(12) United States Patent
Iliopoulos et al.

(10) Patent No.: US 11,485,728 B2
(45) Date of Patent: Nov. 1, 2022

(54) SMALL MOLECULES FOR THE TREATMENT OF AUTOIMMUNE DISEASES AND CANCER

(71) Applicant: Athos Therapeutics, Inc., Los Angeles, CA (US)

(72) Inventors: Dimitrios Iliopoulos, Los Angeles, CA (US); David G. Ho, Monterey Park, CA (US); Iordanis Karagiannidis, North Hollywood, CA (US); Phithi Nguyen, Anaheim, CA (US); Dimitra Chalkia, Fullerton, CA (US)

(73) Assignee: Athos Therapeutics, Inc., Torrance, CA (US)

( * ) Notice: Subject to any disclaimer, the term of this patent is extended or adjusted under 35 U.S.C. 154(b) by 0 days.

(21) Appl. No.: 17/531,397

(22) Filed: Nov. 19, 2021

(65) Prior Publication Data

US 2022/0073498 A1    Mar. 10, 2022

Related U.S. Application Data

(63) Continuation of application No. PCT/US2021/044692, filed on Aug. 5, 2021.

(60) Provisional application No. 63/062,670, filed on Aug. 7, 2020.

(51) Int. Cl.

| | |
|---|---|
| *C07D 401/14* | (2006.01) |
| *C07D 405/14* | (2006.01) |
| *C07D 409/12* | (2006.01) |
| *C07D 409/14* | (2006.01) |
| *C07D 401/04* | (2006.01) |
| *C07D 401/12* | (2006.01) |
| *C07D 405/12* | (2006.01) |
| *C07D 413/14* | (2006.01) |
| *C07D 417/14* | (2006.01) |
| *A61P 1/00* | (2006.01) |
| *A61P 35/00* | (2006.01) |
| *A61P 37/06* | (2006.01) |
| *A61P 1/04* | (2006.01) |
| *A61P 37/00* | (2006.01) |
| *A61P 43/00* | (2006.01) |
| *A61K 31/403* | (2006.01) |
| *A61K 31/4709* | (2006.01) |
| *A61K 31/517* | (2006.01) |

(52) U.S. Cl.
CPC ............ *C07D 401/14* (2013.01); *A61P 1/00* (2018.01); *A61P 35/00* (2018.01); *A61P 37/06* (2018.01); *C07D 405/14* (2013.01); *C07D 409/12* (2013.01); *C07D 409/14* (2013.01)

(58) Field of Classification Search
CPC .. C07D 401/14; C07D 405/14; C07D 409/12; C07D 409/14; C07D 401/04; C07D 401/12; C07D 405/12; C07D 413/14; C07D 417/14; A61P 1/00; A61P 37/06; A61P 35/00; A61P 1/04; A61P 37/00; A61P 43/00; A61K 31/403; A61K 31/4709; A61K 31/517

See application file for complete search history.

(56) References Cited

U.S. PATENT DOCUMENTS

| | | | |
|---|---|---|---|
| 5,710,158 | A | 1/1998 | Myers et al. |
| 2015/0274660 | A1 | 10/2015 | Pliushchev |
| 2019/0201402 | A1 | 7/2019 | Jiang et al. |

FOREIGN PATENT DOCUMENTS

| | | |
|---|---|---|
| WO | WO 92/20642 | 11/1992 |
| WO | WO 04/030672 | 4/2004 |
| WO | WO 06/067614 | 6/2006 |
| WO | WO 07/125331 | 11/2007 |
| WO | WO 12/117048 | 9/2012 |
| WO | WO 13/027794 | 2/2013 |
| WO | WO 15/004533 | 1/2015 |
| WO | WO 16/172332 | 10/2016 |
| WO | WO 17/085053 | 5/2017 |
| WO | WO 18/005799 | 1/2018 |
| WO | WO 19/006322 | 1/2019 |
| WO | WO 19/010180 | 1/2019 |
| WO | WO 20/033585 | 2/2020 |
| WO | WO 20/132409 | 6/2020 |

OTHER PUBLICATIONS

Konze, K. D.. "A chemical tool for in vitro and in vivo precipitation of lysine methyltransferase G9a." ChemMedChem 9.3 (2014): 549-553.*
CAS Registry No. 1239751-08-6.
CAS Registry No. 1239850-93-1.
CAS Registry No. 1284061-91-1.
CAS Registry No. 1408805-43-5.
CAS Registry No. 1409718-73-5.
CAS Registry No. 1957376-97-4.
CAS Registry No. 2134081-16-4.
CAS Registry No. 2373601-00-2.
CAS Registry No. 2398726-29-7.
Ahmed et al., Sep. 20, 2019. In vitro Characterization of Gut Microbiota-Derived Bacterial Strains With Neuroprotective Properties. Front Cell Neurosci. 13:402.

(Continued)

*Primary Examiner* — John M Mauro

(74) *Attorney, Agent, or Firm* — Knobbe, Martens, Olson & Bear, LLP

(57) ABSTRACT

Disclosed herein are quinazolinyl compounds, compositions, and methods of use thereof. The compounds may be used in the treatment of autoimmune disorders or cancer.

12 Claims, 14 Drawing Sheets

(56) References Cited

OTHER PUBLICATIONS

Antignano et al., 2016, G9a regulates group 2 innate lymphoid cell development by repressing the group 3 innate lymphoid cell program, J Exp Med, 213(7):1152-1162.
Antignano et al., May 2014, Methyltransferase G9A regulates T cell differentiation during murine intestinal inflammation. J Clin Invest. 124(5):1945-1955.
Arijs et al., 2009, Mucosal gene signatures to predict response to infliximab in patients with ulcerative colitis, Gut, 58:1612-1619.
Bajer et al., Jul. 7, 2017, Distinct gut microbiota profiles in patients with primary sclerosing cholangitis and ulcerative colitis. World J Gastroenterol. 23(25):4548-4558.
Bannister et al., Mar. 1, 2001, Selective recognition of methylated lysine 9 on histone H3 by the HP1 chromo domain, Nature, 410:120-124.
Bolger et al., 2014, Trimmomatic: a flexible trimmer for Illumina sequence data. Bioinformatics, 30(15):2114-2120.
Buchfink et al., Jan. 2015, Fast and sensitive protein alignment using DIAMOND. Nature Methods 12(1):59-60.
Caporaso et al., May 2010, QIIME allows analysis of high-throughput community sequencing data. Nat Methods 7(5):335-336.
Casciello et al., 2017, G9a in hypoxia: linking tumor hypoxia and epigenetic regulations, Cell Cycle, 16(21):2001-2002.
Gerami et al., May 2012, The cBio cancer genomics portal: an open platform for exploring multidimensional cancer genomics data, Cancer Discov, 2(5):401-404.
Chamie et al., May 2015, Carbonic anhydrase-IX score is a novel biomarker that predicts recurrence and survival for high-risk, nonmetastatic renal cell carcinoma: data from the phase III ARISER clinical trial, Urol Oncol. 33(5):204.e25-204.e33.
Charles et al., 2019, Delineating the active site architecture of G9a lysine methyltransferase through substrate and inhibitor binding mode analysis: a molecular dynamics study, Journal of Biomolecular Structure and Dynamics, 37(10):2581-2591.
Charles et al., 2020, Identification of novel quinoline inhibitors for EHMT2/G9a through virtual screening, Biochimie, 168:220-230 and Supporting Information.
Chen et al., Jul. 2008, A Novel Design of Artificial Membrane for Improving the PAMPA Model, Pharmaceutical Research, 25(7):1511-1520.
Collins et al., Feb. 16, 2010, Survey and summary: a case study in cross-talk: the histone lysine methyltransferases G9a and GLP, Nucleic Acids Res, 38(11):3503-3511.
Delday et al., Jan. 2019, Bacteroides thetaiotaomicron Ameliorates Colon Inflammation in Preclinical Models of Crohn's Disease, Inflammatory Bowel Diseases 25(1):85-96.
Ghose et al., 1998, Prediction of hydrophobic (lipophilic) properties of small organic molecules using fragmental methods; an analysis of ALOGP and CLOGP methods, J. Phys. Chem. A., 102:3762-3772.
Hall et al., Sep. 27, 2002, Establishment and maintenance of a heterochromatin domain, Science, 297:2232-2237.
Herrera-Vazquez et al., 2019, Quinazolines as inhibitors of chromatin-associated proteins in histones, Medicinal Chemistry Research, 28:395-416.
Hooper et al., Feb. 2, 2001, Molecular analysis of commensal host-microbial relationships in the intestine, Science, 291:881-884.
Hua et al., 2014, The H3K9 methyltransferase G9a is a marker of aggressive ovarian cancer that promotes peritoneal metastasis, Mol Cancer, 13:189.
Huang et al., Mar. 26, 2010, G9a and Glp methylate lysine 373 in the tumor suppressor p53, J Biol Chem, 285(13):9636-9641.
Hyun et al., 2017, Writing, erasing and reading histone lysine methylations, Exp Mol Med, 49:e324.
Jenuwein et al., Aug. 10, 2001, Translating the histone code, Science, 293:1074-1080.
Johnson et al., Mar. 2020, The Role of Tissue-resident T Cells in Stress Surveillance and Tissue Maintenance. Cells. 9(3):686.
Kelly et al., Jan. 2004, Commensal anaerobic gut bacteria attenuate inflammation by regulating nuclear-cytoplasmic shuttling of PPAR-γ and relA, Nat Immunol, 5(1):104-112.
Kim et al., 2016, Centrifuge: rapid and sensitive classification of metagenomic sequences. Genome Res 12:1721-1729.
Klatte et al., Apr. 1, 2009, Carbonic anhydrase IX in bladder cancer, Cancer, 115(7):1448-1458.
Leenders et al., 2019, Novel SAR for quinazoline inhibitors of EHMT1 and EHMT2, Bioorganic & Medicinal Chemistry Letters. 29:2516-2524.
Liao et al., Jun. 2011, Software and resources for computational medicinal chemistry, Future Med. Chem., 3(8):1057-1085.
Liu et al., 2009, Discovery of a 2,4-diamino-7-aminoalkoxyquinazoline as a potent and selective inhibitor of histone lysine methyltransferase G9a, J. Med. Chem., 52:7950-7953.
Liu et al., 2010, Protein lysine methyltransferase G9a inhibitors: design, synthesis, and structure activity relationships of 2,4-diamino-7-aminoalkoxy-quinazolines, J. Med. Chem., 53:5844-5857.
Liu et al., 2011, Optimization of cellular activity of G9a inhibitors 7-aminoalkoxy-quinazolines, Journal of Medicinal Chemistry, 54:6139-6150.
Liu et al., Nov. 14, 2013, Discovery of an in Vivo Chemical Probe of the Lysine Methyltransferases G9a and GLP, J. Med. Chem., 56(21):8931-8942.
Ma et al., 2014, Structure-activity relationship studies of SETD8 inhibitors, Medicinal Chemistry Communications, 5:1892-1898.
MacDonald et al., 2019, Pathway-Based High-Throughput Chemical Screen Identifies Compounds That Decouple Heterchromatin Transformation, SLAS Discovery, 24(8):802-816 and Supplemental Material.
Miao et al., 2008, Histone methylation patterns are cell-type specific in human monocytes and lymphocytes and well maintained at core genes, J Immunol, 180:2264-2269.
Mikkelsen et al., Aug. 2, 2007, Genome-wide maps of chromatin state in pluripotent and lineage-committed cells, Nature, 448:553-560.
Milite et al., 2019, Discovery of a novel chemotype of histone lysine methyltransferase EHMT1/2 (GLP/G9a) inhibitors: rational design, synthesis, biological evaluation, and co-crystal structure, J. Med. Chem, 62:2666-2689.
Mirallai et al., 2015, The Conversion of 4-Anilinoquinazoline- and 3-Aryl-4-imino-3,4-dihydro-quinazoline-2-carbonitriles into Benzo[4,5]imidazole[1,2-c]quinazoline-6-carbonitriles via Oxidative and Nonoxidative C—N Couplings, The Journal of Organic Chemistry. 80:8329-8340.
Mukhopadhya et al., 2011, A comprehensive evaluation of colonic mucosal isolates of sutterella wadsworthensis from inflammatory bowel disease. PloS One. 6:1-10.
Overington et al., Dec. 2006, How many drug targets are there?, Nature Reviews/Drug Discovery, 5:993-996.
Peterson et al., Jul. 1992, Characterization of the enterocyte-like brush border cytoskeleton of the C2BBe clones of the human intestinal cell line, Caco-2. J Cell Sci. 102:581-600.
Portela et al., 2010, Epigenetic modifications and human disease, Nat Biotechnol, 28:1057-1068.
Rabal et al., 2018, Discovery of reversible DNA methyltrasnferase and lysine methyltrasnferase G9a inhibitors with antitumoral in vivo efficacy, J. Med. Chem., 61:6518-6545.
Ray et al., Jan. 10, 2019, Epigenetics, DNA Organization, and Inflammatory Bowel Disease. Inflamm Bowel Dis. 25(2):235-247.
Roda et al., Sep. 14, 2010, Intestinal epithelial cells in inflammatory bowel diseases. World J Gastroenterol. 16(34):4264-4271.
Rowe et al., 2006, Handbook of Pharmaceutical Excipients, 5th ed., pp. 253-254, 624-625.
Safdari et al., Jul. 2016, Effects of pro-inflammatory cytokines, lipopolysaccharide and COX-2 mediators on human colonic neuromuscular function and epithelial permeability, Cytokine, 83:231-238.
Segata et al., 2011, Metagenomic biomarker discovery and explanation, Genome Biol 12:R60.
Shinkai et al., 2011, H3K9 methyltrasnferase G9a and the related molecule GLP, Genes & Development 25:781-788.

(56) References Cited

OTHER PUBLICATIONS

Srimongkolpithak et al., Dec. 2014, Identification of 2,4-diamoni-6,7-dimethoxyquinoline derivatives as G9a inhibitors, Med. Chem. Comm., 5(12):1821-1828.
Sweis et al., 2014, Discovery and development of potent and selective inhibitors of histone methyltransferase G9a, ACS Med. Chem. Letters, 5:205-209 and Supporting Information.
Vedadi et al., Aug. 1, 2012, A chemical probe selectively inhibits G9a and GLP methyltransferase activity in cells, Nat Chem Biol., 7(8):566-574.
Wrzosek et al., 2013, Bacteroides thetaiotaomicron and faecalibacterium prausnitzii influence the production of mucus glycans and the development of goblet cells in the colonic epithelium of a gnotobiotic model rodent. BMC Biol 11:61.
Xiong et al., Mar. 9, 2017, Discovery of Potent and Selective Inhibitors for G9a-Like Protein (GLP) Lysine Methyltransferase, J. Med. Chem., 60(5):1876-1891.
Karthikeyan et al., 2017, N-(1H-pyrazol-3-yl)quinazolin-4-amines as a novel class of casein kinase1 δ/ε inhibitors: synthesis, biological evaluation and molecular modeling studies, Bioorganic & Medicinal Chemistry Letters, doi: http//dx/doi.org/10.1016/j.bmcl.2017.04.080.

\* cited by examiner

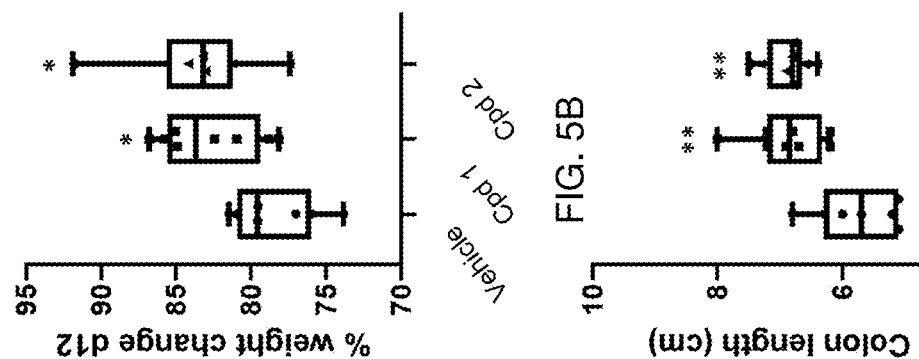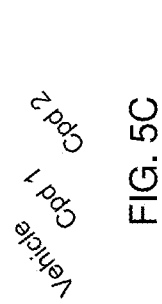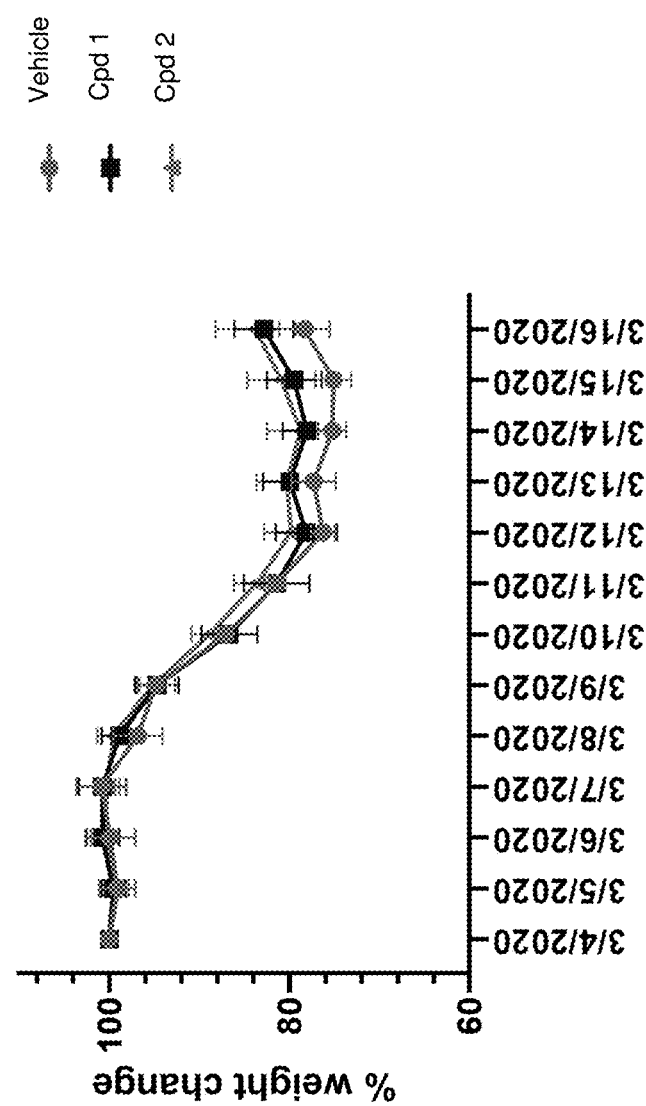
FIG. 5A
FIG. 5B
FIG. 5C

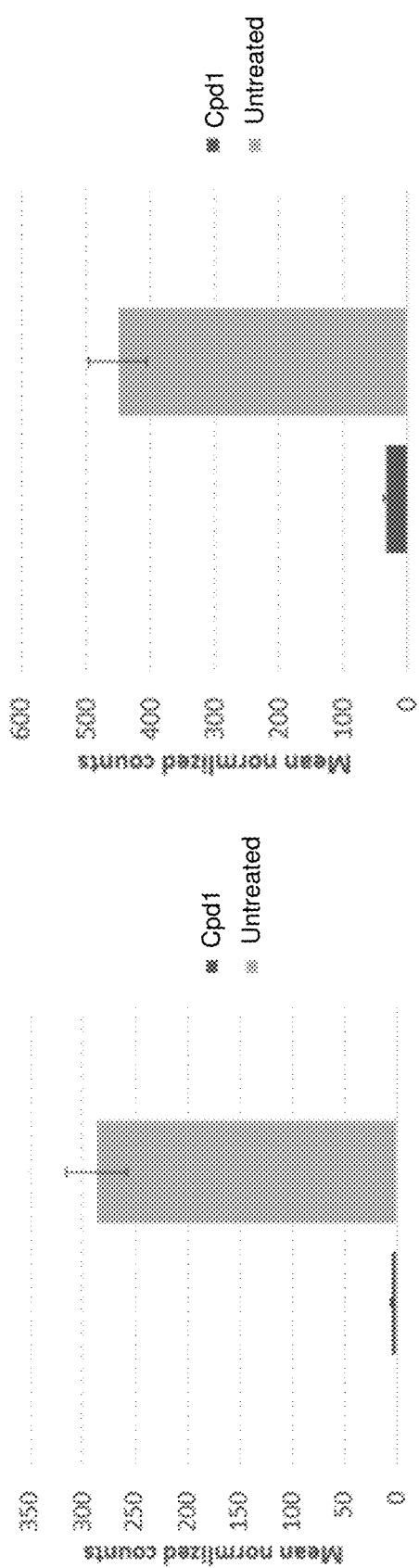
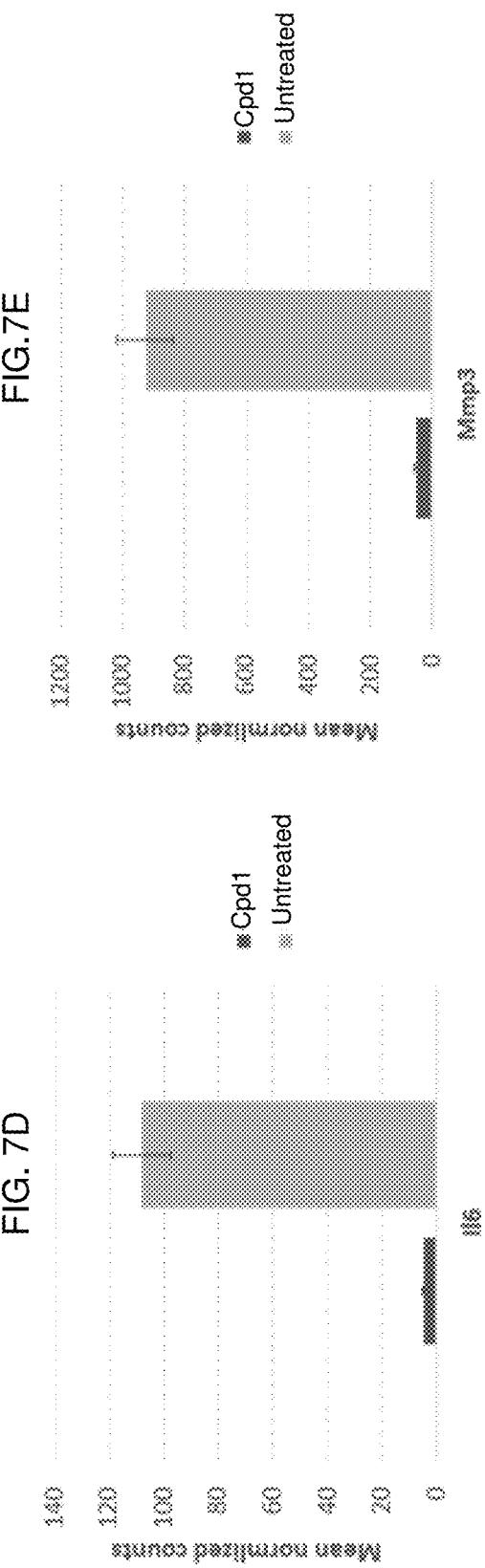
FIG. 7D
FIG. 7E
FIG. 7F
FIG. 7G

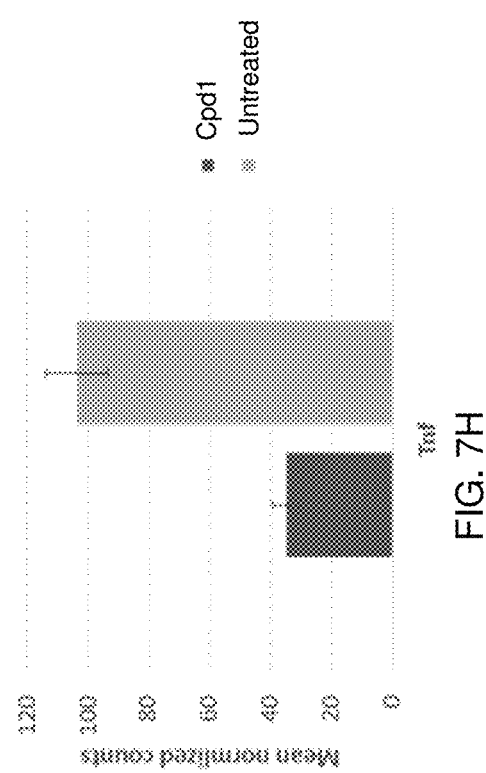

SMALL MOLECULES FOR THE TREATMENT OF AUTOIMMUNE DISEASES AND CANCER

CROSS REFERENCE TO RELATED APPLICATIONS

The present application is a continuation of PCT/US2021/044692, filed Aug. 5, 2021, which claims the benefit of priority to U.S. Provisional Patent Application No. 63/062,670, filed Aug. 7, 2020. Each of the foregoing applications is fully incorporated herein by reference in its entirety for all purposes. All applications for which a foreign or domestic priority claim is identified in the Application Data Sheet as filed with the present application are hereby incorporated by reference herein under 37 C.F.R. § 1.57.

BACKGROUND

Field

The present application relates to the fields of chemistry and medicine. More specifically, the application relates to compounds that are useful in the treatment of autoimmune disorders and cancer. Several embodiments pertain to quinazolinyl compounds, their methods of manufacture, and use.

Description of the Related Technology

Histone post-translational modifications are epigenetic mechanisms that affect the structure of the chromatin, leading to gene expression alterations and ultimately contributing to the pathogenesis of different human diseases, including autoimmune diseases and cancer. Specifically, the N-terminal tails of histones are subject to reversible covalent modifications, including acetylation, methylation, phosphorylation, ubiquitination and sumoylation. These modifications regulate the ability of transcription factors to access the underlying DNA by modifying histone affinity for its negatively charged sugar backbone, affecting replication, transcription and chromatin stability.

SUMMARY

Several embodiments disclosed herein pertain to quinazolinyl compounds, methods of making quinazolinyl compounds, compositions comprising quinazolinyl compounds, and methods of treatment using quinazolinyl compounds. In several embodiments, the quinazolinyl compound is used to treat an autoimmune disorder (e.g., in a method of treating a subject having an autoimmune disorder). In some embodiments, the autoimmune disorder is selected from the group consisting of Ulcerative Colitis, Crohn's disease, systemic lupus erythematosus, psoriasis, rheumatoid arthritis, type 1 diabetes, multiple sclerosis, celiac disease, Graft versus host disease (GVHD), Sjogren syndrome, Graves' Disease, Hashimoto's Thyroiditis, Autoimmune Hepatitis, Behcet's Disease, atopic dermatitis, Castleman disease, Allergic Rhinitis, Eczema, Dressler's Syndrome, Eosinophilic esophagitis, Fibromyalgia, Guillain-Barre Syndrome, Juvenile arthritis, Kawasaki disease, Mooren's ulcer, mixed connective tissue disease, Parry Romberg syndrome, primary biliary cirrhosis, primary sclerosing cholangitis, psoriatic arthritis, sarcoidosis, scleroderma, undifferentiated connective tissue disease, uveitis, vasculitis and vitiligo.

In several embodiments, the quinazolinyl compound is used to treat a cancer. In some embodiments, the cancer is selected from the group consisting of colorectal, gastric, stomach, esophageal, liver, pancreatic, breast, prostate, bladder, renal, ovarian, lung, melanoma, and multiple myeloma.

In several embodiments, the quinazolinyl compound is a compound of Formula (I):

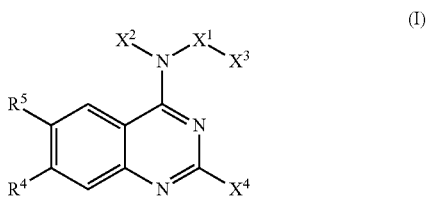

or a stereoisomer, tautomer, or pharmaceutically acceptable salt thereof.

In some embodiments, $X^1$ is $CH_2$ or a covalent bond.

In some embodiments, $X^2$ is hydrogen or optionally substituted $C_1$-$C_{10}$ alkyl and $X^3$ is selected from the group consisting of —CN, optionally substituted $C_1$-$C_{10}$ alkyl, optionally substituted 2-10 membered heteroalkyl, optionally substituted 3-10 membered carbocyclyl, optionally substituted (carbocyclyl)alkyl, optionally substituted (heterocyclyl)alkyl, optionally substituted 6-10 membered aryl, optionally substituted 3-10 membered heterocyclyl, or optionally substituted 5-10 membered heteroaryl; or alternatively, $X^2$ and $X^3$ are taken together with the atoms to which they are attached to form an optionally substituted 3-10 membered heterocyclyl.

In some embodiments, $X^4$ is selected from the group consisting of —CN, —$OR^1$, —$SR^1$, halogen, optionally substituted $C_1$-$C_{10}$ alkyl, optionally substituted $C_1$-$C_{10}$ alkenyl, optionally substituted $C_1$-$C_{10}$ alkynyl, optionally substituted 3-10 membered carbocyclyl, optionally substituted 6-10 membered aryl, optionally substituted 3-10 membered heterocyclyl, optionally substituted 5-10 membered heteroaryl, and —$NR^2R^3$.

In some embodiments, $R^1$ is hydrogen or an optionally substituted $C_1$-$C_{10}$ alkyl;

In some embodiments, each of $R^2$ and $R^3$ is independently selected from hydrogen and optionally substituted $C_{1-10}$ alkyl; or alternatively, $R^2$ and $R^3$ attached to the same nitrogen atom may be together with the atom to which they are attached, form an optionally substituted 3-10 membered heterocyclyl or an optionally substituted 5-10 membered heteroaryl.

In some embodiments, $R^4$ is —$OR^9$ or (heterocyclyl)alkynyl.

In some embodiments, $R^9$ is selected from the group consisting of methyl, optionally substituted 2-10 membered heteroalkyl, and (heterocyclyl)alkyl.

In some embodiments, $R^5$ is selected from the group consisting of hydrogen, halogen, and —OMe.

Several embodiments pertain to a compound of Formula (I):

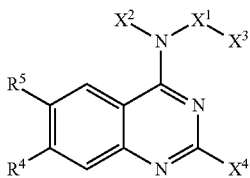

where $X^1$ is —$(CH_2)_o$— or a covalent bond; o is an integer equal to 1, 2, 3, 4, 5, or 6; $X^2$ is hydrogen and $X^3$ is selected from the group consisting of —CN, optionally substituted $C_1$-$C_{10}$ alkyl, optionally substituted 2-10 membered heteroalkyl, optionally substituted 3-10 membered carbocyclyl, optionally substituted (carbocyclyl)alkyl, optionally substituted (heterocyclyl)alkyl, optionally substituted 6-10 membered aryl, optionally substituted 3-10 membered heterocyclyl, or optionally substituted 5-10 membered heteroaryl; or alternatively, $X^2$ and $X^3$ are taken together with the atoms to which they are attached to form an optionally substituted 3-10 membered heterocyclyl; $X^4$ is selected from the group consisting of —CN, —$OR^1$, —$SR^1$, halogen, optionally substituted $C_1$-$C_{10}$ alkyl, optionally substituted $C_1$-$C_{10}$ alkenyl, optionally substituted $C_1$-$C_{10}$ alkynyl, optionally substituted 3-10 membered carbocyclyl, optionally substituted 6-10 membered aryl, optionally substituted 3-10 membered heterocyclyl, optionally substituted 5-10 membered heteroaryl, and —$NR^2R^3$; $R^1$ is hydrogen or an optionally substituted $C_1$-$C_{10}$ alkyl; each of $R^2$ and $R^3$ is independently selected from hydrogen and optionally substituted $C_{1-10}$ alkyl; or alternatively, $R^2$ and $R^3$ attached to the same nitrogen atom may be together with the atom to which they are attached, form an optionally substituted 3-10 membered heterocyclyl or an optionally substituted 5-10 membered heteroaryl; $R^4$ is —$OR^9$ or (heterocyclyl)alkynyl; $R^9$ is selected from the group consisting of methyl, optionally substituted 2-10 membered heteroalkyl, and (heterocyclyl)alkyl; and $R^5$ is selected from the group consisting of hydrogen, halogen, and —OMe; or a stereoisomer, tautomer, or pharmaceutically acceptable salt thereof.

In several embodiments, if $X^3$ is

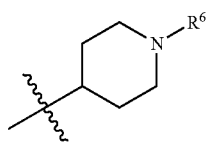

wherein $R^6$ is unsubstituted benzyl, unsubstituted 3-10 membered carbocyclyl, or $C_1$-$C_{10}$ alkyl optionally substituted with amine, if $R^2$ and $R^3$ are present, they come together to form an optionally substituted 5-membered heteroaryl or an optionally substituted 4-membered heterocyclyl; and provided that if $X^3$ is

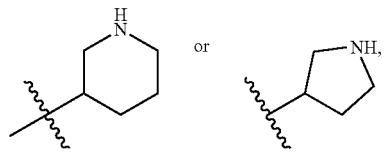 [SMILES: *C1CCCNC1 ; "or" ; *C1CCNC1]

$R^4$ is

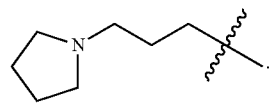

In several embodiments, the compound of Formula (I) is further represented by a compound of Formula (Ia):

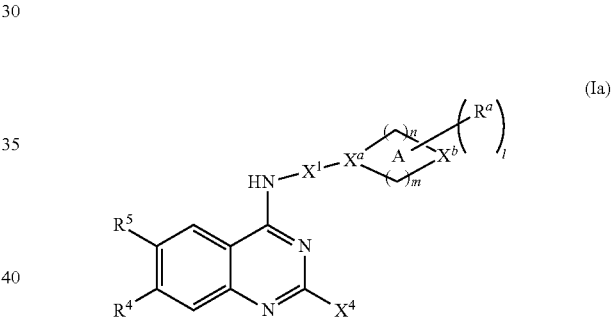

wherein ring "A" is a cycloalkyl ring or a heterocyclyl ring; $X^a$ is selected from the group consisting of CH and N; m is independently an integer selected from 0, 1, 2, and 3; n is independently an integer selected from 0, 1, 2, and 3; l is an integer selected from 0, 1, 2, and 3; $X^b$ is selected from the group consisting of $CH_2$, $NR^b$, O, and $SO_2$; $R^a$ is optionally present and can be provided at any position of the "A" ring by replacing one or more —H of any carbon or nitrogen atom present within the "A" ring; $R^a$ is selected from the group consisting of amino, —OH, and optionally substituted $C_1$-$C_6$ alkyl; and $R^b$ is selected from the group consisting of hydrogen, optionally substituted $C_1$-$C_6$ alkyl, and C-carboxy. In several embodiments, n is 1 and m is 3. In several embodiments, $X^b$ is O or $SO_2$. In several embodiments, the compound is selected from the group consisting of Compound 1, 6, 11, 14, 15, 19, 24, 26, 28, 66, 80, 81, 82, 83, 84, 85, 86, 87, 88, 89, 90, 91, 92, 93, 94, 95, 96, 97, 98, 99, 100, 101, 102, 105, 106, 107, 108, 116, 117, 119, 120, 121, 122, 123, 124, 125, 126, 127, 128, 129, 131, 136, 137, 139, 140, 141, 142, 143, 144, 145, 146, 147, 148, 149, 164, 165, 173, 174, 175, 177, 178, 179, 180, 181, 182, 183, 184, 185, 186, 187, 188, 189, 190, 191, 192, 193, 194, 195, 196, 197, 198, 199, 200, 201, or a stereoisomer, tautomer, or pharmaceutically acceptable salt of any of the foregoing.

In several embodiments, the compound of Formula (I) is further represented by a compound of Formula (Ib):

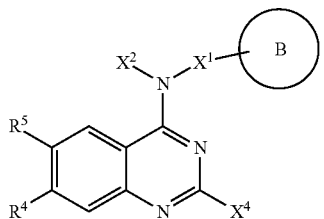

(Ib)

wherein $X^3$ is represented by ring "B";
wherein the "B" ring is an unsaturated ring selected from the group consisting of optionally substituted cyclopentenyl, optionally substituted phenyl, optionally substituted furyl, optionally substituted thienyl, optionally substituted pyrrolyl, optionally substituted oxazolyl, optionally substituted thiazolyl, optionally substituted imidazolyl, optionally substituted benzimidazolyl, optionally substituted pyrazolyl, optionally substituted isoxazolyl, optionally substituted triazolyl, optionally substituted pyridinyl, optionally substituted pyridazinyl, optionally substituted pyrimidinyl, optionally substituted pyrazinyl, optionally substituted indolyl, optionally substituted isoindolyl, and optionally substituted benzothienyl. In several embodiments, the "B" ring is selected from any of the following:

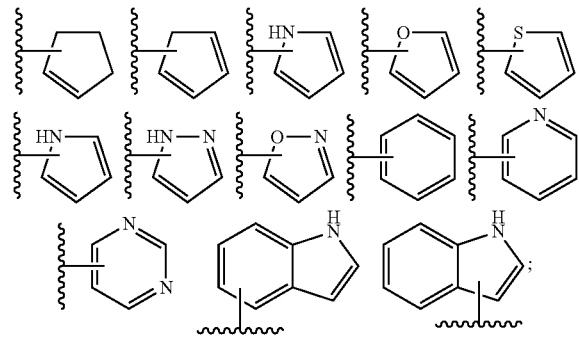

any one of which may be optionally substituted by replacing one or more —H atoms of any carbon or nitrogen atom present on the "B" ring.

In several embodiments, optional substitutions of the "B" ring are selected from one or more amino, —OH, optionally substituted $C_1$-$C_6$ alkyl, and halogen.

In several embodiments, the compound of Formula (I) is further represented by a compound of Formula (Ic):

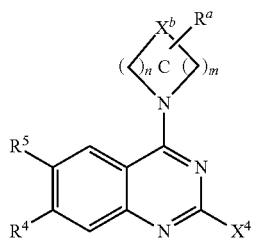

(Ic)

where m is independently an integer selected from 0, 1, 2, and 3; n is independently an integer selected from 0, 1, 2, and 3; $X^b$ is selected from the group consisting of $CH_2$, $NR^b$, O, and $SO_2$; $R^a$ is optionally present and can be provided at any position of the "C" ring by replacing one or more —H of any carbon or nitrogen atom present within the "C" ring; $R^a$ is selected from the group consisting of amino, N-amido, —OH, optionally substituted $C_1$-$C_6$ alkyl; and $R^b$ is selected from $C_1$-$C_6$ alkyl and C-carboxy.

In several embodiments, the compound of Formula (I) is further represented by a compound of Formula (Id):

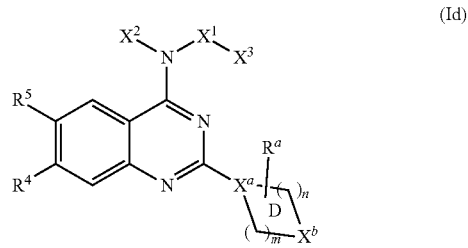

(Id)

wherein ring "D" is a cycloalkyl ring or a heterocyclyl ring; $X^a$ is selected from the group consisting of CH and N; m is independently an integer selected from 0, 1, 2, and 3; n is independently an integer selected from 0, 1, 2, and 3; $X^b$ is selected from the group consisting of $CH_2$, $NR^h$, O, and $SO_2$; $R^a$ is optionally present and can be provided at any position of the "D" ring by replacing one or more —H of any carbon or nitrogen atom present within the "D" ring; $R^a$ is selected from the group consisting of halogen, amino, —OH, optionally substituted $C_1$-$C_6$ alkyl; and $R^h$ is selected from the group consisting of hydrogen, optionally substituted $C_1$-$C_6$ alkyl, and C-carboxy. In several embodiments, n is 1 and m is 2. In several embodiments, n is 1 and m is 3. In several embodiments, n is 2 and m is 2.

In several embodiments, the compound of Formula (I) is further represented by a compound of Formula (Ie):

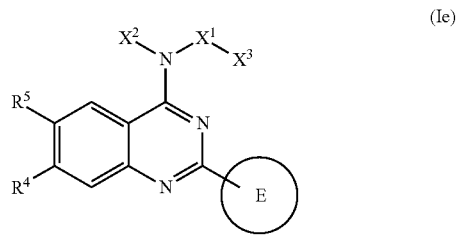

(Ie)

wherein $X^4$ is represented by ring "E"; wherein the "E" ring is an unsaturated ring selected from the group consisting of optionally substituted cyclopentenyl, optionally substituted phenyl, optionally substituted furyl, optionally substituted thienyl, optionally substituted pyrrolyl, optionally substituted oxazolyl, optionally substituted thiazolyl, optionally substituted imidazolyl, optionally substituted benzimidazolyl, optionally substituted pyrazolyl, optionally substituted isoxazolyl, optionally substituted triazolyl, optionally substituted pyridinyl, optionally substituted pyridazinyl, optionally substituted pyrimidinyl, optionally substituted pyrazinyl, optionally substituted indolyl, optionally substituted isoindolyl, and optionally substituted benzothienyl. In several embodiments, the "E" ring is selected from any of the following:

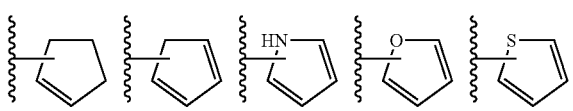

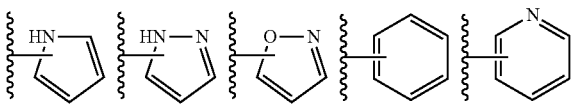

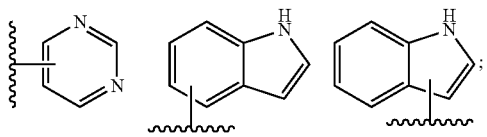

any one of which may be optionally substituted by replacing one or more —H atoms of any carbon or nitrogen atom present on the "E" ring.

In several embodiments, the optional substitutions of the "E" ring are selected from one or more of amino, —OH, optionally substituted $C_1$-$C_6$ alkyl, and halogen.

In several embodiments, the compound of Formula (I) is further represented by a compound of Formula (If):

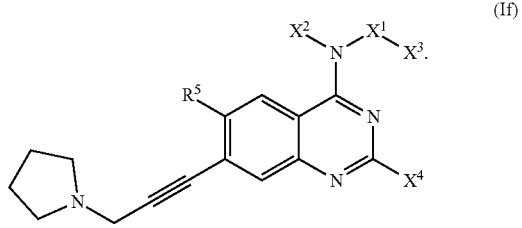

where the variables are as defined elsewhere herein.

In several embodiments, $X^3$ is a substituted 6-membered heterocyclyl. In several embodiments, $X^3$ is an unsubstituted 6-membered heterocyclyl. In several embodiments, $X^3$ is an unsubstituted 6-membered aryl. In several embodiments, $X^3$ is an unsubstituted 2-10 membered heteroalkyl.

In several embodiments, $X^4$ is an optionally substituted 4-6 membered heterocyclyl. In several embodiments, $X^4$ is a 5-membered heteroaryl. In several embodiments, $X^4$ is —CN.

In several embodiments, $X^1$ is a covalent bond. In several embodiments, $X^1$ is $CH_2$.

In several embodiments, $X^2$ is hydrogen.

In several embodiments, $R^4$ is

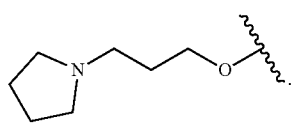 [SMILES: *OCCCN1CCCC1]

In several embodiments, $R^5$ is —OMe.

In several embodiments, the compound of Formula (I) is further represented by Formula (Ig):

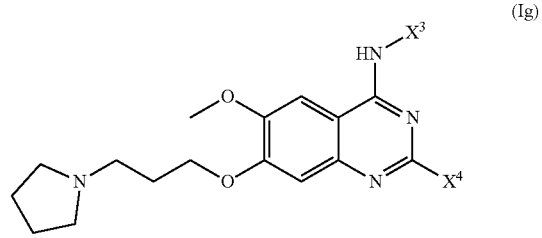

wherein $X^3$ is selected from the group consisting of optionally substituted 2-10 membered heteroalkyl, optionally substituted 3-10 membered heterocyclyl, or optionally substituted 5-10 membered heteroaryl; and $X^4$ is —CN or —$NR^2R^3$.

In several embodiments, the compound of Formula (I) is further represented by Formula (Ih):

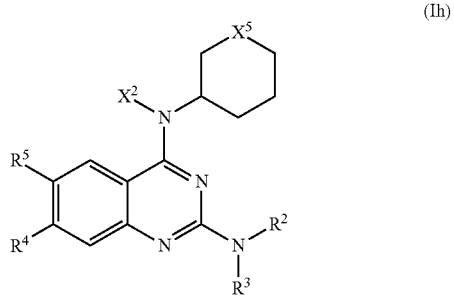

wherein $X^5$ is oxygen or sulfonyl.

In several embodiments, the compound of Formula (I) is further represented by Formula (Ij):

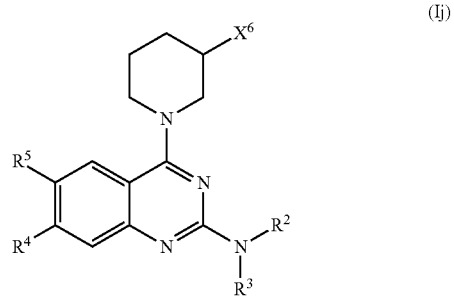

wherein $X^6$ is selected from the group consisting of hydrogen, —$NH_2$, —OH, and N-amide.

In several embodiments, the compound of Formula (I) is further represented by Formula (Ik):

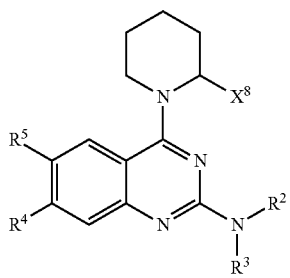

(Ik)

wherein X⁸ is selected from the group consisting of hydrogen, —NH₂, —OH, and N-amide.

In several embodiments, the compound is selected from

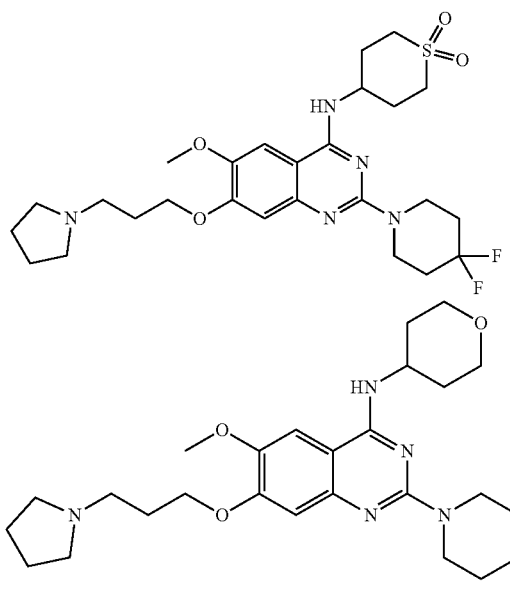

and or a stereoisomer, tautomer, or pharmaceutically acceptable salt thereof.

Some embodiments pertain to a pharmaceutical composition comprising a therapeutically effective amount of a compound as described above and a pharmaceutically acceptable excipient.

Some embodiments pertain to a method of treating an autoimmune disorder, comprising administering to a subject in need thereof a compound of Formula (I):

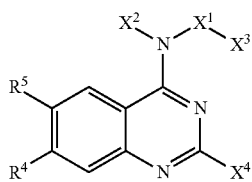

(I)

wherein $X^1$ is CH₂ or a covalent bond; $X^2$ is hydrogen and $X^3$ is selected from the group consisting of —CN, optionally substituted $C_1$-$C_{10}$ alkyl, optionally substituted 2-10 membered heteroalkyl, optionally substituted 3-10 membered carbocyclyl, optionally substituted (carbocyclyl)alkyl, optionally substituted (heterocyclyl)alkyl, optionally substituted 6-10 membered aryl, optionally substituted 3-10 membered heterocyclyl, or optionally substituted 5-10 membered heteroaryl; or alternatively, $X^2$ and $X^3$ are taken together with the atoms to which they are attached to form an optionally substituted 3-10 membered heterocyclyl; $X^4$ is selected from the group consisting of —CN, —OR¹, —SR¹, halogen, optionally substituted $C_1$-$C_{10}$ alkyl, optionally substituted $C_1$-$C_{10}$ alkenyl, optionally substituted $C_1$-$C_{10}$ alkynyl, optionally substituted 3-10 membered carbocyclyl, optionally substituted 6-10 membered aryl, optionally substituted 3-10 membered heterocyclyl, optionally substituted 5-10 membered heteroaryl, and —NR²R³; R¹ is hydrogen or an optionally substituted $C_1$-$C_{10}$ alkyl; each of R² and R³ is independently selected from hydrogen and optionally substituted $C_1$-$C_{10}$ alkyl; or alternatively, R² and R³ attached to the same nitrogen atom may be together with the atom to which they are attached, form an optionally substituted 3-10 membered heterocyclyl or an optionally substituted 5-10 membered heteroaryl; R⁴ is —OR⁹ or (heterocyclyl)alkynyl; R⁹ is selected from the group consisting of methyl, optionally substituted 2-10 membered heteroalkyl, and (heterocyclyl)alkyl; and R⁵ is selected from the group consisting of hydrogen, halogen, and —OMe; or a stereoisomer, tautomer, or pharmaceutically acceptable salt thereof.

Some embodiments pertain to a method of treating an autoimmune disorder or cancer, comprising administering to a subject in need thereof a compound as disclosed elsewhere herein, a pharmaceutical composition comprising that compound, a compound having the following structure:

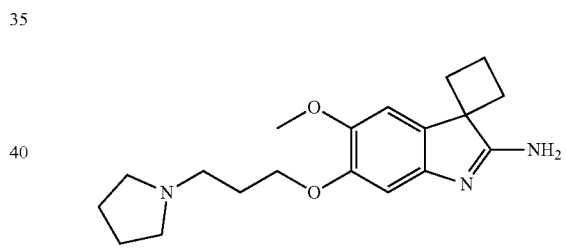

or a compound according to Formula (II):

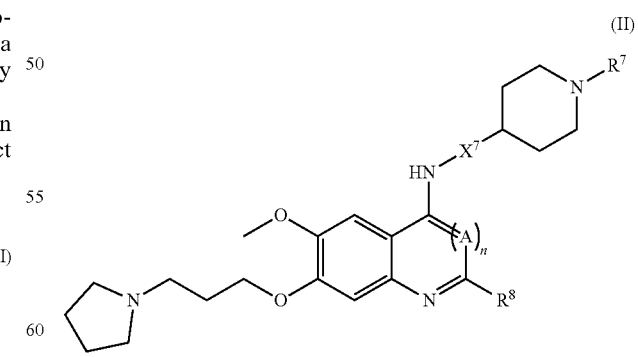

(II)

wherein: $X^7$ is CH₂ or a covalent bond; R⁷ is $C_1$-$C_6$ alkyl or 3-6 membered carbocyclyl; R⁸ is selected from the group consisting of cyclohexyl, 5-6 membered heteroaryl optionally substituted with methyl, or 5-7 membered heterocyclyl optionally substituted with fluoro, oxo, or $C_1$-$C_6$ alkyl; A is selected from the group consisting of N, CH, or $CH_2$; n is independently an integer selected from 0, 1, and 2; or a stereoisomer, tautomer, or pharmaceutically acceptable salt thereof.

Some embodiments pertain to a method of treating an autoimmune disorder, comprising administering a compound as disclosed herein or a pharmaceutical composition as disclosed herein to a patient having an autoimmune disorder. In several embodiments, the autoimmune disorder is selected from the group consisting of Ulcerative Colitis, Crohn's disease, systemic lupus erythematosus, psoriasis, rheumatoid arthritis, type 1 diabetes, multiple sclerosis, celiac disease, Graft versus host disease (GVHD), Sjogren syndrome, Graves' Disease, Hashimoto's Thyroiditis, Autoimmune Hepatitis, Behcet's Disease, atopic dermatitis, Castleman disease, Allergic Rhinitis, Eczema, Dressler's Syndrome, Eosinophilic esophagitis, Fibromyalgia, Guillain-Barre Syndrome, Juvenile arthritis, Kawasaki disease, Mooren's ulcer, mixed connective tissue disease, Parry Romberg syndrome, primary biliary cirrhosis, primary sclerosing cholangitis, psoriatic arthritis, sarcoidosis, scleroderma, undifferentiated connective tissue disease, uveitis, vasculitis and vitiligo. In several embodiments, the autoimmune disorder is selected from the group consisting of Ulcerative Colitis, Crohn's disease, systemic lupus erythematosus, psoriasis, rheumatoid arthritis, type 1 diabetes, multiple sclerosis, and celiac disease. In several embodiments, the autoimmune disorder is Crohn's disease. In several embodiments, the autoimmune disorder is Ulcerative Colitis.

Some embodiments pertain to a method of treating cancer, comprising administering a compound as disclosed herein or a pharmaceutical composition as disclosed herein to a patient having cancer. In several embodiments, the cancer is selected from the group consisting of colorectal, gastric, stomach, esophageal, liver, pancreatic, breast, prostate, bladder, renal, ovarian, lung, melanoma, and multiple myeloma.

BRIEF DESCRIPTION OF THE DRAWINGS

FIG. 5A is a graph showing the percent weight change in mice after treatment with selected compounds.

FIG. 5B is a chart showing the percent weight change of mice after exposure to selected conditions.

FIG. 5C is a chart showing the colon lengths of mice after exposure to selected conditions.

FIGS. 7D-7G. Colon tissue gene expression. Mice with TNBS-induced Colitis and a compound as disclosed herein showed significantly reduced expression of marker genes for patients with untreated or refractory Ulcerative Colitis (marker genes for Infliximab response, a mouse/human chimeric monoclonal IgG1 antibody to tumor necrosis factor alpha (TNFa), were taken from a published study.

FIG. 7H provides data for mice with TNBS-induced Colitis and treated with a compound as disclosed herein. Treated mice showed significantly reduced expression of the pro-inflammatory cytokine TNF.

DETAILED DESCRIPTION

Figure 1:
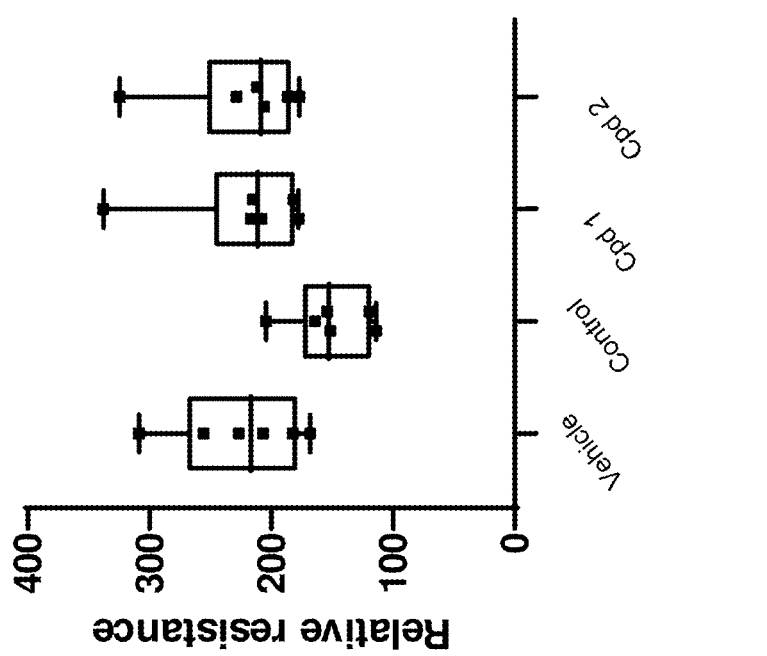
FIG. 1 is a chart showing the relative transepithelial resistance of CaCo-2 cells after 24 hours of exposure to selected conditions.

Several embodiments disclosed herein pertain to quinazolinyl compounds, methods of using quinazolinyl compounds, compositions comprising quinazolinyl compounds, and methods of treatment using quinazolinyl compounds. In several embodiments, the quinazoline compounds comprise a quinazoline core. In several embodiments, the quinazoline compound comprises a cyclic substituent bonded to the quinazoline ring at the 2-position. In several embodiments, the quinazoline compound comprises an amine substituent bonded to the quinazoline ring at the 4-position. In several embodiments, the quinazoline compound comprises the amine at the 4-position comprising a cyclic substituent (either pendant or directly bonded to the amine) or the amine is part of a cyclic substituent. In several embodiments, the quinazoline compound comprises a methoxy group at the 6-position. In several embodiments, the quinazoline compound comprises an alkoxy group at the 7-position. In several embodiments, the quinazoline compound comprises a pendant cyclic group at the 7-position, connected to the bicycle either with an alkyne or an alkoxy group. The following description provides context and examples, but should not be interpreted to limit the scope of the inventions covered by the claims that follow in this specification or in any other application that claims priority to this specification. No single component or collection of components is essential or indispensable. Any feature, structure, component, material, step, or method that is described and/or illustrated in any embodiment in this specification can be used with or instead of any feature, structure, component, material, step, or method that is described and/or illustrated in any other embodiment in this specification.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

When referring to numerical values, the terms "or ranges including and/or spanning the aforementioned values" (and variations thereof) is meant to include any range that includes or spans the aforementioned values. For example, when the temperature of a reaction is expressed as "20° C., 30° C., 40° C., 50° C., or ranges including and/or spanning the aforementioned values," this includes the particular temperature provided or temperature ranges spanning from 20° C. to 50° C., 20° C. to 40° C., 20° C. to 30° C., 30° C. to 50° C., 30° C. to 40° C., or 40° C. or 50° C.

As used herein, "$C_a$ to $C_b$" or "$C_{a-b}$" (or similar language) in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "haloalkyl" refers to a straight- or branched-chain alkyl group having from 1 to 12 carbon atoms in the chain, substituting one or more hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, —$CH_2CF_2CF_3$ and other groups that in light of the ordinary skill in the art and the teachings provided herein, would be considered equivalent to any one of the foregoing examples.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "polyethylene glycol" refers to the formula

wherein n is an integer greater than one and R is a hydrogen or alkyl. The number of repeat units "n" may be indicated by referring to a number of members. Thus, for example, "2- to 5-membered polyethylene glycol" refers to n being an integer selected from two to five. In some embodiments, R is selected from methoxy, ethoxy, n-propoxy, 1-methylethoxy (isopropoxy), n-butoxy, iso-butoxy, sec-butoxy, and tert-butoxy.

As used herein, "heteroalkyl" refers to a straight or branched hydrocarbon chain containing one or more heteroatoms. A heteroatom is given its plain and ordinary meaning in organic chemistry, which includes an element other than carbon, including but not limited to, nitrogen (e.g., amino, etc.), oxygen (e.g., alkoxy, ether, hydroxyl, etc.), sulfur, and halogens. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. In various embodiments, the heteroalkyl may have from 1 to 4 heteroatoms, from 1 to 3 heteroatoms, 1 or 2 heteroatoms, or 1 heteroatom. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. In various embodiments, a heteroaryl contains from 1 to 4 heteroatoms, from 1 to 3 heteroatoms, from 1 to 2 heteroatoms, or 1 heteroatom. For example, in various embodiments, a heteroaryl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations.

In various embodiments, a heterocyclyl contains from 1 to 4 heteroatoms, from 1 to 3 heteroatoms, from 1 to 2 heteroatoms, or 1 heteroatom. For example, in various embodiments, a heterocyclyl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline. A sulfur of the heterocyclyl ring may be provided as a dioxide (e.g., —S(O)$_2$—).

A "(heterocyclyl)alkyl" is a heterocyclyl group connected, as a substituent, via an alkylene group. Examples include, but are not limited to, imidazolinylmethyl and indolinylethyl.

A "(heterocyclyl)alkynyl" is a heterocyclyl group connected, as a substitutent, via an alkynylene group.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, —NH$_2$, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" or "—SO$_2$—" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A sulfonyl can be provided in a heterocyclyl ring.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a "natural amino acid side chain" refers to the side-chain substituent of a naturally occurring amino acid. Naturally occurring amino acids have a substituent attached to the α-carbon. Naturally occurring amino acids include Arginine, Lysine, Aspartic acid, Glutamic acid, Glutamine, Asparagine, Histidine, Serine, Threonine, Tyrosine, Cysteine, Methionine, Tryptophan, Alanine, Isoleucine, Leucine, Phenylalanine, Valine, Proline, and Glycine.

As used herein, a "non-natural amino acid side chain" refers to the side-chain substituent of a non-naturally occurring amino acid. Non-natural amino acids include β-amino acids (β$^3$ and β$^2$), Homo-amino acids, Proline and Pyruvic acid derivatives, 3-substituted Alanine derivatives, Glycine derivatives, Ring-substituted Phenylalanine and Tyrosine Derivatives, Linear core amino acids and N-methyl amino acids. Exemplary non-natural amino acids are available from Sigma-Aldridge, listed under "unnatural amino acids & derivatives." See also, Travis S. Young and Peter G. Schultz, "Beyond the Canonical 20 Amino Acids: Expanding the Genetic Lexicon," J. Biol. Chem. 2010 285: 11039-11044, which is incorporated by reference in its entirety.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from $C_1$-$C_6$ alkyl (optionally substituted with —OH or C-carboxy), $C_1$-$C_6$ alkenyl, $C_1$-$C_6$ alkynyl, $C_1$-$C_6$ heteroalkyl, $C_3$-$C_7$ carbocyclyl (optionally substituted with halo, —OH, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with N-amido, —OH, halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —O—NH$_2$, and oxo (=O). Wherever a group is described as "optionally substituted" or as comprising one or more "optional substitutions," that group can be substituted with the above substituents.

Two substituents may come together with the atom or atoms to which they are attached to form a ring that is spiro or fused with the rest of the compound.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by ～, followed by the number of carbon atoms, followed by a "*". For example,

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group (e.g., 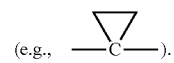).

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

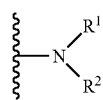

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

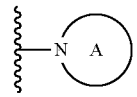

where ring A is a heterocyclyl ring containing the depicted nitrogen.

When a cyclic structure is shown as follows:

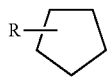

what is meant is the R group may be attached to any position of the ring by replacing an —H of the ring with —R. For example, for the following ring:

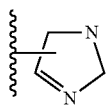

includes any of the following ring structures:

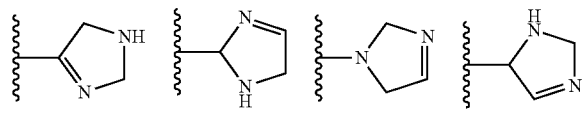

where "⌇" indicates a bond to a remaining portion of the structure.

Similarly, when two "adjacent" R groups are said to form a ring "together with the atoms to which they are attached," it is meant that the collective unit of the atoms, intervening bonds, and the two R groups are the recited ring. For example, when the following substructure is present:

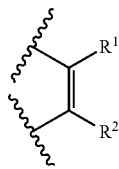

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

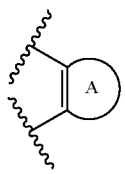

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

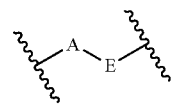

includes the substituent being oriented such that the A is attached at the leftmost attachment point of the molecule as well as the case in which A is attached at the rightmost attachment point of the molecule.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

"Subject" (or "patient") as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject.

As used herein, the term "weight percent," when referring to a component, is the weight of the component divided by the weight of the composition that includes the component, multiplied by 100%. For example, the weight percent of component A when 5 grams of component A is added to 95 grams of component B is 5% (e.g., 5 g A/(5 g A+95 g B)×100%).

Introduction

As disclosed elsewhere herein, histone post-translational modifications are epigenetic mechanisms that affect the structure of the chromatin, leading to gene expression alterations and ultimately contributing to the pathogenesis of different human diseases, including autoimmune diseases and cancer. Specifically, the N-terminal tails of histones are subject to reversible covalent modifications, including acetylation, methylation, phosphorylation, ubiquitination and sumoylation. These modifications regulate the ability of transcription factors to access the underlying DNA by modifying histone affinity for its negatively charged sugar backbone, affecting replication, transcription and chromatin stability. Thus, identification of drugs targeting these histone modifying enzymes could provide novel therapeutic agents for different human diseases.

Histones could be methylated by different histone methyltransferases (HMTs) and methylation could be removed by proteins called histone demethylases (HDMs). Methylation of histone tails could occur either at lysine or arginine residues on histones H3 and H4. Lysines can be mono-, di- and tri-methylated, whereas arginines could be only mono- or di-methylated. G9A (also called EHMT2) is a nuclear histone lysine methyltransferase that belongs in the Su(var) 3-9 family that catalyzes histone H3 lysine 9 dimethylation (H3K9me2), which is a reversible modification generally associated with transcriptional gene silencing. Structurally, it is composed by ankyrin repeats which could recognize H3K9me1/2 and also by a catalytic SET domain, responsible for the enzymatic activity. In addition to histone methylation, G9A has also non-histone targets, including the tumor suppressor gene p53.

G9A is an important regulator of the immune system, particularly affecting T cell populations. Specifically, G9A-mediated H3K9me2-dependent regulation of T cell responses are associated with T cells function, including T regulatory cells, as well as the development of different autoimmune diseases, including inflammatory bowel diseases, lupus, type 1 diabetes. Furthermore, G9A has been shown to affect innate lymphoid cells, which are key regulators of disease-associated immune mechanisms and interestingly, mice that did not have the G9A gene were resistant to develop allergic lung inflammation. Taken together, G9A has a pro-inflammatory role contributing in the pathogenesis of multiple autoimmune disorders, thus its inhibition could have therapeutic effects.

G9A has been identified to have oncogenic function, involved in the pathogenesis of different cancer types. Specifically, G9A expression levels are increased in esophageal, liver, non-small cell lung cancer, melanomas, multiple myeloma, breast, prostate, stomach, pancreatic, colorectal, uterine and bladder cancers. Furthermore, high G9A levels have been also associated with poor prognosis. Furthermore, there is strong evidence regarding the correlation between G9A effects on cell adhesion molecules and G9A increase activity during hypoxia, supporting G9A role as a key factor for metastasis. Taken together, these findings show the importance of G9A in oncogenesis and suggest that targeting G9A activity could consist a novel strategy for the treatment of several cancer types.

Several embodiments disclosed herein pertain to substituted quinazoline compounds. In several embodiments, the compounds disclosed herein are useful for the treatment of one or more disease states. In several embodiments, the compounds may be useful in the treatment of autoimmune disorders. In several embodiments, the compounds are useful in the treatment of cancer. In several embodiments, the compounds target G9A. In several embodiments, the compounds treat G9A mediated inflammation.

Compounds

Several embodiments disclosed herein pertain to quinazolinyl compounds, methods of using quinazolinyl compounds, compositions comprising quinazolinyl compounds, and methods of treatment using quinazolinyl compounds. Quinazolinyl compounds may be represented by the following structure and numbering convention:

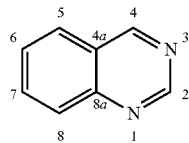

In several embodiments, the quinazolinyl compound is substituted at one or more of the 2-position, the 4-position, the 6-position, the 7-position, or combinations of any one of the foregoing.

In several embodiments, the quinazoline compound comprises a cyclic substituent bonded to the quinazoline ring at the 2-position. In several embodiments, the quinazoline compound comprises an amine substituent bonded to the quinazoline ring at the 4-position. In several embodiments, the quinazoline compound comprises the amine at the 4-position comprising a cyclic substituent (either pendant or directly bonded to the amine) or the amine is part of a cyclic substituent. In several embodiments, the quinazoline compound comprises a methoxy group at the 6-position. In several embodiments, the quinazoline compound comprises an alkoxy group at the 7-position. In several embodiments, the quinazoline compound comprises a pendant cyclic group at the 7-position, connected to the bicycle either with an alkyne or an alkoxy group.

As disclosed elsewhere herein, in several embodiments, the quinazolinyl compound is substituted at the 2-position. In several embodiments, the substituent at the 2-position may include a cyano, alkoxy, thioalkyl, optionally substituted alkyl, optionally substituted alkenyl, optionally substituted alkynyl, optionally substituted carbocyclyl, optionally substituted aryl, optionally substituted heterocyclyl, optionally substituted heteroaryl, or optionally substituted amino. In several embodiments, the substituent at the 2-position is selected from the group consisting of —CN, —OR$^1$, —SR$^1$, optionally substituted $C_1$-$C_{10}$ alkyl, optionally substituted $C_1$-$C_{10}$ alkenyl, optionally substituted $C_1$-$C_{10}$ alkynyl, optionally substituted 3-10 membered carbocyclyl, optionally substituted 6-10 membered aryl, optionally substituted 3-10 membered heterocyclyl, optionally substituted 5-10 membered heteroaryl, and amino.

In several embodiments, the 2-position substituent may be optionally substituted as disclosed herein. In several embodiments, when the 2-position substituent comprises one or more additional optional substituents, the one or more optional substitutions may be independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl, $C_3$-$C_7$-carbocyclyl-$C_1$-$C_6$-alkyl, 5-10 membered heterocyclyl, 5-10 membered heterocyclyl-$C_1$-$C_6$-alkyl, aryl, aryl($C_1$-$C_6$)alkyl, 5-10 membered heteroaryl, 5-10 membered heteroaryl($C_1$-$C_6$)alkyl, halo, cyano, hydroxy, $C_1$-$C_6$ alkoxy, $C_1$-$C_6$ alkoxy($C_1$-$C_6$)alkyl, aryloxy, sulfhydryl, halo($C_1$-$C_6$)alkyl, halo($C_1$-$C_6$)alkoxy, $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —O—NH$_2$, and oxo (=O). In several embodiments, when the 2-position substituent comprises one or more additional optional substituents, the one or more optional substitutions may be independently selected from $C_1$-$C_6$ alkyl, $C_1$-$C_6$ heteroalkyl, $C_3$-$C_7$ carbocyclyl, $C_3$-$C_7$-carbocyclyl-$C_1$-$C_6$-alkyl, 5-10 membered heterocyclyl, 5-10 membered heteroaryl, halo, cyano, hydroxy, $C_1$-$C_6$ alkoxy, amino, C-amido, N-amido, C-carboxy, O-carboxy, acyl, and oxo (=O). In several embodiments, when the 2-position substituent comprises one or more additional optional substituents, the one or more optional substitutions may be independently selected from $C_1$-$C_6$ alkyl, $C_1$-$C_6$ heteroalkyl, and fluoro.

As disclosed elsewhere herein, in several embodiments, the quinazolinyl compound is substituted at the 4-position with an amine. In several embodiments, the quinazoline compound comprises the amine at the 4-position comprising a cyclic substituent (either pendant or directly bonded to the amine) or the amine is part of a cyclic substituent. In several embodiments, the substituent at the 4-position may be an optionally substituted heterocyclyl or an amine substituted with —CN, optionally substituted alkyl, optionally substituted heteroalkyl, optionally substituted carbocyclyl, optionally substituted (carbocyclyl)alkyl, optionally substituted (heterocyclyl)alkyl, optionally substituted aryl, optionally substituted heterocyclyl, or optionally substituted heteroaryl. In several embodiments, the substituent at the 4-position is selected from an optionally substituted 3-10 membered heterocyclyl and amine substituted with one or more substituents selected from —CN, optionally substituted $C_1$-$C_{10}$ alkyl, optionally substituted 2-10 membered heteroalkyl, optionally substituted 3-10 membered carbocyclyl, optionally substituted (carbocyclyl)alkyl, optionally substituted (heterocyclyl)alkyl, optionally substituted 6-10 membered aryl, optionally substituted 3-10 membered heterocyclyl, optionally substituted 5-10 membered heteroaryl, optionally substituted acyl, optionally substituted O-carboxy, optionally substituted C-carboxy, optionally substituted C-amido, optionally substituted N-amido, optionally substituted O-carbamyl, or optionally substituted N-carbamyl.

In several embodiments, the 4-position substituent may be optionally substituted as disclosed herein. In several embodiments, when the 4-position substituent comprises one or more additional optional substituents, the one or more optional substitutions may be independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl, $C_3$-$C_7$-carbocyclyl-$C_1$-$C_6$-alkyl, 5-10 membered heterocyclyl, 5-10 membered heterocyclyl-$C_1$-$C_6$-alkyl, aryl, aryl($C_1$-$C_6$)alkyl, 5-10 membered heteroaryl, 5-10 membered heteroaryl($C_1$-$C_6$)alkyl, halo, cyano, hydroxy, $C_1$-$C_6$ alkoxy, $C_1$-$C_6$ alkoxy($C_1$-$C_6$)alkyl, aryloxy, sulfhydryl, halo($C_1$-$C_6$)alkyl, halo($C_1$-$C_6$)alkoxy, $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —O—NH$_2$, and oxo. In several embodiments, when the 4-position substituent comprises one or more additional optional substituents, the one or more optional substitutions may be independently selected from $C_1$-$C_6$ alkyl, $C_1$-$C_6$ heteroalkyl, $C_3$-$C_7$ carbocyclyl, $C_3$-$C_7$-carbocyclyl-$C_1$-$C_6$-alkyl, 5-10 membered heterocyclyl, 5-10 membered heteroaryl, halo, cyano, hydroxy, $C_1$-$C_6$ alkoxy, amino, C-amido, N-amido, C-carboxy, O-carboxy, acyl, and oxo. In several embodiments, when the 4-position substituent comprises one or more additional optional substituents, the one or more optional substitutions may be independently selected from $C_1$-$C_6$ alkyl, $C_1$-$C_6$ heteroalkyl, $C_3$-$C_7$ carbocyclyl optionally substituted with halo, 5-10 membered heterocyclyl optionally substituted with —OH, halo, cyano, hydroxy, $C_1$-$C_6$ alkoxy, amino, N-amido, acyl, —O—$NH_2$, and oxo.

As disclosed elsewhere herein, in several embodiments, the quinazolinyl compound is substituted at the 6-position with hydrogen, halogen, or alkoxy. In several embodiments, the substituent is fluoro or methoxy.

As disclosed elsewhere herein, in several embodiments, the quinazolinyl compound is substituted at the 7-position with alkoxy or (heterocyclyl)alkynyl. In several embodiments, the alkoxy comprises alkyl, optionally substituted 2-10 membered heteroalkyl, or (heterocyclyl)alkyl.

In several embodiments, the 7-position may be optionally substituted as described herein. In several embodiments, when the 7-position substituent comprises one or more additional optional substituents, the one or more optional substitutions may be independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl, $C_3$-$C_7$-carbocyclyl-$C_1$-$C_6$-alkyl, 5-10 membered heterocyclyl, 5-10 membered heterocyclyl-$C_1$-$C_6$-alkyl, aryl, aryl($C_1$-$C_6$)alkyl, 5-10 membered heteroaryl, 5-10 membered heteroaryl($C_1$-$C_6$)alkyl, halo, cyano, hydroxy, $C_1$-$C_6$ alkoxy, $C_1$-$C_6$ alkoxy($C_1$-$C_6$)alkyl, aryloxy, sulfhydryl, halo($C_1$-$C_6$)alkyl, halo($C_1$-$C_6$)alkoxy, $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —O—$NH_2$, and oxo. In several embodiments, when the 7-position substituent comprises one or more additional optional substituents, the one or more optional substitutions may be independently selected from $C_1$-$C_6$ alkyl, $C_1$-$C_6$ heteroalkyl, $C_3$-$C_7$ carbocyclyl, $C_3$-$C_7$-carbocyclyl-$C_1$-$C_6$-alkyl, 5-10 membered heterocyclyl, 5-10 membered heteroaryl, halo, cyano, hydroxy, $C_1$-$C_6$ alkoxy, amino, C-amido, N-amido, C-carboxy, O-carboxy, acyl, and oxo. In several embodiments, when the 7-position substituent comprises one or more additional optional substituents, the one or more optional substitutions may be independently selected from $C_1$-$C_6$ alkyl and amino.

Several embodiments relate to a pharmaceutical composition comprising a therapeutically effective amount of a compound as described herein and a pharmaceutically acceptable excipient.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Compounds of Formula (I)

Several embodiments pertain to quinazolinyl compounds having the structure of Formula (I) (or a stereoisomer, tautomer or pharmaceutically acceptable salt thereof):

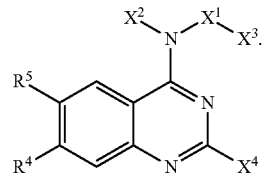

Formula (I)

In several embodiments, the variable groups of Formula (I) are as disclosed elsewhere herein. For brevity, the variables defined for one formula may be used to define the same variable in another formula. For example, in several embodiments, the variables for Formula (I) are as disclosed elsewhere herein for Formula (I) and/or as disclosed elsewhere herein for any other formula having variables shared with those provided in Formula (I). As one illustration using $R^4$, where $R^4$ is defined in one manner for Formula (Ia), that same definition of $R^4$ may be used for Formula (I), even if that particular definition for $R^4$ is not specifically provided with respect to the Formula (I). Likewise, where $R^4$ is defined in one manner for Formula (I), that same definition of $R^4$ may be used for Formula (Ia) (or other formulae), even if that definition for $R^4$ is not specifically provided with respect to Formula (Ia).

In several embodiments, $X^1$ is —$(CH_2)_o$— or a covalent bond. In several embodiments, o is an integer equal to 1, 2, 3, 4, 5, or 6. In several embodiments, $X^1$ is an optionally substituted $C_1$-$C_{10}$ alkylene. In several embodiments, $X^2$ is hydrogen or optionally substituted $C_1$-$C_{10}$ alkyl. In several embodiments, $X^2$ is hydrogen or optionally substituted $C_1$-$C_{10}$ alkyl. In several embodiments, $X^3$ is selected from the group consisting of —CN, —OH, optionally substituted $C_1$-$C_{10}$ alkyl, optionally substituted 2-10 membered heteroalkyl, optionally substituted 3-10 membered carbocyclyl, optionally substituted (carbocyclyl)alkyl, optionally substituted (heterocyclyl)alkyl, optionally substituted 6-10 membered aryl, optionally substituted 3-10 membered heterocyclyl, optionally substituted 5-10 membered heteroaryl, optionally substituted amino, optionally substituted sulfonyl, optionally substituted acyl, optionally substituted O-carboxy, optionally substituted C-carboxy, optionally substituted C-amido, optionally substituted N-amido, optionally substituted O-carbamyl, or optionally substituted N-carbamyl. In several embodiments, $X^2$ and $X^3$ are taken together with the atoms to which they are attached to form an optionally substituted 3-10 membered heterocyclyl. The optional substituents may be selected from substituents as disclosed elsewhere herein.

In several embodiments, the $X^3$ may be represented by Formula (IX3):

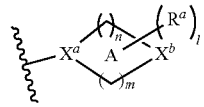

Formula (IX3)

where $X^a$ is selected from the group consisting of CH and N, m is independently an integer selected from 0, 1, 2, 3, or 4; n is independently an integer selected from 0, 1, 2, 3, or 4; $X^b$ is selected from the group consisting of $CH_2$, NH, O, S, and $SO_2$; each instance of $R^a$, where present, is independently selected from the group consisting of amino, —OH, halogen, cyano, hydroxy, optionally substituted $C_1$-$C_6$ alkyl, C-carboxy, and optionally substituted $C_1$-$C_6$ alkoxy($C_1$-$C_6$) alkyl; l is an integer selected from 0, 1, 2, 3, or 4. In several embodiments, ring "A" is a cycloalkyl ring or a heterocyclyl ring. As disclosed elsewhere herein and as will be readily appreciated by those skilled in the art, each $R^a$ can be provided at any position of the "A" ring by replacing one or more —H atoms of any carbon or nitrogen atom present within the "A" ring (including any —H atom that may be present on $X^b$ and $X^a$, where applicable). The optional substituents of the "A" ring may be selected from substituents as disclosed elsewhere herein. In several embodiments, when a substituent of the "A" ring is optionally substituted with one or more optional substitutions, the one or more optional substitutions may be independently selected from the group consisting of $C_1$-$C_3$ alkyl, halo, and $C_1$-$C_3$ alkoxy.

In several embodiments, n is 0 and m is 1. In several embodiments, n is 1 and m is 1. In several embodiments, n is 1 and m is 3. In several embodiments, n is 2 and m is 2. In several embodiments, n is 3 and m is 2.

In several embodiments, $X^b$ is selected from the group consisting of O, $SO_2$, —N($R^a$), —C($R^a$)H, and —C($R^a$)$_2$.

In several embodiments, the 4-position substituent of Formula (I) (e.g., —N($X^2$)—$X^1$—$X^3$) is represented by one of the following structures:

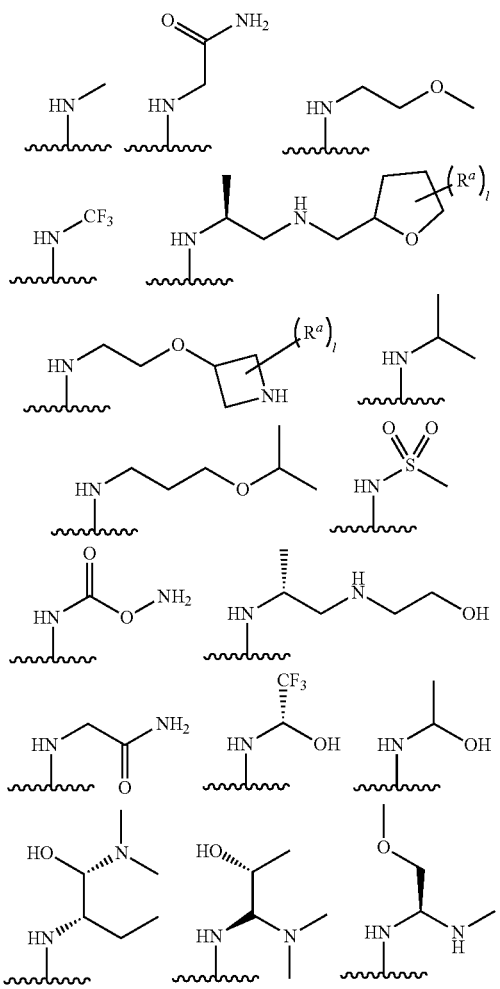
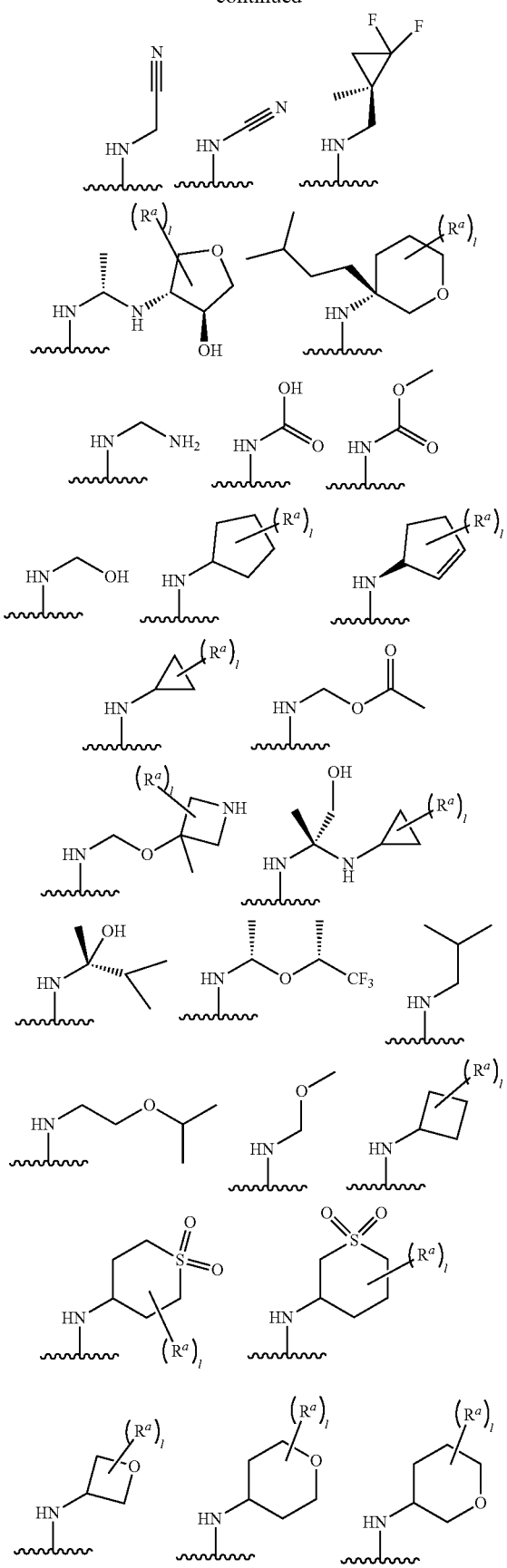

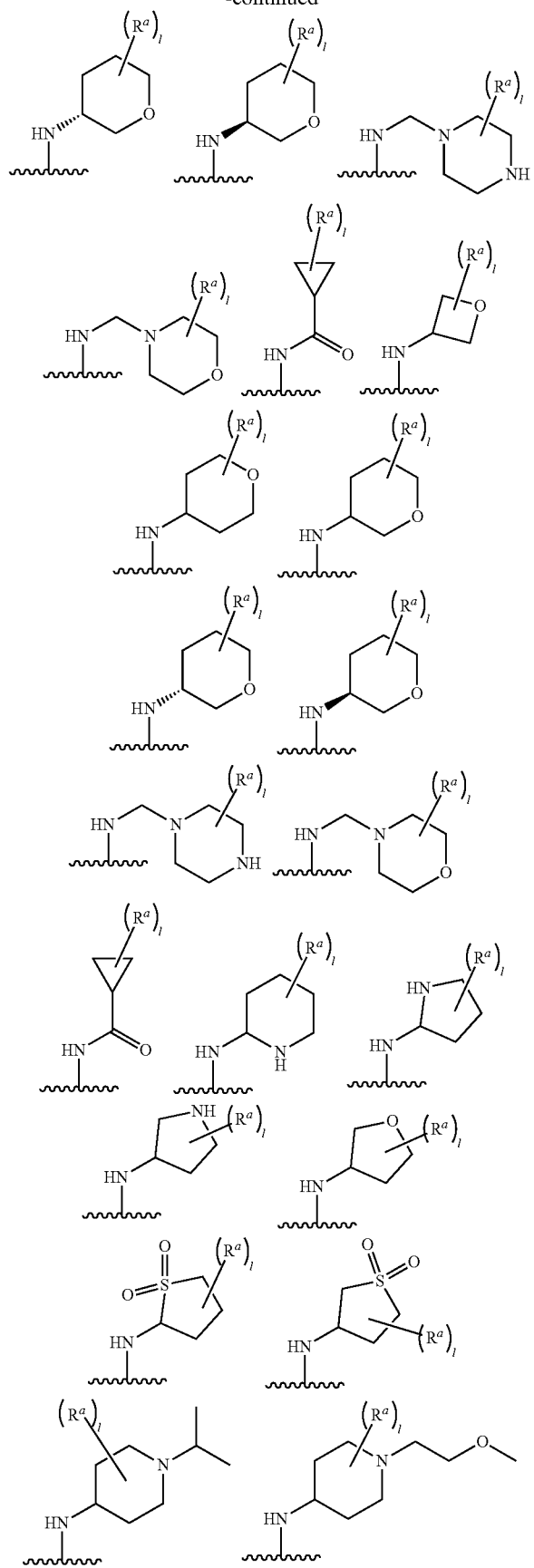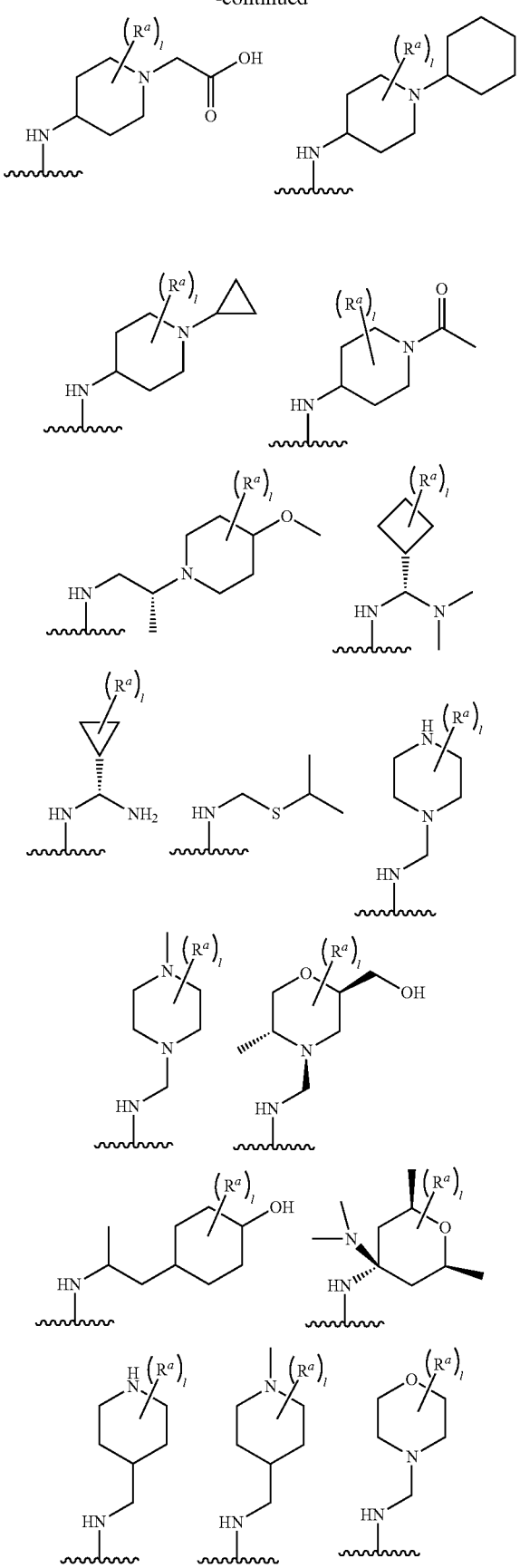

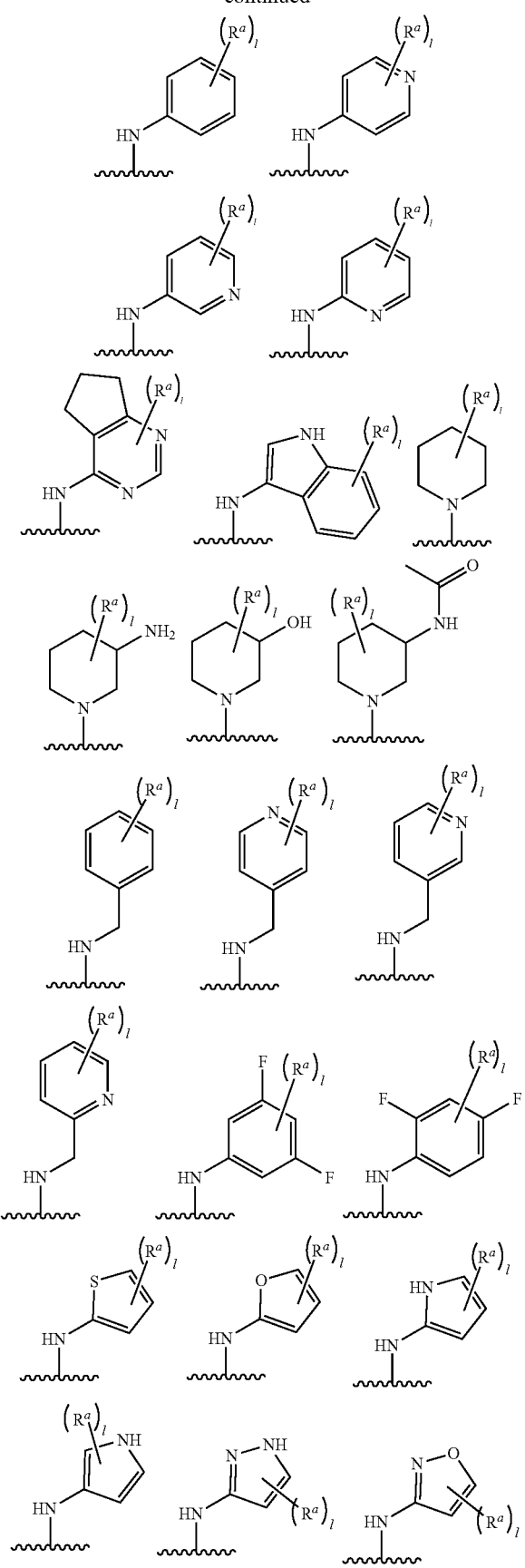

any one of which may be further optionally substituted by replacing one or more —H atoms of any carbon or nitrogen atom present within the —N(X$^2$)—X$^1$—X$^3$. In several embodiments, when —N(X$^2$)—X$^1$—X$^3$ substituent comprises one or more optional substitutions, the optional substitutions are as disclosed elsewhere herein. In several embodiments, when —N(X$^2$)—X$^1$—X$^3$ comprises one or more optional substitutions, the one or more optional substitutions may be independently selected from the group consisting of C$_1$-C$_3$ alkyl, halo, cyano, hydroxy, amino, C$_1$-C$_3$ alkoxy, 3-6 membered carbocyclyl, and 3-6 membered heterocyclyl. In several embodiments, R$^a$ and l are as defined elsewhere herein.

In several embodiments, where one or more of X$^1$, X$^2$, or X$^3$ is described as optionally substituted, the optional substituents may be selected from substituents as disclosed elsewhere herein. In several embodiments, where one or more of X$^1$, X$^2$, or X$^3$ is described as optionally substituted, the optional substitution(s) may be independently selected from the group consisting of C$_1$-C$_3$ alkyl, halogen, —OH, —CN, and C$_1$-C$_3$ alkoxy.

In several embodiments, X$^4$ is as disclosed elsewhere herein. In several embodiments, X$^4$ is selected from the group consisting of —CN, —OR$^1$, —SR$^1$, halogen, optionally substituted C$_1$-C$_{10}$ alkyl, optionally substituted C$_1$-C$_{10}$ alkenyl, optionally substituted C$_1$-C$_{10}$ alkynyl, optionally substituted 3-10 membered carbocyclyl, optionally substituted 6-10 membered aryl, optionally substituted 3-10 membered heterocyclyl, optionally substituted 5-10 membered heteroaryl, and —NR$^2$R$^3$. The optional substituents may be selected from substituents as disclosed elsewhere herein. In several embodiments, when X$^4$ comprises one or more optional substitutions, the one or more optional substitutions may be independently selected from the group consisting of C$_1$-C$_3$ alkyl, halo, cyano, hydroxy, and C$_1$-C$_3$ alkoxy.

In several embodiments, R$^1$ is hydrogen or an optionally substituted C$_1$-C$_{10}$ alkyl. The optional substituents may be selected from substituents as disclosed elsewhere herein. In several embodiments, when R$^1$ comprises one or more optional substitutions, the one or more optional substitutions may be independently selected from the group consisting of C$_1$-C$_3$ alkyl, halo, cyano, hydroxy, and C$_1$-C$_3$ alkoxy.

In several embodiments, each of $R^2$ and $R^3$ is independently selected from hydrogen and optionally substituted $C_{1-10}$ alkyl; or alternatively, $R^2$ and $R^3$ attached to the same nitrogen atom may be together with the atom to which they are attached, form an optionally substituted 3-10 membered heterocyclyl or an optionally substituted 5-10 membered heteroaryl. The optional substituents may be selected from substituents as disclosed elsewhere herein. In several embodiments, when $R^2$ and/or $R^3$ comprises one or more optional substitutions, the one or more optional substitutions may be independently selected from the group consisting of $C_1$-$C_3$ alkyl, halo, cyano, hydroxy, and $C_1$-$C_3$ alkoxy.

In several embodiments, $X^4$ is represented by Formula (IX4):

Formula (IX4)

where $X^f$ is selected from the group consisting of CH and N, b is independently an integer selected from 0, 1, 2, 3, or 4; c is independently an integer selected from 0, 1, 2, 3, or 4; $X^g$ is selected from the group consisting of $CH_2$, NH, O, S, and $SO_2$; each instance of $R^f$, where present, is independently selected from the group consisting of amino, —OH, halogen, cyano, hydroxy, optionally substituted $C_1$-$C_6$ alkyl, C-carboxy, and optionally substituted $C_1$-$C_6$ alkoxy($C_1$-$C_6$) alkyl; d is an integer selected from 0, 1, 2, 3, or 4. In several embodiments, ring "D" is a cycloalkyl ring or a heterocyclyl ring. As disclosed elsewhere herein and as will be readily appreciated by those skilled in the art, each $R^f$ can be provided at any position of the "D" ring by replacing one or more —H atoms of any carbon or nitrogen atom present within the "D" ring (including any —H atom that may be present on $X^f$ and $X^g$, where applicable). The optional substituents of the "D" ring may be selected from substituents as disclosed elsewhere herein. In several embodiments, when a substituent of the "D" ring is optionally substituted with one or more optional substitutions, the one or more optional substitutions may be independently selected from the group consisting of $C_1$-$C_3$ alkyl, halo, and $C_1$-$C_3$ alkoxy.

In several embodiments, n is 0 and m is 1. In several embodiments, n is 1 and m is 1. In several embodiments, n is 1 and m is 3. In several embodiments, n is 2 and m is 2. In several embodiments, n is 3 and m is 2.

In several embodiments, $X^g$ is selected from the group consisting of O, $SO_2$, —N($R^f$), —C($R^f$)H, and —C($R^f$)$_2$.

In several embodiments, the 2-position substituent of Formula (I) (e.g., $X^4$) is represented by one of the following structures:

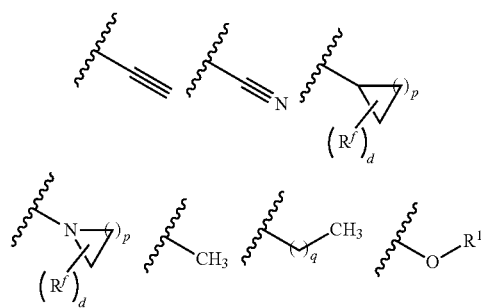

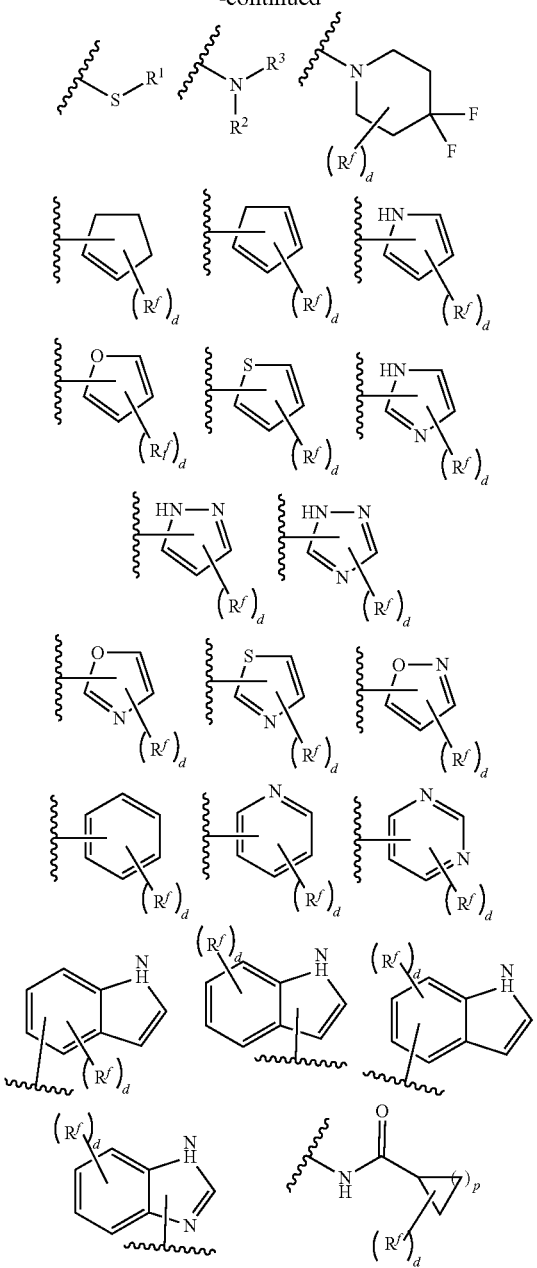

where p is an integer equal to 1, 2, 3, 4, or 5; q is an integer equal to 1, 2, 3, 4, 5, 6, 7, 8, 9, or 10; where the variables are as provided elsewhere herein; and/or where any one of these structures may be optionally substituted by replacing one or more —H atoms of any carbon or nitrogen atom present on $X^4$. In several embodiments, when $X^4$ comprises one or more optional substitutions, the one or more optional substitutions may be independently selected from the group consisting of $C_1$-$C_3$ alkyl, halo, cyano, hydroxy, and $C_1$-$C_3$ alkoxy. In several embodiments, $R^f$ and d are as defined elsewhere herein.

In several embodiments, $R^4$ is —$OR^9$ or (heterocyclyl) alkynyl. In several embodiments, $R^9$ is selected from the group consisting of hydrogen, $C_1$-$C_3$ alkyl (e.g., methyl), optionally substituted 2-10 membered heteroalkyl, optionally substituted (carbocyclyl)alkyl, optionally substituted (heterocyclyl)alkyl, optionally substituted (aryl)alkyl and optionally substituted (heteroaryl)alkyl. In several embodiments, the heterocyclyl or carbocyclyl comprises 3 to 10 ring members (e.g., 3-6 members, 3-7 members, etc.). In several embodiments, the heteroaryl or aryl comprises 6 to 10 ring members. In several embodiments, $R^9$ is (amino) $C_1$-$C_6$ alkyl. In several embodiments, the heterocyclyl ring is a pyrrolidinyl ring.

In several embodiments, $R^4$ is represented by the one of the following formulae:

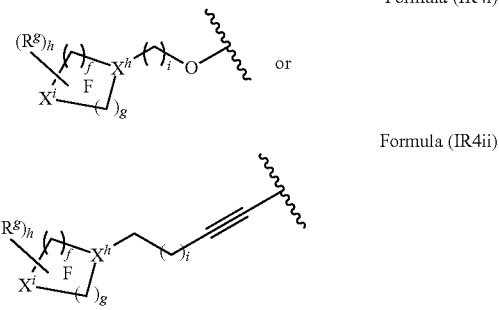

Formula (IR4i) or

Formula (IR4ii)

where $X^h$ is selected from the group consisting of CH and N, f is independently an integer selected from 0, 1, 2, 3, or 4; g is independently an integer selected from 0, 1, 2, 3, or 4; $X^i$ is selected from the group consisting of $CH_2$, NH, O, S, and $SO_2$; each instance of $R^g$, where present, is independently selected from the group consisting of amino, —OH, halogen, cyano, hydroxy, optionally substituted $C_1$-$C_6$ alkyl, C-carboxy, and optionally substituted $C_1$-$C_6$ alkoxy($C_1$-$C_6$) alkyl; h is an integer selected from 0, 1, 2, 3, or 4; and i is an integer selected from 1, 2, 3, 4, 5, 6, or 7 (including ranges spanning the aforementioned values). In several embodiments, ring "F" is a cycloalkyl ring or a heterocyclyl ring. As disclosed elsewhere herein and as will be readily appreciated by those skilled in the art, each $R^g$ can be provided at any position of the "F" ring by replacing one or more —H atoms of any carbon or nitrogen atom present within the "F" ring (including any —H atom that may be present on $X^h$ and $X^i$, where applicable). The optional substituents of the "F" ring may be selected from substituents as disclosed elsewhere herein. In several embodiments, when a substituent of the "F" ring is optionally substituted with one or more optional substitutions, the one or more optional substitutions may be independently selected from the group consisting of $C_1$-$C_3$ alkyl, halo, and $C_1$-$C_3$ alkoxy. In several embodiments, i is 1 or 3.

In several embodiments, $R^4$ is 3-(pyrrolidin-1-yl) propoxy or 3-(pyrrolidin-1-yl)prop-1-yn-1-yl, as shown in the following structures, respectively:

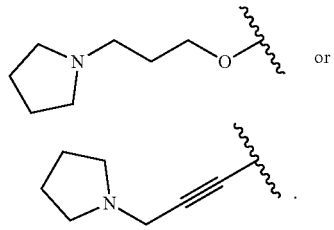

In several embodiments, $R^5$ is selected from the group consisting of hydrogen, halogen, and —$C_{1-6}$ alkoxy. In several embodiments, $R^5$ is selected from the group consisting of hydrogen, halogen, and —OMe.

In several embodiments, provided that if $X^3$ is

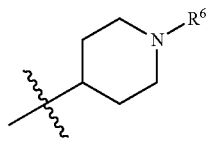

wherein $R^6$ is unsubstituted benzyl, unsubstituted 3-10 membered carbocyclyl, or $C_1$-$C_{10}$ alkyl optionally substituted with amine, if $R^2$ and $R^3$ are present, they come together to form an optionally substituted 5-membered heteroaryl or an optionally substituted 4-membered heterocyclyl.

In several embodiments, provided that if $X^3$ is

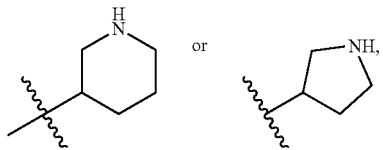 [SMILES: *C1CCCNC1 ; "or" ; *C1CCNC1]

$R^4$ is

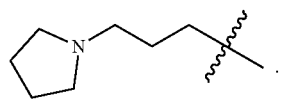 [SMILES: *CCCN1CCCC1]

In several embodiments, $X^3$ is a substituted 6-membered heterocyclyl. In several embodiments, $X^3$ is an unsubstituted 6-membered heterocyclyl. In several embodiments, $X^3$ is an unsubstituted 6-membered aryl. In several embodiments, $X^3$ is an unsubstituted 2-10 membered heteroalkyl.

In several embodiments, $X^4$ is an optionally substituted 4-6 membered heterocyclyl. In several embodiments, $X^4$ is a 5-membered heteroaryl. In several embodiments, $X^4$ is —CN.

In several embodiments, $X^1$ is a covalent bond. In several embodiments, $X^1$ is $CH_2$.

In several embodiments, $X^2$ is hydrogen.

In several embodiments, $R^4$ is

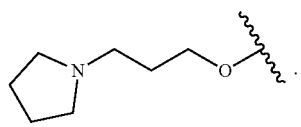 [SMILES: *OCCCN1CCCC1]

In several embodiments, $R^5$ is —OMe.

In several embodiments, where Formula (I) comprises Formula (IX3) where n is 2, m is 2, and $R^a$ is isopropyl, $X^b$ is not N. In several embodiments, where Formula (I) comprises Formula (IX3) where n is 2, m is 2, and $X^b$ comprises an $R^a$ substituent, that $R^a$ substituent is not isopropyl. In several embodiments, where n is 2, m is 2 and $R^a$ is isopropyl, $X^b$ is not N. In several embodiments, where n is 2, m is 2 and $R^a$ is isopropyl, $X^b$ is not N. In several embodiments, where Formula (I) comprises Formula (IX3)

where n is 2, m is 2, and $X^b$ comprises an $R^a$ substituent, that $R^a$ substituent is not a $C_3$ alkyl. In several embodiments, where Formula (I) comprises Formula (IX3) where n is 2, m is 2, and $X^b$ is N and comprises an $R^a$ substituent, that $R^a$ substituent on $X^b$ is not a $C_3$ alkyl. In several embodiments, where Formula (I) comprises Formula (IX3) where n is 2, m is 2, and $X^b$ is N and comprises an $R^a$ substituent, that $R^a$ substituent on $X^b$ is not methyl. In several embodiments, where Formula (I) comprises Formula (IX3) where n is 2, m is 2, and $X^b$ is N and comprises an $R^a$ substituent, that $R^a$ substituent on $X^b$ is not a $C_3$ alkyl or $C_3$ carbocyclyl. In several embodiments, where Formula (I) comprises Formula (IX3) where n is 2, m is 2, and $X^b$ is N and comprises an $R^a$ substituent, that $R^a$ substituent on $X^b$ is not a $C_7$ (carbocyclyl)alkyl. In several embodiments, where Formula (I) comprises Formula (IX3) where n is 2, m is 2, and $X^b$ is N and comprises an $R^a$ substituent, that $R^a$ substituent on $X^b$ is not a $C_6$ alkyl or $C_6$ carbocyclyl. In several embodiments, Formula (I) lacks a compound having a 7-membered heterocyclyl group and/or a 7-membered carbocyclyl group. In several embodiments, where Formula (I) includes a 6-membered heterocyclyl group and/or 6-membered carbocyclyl group, Formula (I) lacks a 7-membered heterocyclyl group and/or 7-membered carbocyclyl group. In several embodiments, where Formula (I) includes a 6-membered heterocyclyl group, 6-membered carbocyclyl group, a 7-membered heterocyclyl group, and/or 7-membered carbocyclyl group, those cyclic groups may be substituted or may lack a substitution.

Some Embodiments of Compounds of Formula (I)

In several embodiments, the compound of Formula (I) may be selected from any of the following:

1

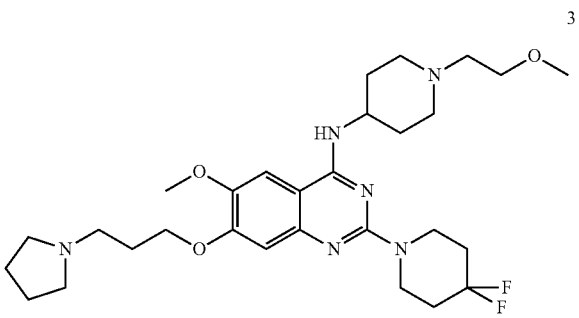

2

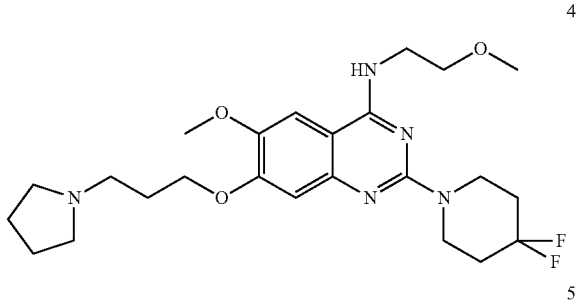

-continued

3

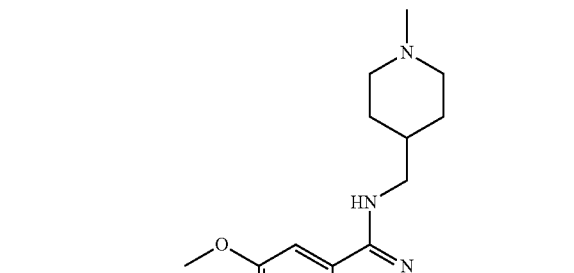

4

5

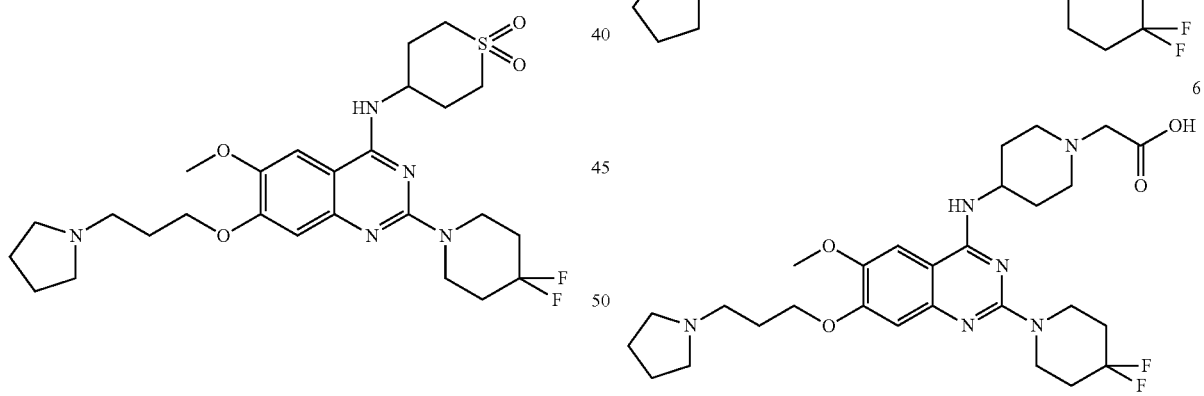

6

7

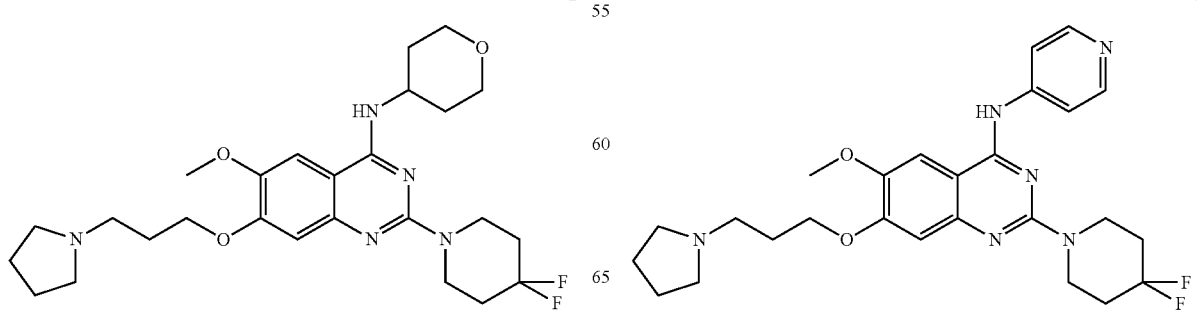

-continued
8
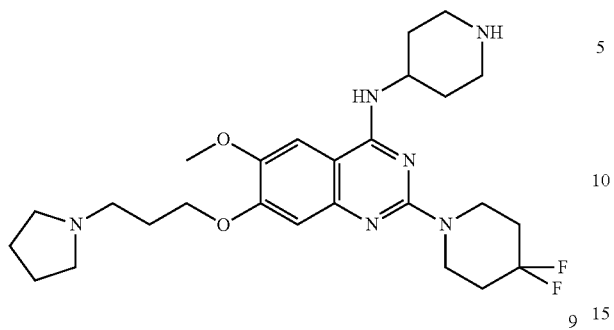
9
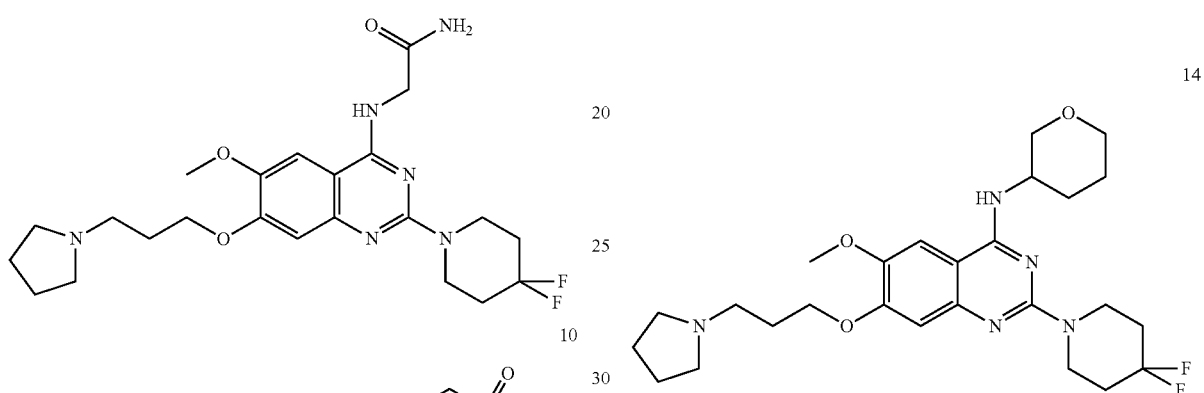
10
11
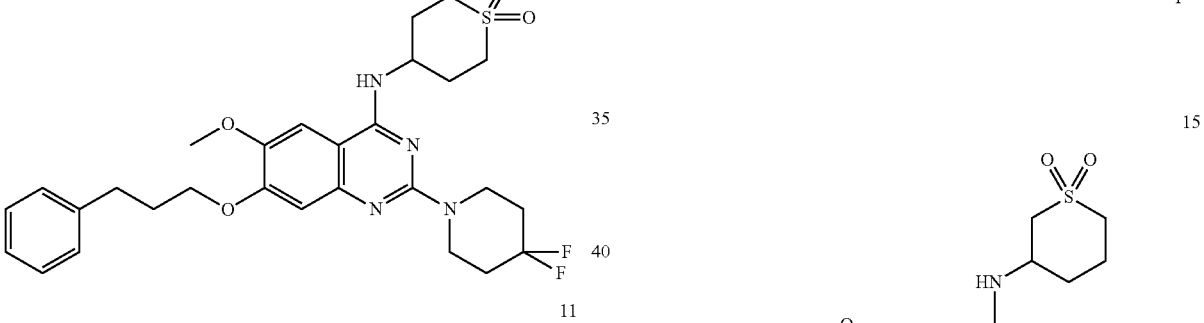
12
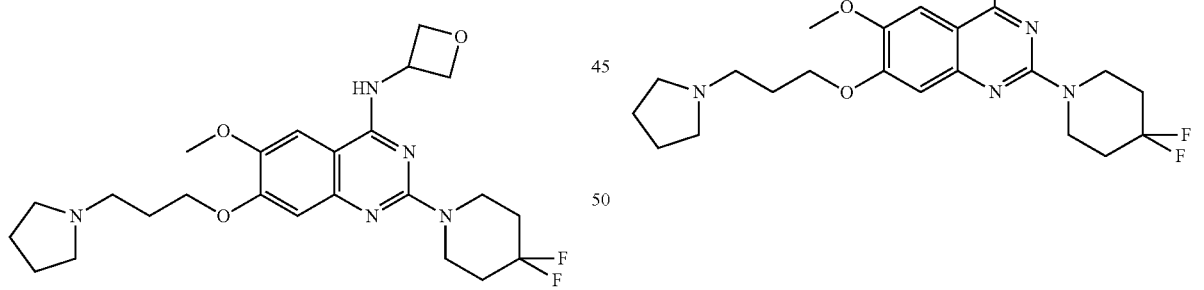
-continued
13
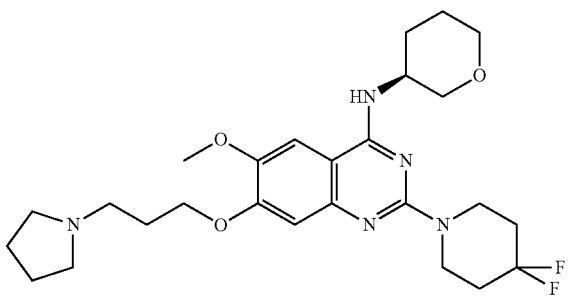
14
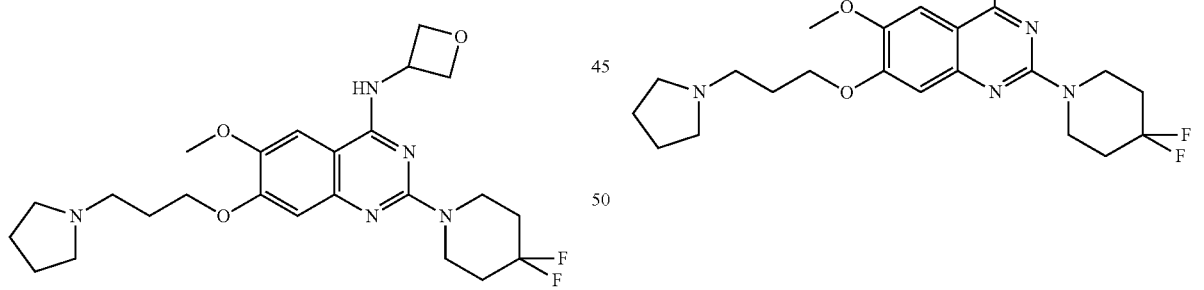
15
16
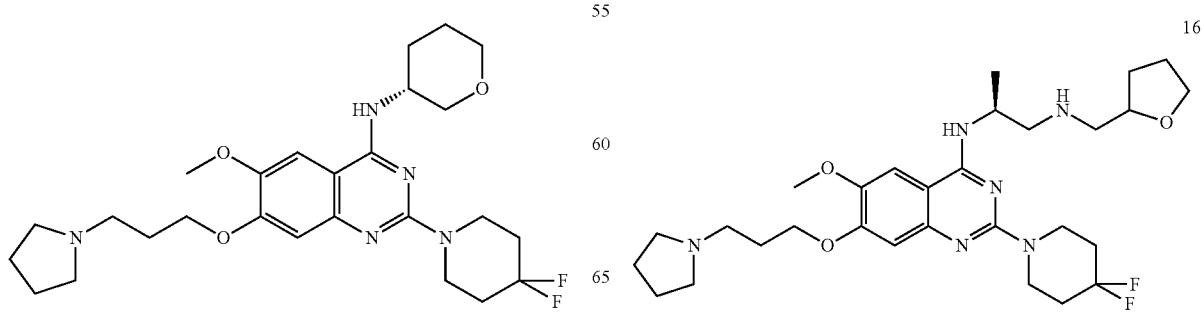

17
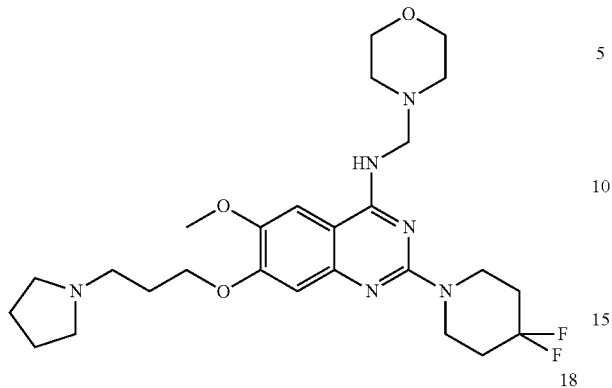
18
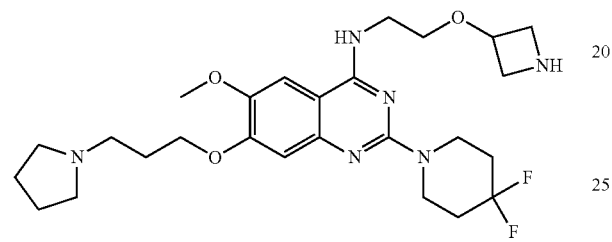
19
20
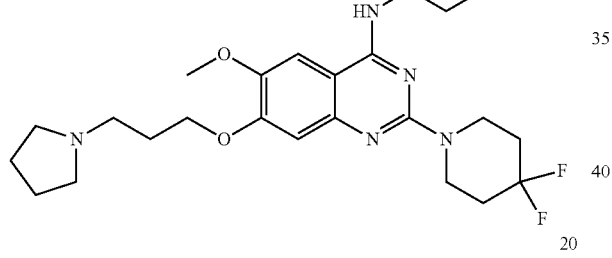
21
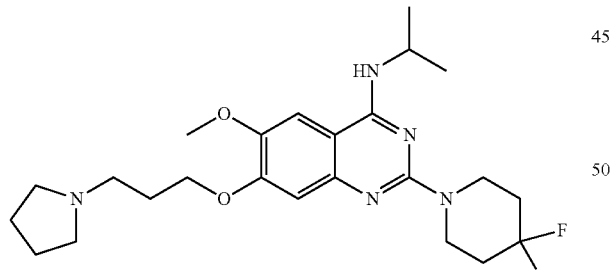
22
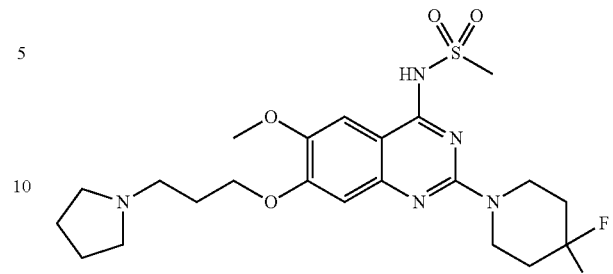
23
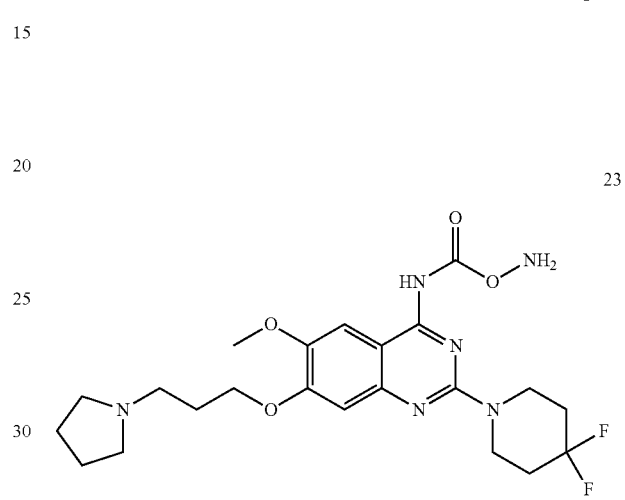
24
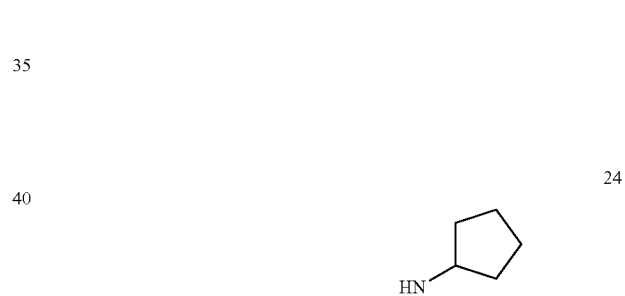
25
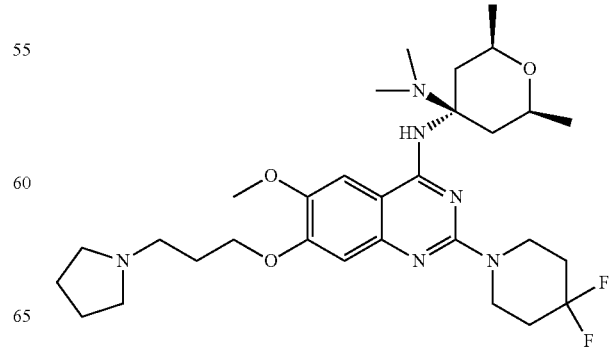

26
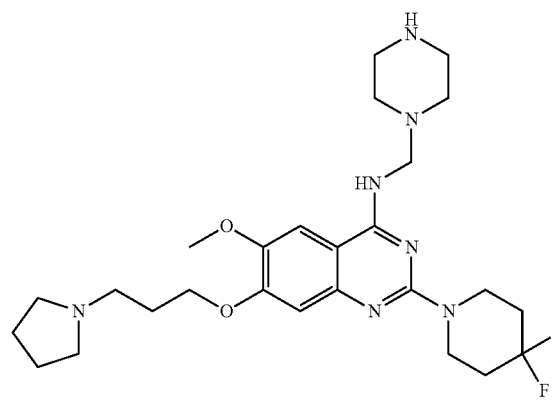
27
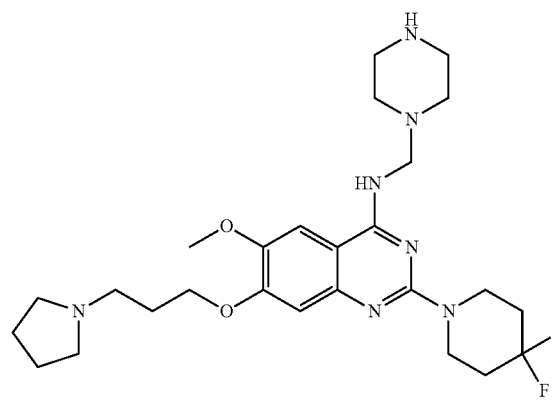
28
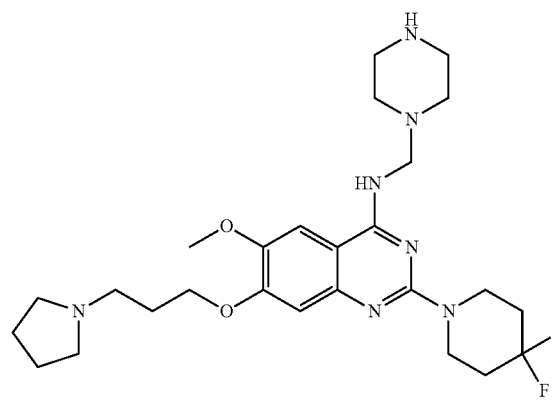
29
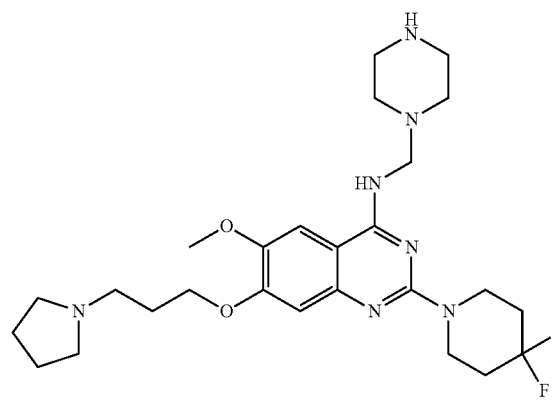
30
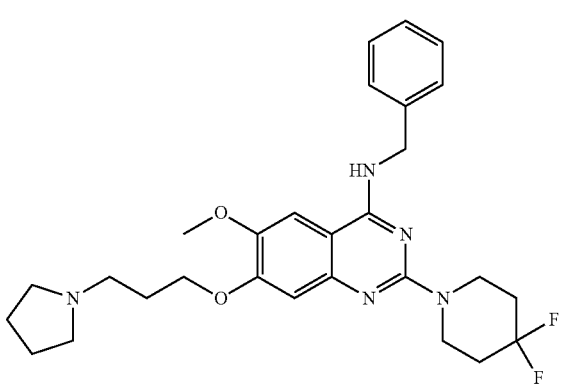
31
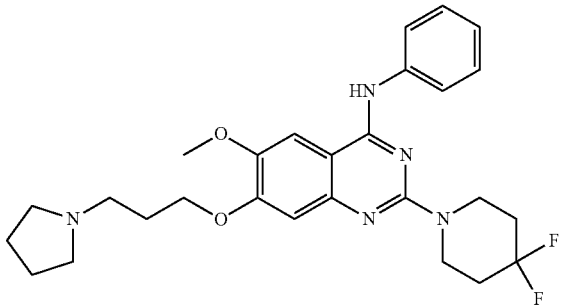
32
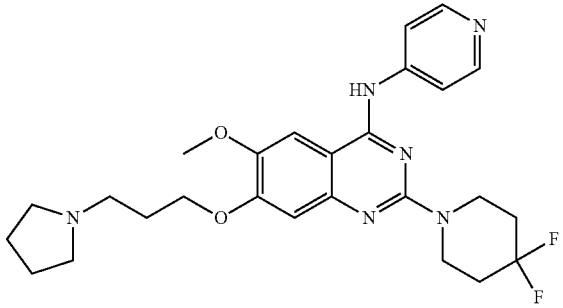
33
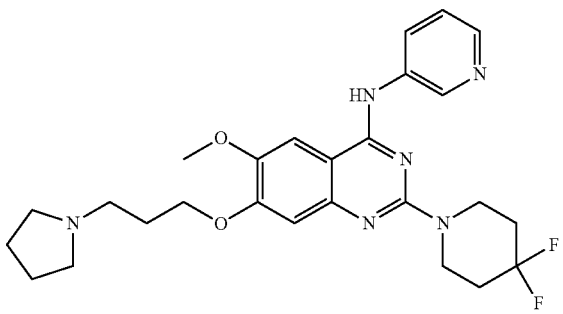

-continued
34
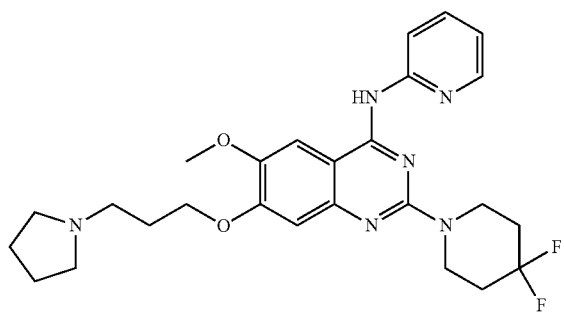
35
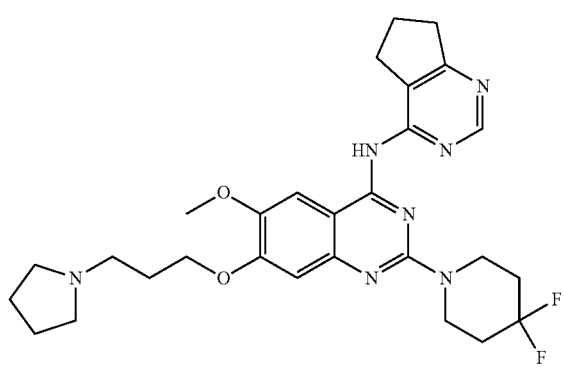
36
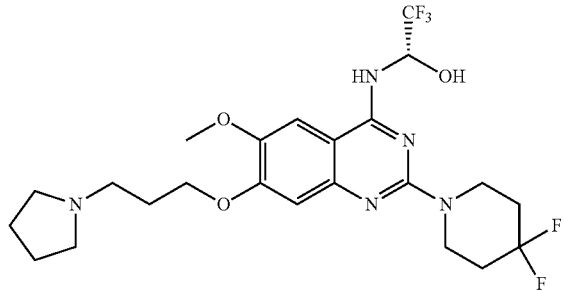
37
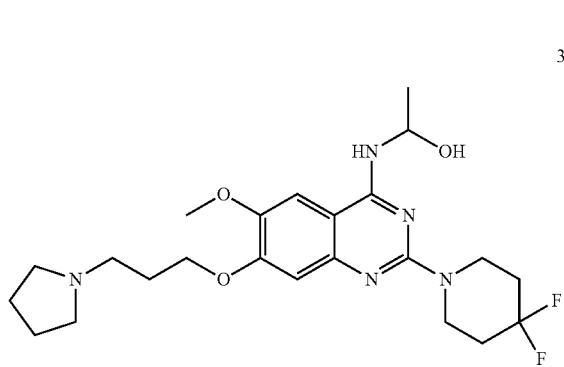
-continued
38
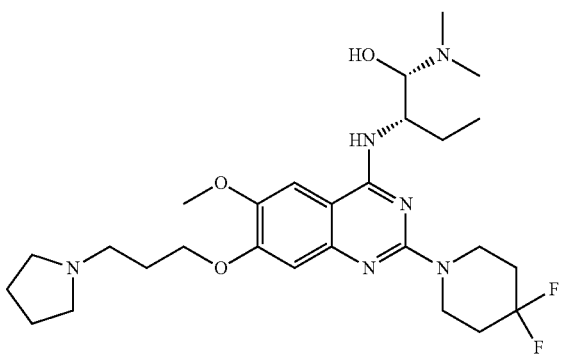
39
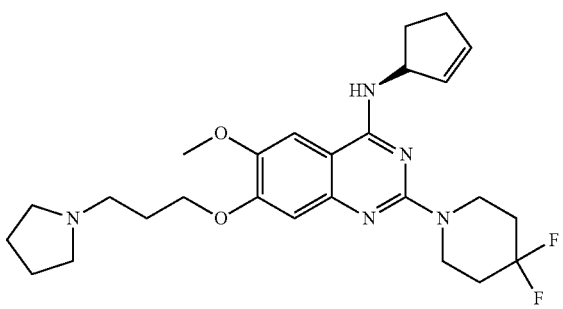
40
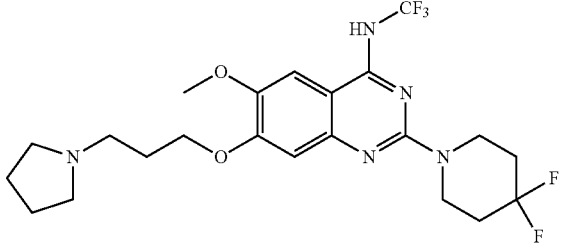
41
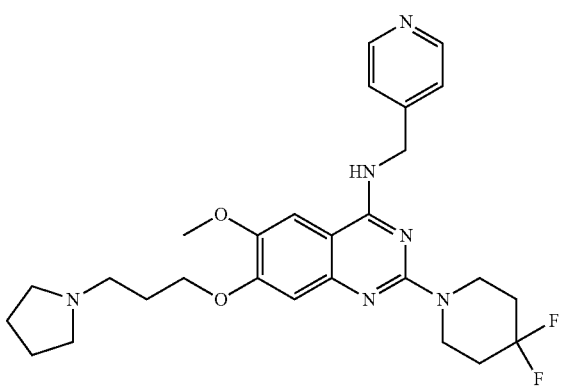

42
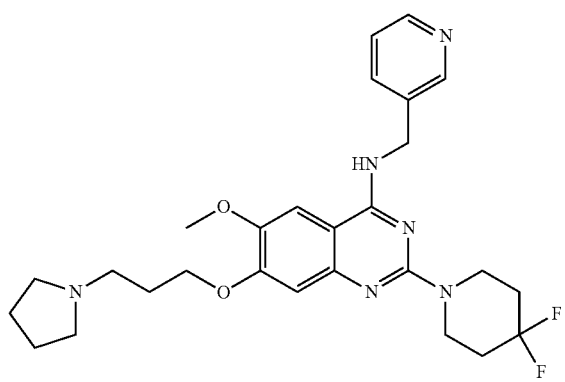
43
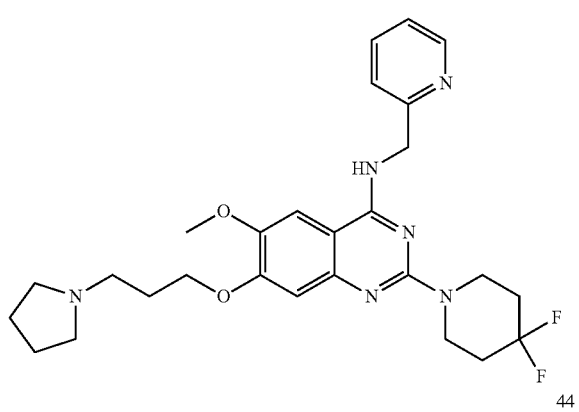
44
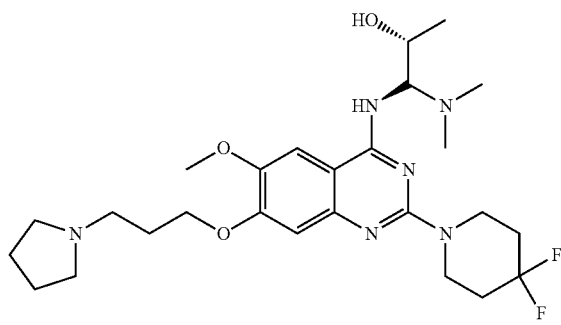
45
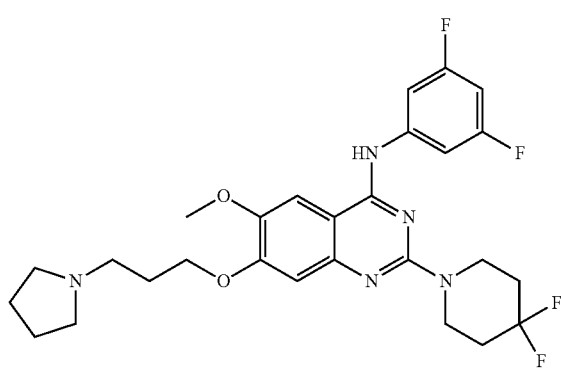
46
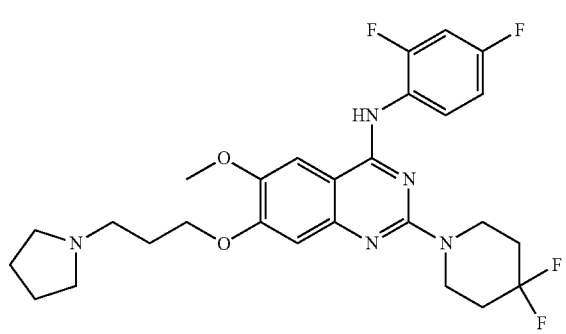
47
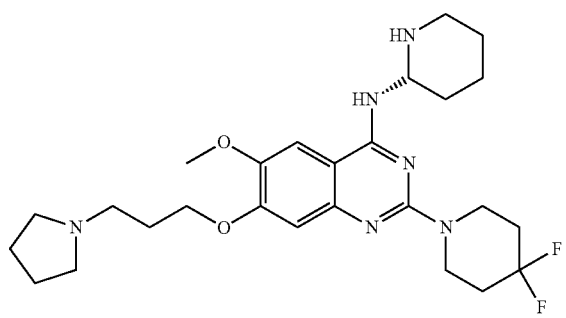
48
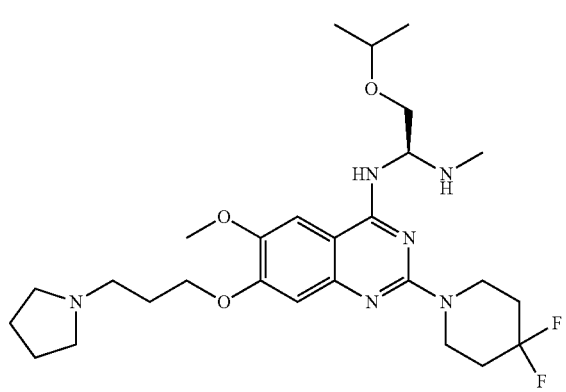
49
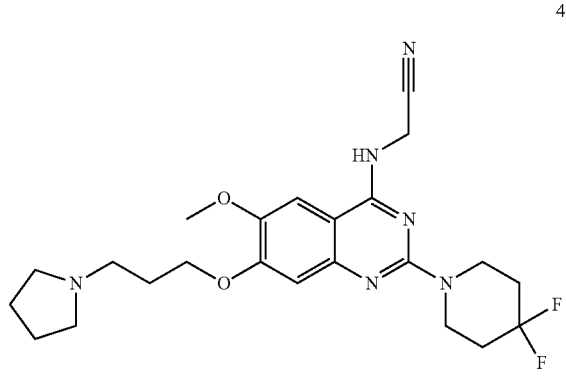

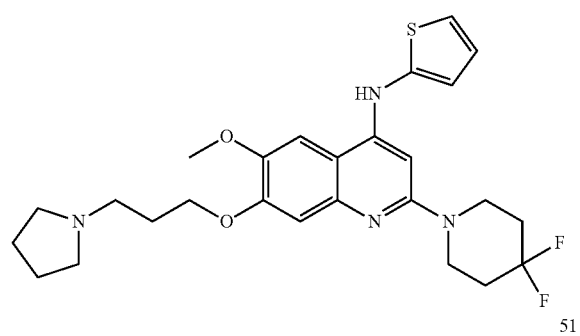
50
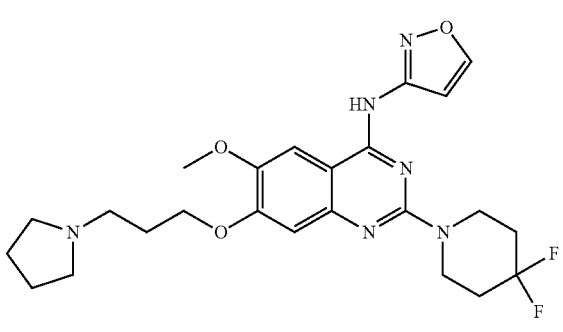
55
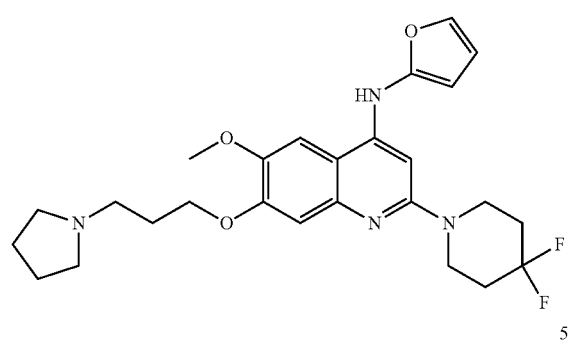
51
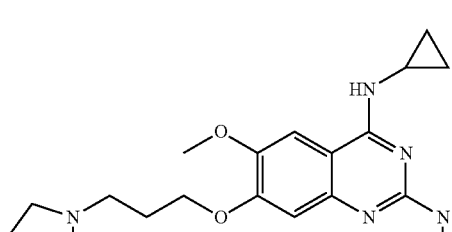
56
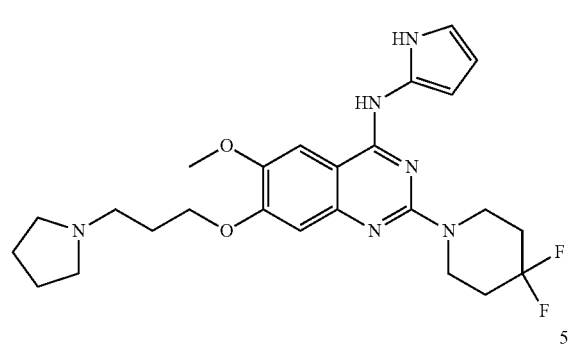
52
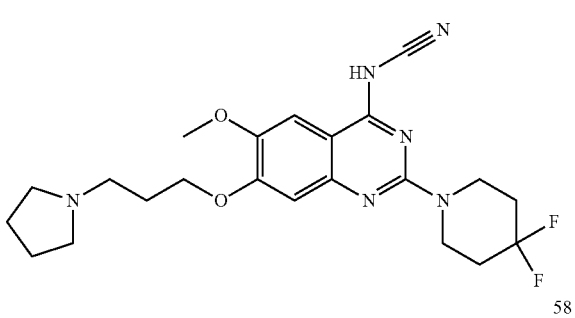
57
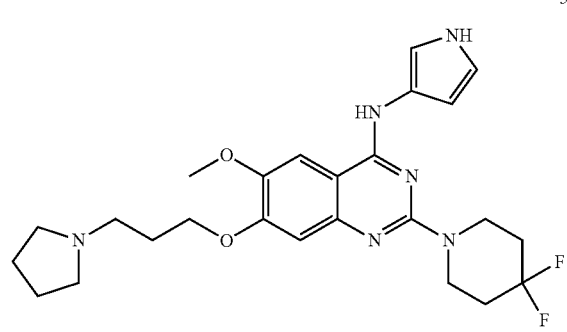
53
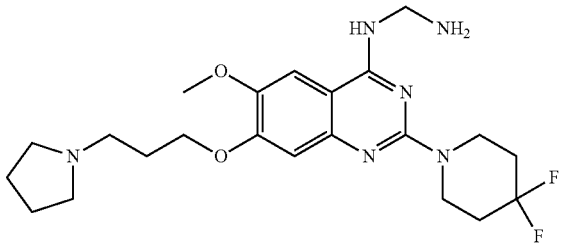
58
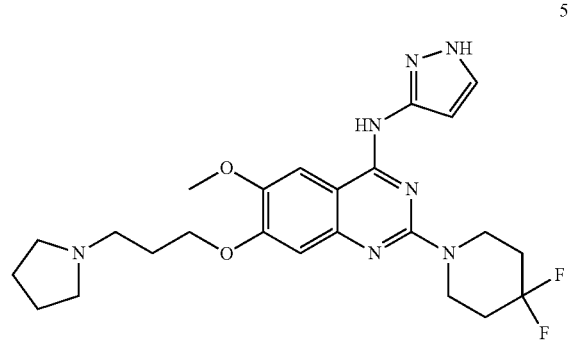
54
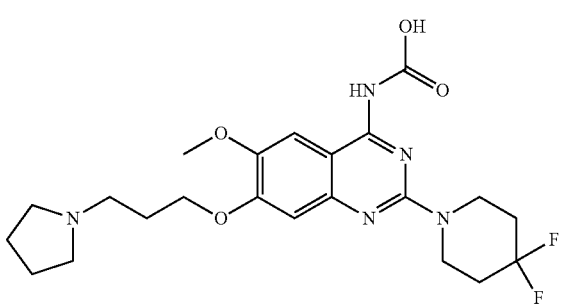
59

53
-continued
60
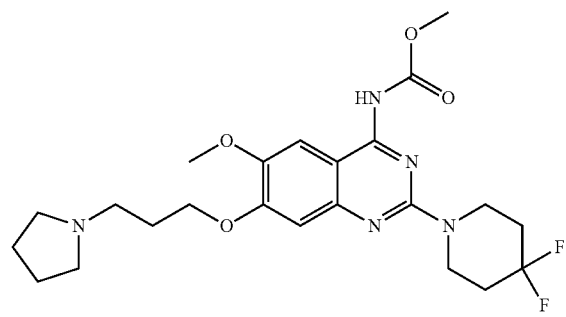
61
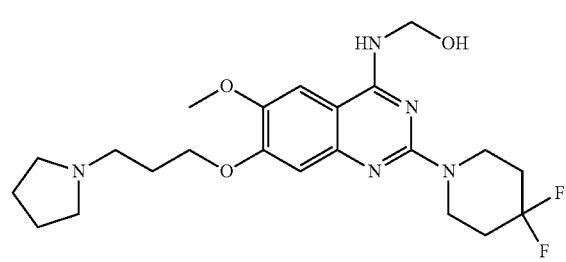
62
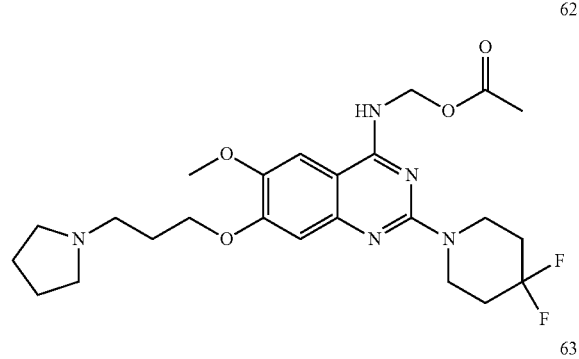
63
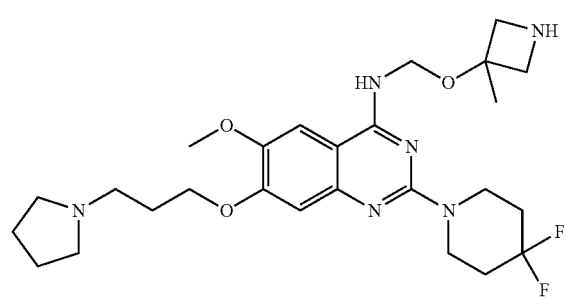
64
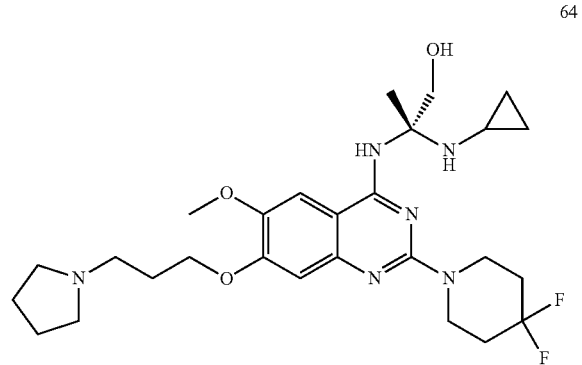
54
-continued
65
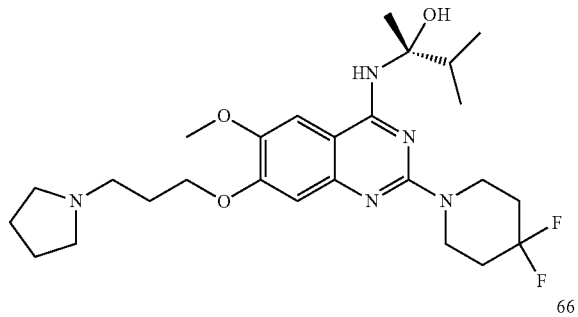
66
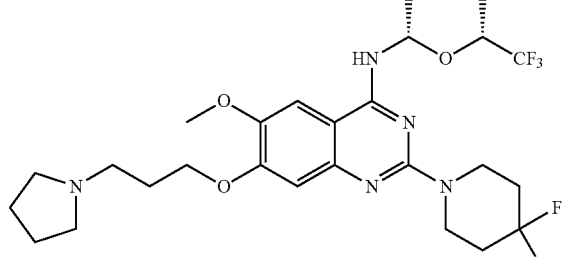
67
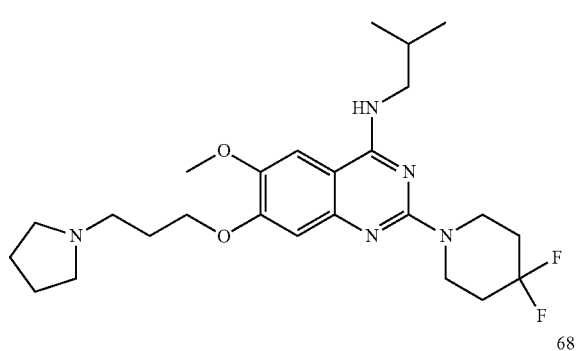
68
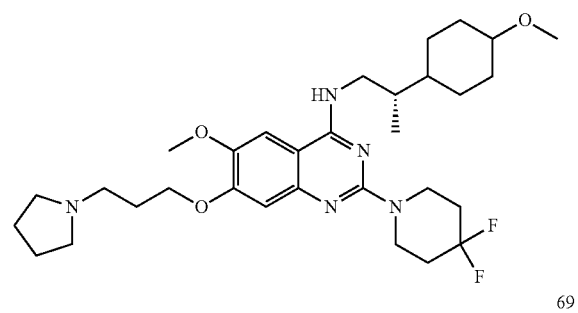
69
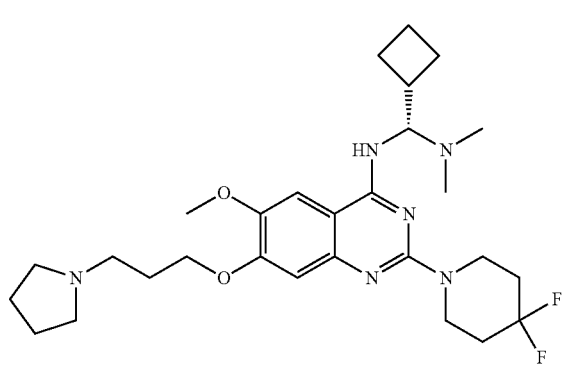

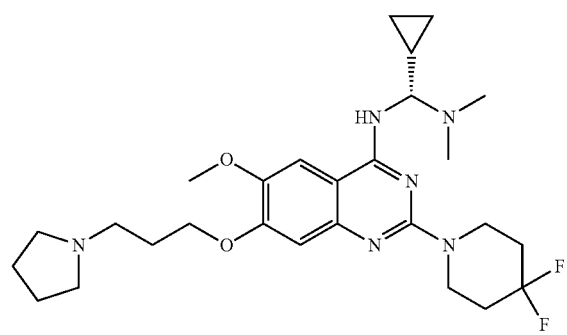
70
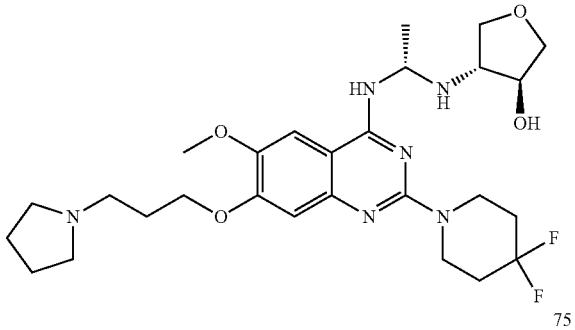
74
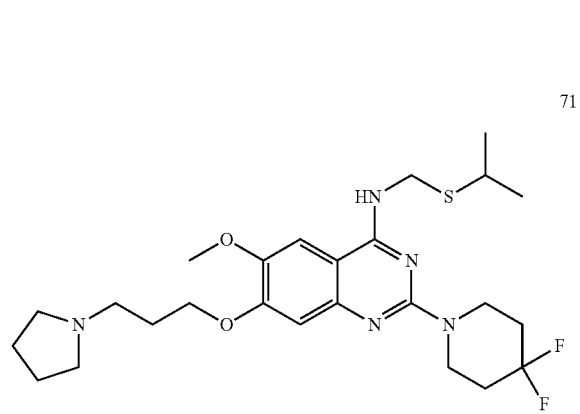
71
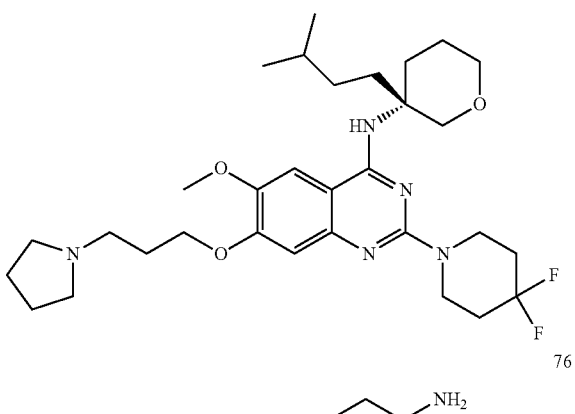
75
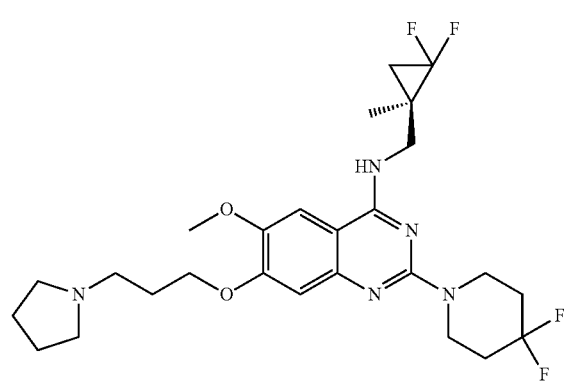
72
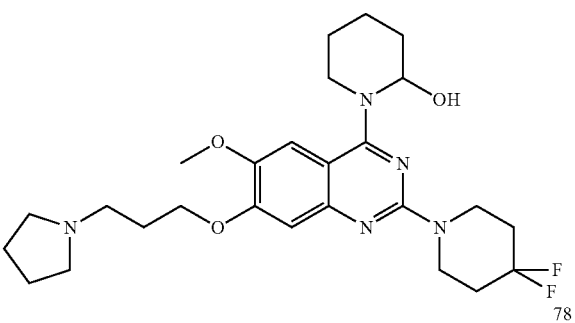
76
73
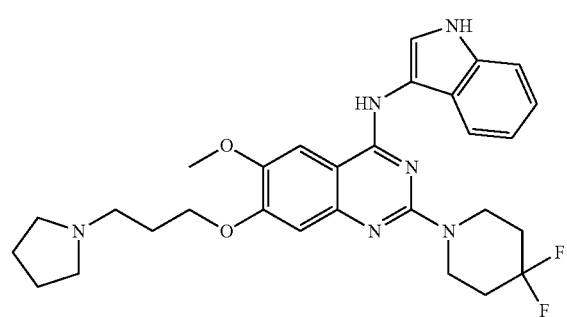
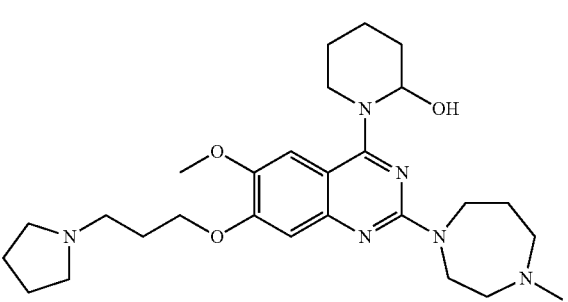
77
78

79
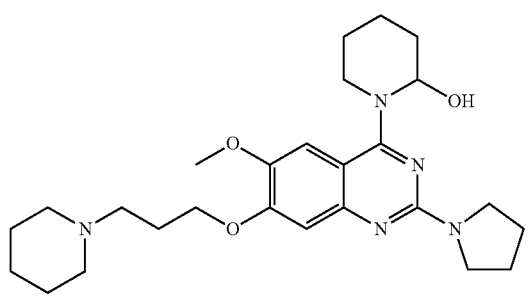
80
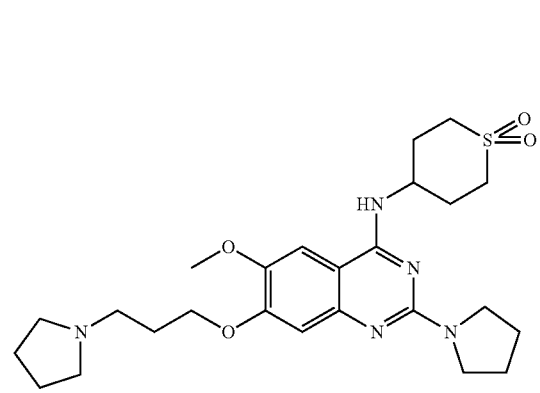
81
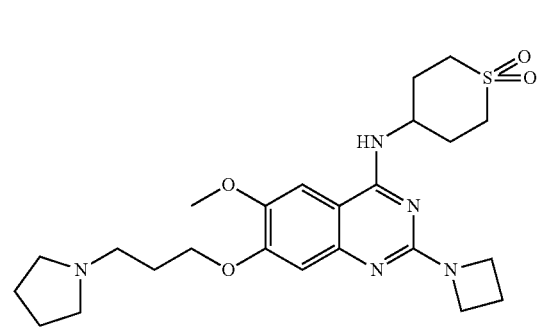
82
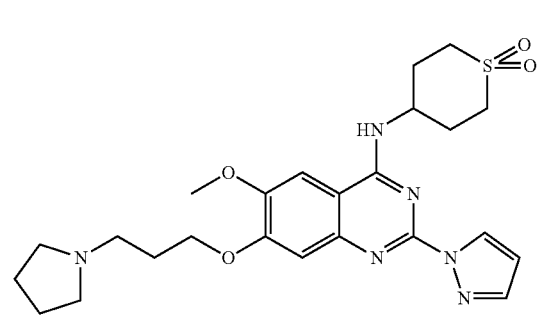
83
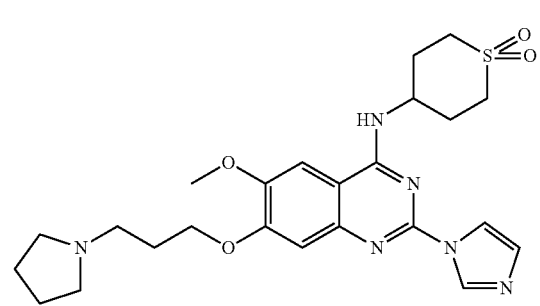
84
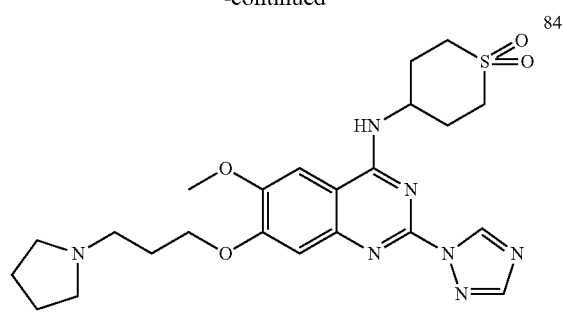
85
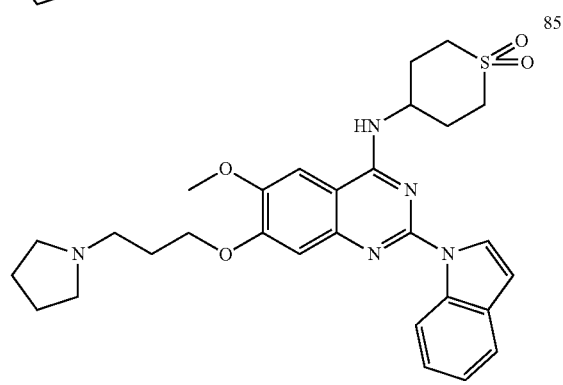
86
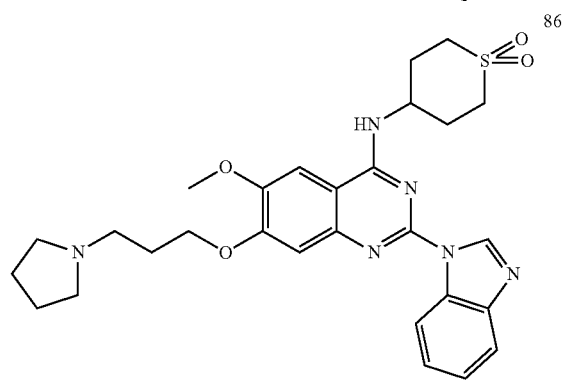
87
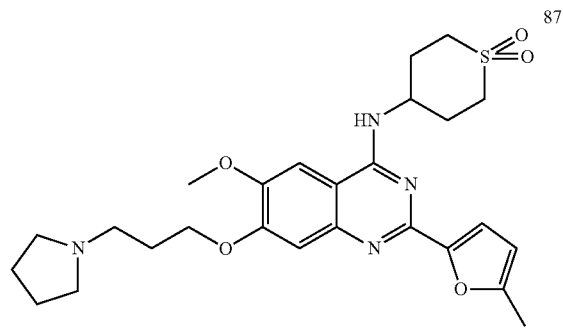
88
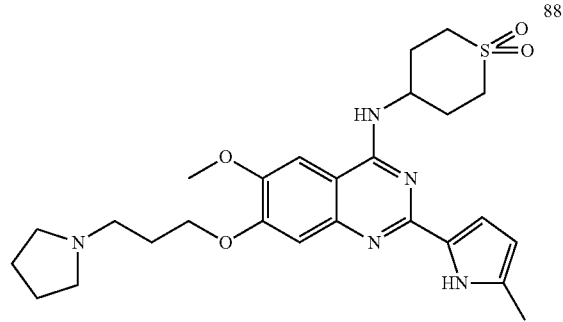

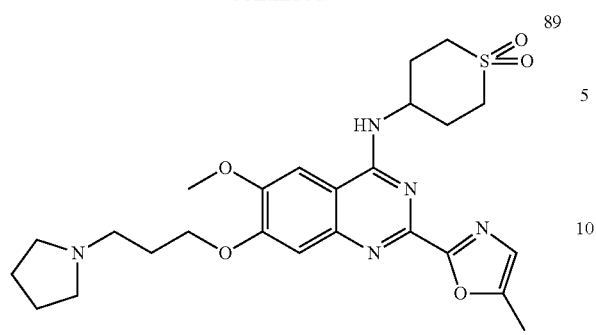
89
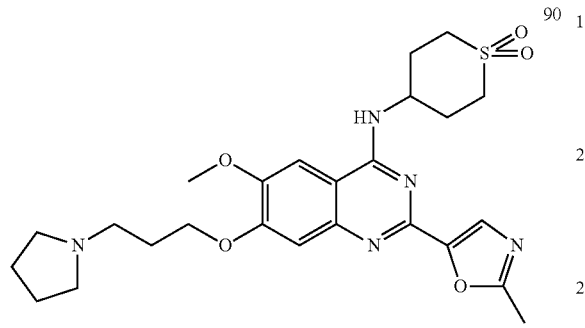
90
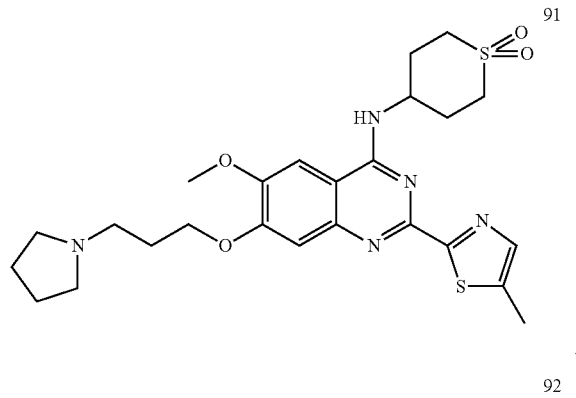
91
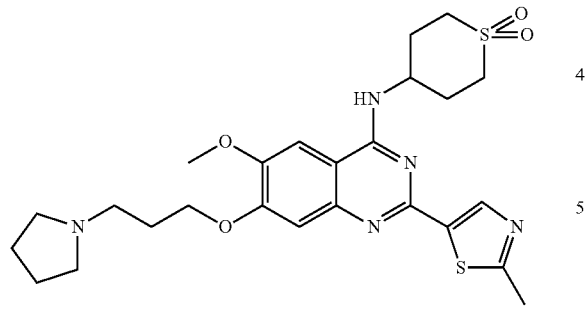
92
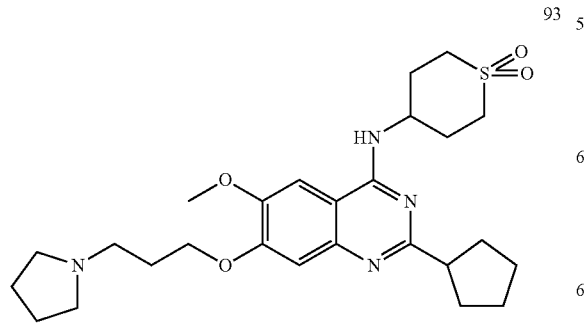
93
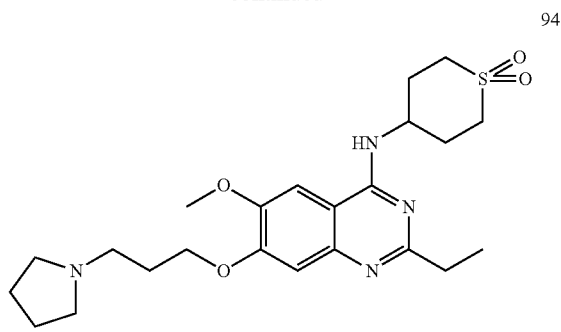
94
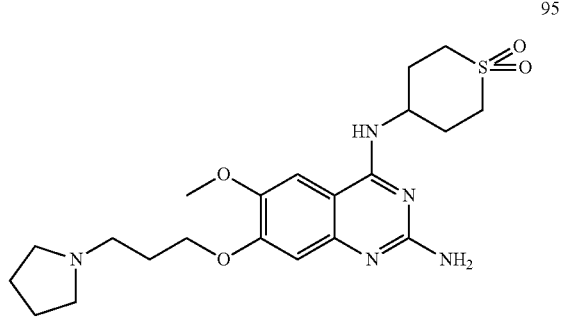
95
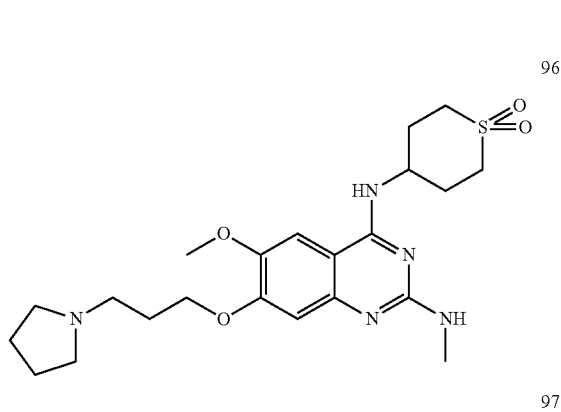
96
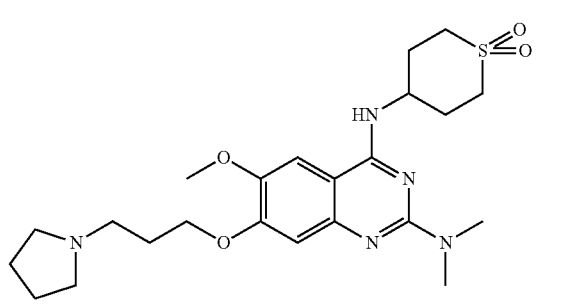
97
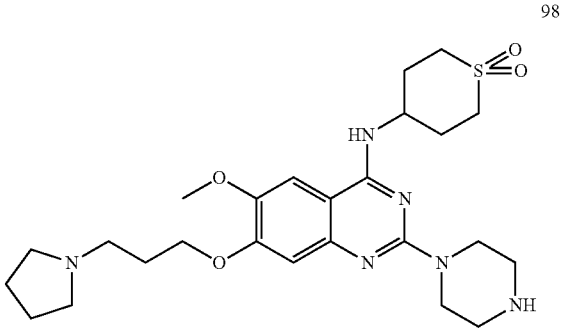
98

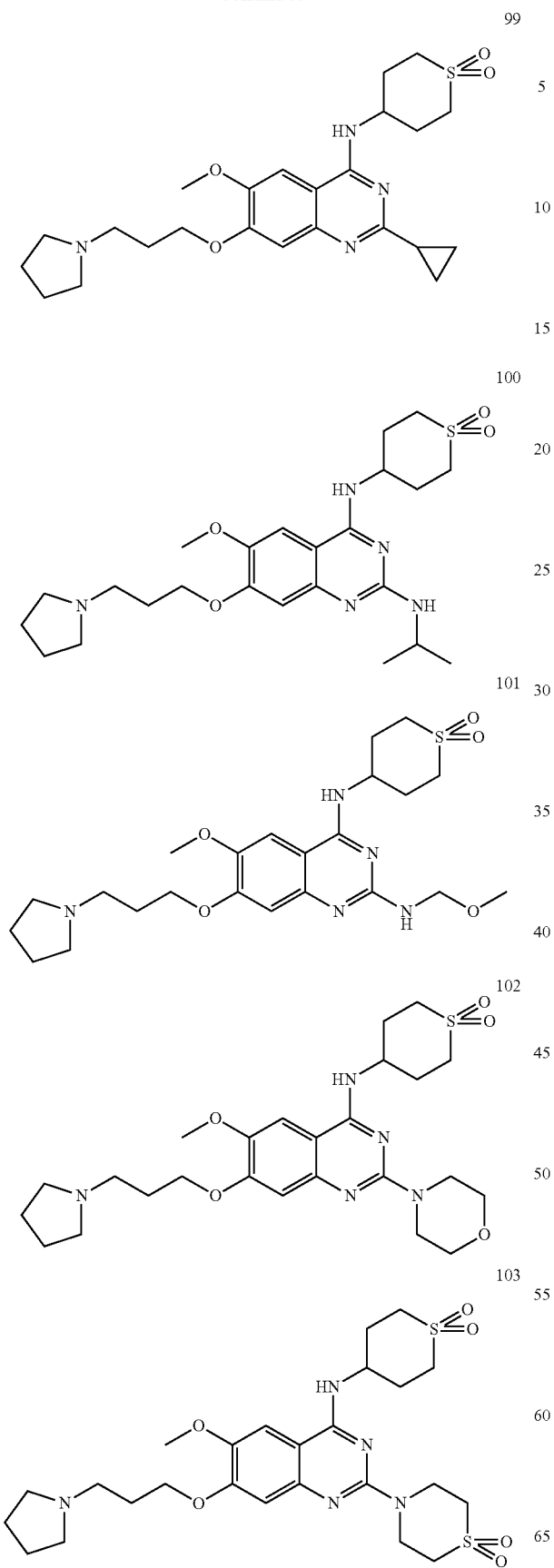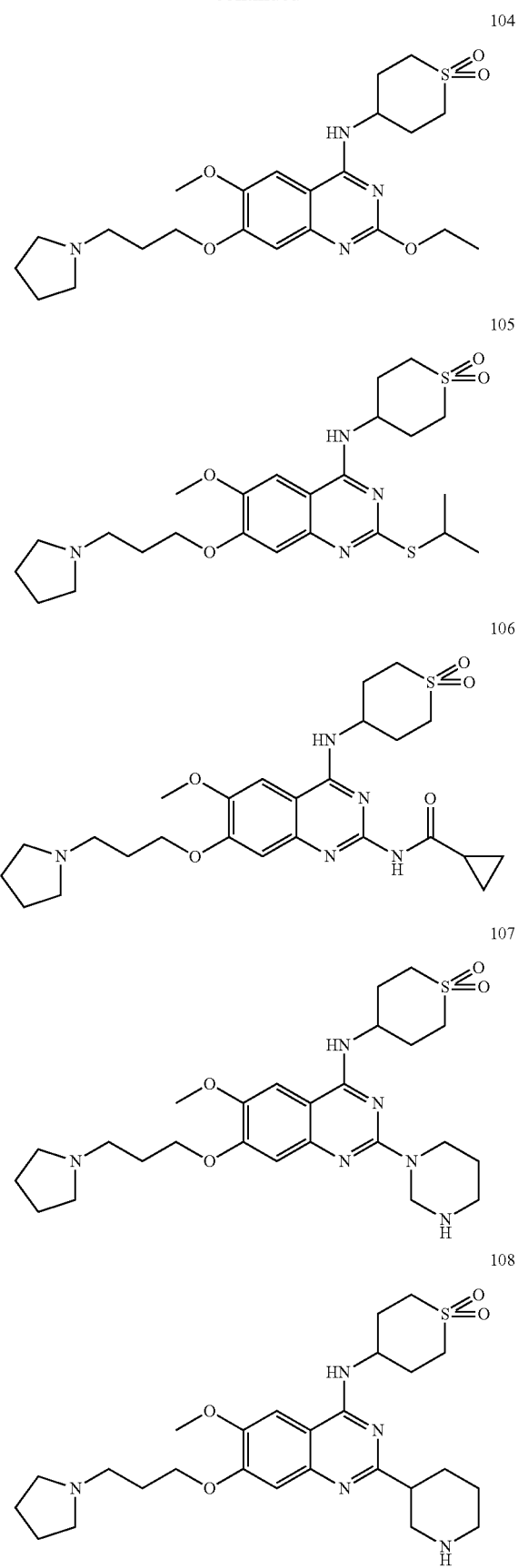

-continued
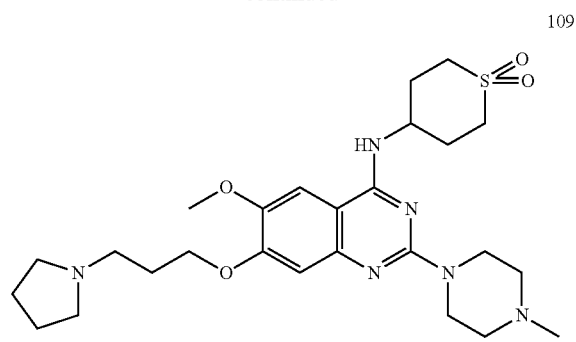
109
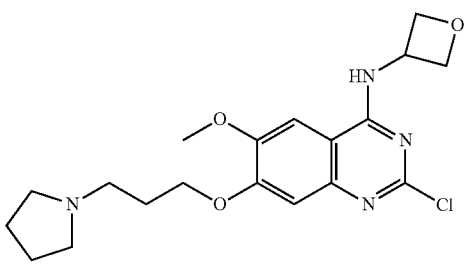
114
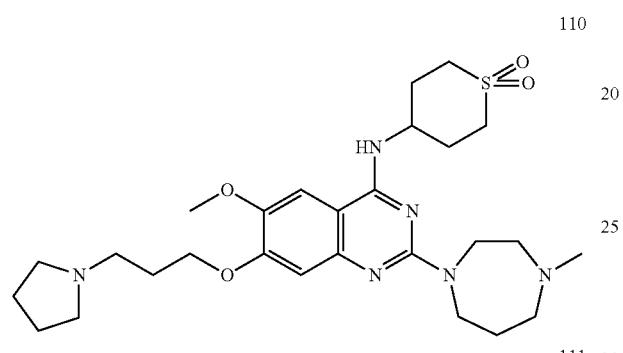
110
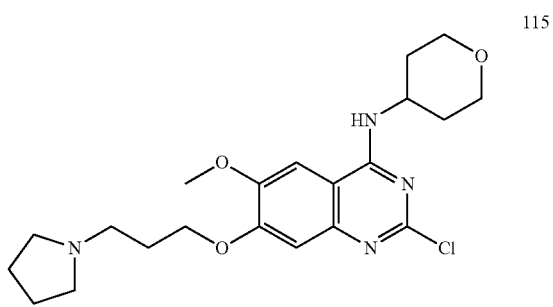
115
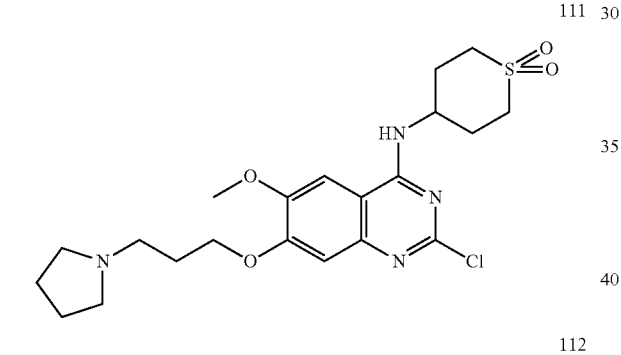
111
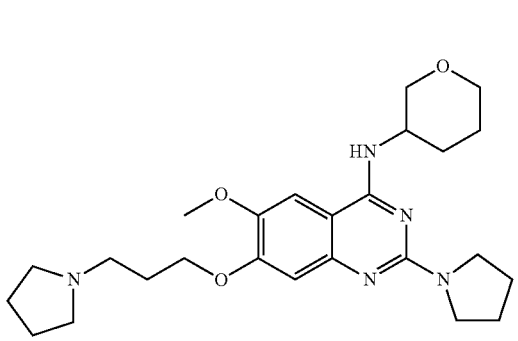
116
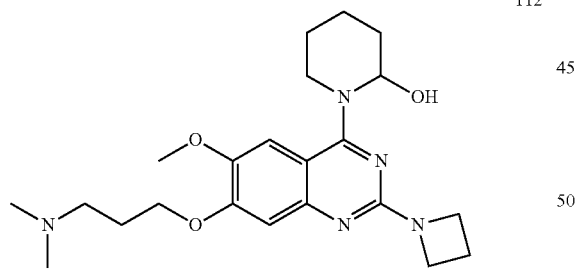
112
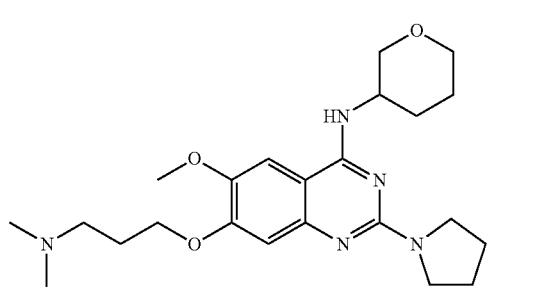
117
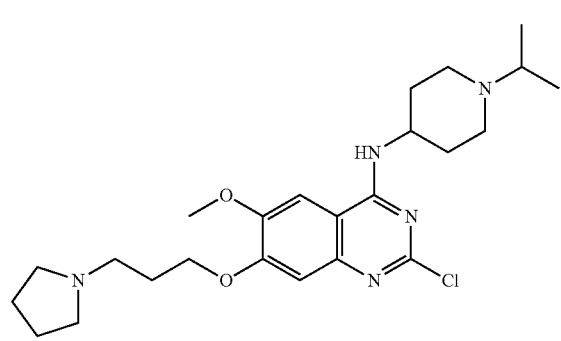
113
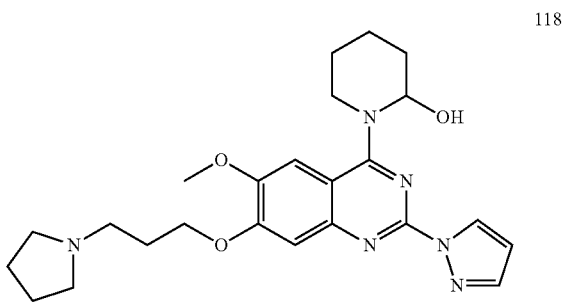
118

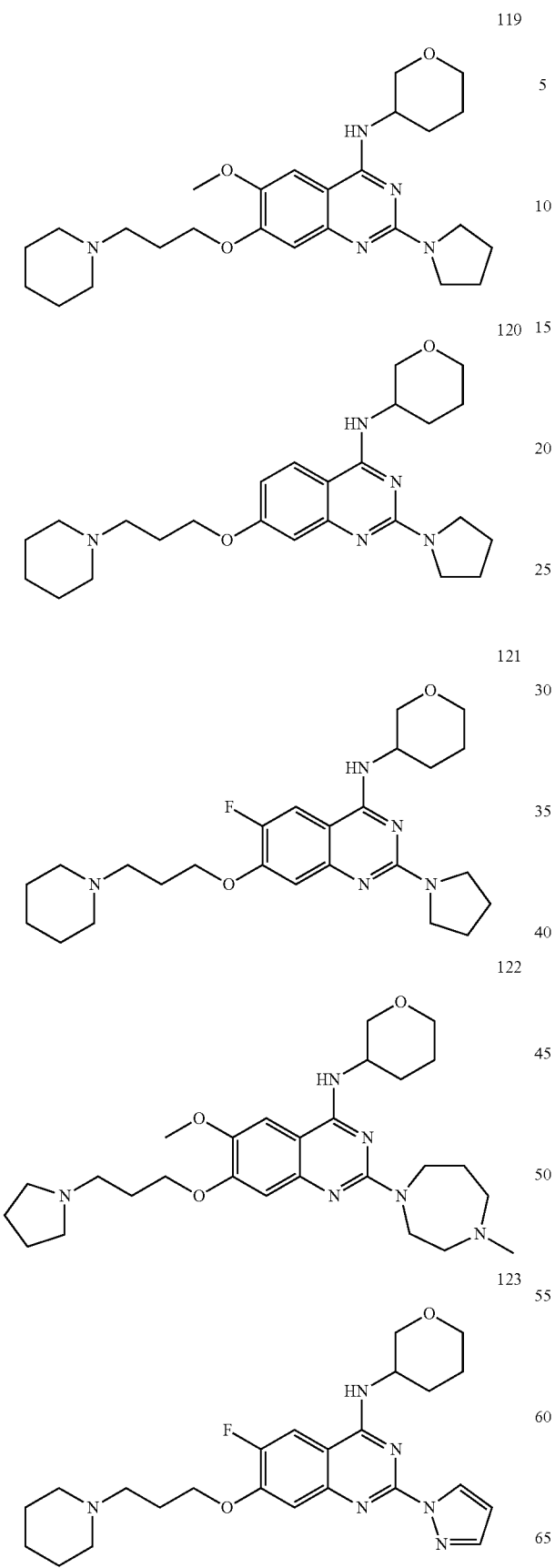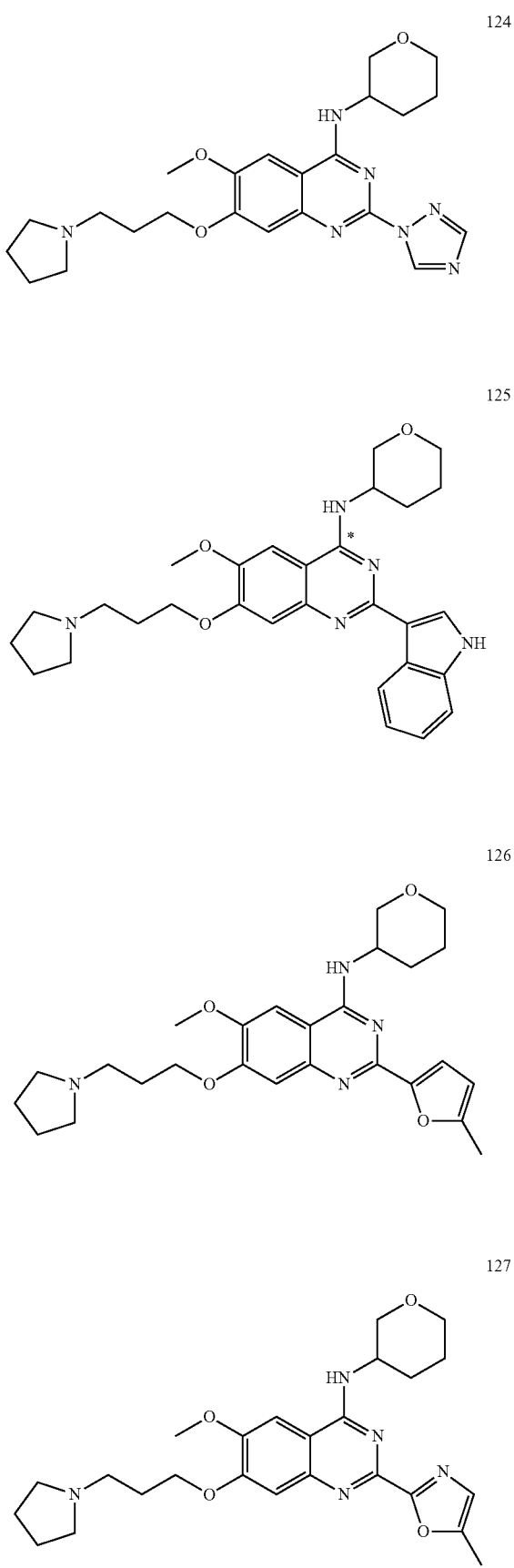

-continued
128
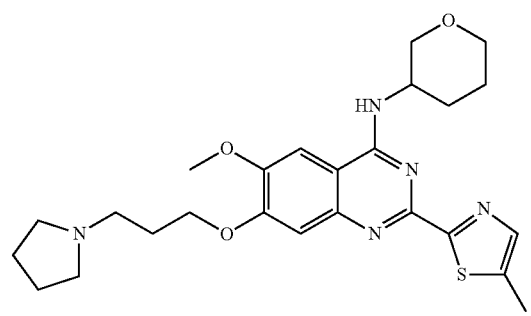
129
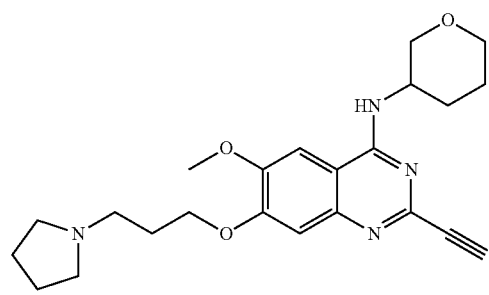
130
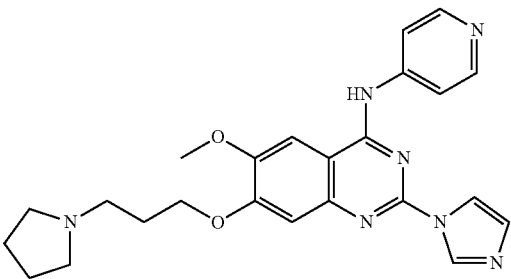
131
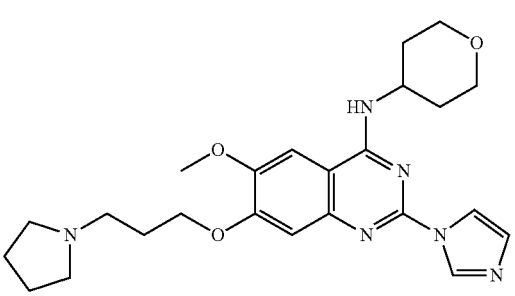
132
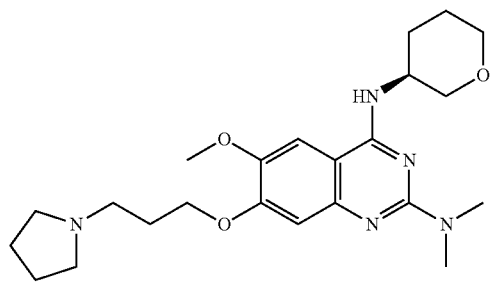
-continued
133
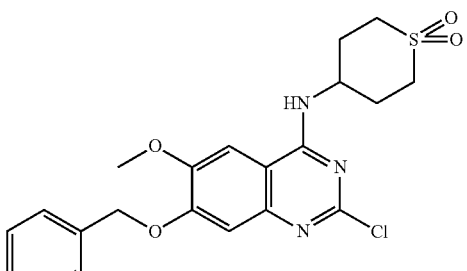
134
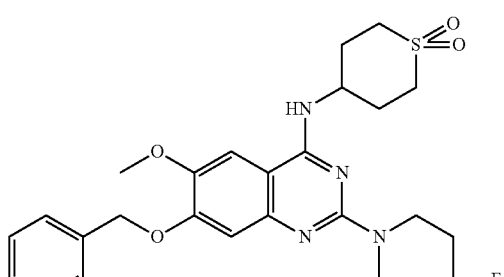
136
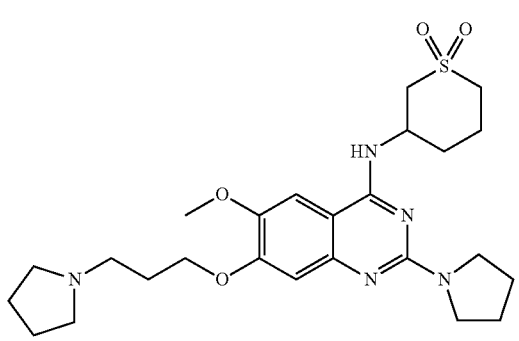
137
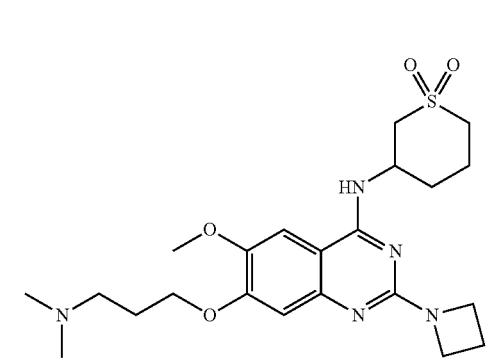
139
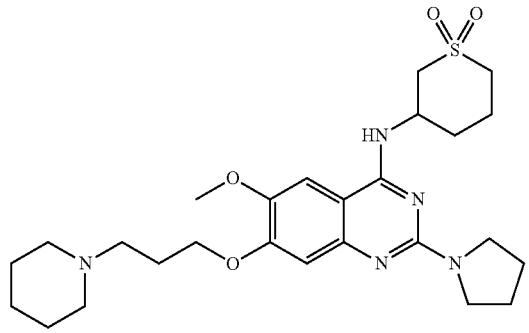

-continued
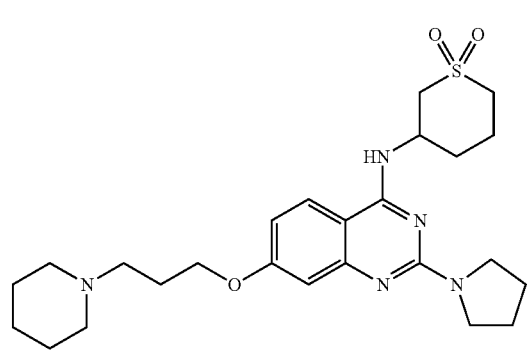
140
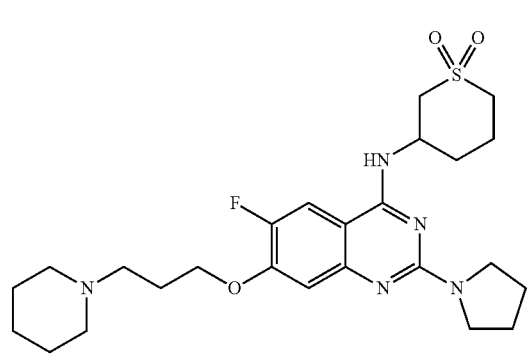
141
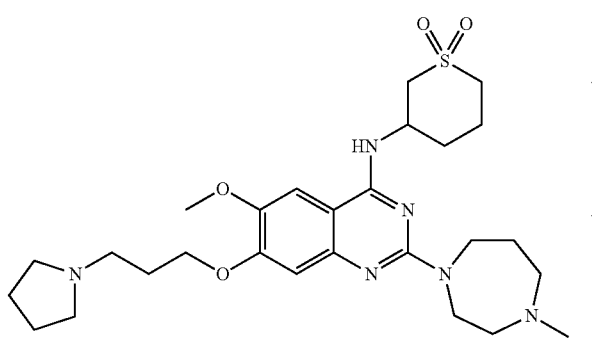
142
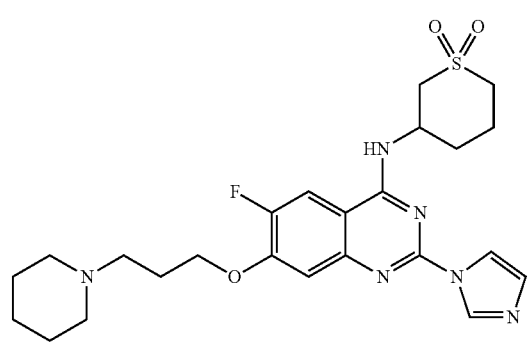
143
-continued
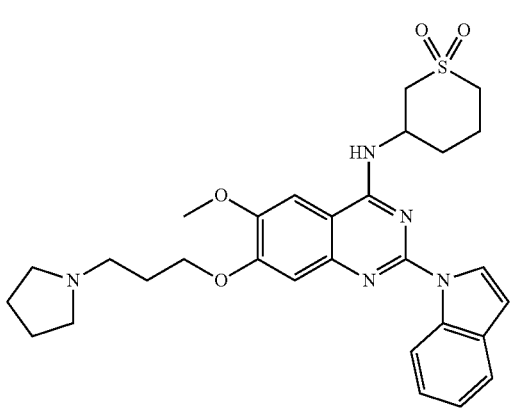
144
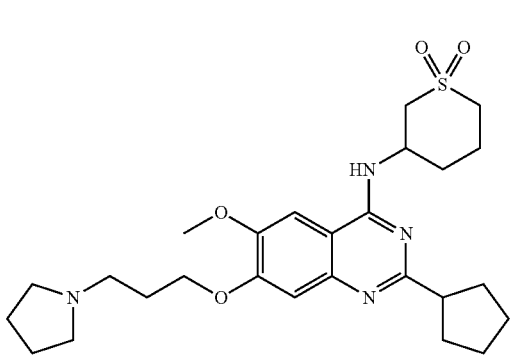
145
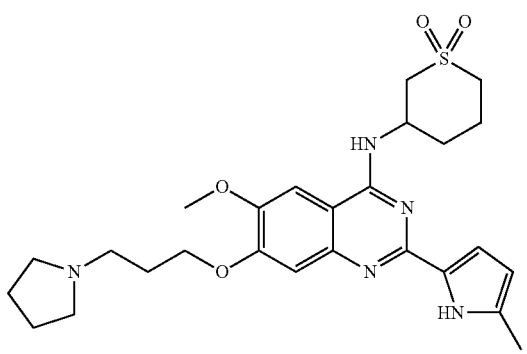
146
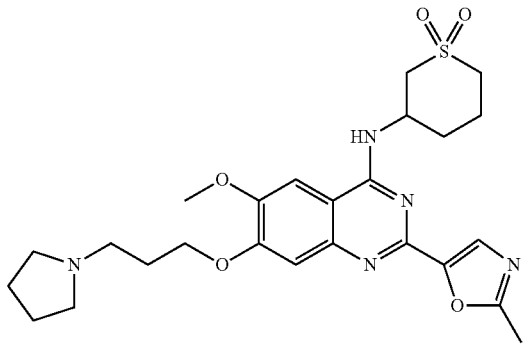
147

-continued
148
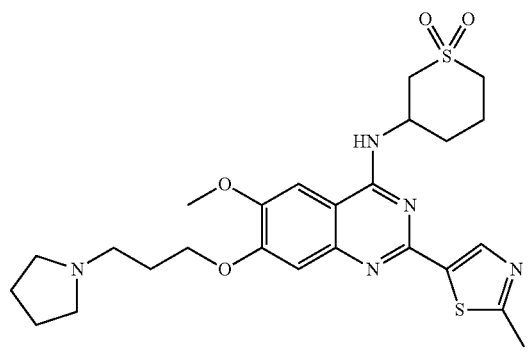
149
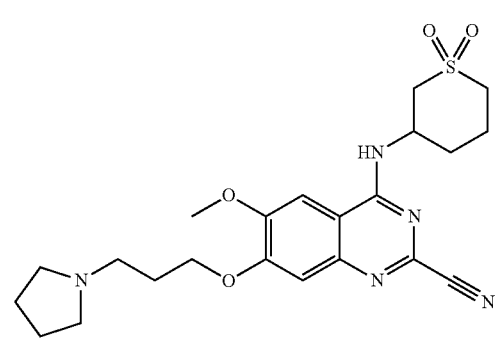
150
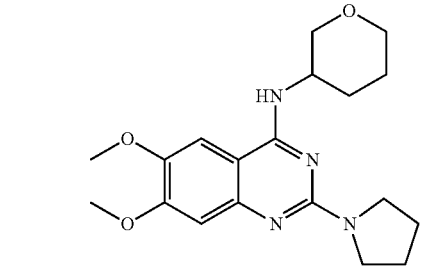
151
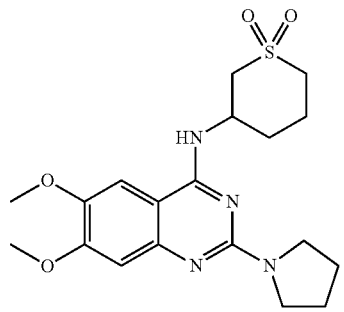
152
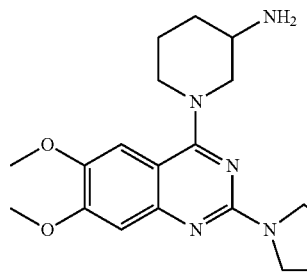
-continued
153
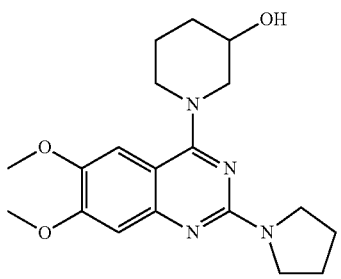
154
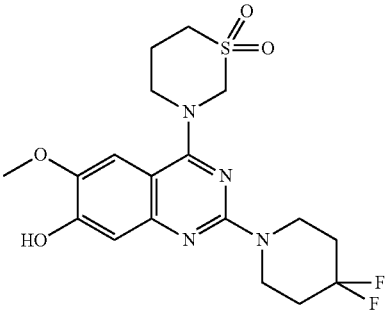
156
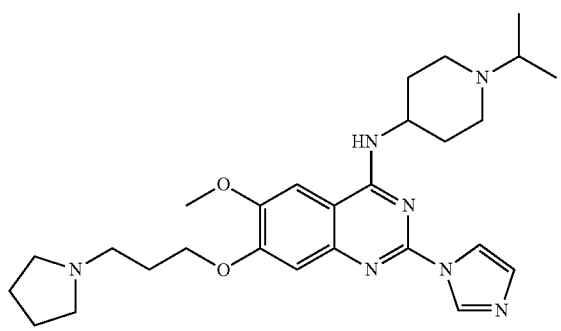
157
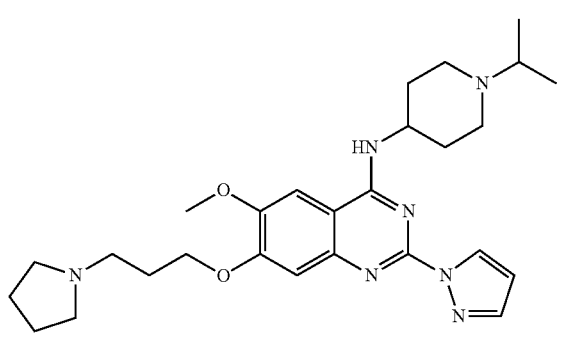
158
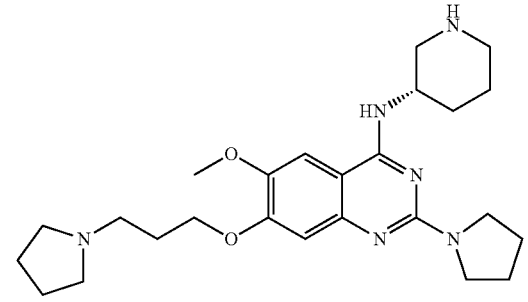

159 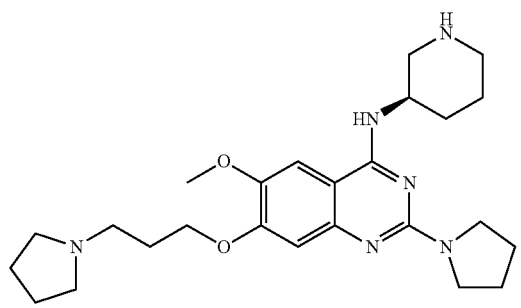
160 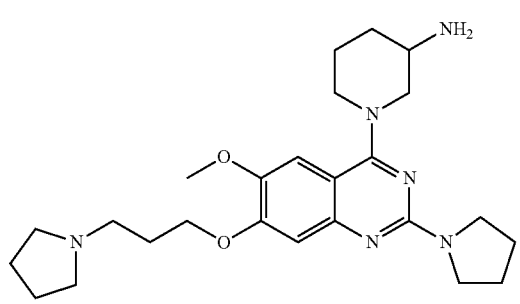
161 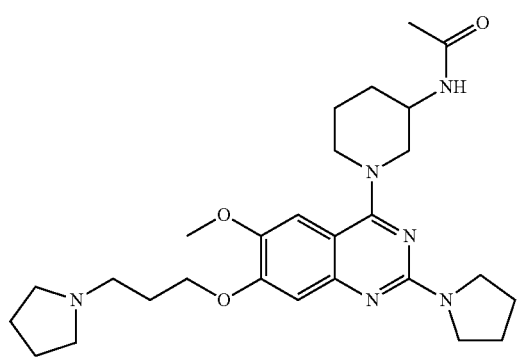
162 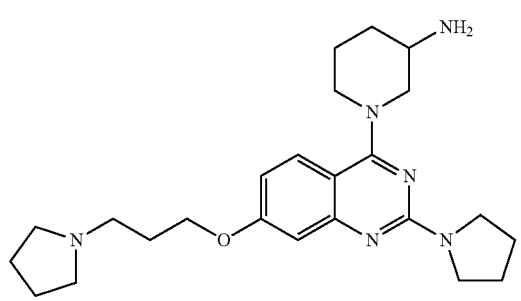
163 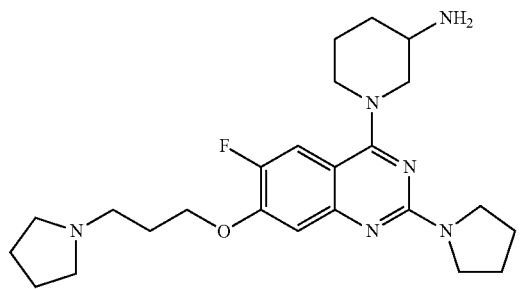
164 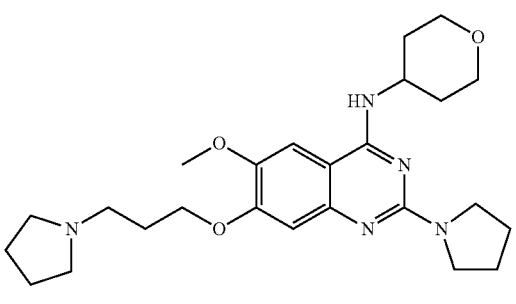
165 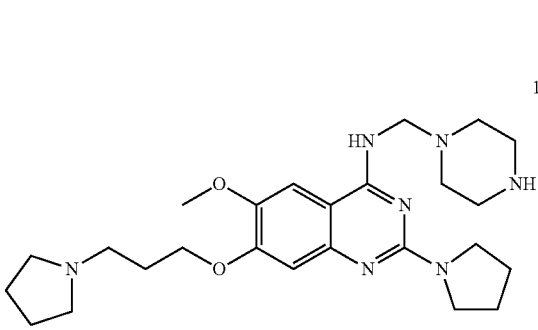
166 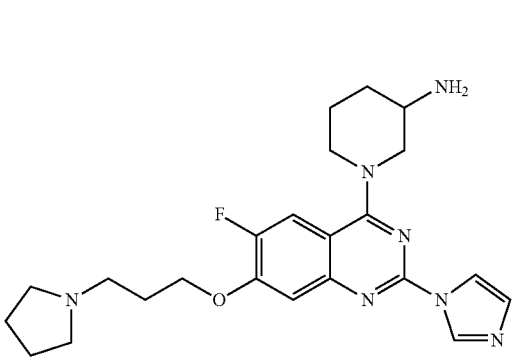
167 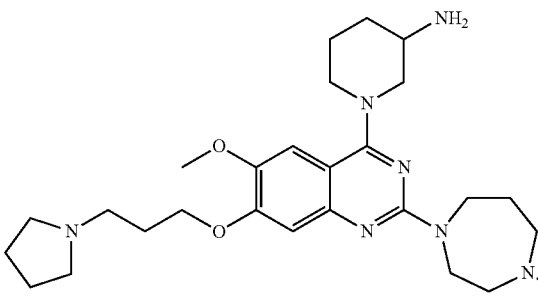
168 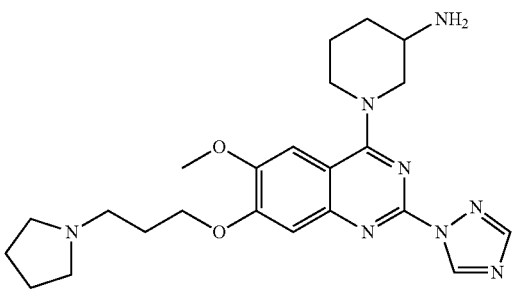

-continued
169
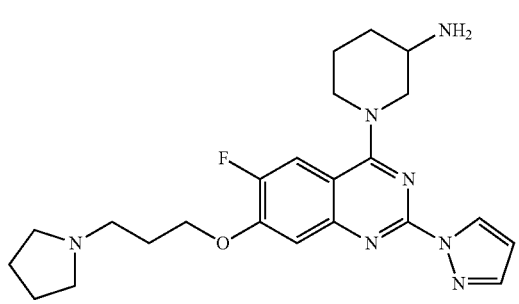
170
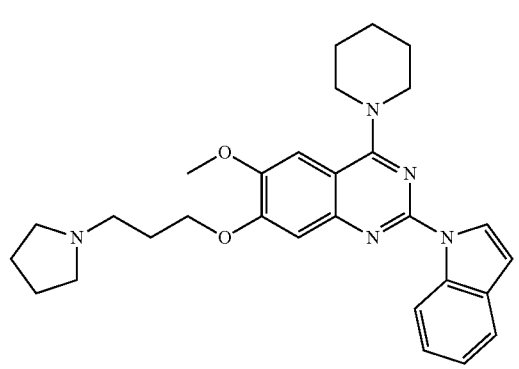
171
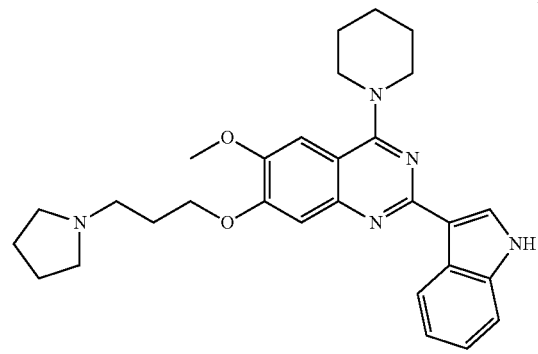
172
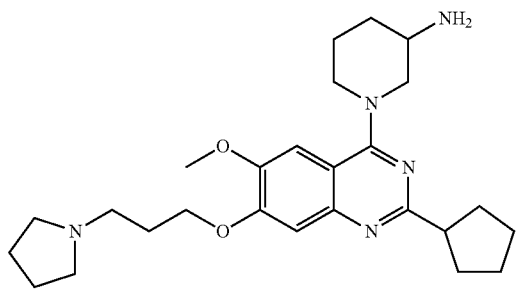
173
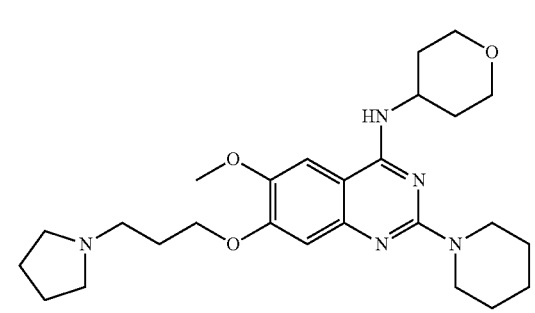
-continued
174
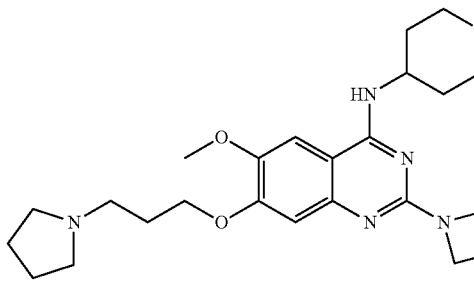
175
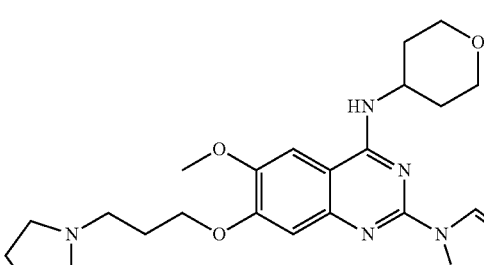
177
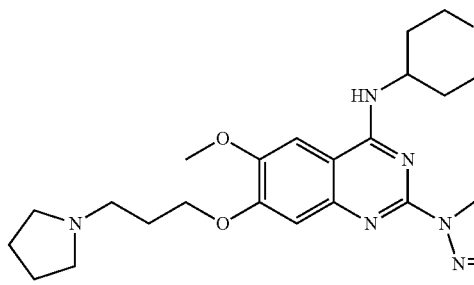
178
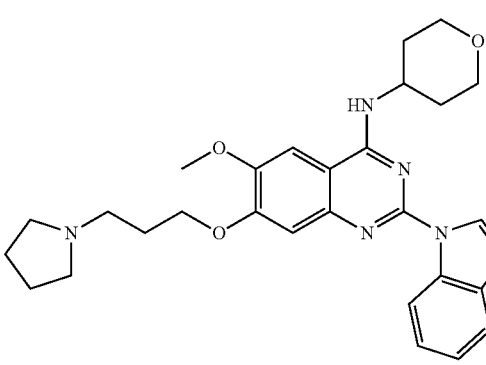
179
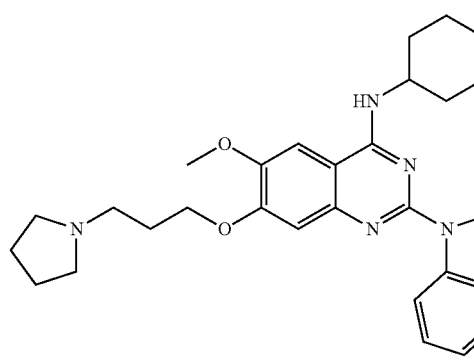

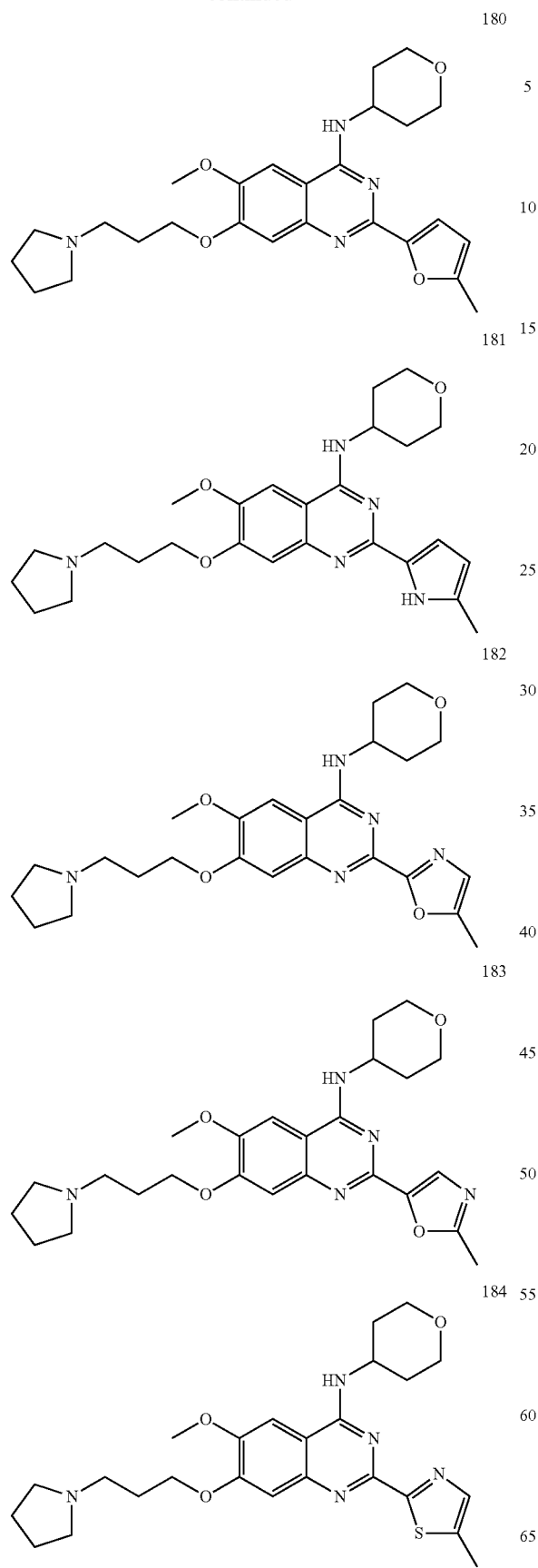
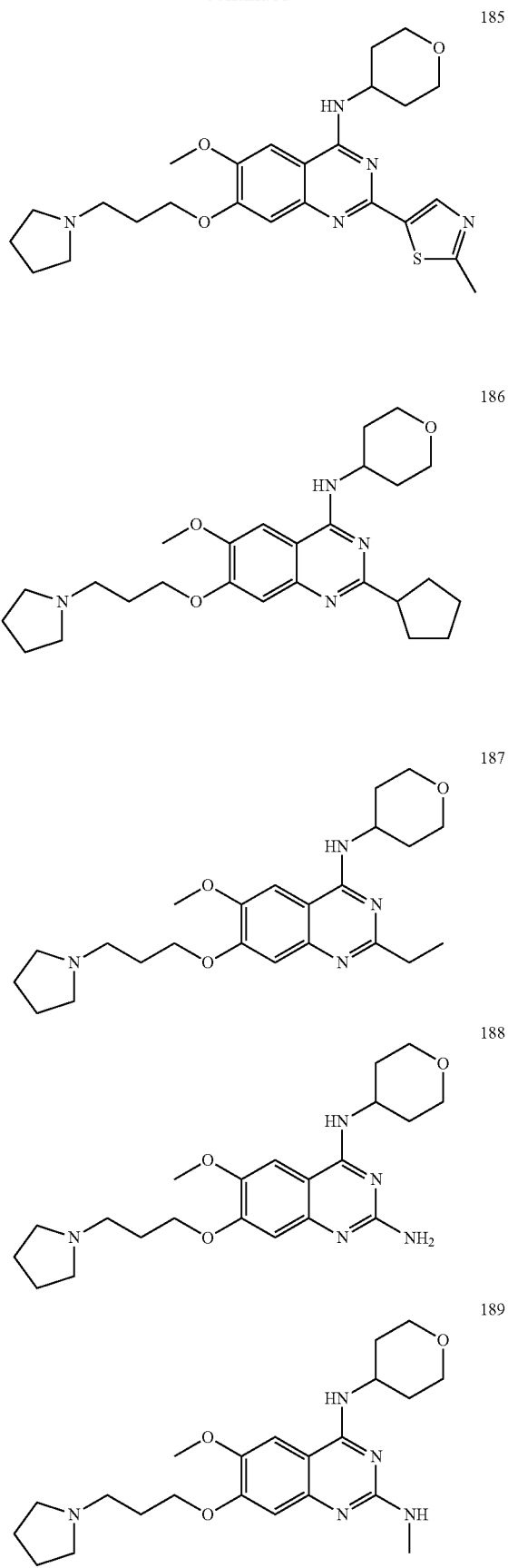

190
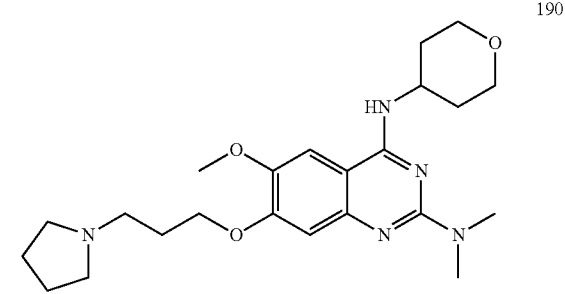
191
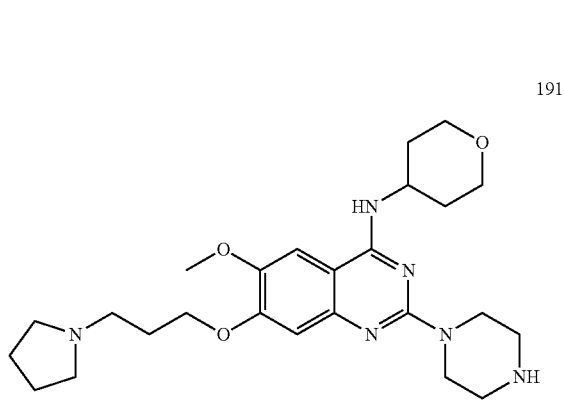
192
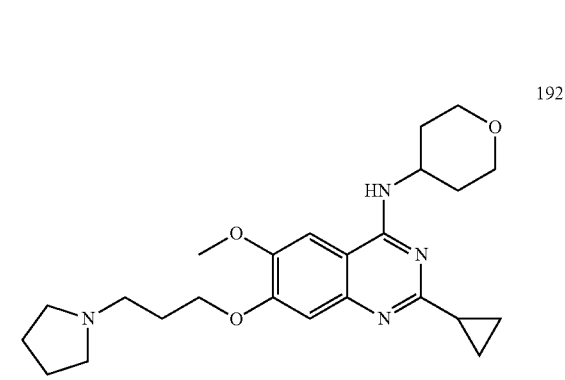
193
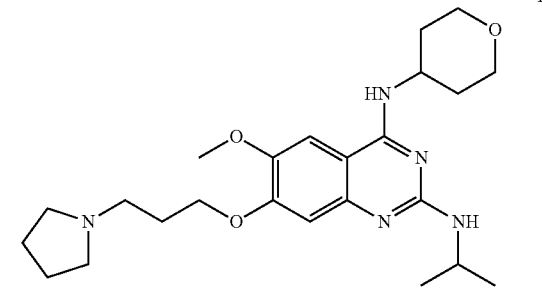
194
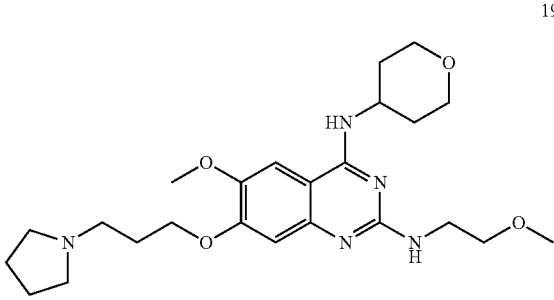
195
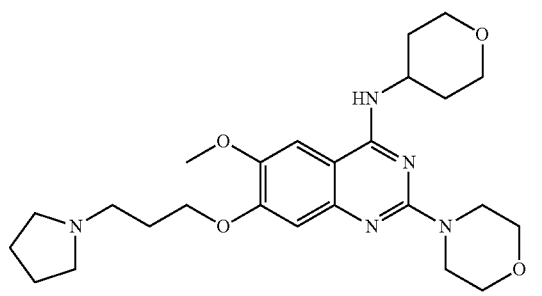
196
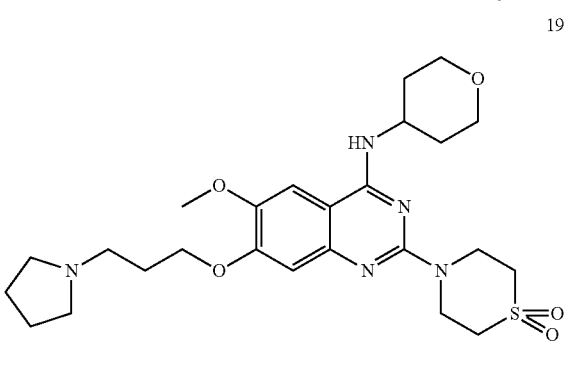
197
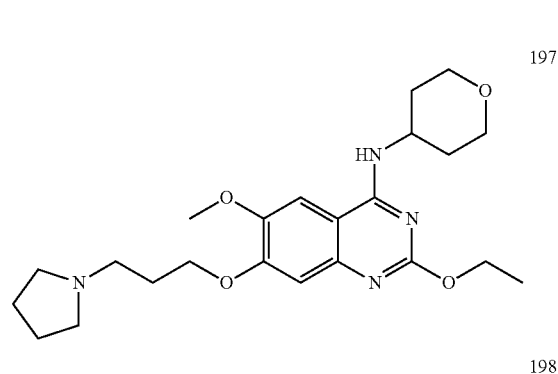
198
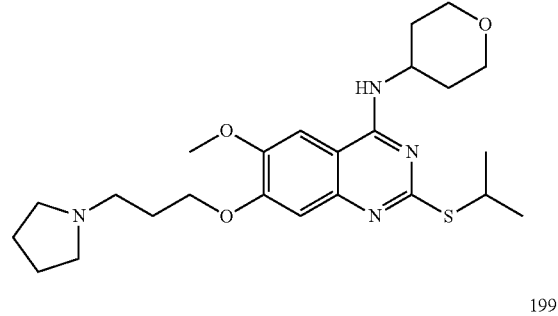
199

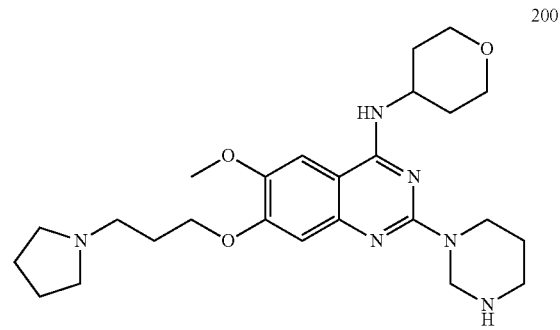
200
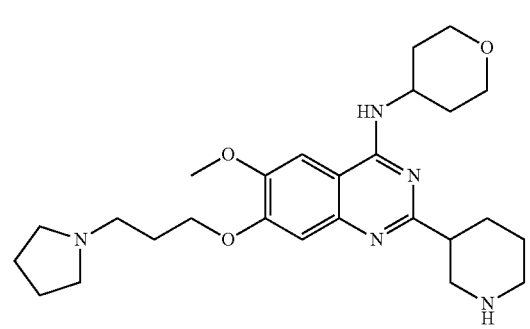
201
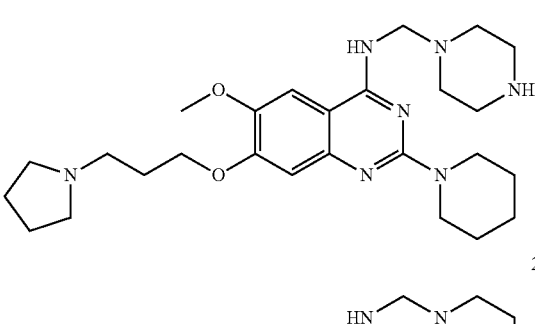
202
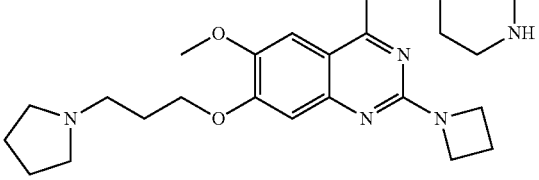
203
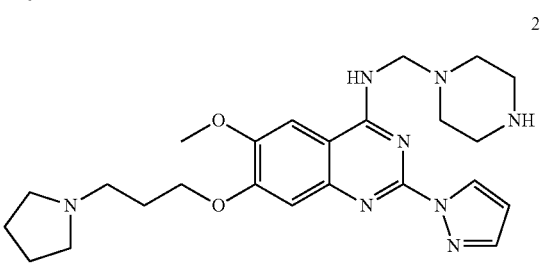
204
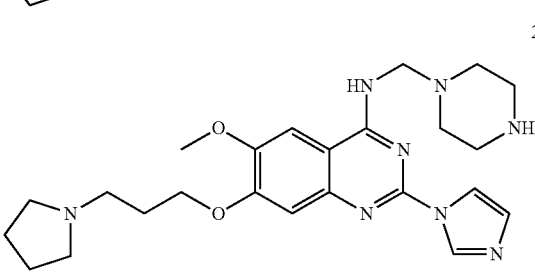
205
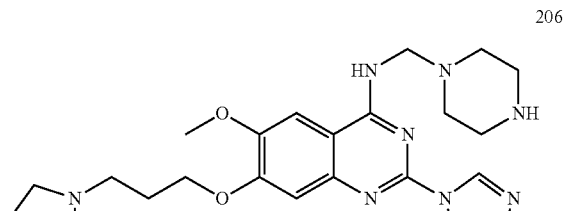
206
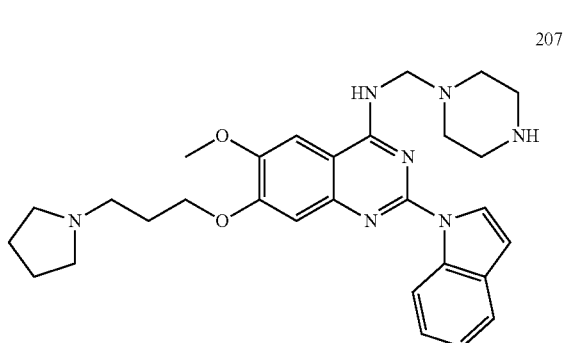
207
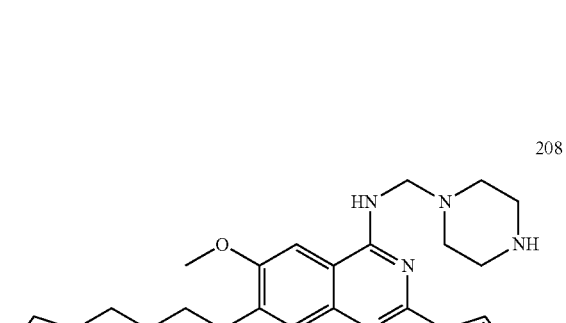
208
209
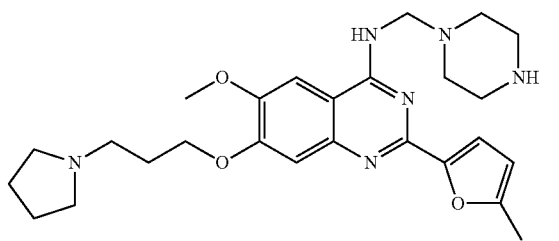
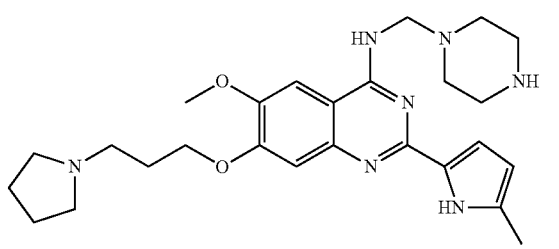
210

211
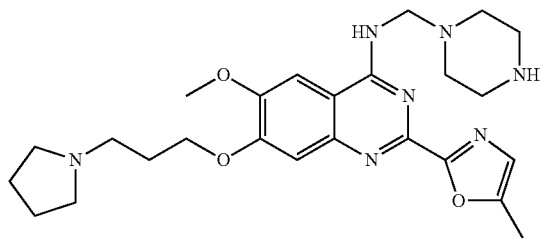
212
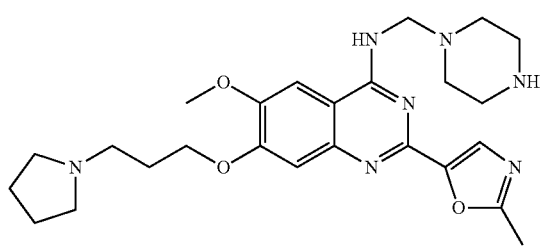
213
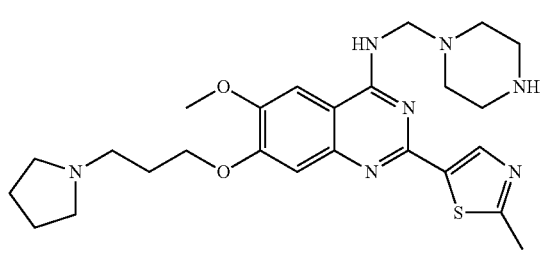
214
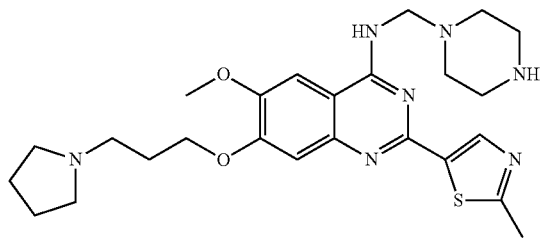
215
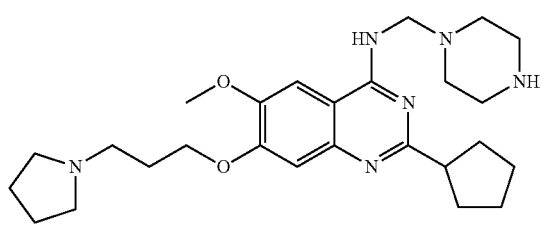
216
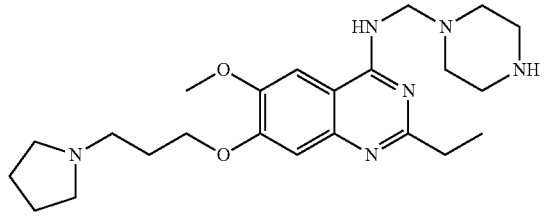
217
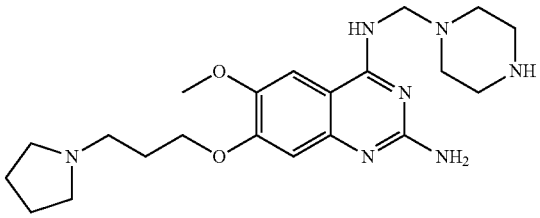
218
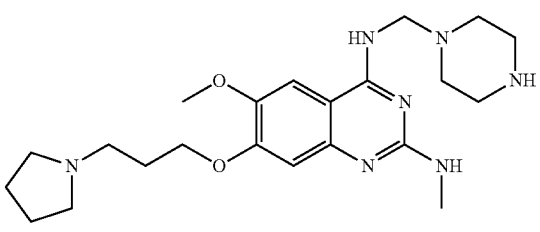
219
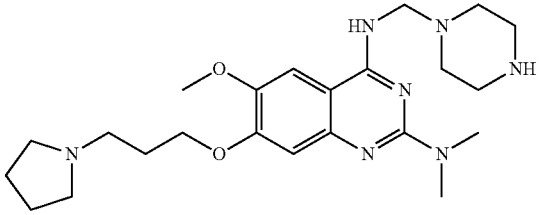
220
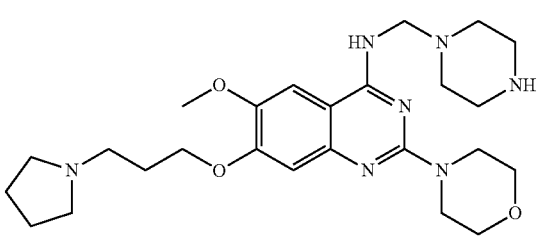
221
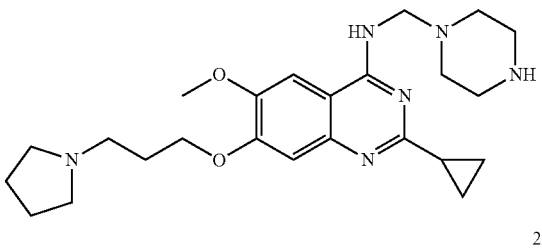
222
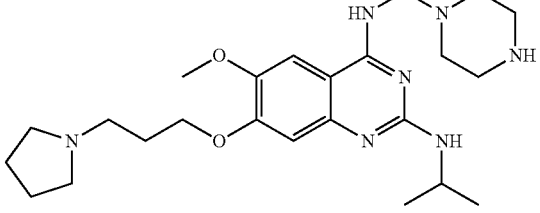

-continued
223
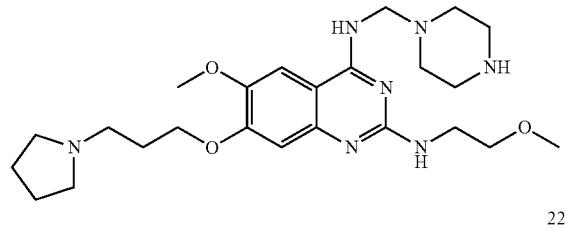
224
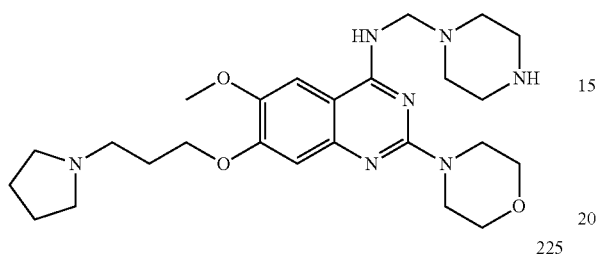
225
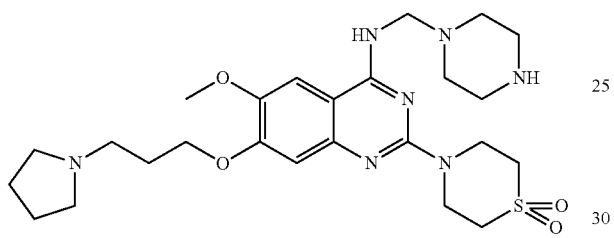
230
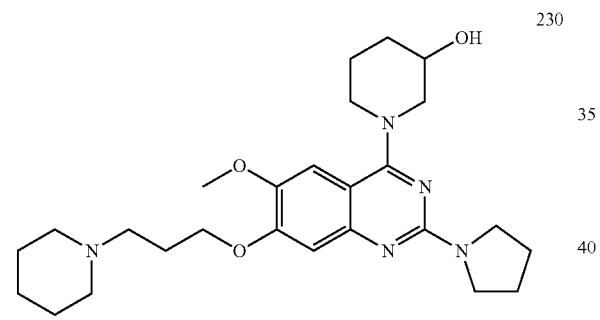
231
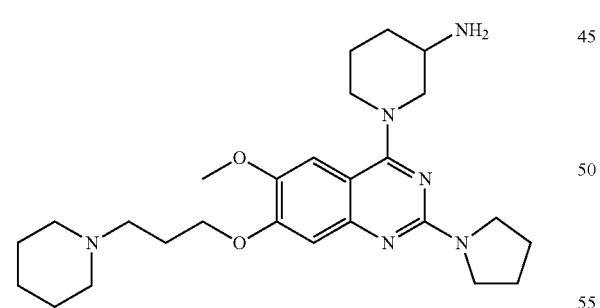
232
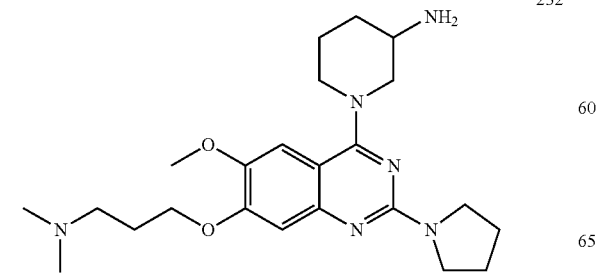
-continued
233
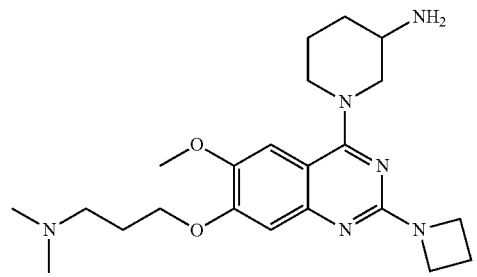
234
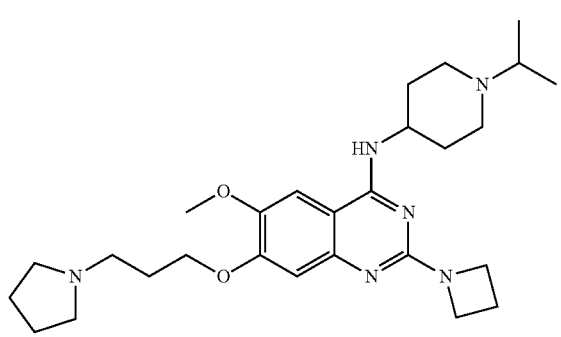
235
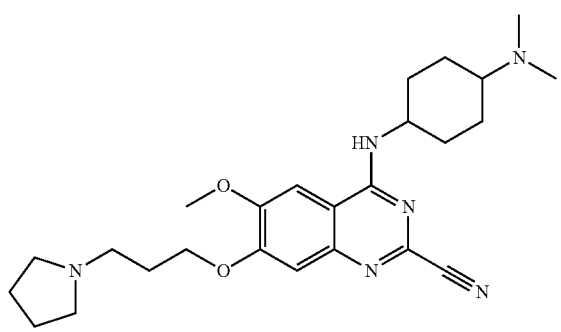
236
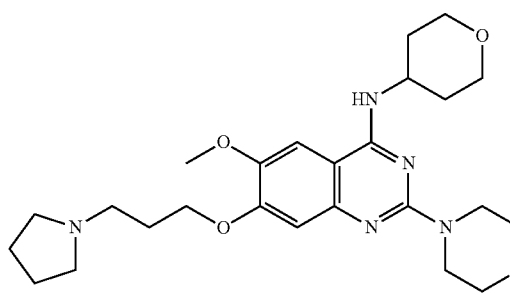
237
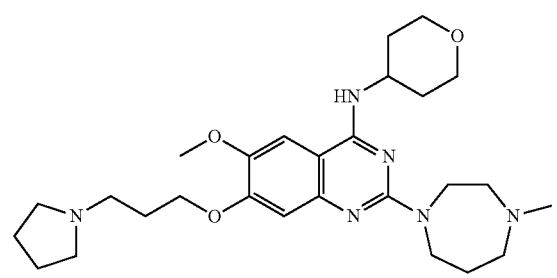

238
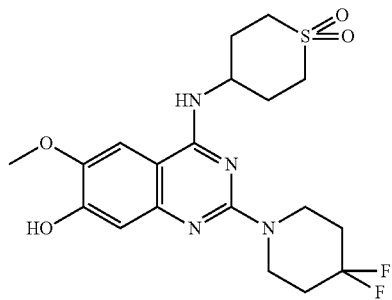
239
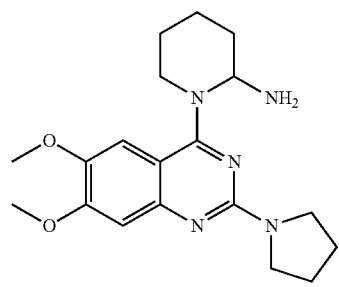
240
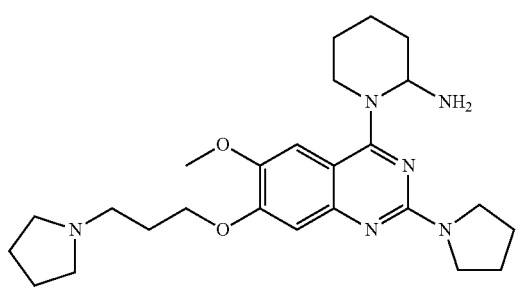
241
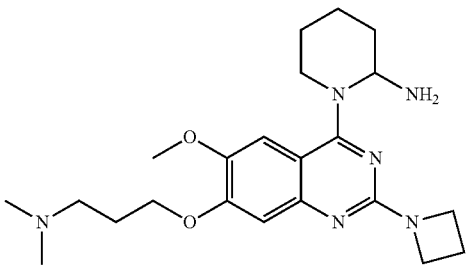
242
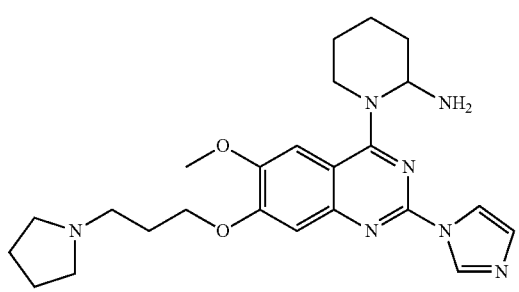
243
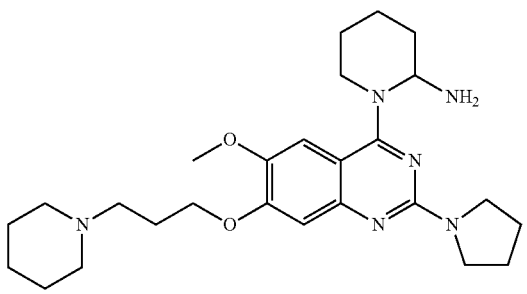
244
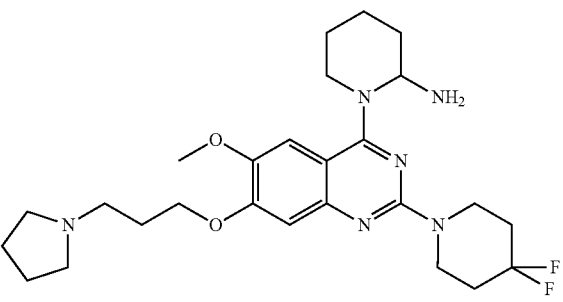
245
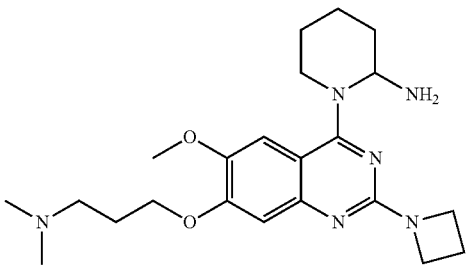
246
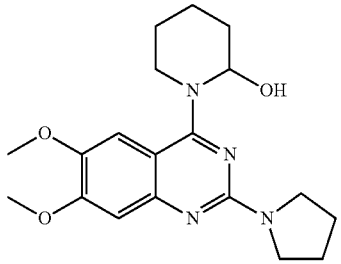
247
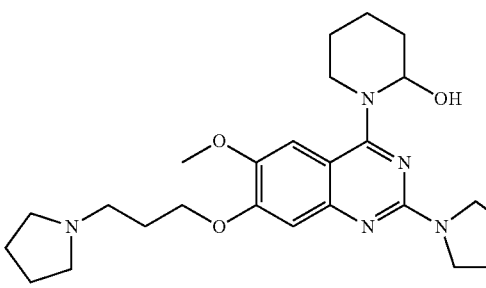

248 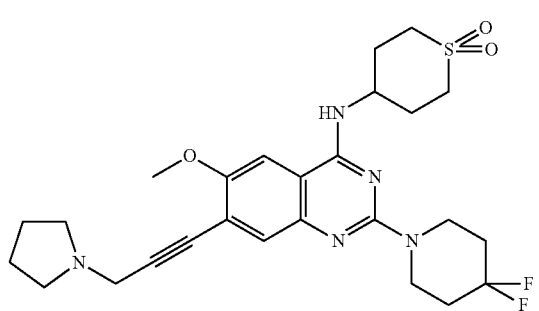
249 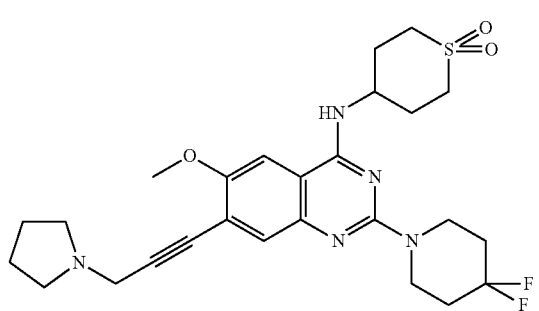
250
251
252
253 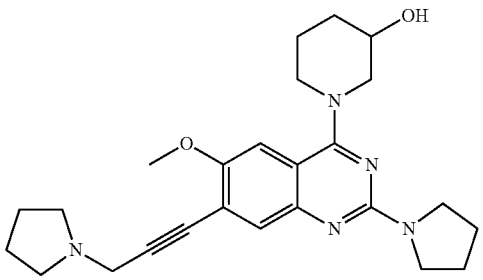
254 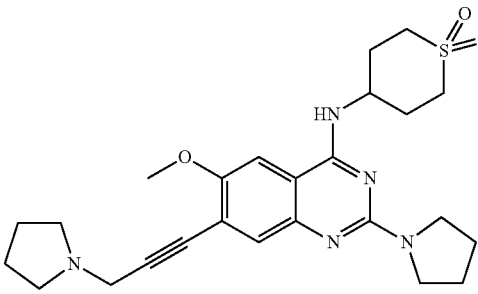
255 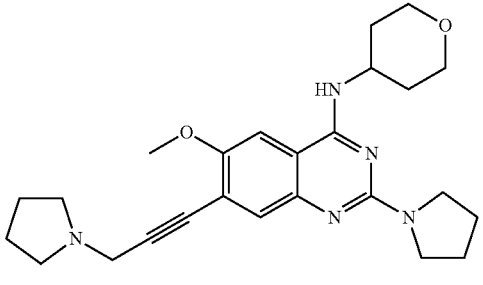
256 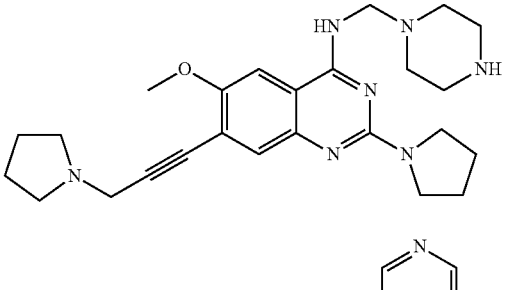
257 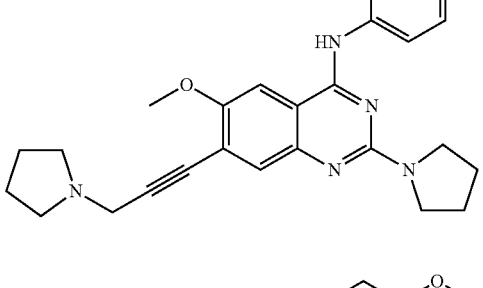
258 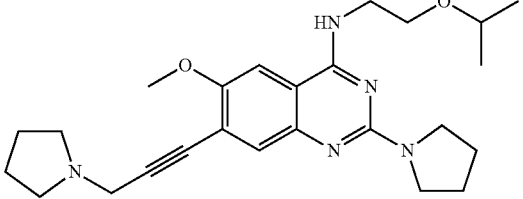

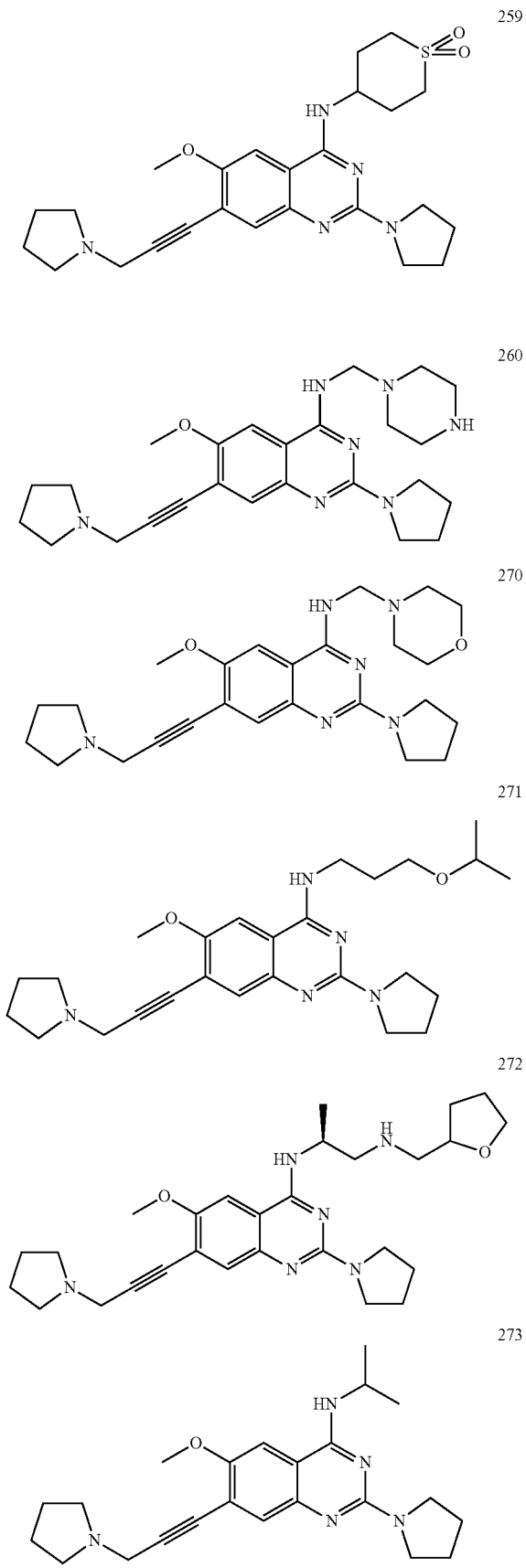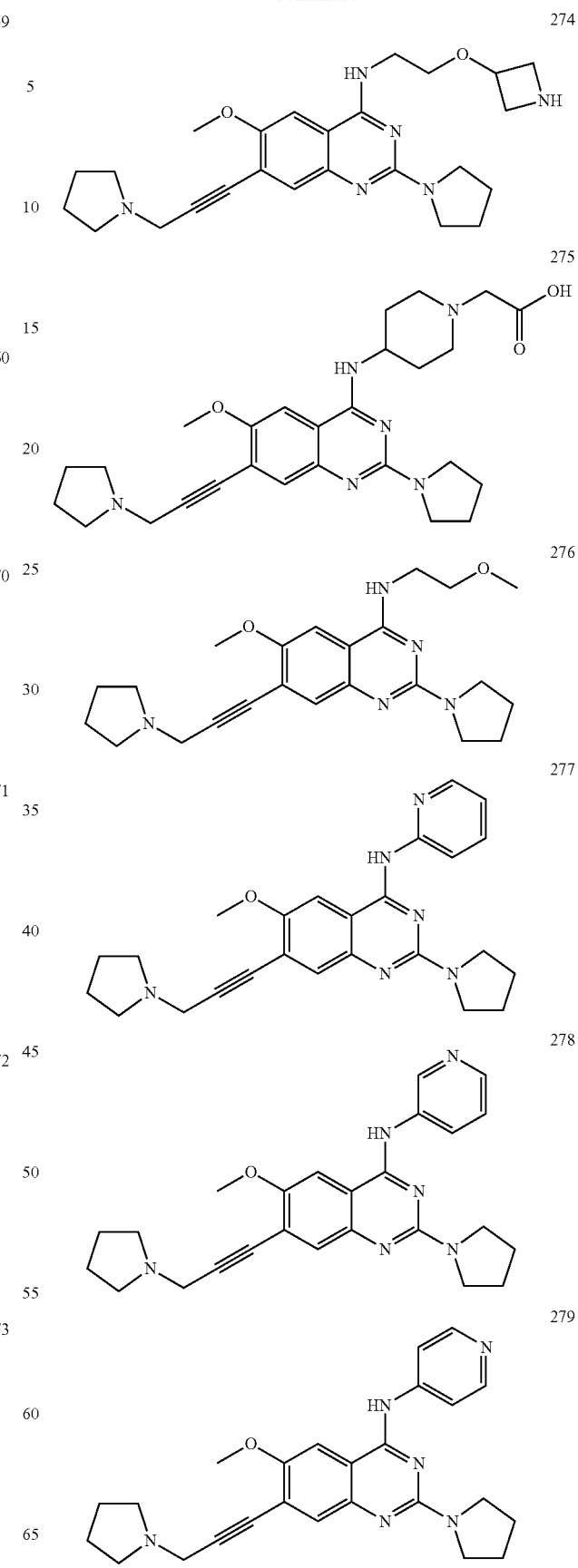

-continued
280
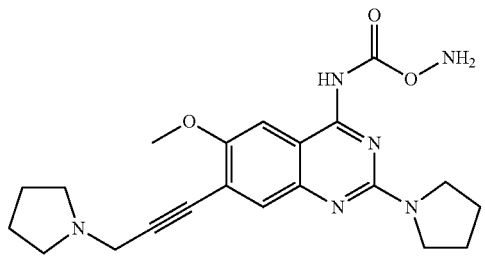
281
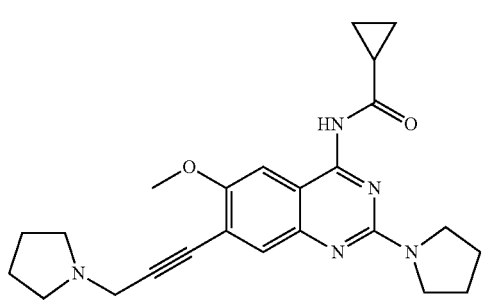
282
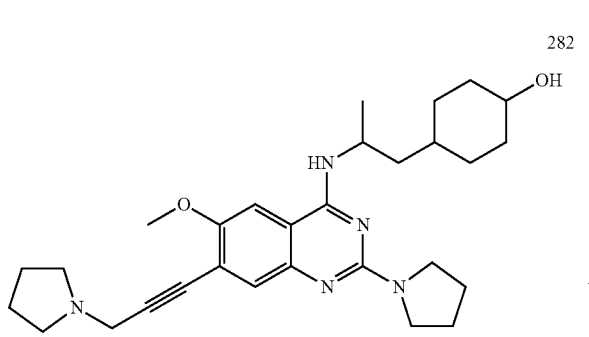
283
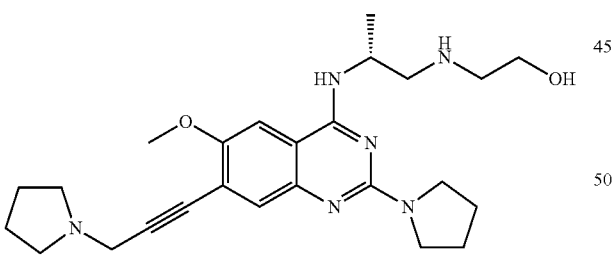
284
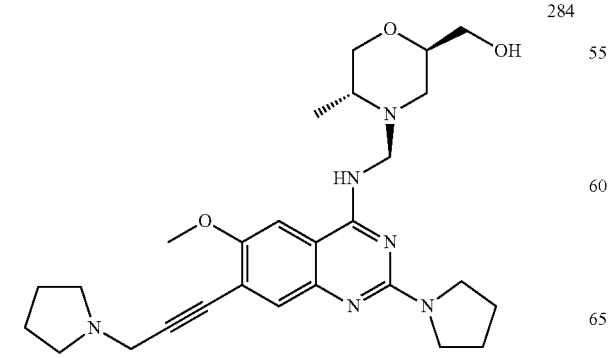
-continued
285
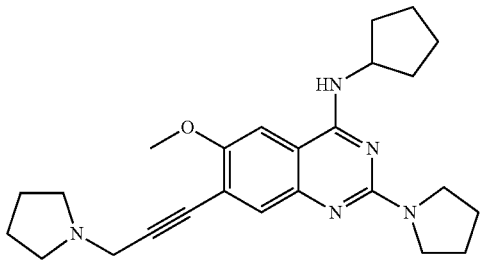
286
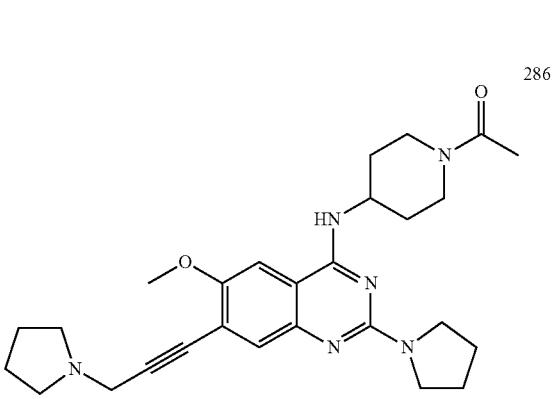
287
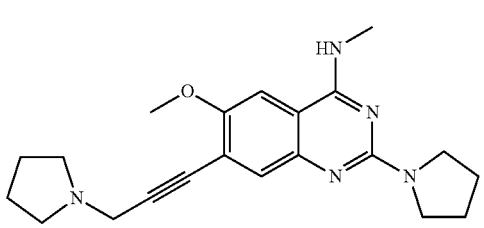
288
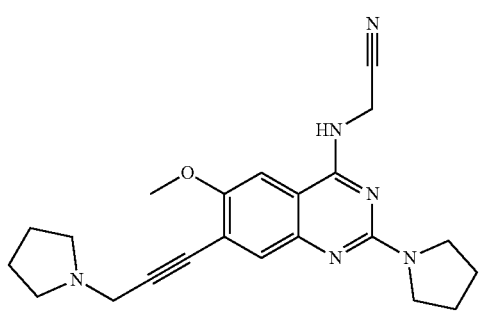
289
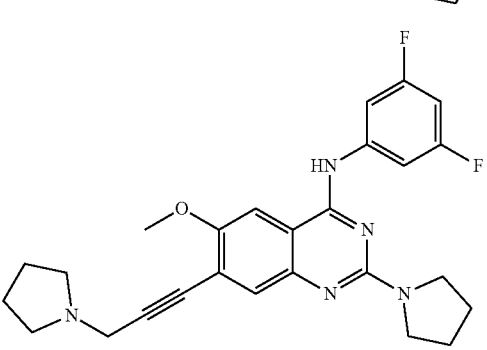

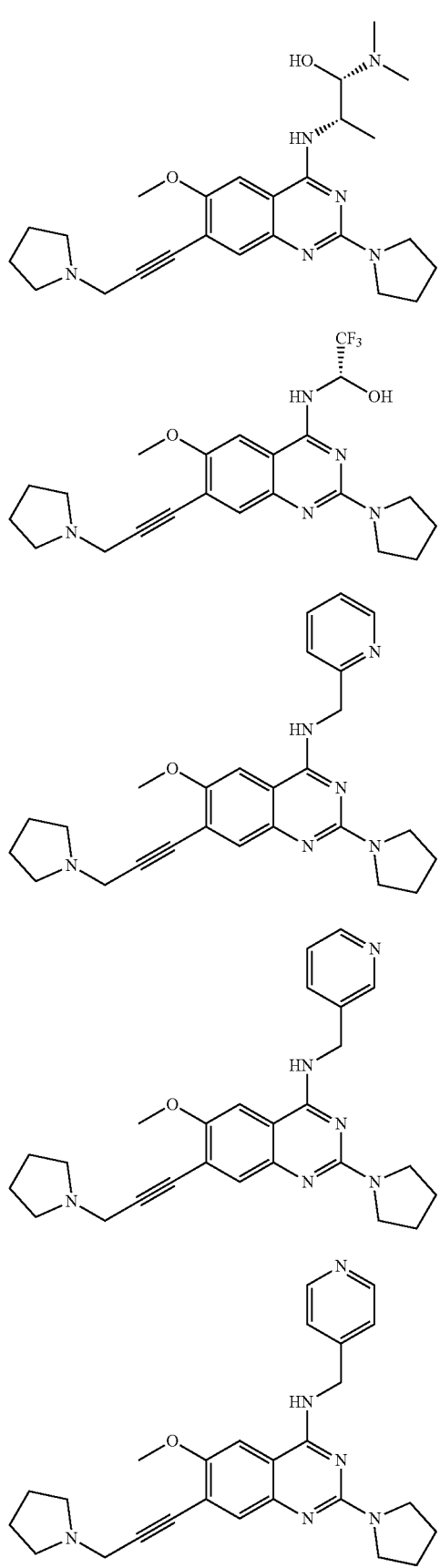
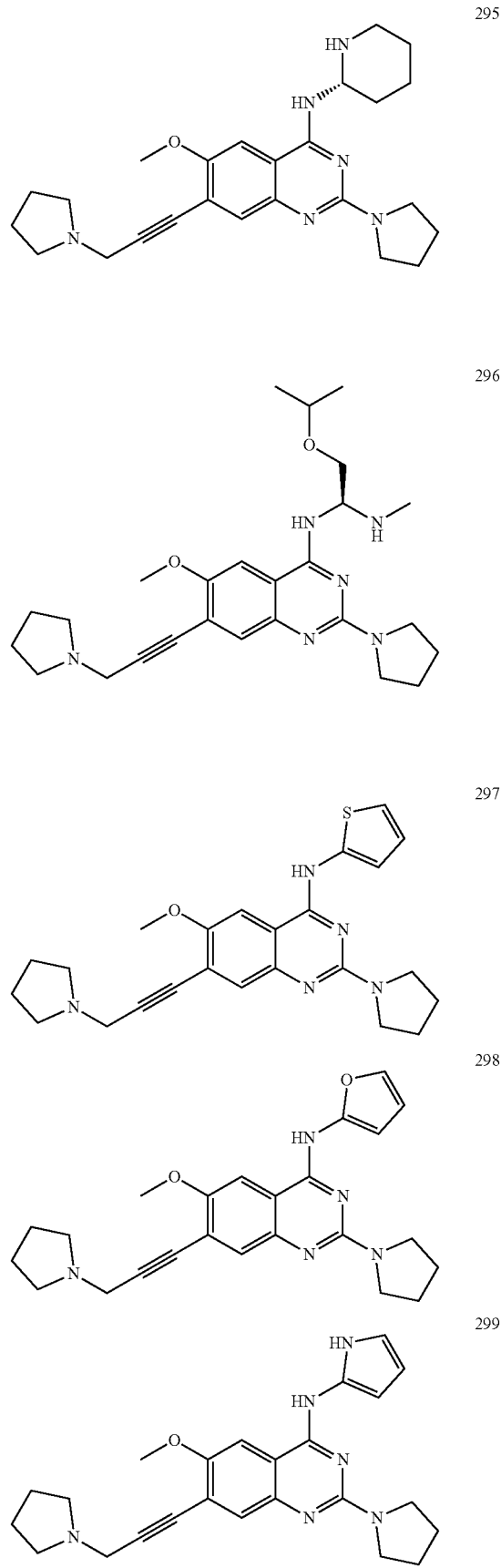

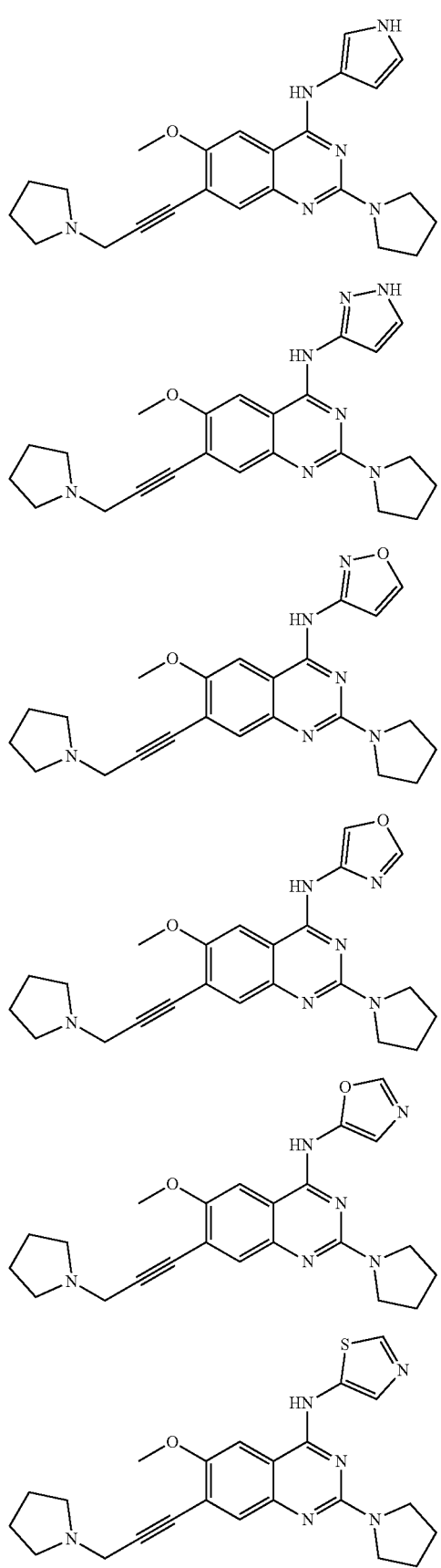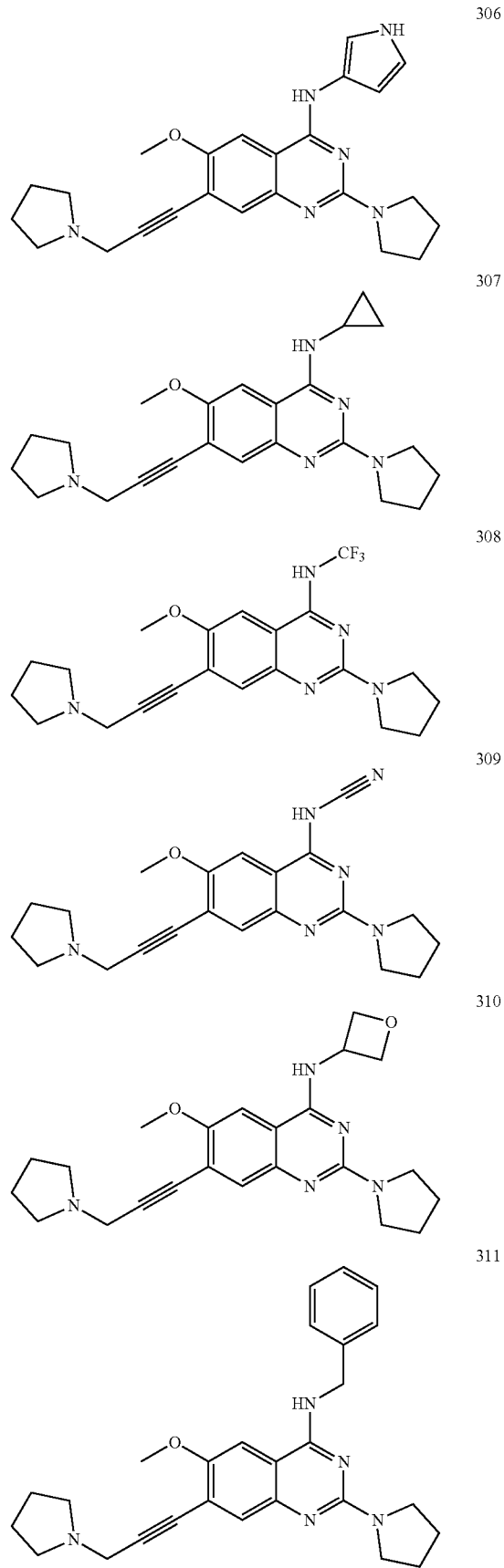

315
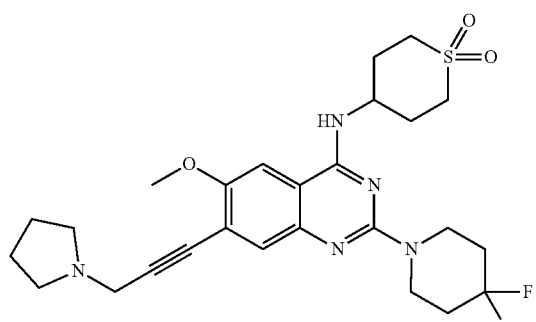
316
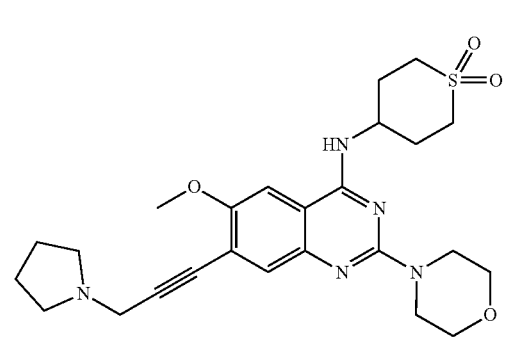
318
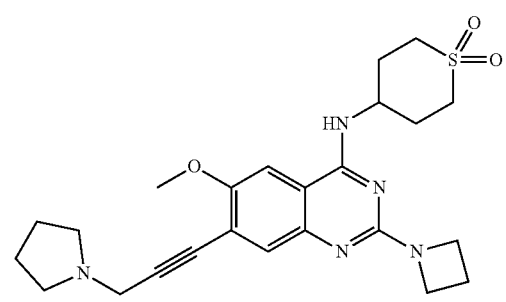
319
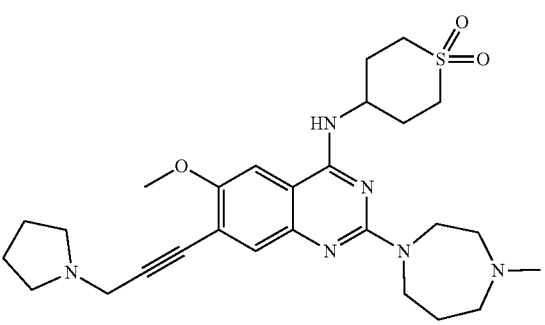
320
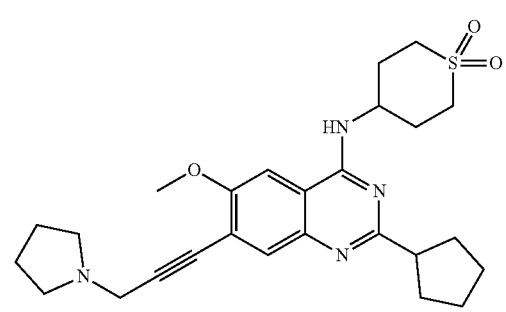
321
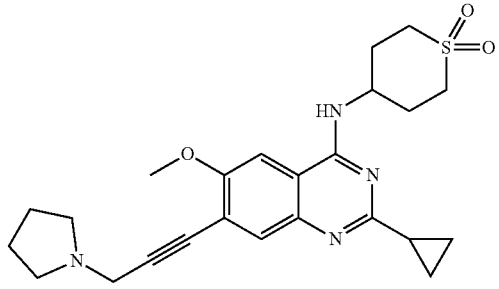
322
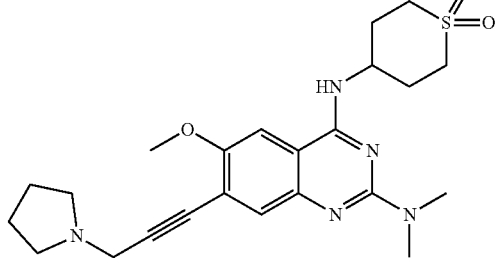
323
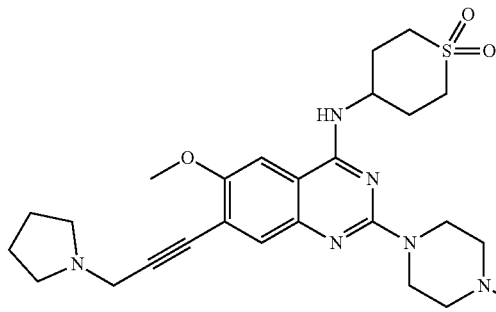
324
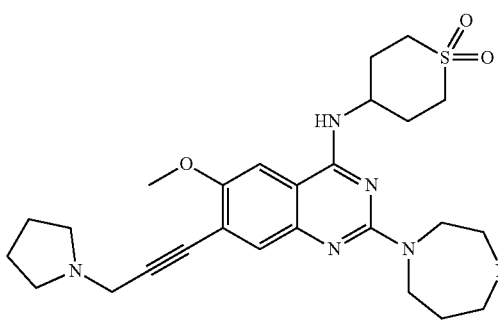
325
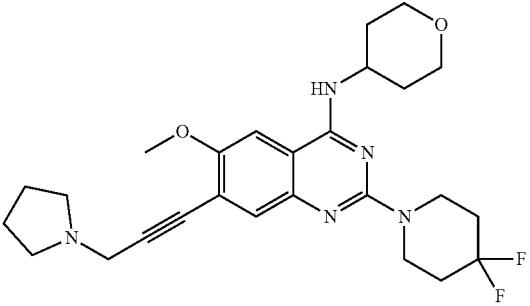

-continued
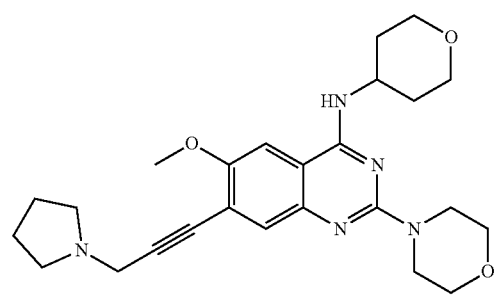
326
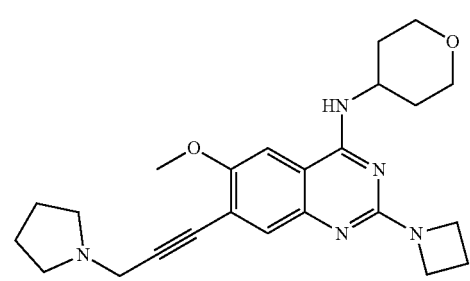
328
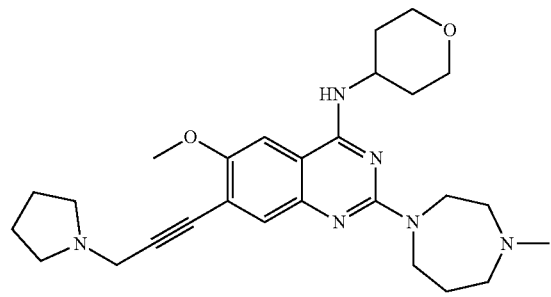
329
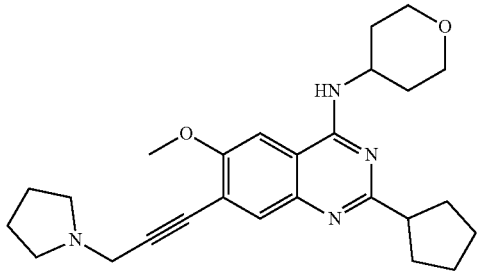
330
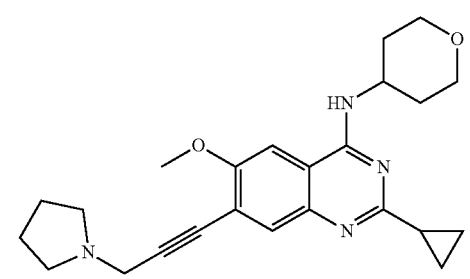
331
-continued
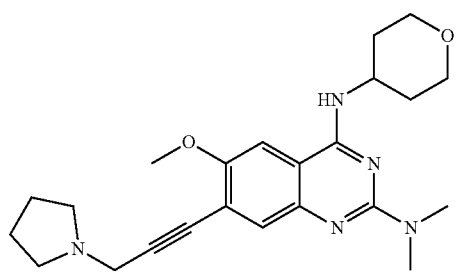
332
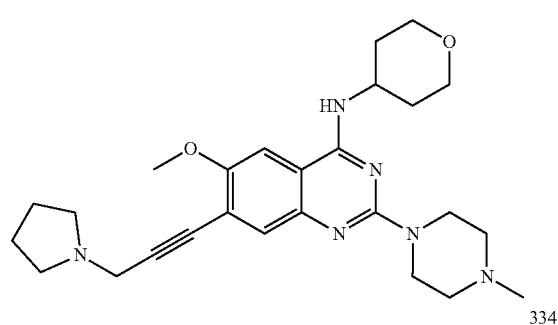
333
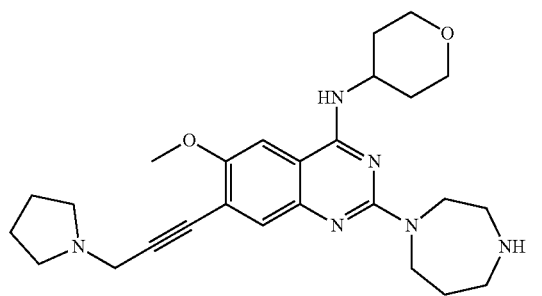
334
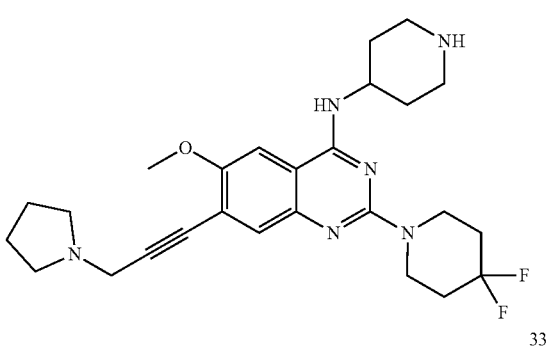
335
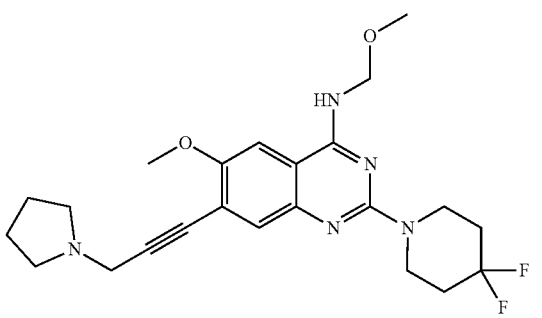
336

337 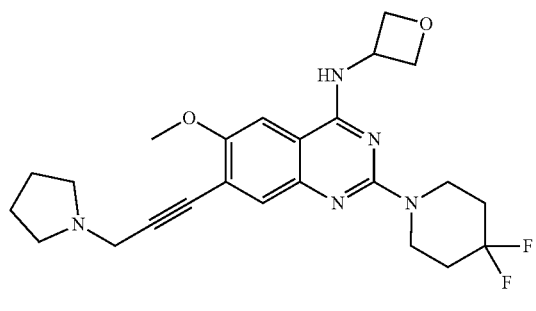
338 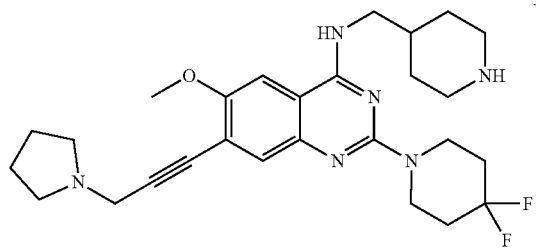
339 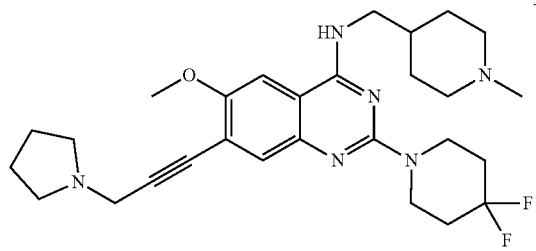
340 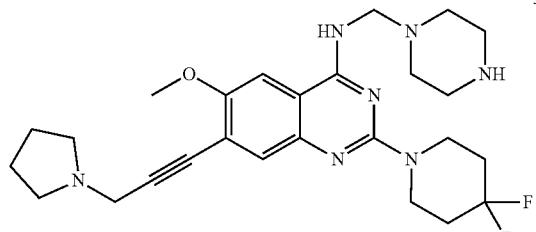
341 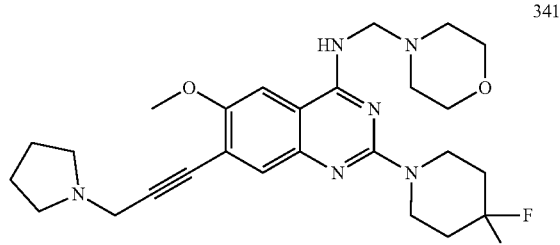
342 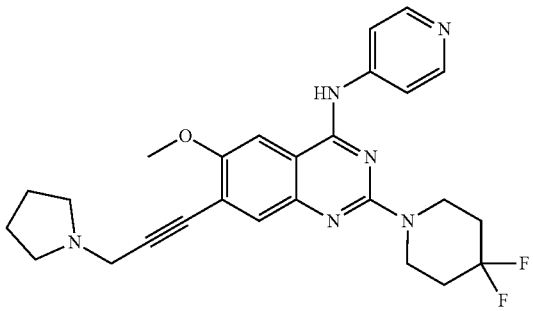
343 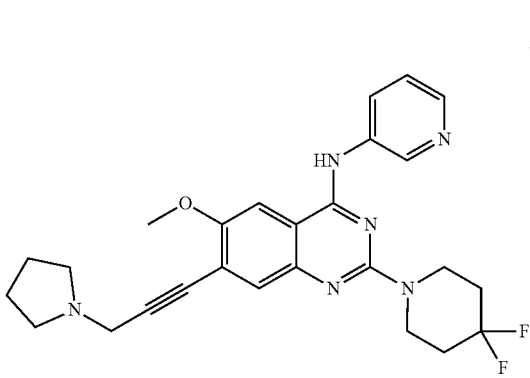
344 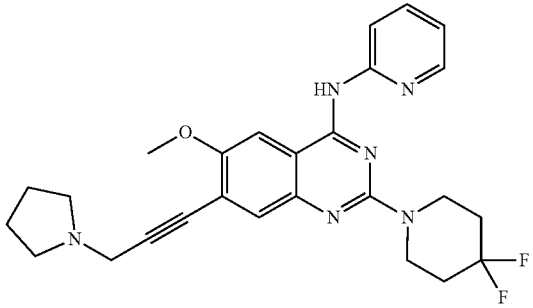
345 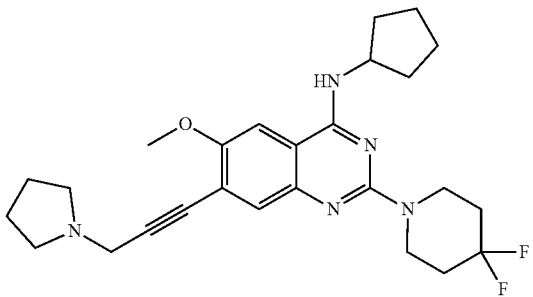

346
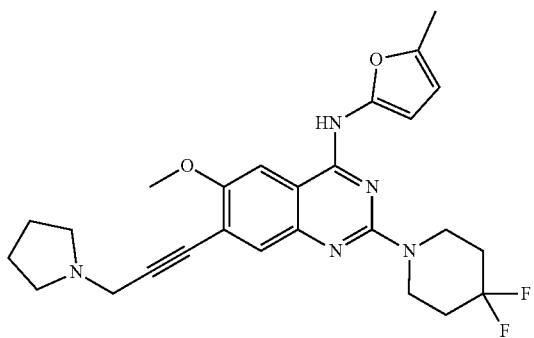
347
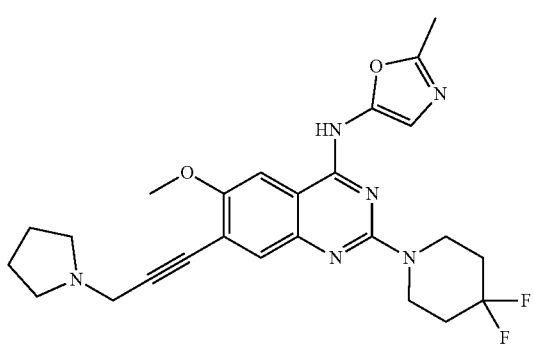
348
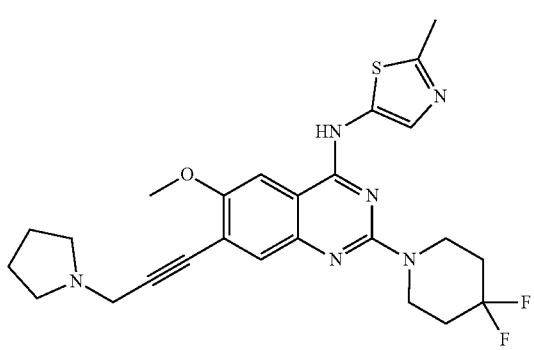
349
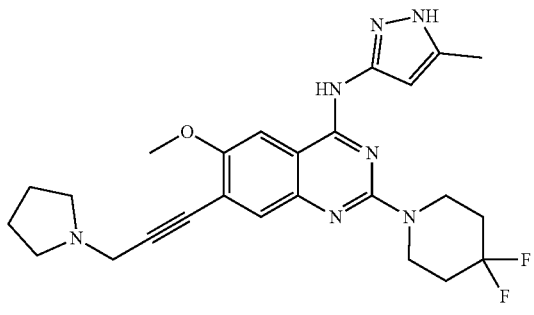
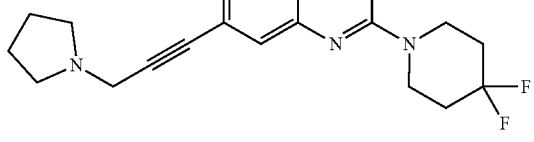
350
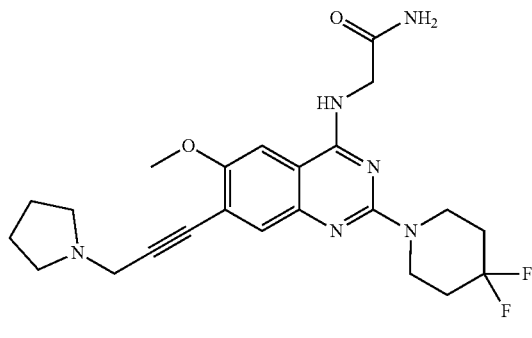
351
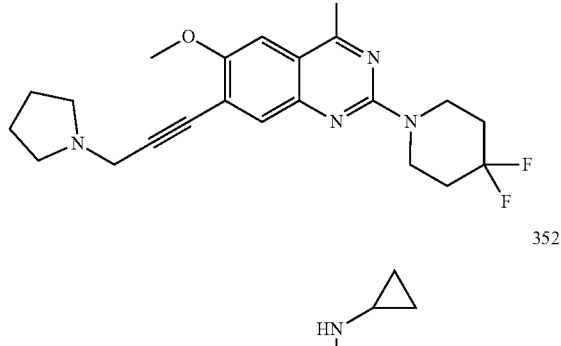
352
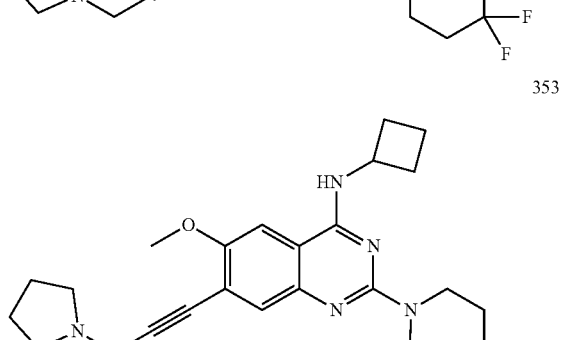
353
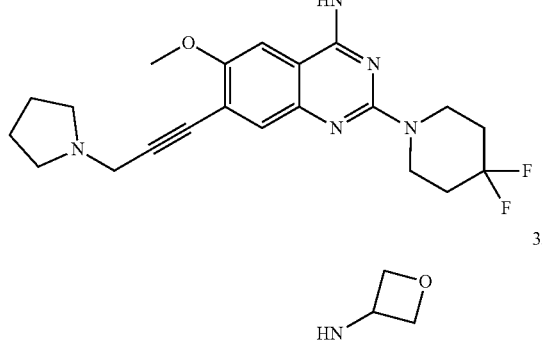
354
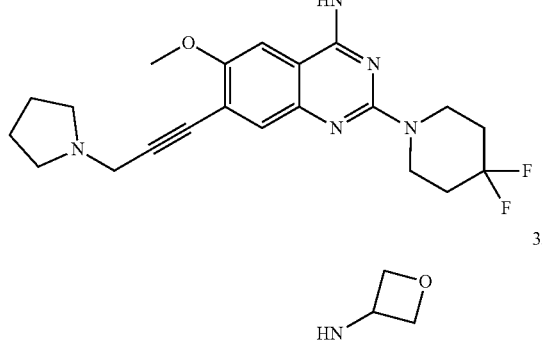

355
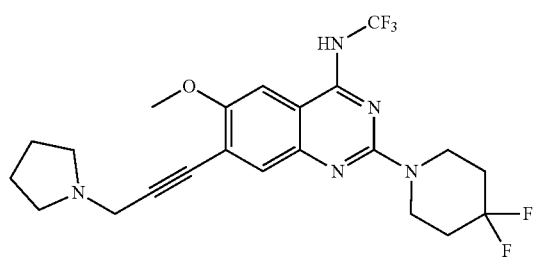
356
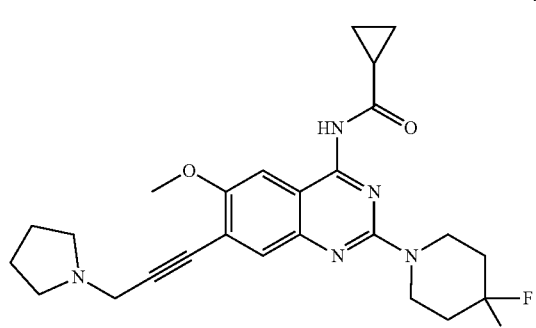
357
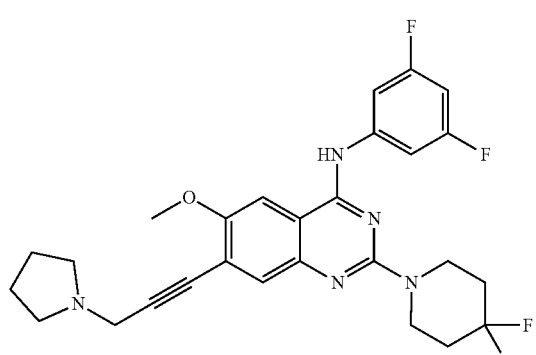
358
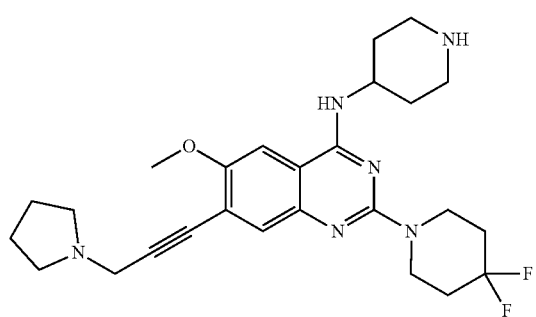
359
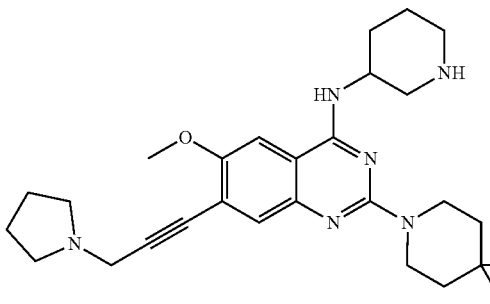
360
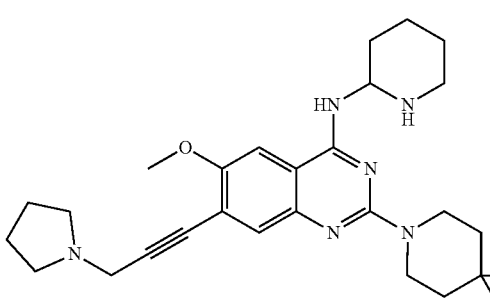
361
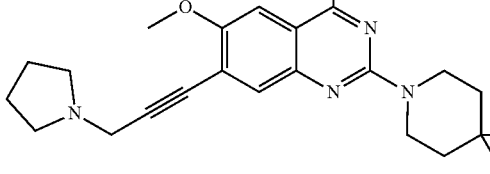
362
363
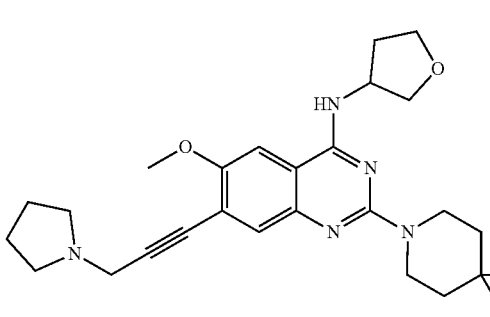

364
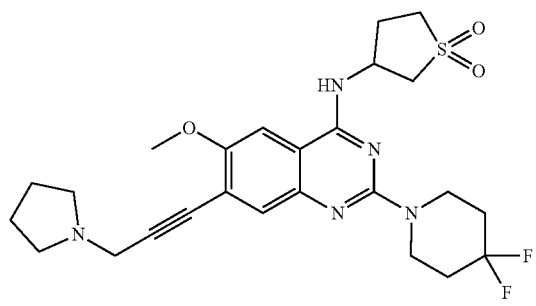
365
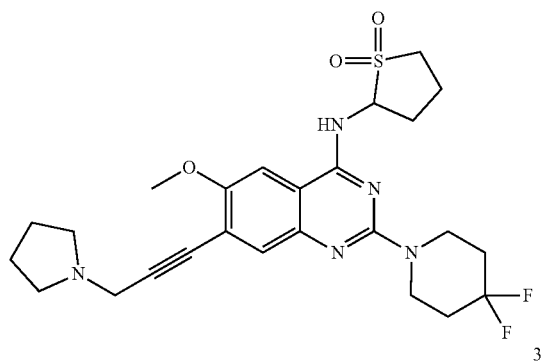
366
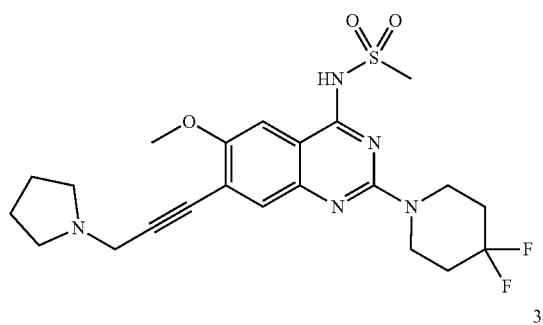
367
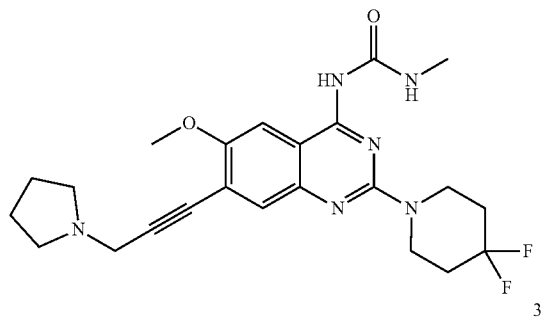
368
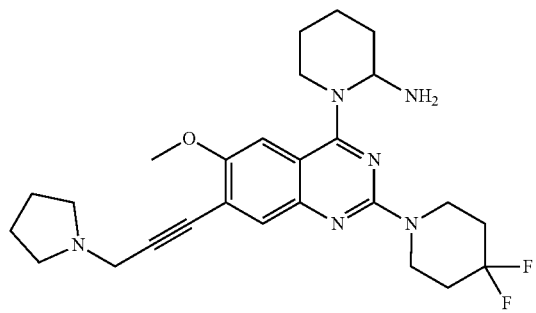
369
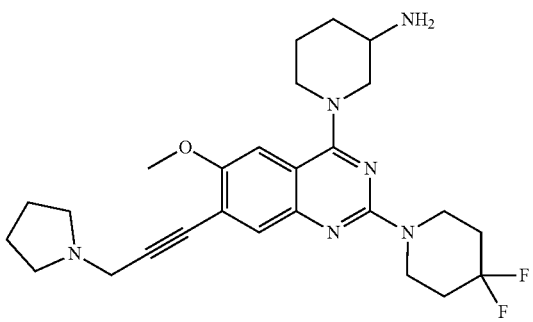
370
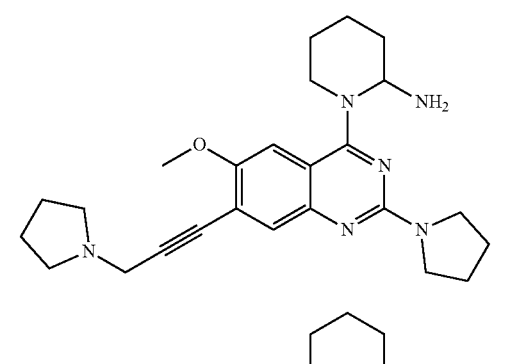
371
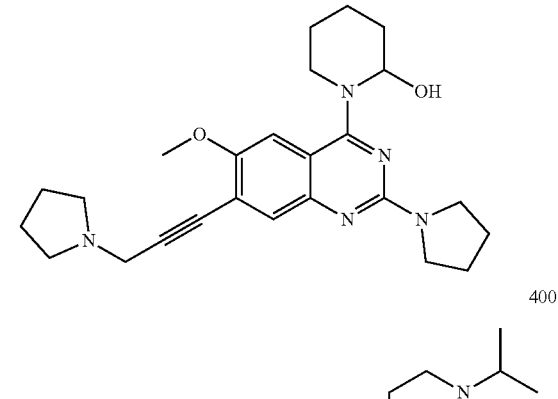
400
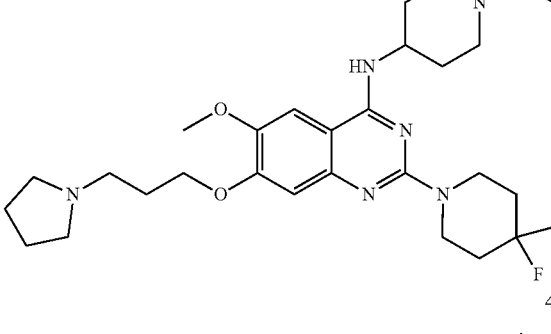
401
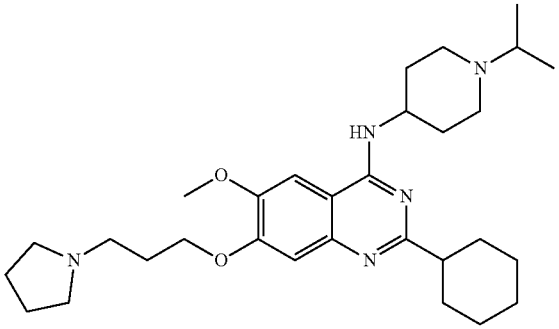

402
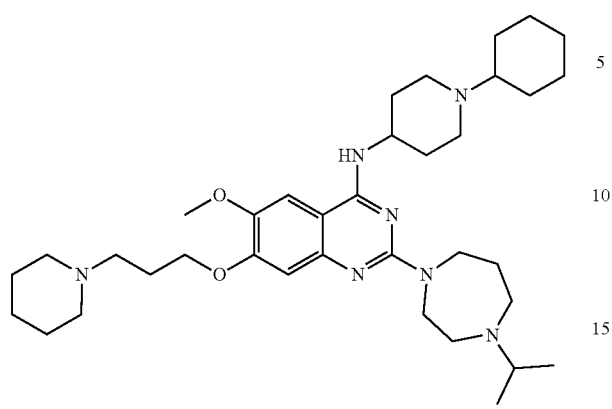
403
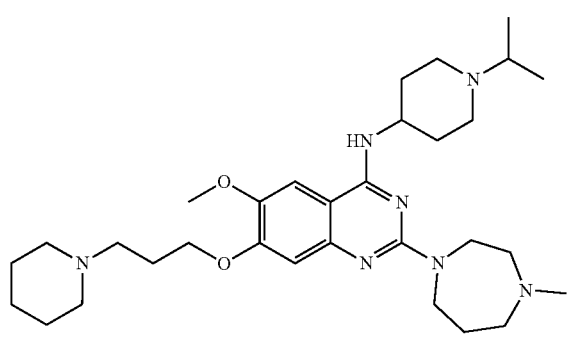
404
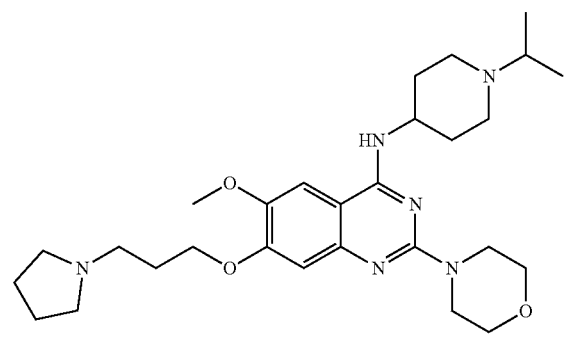
405
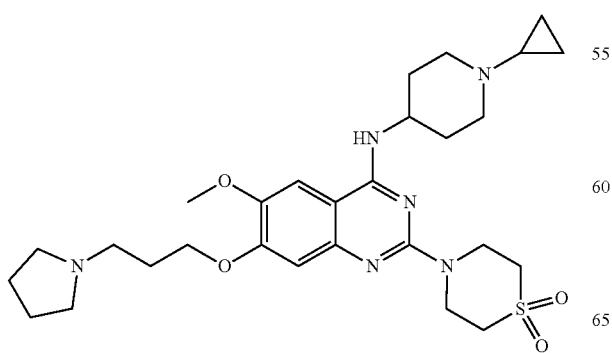
407
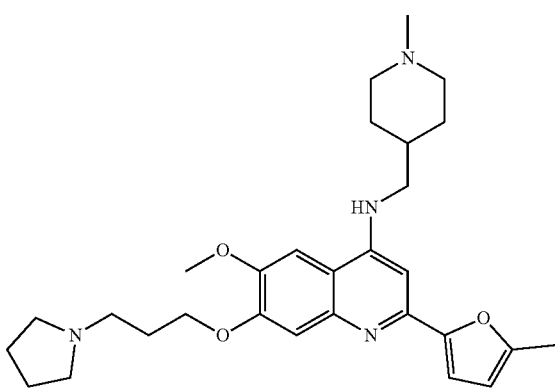
408
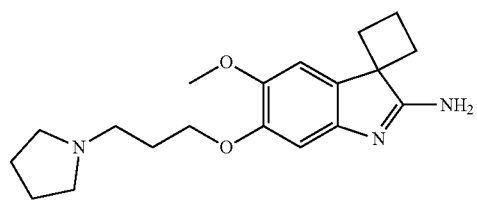
409
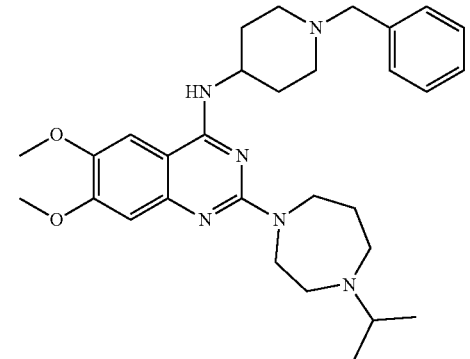
410
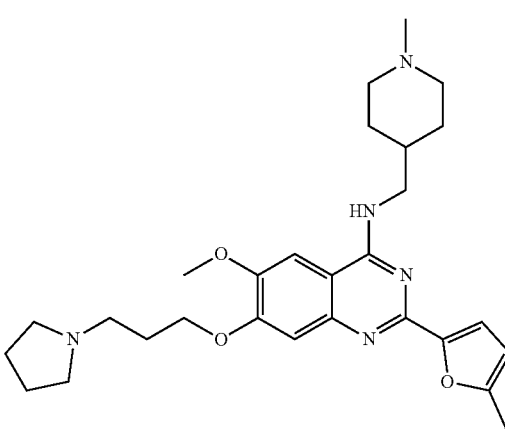

-continued

411
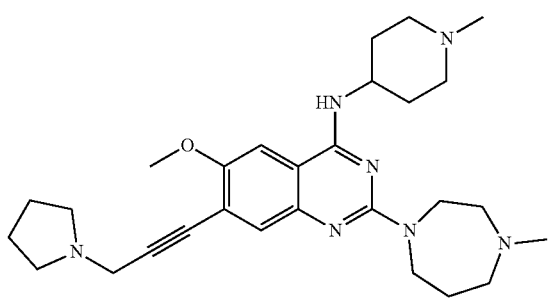

412
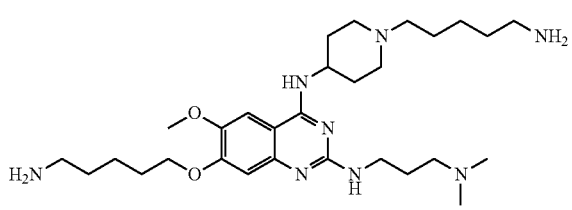

413
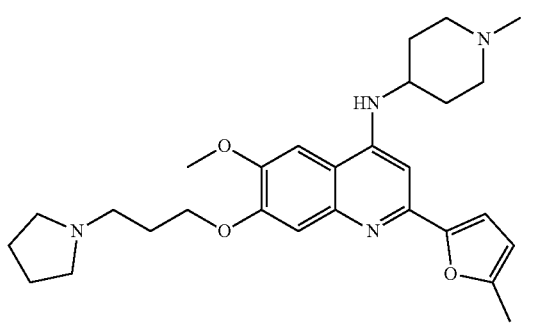

414
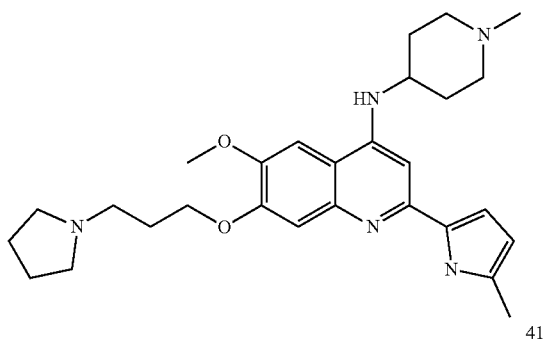

415
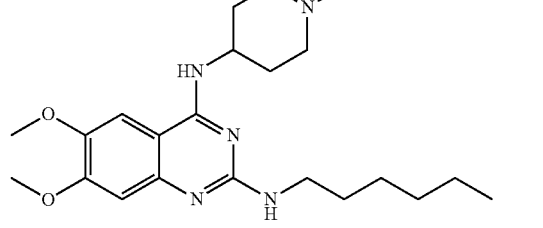

In some embodiments, Formula (I) does not include one or more of structures (e.g., 158, 159, 400, 401, 402, 403, 404, 405, 406, 407, 408, 409, 410, 411, 412, 413, 414, or 415.

In some embodiments, the quinazolinyl compounds having the structure of Formula of Formula (I) is selected from one or more of the following:

4-((2-(4,4-difluoropiperidin-1-yl)-6-methoxy-7-(3-(pyrrolidin-1-yl)propoxy)quinazolin-4-yl)amino)tetrahydro-2H-thiopyran 1,1-dioxide;

2-(4,4-difluoropiperidin-1-yl)-6-methoxy-7-(3-(pyrrolidin-1-yl)propoxy)-N-(tetrahydro-2H-pyran-4-yl)quinazolin-4-amine;

2-(4,4-difluoropiperidin-1-yl)-6-methoxy-N-(1-(2-methoxyethyl)piperidin-4-yl)-7-(3-(pyrrolidin-1-yl)propoxy)quinazolin-4-amine;

2-(4,4-difluoropiperidin-1-yl)-6-methoxy-N-(2-methoxyethyl)-7-(3-(pyrrolidin-1-yl)propoxy)quinazolin-4-amine;

2-(4,4-difluoropiperidin-1-yl)-6-methoxy-N-((1-methylpiperidin-4-yl)methyl)-7-(3-(pyrrolidin-1-yl)propoxy)quinazolin-4-amine;

2-(4-((2-(4,4-difluoropiperidin-1-yl)-6-methoxy-7-(3-(pyrrolidin-1-yl)propoxy)quinazolin-4-yl)amino)piperidin-1-yl)acetic acid;

2-(4,4-difluoropiperidin-1-yl)-6-methoxy-N-(pyridin-4-yl)-7-(3-(pyrrolidin-1-yl)propoxy)quinazolin-4-amine;

2-(4,4-difluoropiperidin-1-yl)-6-methoxy-N-(piperidin-4-yl)-7-(3-(pyrrolidin-1-yl)propoxy)quinazolin-4-amine;

2-((2-(4,4-difluoropiperidin-1-yl)-6-methoxy-7-(3-(pyrrolidin-1-yl)propoxy)quinazolin-4-yl)amino)acetamide;

4-((2-(4,4-difluoropiperidin-1-yl)-6-methoxy-7-(3-(pyrrolidin-1-yl)propoxy)quinazolin-4-yl)amino)tetrahydro-2H-thiopyran 1,1-dioxide;

2-(4,4-difluoropiperidin-1-yl)-6-methoxy-N-(oxetan-3-yl)-7-(3-(pyrrolidin-1-yl)propoxy)quinazolin-4-amine;

(R)-2-(4,4-difluoropiperidin-1-yl)-6-methoxy-7-(3-(pyrrolidin-1-yl)propoxy)-N-(tetrahydro-2H-pyran-3-yl)quinazolin-4-amine;

(S)-2-(4,4-difluoropiperidin-1-yl)-6-methoxy-7-(3-(pyrrolidin-1-yl)propoxy)-N-(tetrahydro-2H-pyran-3-yl)quinazolin-4-amine;

2-(4,4-difluoropiperidin-1-yl)-6-methoxy-7-(3-(pyrrolidin-1-yl)propoxy)-N-(tetrahydro-2H-pyran-3-yl)quinazolin-4-amine;

3-((2-(4,4-difluoropiperidin-1-yl)-6-methoxy-7-(3-(pyrrolidin-1-yl)propoxy)quinazolin-4-yl)amino)tetrahydro-2H-thiopyran 1,1-dioxide;

(2S)—N2-(2-(4,4-difluoropiperidin-1-yl)-6-methoxy-7-(3-(pyrrolidin-1-yl)propoxy)quinazolin-4-yl)-N1-((tetrahydrofuran-2-yl)methyl)propane-1,2-diamine;

2-(4,4-difluoropiperidin-1-yl)-6-methoxy-N-(morpholinomethyl)-7-(3-(pyrrolidin-1-yl)propoxy)quinazolin-4-amine;

2-(4,4-difluoropiperidin-1-yl)-6-methoxy-N-(morpholinomethyl)-7-(3-(pyrrolidin-1-yl)propoxy)quinazolin-4-amine;

1-(4-((2-(4,4-difluoropiperidin-1-yl)-6-methoxy-7-(3-(pyrrolidin-1-yl)propoxy)quinazolin-4-yl)amino)piperidin-1-yl)ethan-1-one;

2-(4,4-difluoropiperidin-1-yl)-N-isopropyl-6-methoxy-7-(3-(pyrrolidin-1-yl)propoxy)quinazolin-4-amine;

2-(4,4-difluoropiperidin-1-yl)-N-(3-isopropoxypropyl)-6-methoxy-7-(3-(pyrrolidin-1-yl)propoxy)quinazolin-4-amine;

N-(2-(4,4-difluoropiperidin-1-yl)-6-methoxy-7-(3-(pyrrolidin-1-yl)propoxy)quinazolin-4-yl)methanesulfonamide;

N-((aminooxy)carbonyl)-2-(4,4-difluoropiperidin-1-yl)-6-methoxy-7-(3-(pyrrolidin-1-yl)propoxy)quinazolin-4-amine;

N-cyclopentyl-2-(4,4-difluoropiperidin-1-yl)-6-methoxy-7-(3-(pyrrolidin-1-yl)propoxy)quinazolin-4-amine;

(2R,4r,6S)—N-(2-(4,4-difluoropiperidin-1-yl)-6-methoxy-7-(3-(pyrrolidin-1-yl)propoxy)quinazolin-4-yl)-N',N',2,6-tetramethyltetrahydro-4H-pyran-4,4-diamine;

2-(4,4-difluoropiperidin-1-yl)-6-methoxy-N-(piperazin-1-ylmethyl)-7-(3-(pyrrolidin-1-yl)propoxy)quinazolin-4-amine;

(R)-2-((2-((2-(4,4-difluoropiperidin-1-yl)-6-methoxy-7-(3-(pyrrolidin-1-yl)propoxy)quinazolin-4-yl)amino)propyl)amino)ethan-1-ol;

((2R,5R)-4-(((2-(4,4-difluoropiperidin-1-yl)-6-methoxy-7-(3-(pyrrolidin-1-yl)propoxy)quinazolin-4-yl)amino)methyl)-5-methylmorpholin-2-yl)methanol;

4-(2-((2-(4,4-difluoropiperidin-1-yl)-6-methoxy-7-(3-(pyrrolidin-1-yl)propoxy)quinazolin-4-yl)amino)propyl)cyclohexan-1-ol;

N-benzyl-2-(4,4-difluoropiperidin-1-yl)-6-methoxy-7-(3-(pyrrolidin-1-yl)propoxy)quinazolin-4-amine;

2-(4,4-difluoropiperidin-1-yl)-6-methoxy-N-phenyl-7-(3-(pyrrolidin-1-yl)propoxy)quinazolin-4-amine;

2-(4,4-difluoropiperidin-1-yl)-6-methoxy-N-(pyridin-4-yl)-7-(3-(pyrrolidin-1-yl)propoxy)quinazolin-4-amine;

2-(4,4-difluoropiperidin-1-yl)-6-methoxy-N-(pyridin-3-yl)-7-(3-(pyrrolidin-1-yl)propoxy)quinazolin-4-amine;

2-(4,4-difluoropiperidin-1-yl)-6-methoxy-N-(pyridin-2-yl)-7-(3-(pyrrolidin-1-yl)propoxy)quinazolin-4-amine;

2-(4,4-difluoropiperidin-1-yl)-N-(6,7-dihydro-5H-cyclopenta[d]pyrimidin-4-yl)-6-methoxy-7-(3-(pyrrolidin-1-yl)propoxy)quinazolin-4-amine;

(S)-1-((2-(4,4-difluoropiperidin-1-yl)-6-methoxy-7-(3-(pyrrolidin-1-yl)propoxy)quinazolin-4-yl)amino)-2,2,2-trifluoroethan-1-ol;

1-((2-(4,4-difluoropiperidin-1-yl)-6-methoxy-7-(3-(pyrrolidin-1-yl)propoxy)quinazolin-4-yl)amino)ethan-1-ol;

(1S,2S)-2-((2-(4,4-difluoropiperidin-1-yl)-6-methoxy-7-(3-(pyrrolidin-1-yl)propoxy)quinazolin-4-yl)amino)-1-(dimethylamino)butan-1-ol;

(R)—N-(cyclopent-2-en-1-yl)-2-(4,4-difluoropiperidin-1-yl)-6-methoxy-7-(3-(pyrrolidin-1-yl)propoxy)quinazolin-4-amine;

2-(4,4-difluoropiperidin-1-yl)-6-methoxy-7-(3-(pyrrolidin-1-yl)propoxy)-N-(trifluoromethyl)quinazolin-4-amine;

2-(4,4-difluoropiperidin-1-yl)-6-methoxy-N-(pyridin-4-ylmethyl)-7-(3-(pyrrolidin-1-yl)propoxy)quinazolin-4-amine;

2-(4,4-difluoropiperidin-1-yl)-6-methoxy-N-(pyridin-3-ylmethyl)-7-(3-(pyrrolidin-1-yl)propoxy)quinazolin-4-amine;

2-(4,4-difluoropiperidin-1-yl)-6-methoxy-N-(pyridin-2-ylmethyl)-7-(3-(pyrrolidin-1-yl)propoxy)quinazolin-4-amine;

(1S,2R)-1-((2-(4,4-difluoropiperidin-1-yl)-6-methoxy-7-(3-(pyrrolidin-1-yl)propoxy)quinazolin-4-yl)amino)-1-(dimethylamino)propan-2-ol;

N-(3,5-difluorophenyl)-2-(4,4-difluoropiperidin-1-yl)-6-methoxy-7-(3-(pyrrolidin-1-yl)propoxy)quinazolin-4-amine;

N-(2,4-difluorophenyl)-2-(4,4-difluoropiperidin-1-yl)-6-methoxy-7-(3-(pyrrolidin-1-yl)propoxy)quinazolin-4-amine;

(S)-2-(4,4-difluoropiperidin-1-yl)-6-methoxy-N-(piperidin-2-yl)-7-(3-(pyrrolidin-1-yl)propoxy)quinazolin-4-amine;

(S)—N-(2-(4,4-difluoropiperidin-1-yl)-6-methoxy-7-(3-(pyrrolidin-1-yl)propoxy)quinazolin-4-yl)-2-isopropoxy-N'-methylethane-1,1-diamine;

2-((2-(4,4-difluoropiperidin-1-yl)-6-methoxy-7-(3-(pyrrolidin-1-yl)propoxy)quinazolin-4-yl)amino)acetonitrile;

2-(4,4-difluoropiperidin-1-yl)-6-methoxy-7-(3-(pyrrolidin-1-yl)propoxy)-N-(thiophen-2-yl)quinazolin-4-amine;

2-(4,4-difluoropiperidin-1-yl)-N-(furan-2-yl)-6-methoxy-7-(3-(pyrrolidin-1-yl)propoxy)quinazolin-4-amine;

2-(4,4-difluoropiperidin-1-yl)-6-methoxy-N-(1H-pyrrol-2-yl)-7-(3-(pyrrolidin-1-yl)propoxy)quinazolin-4-amine;

2-(4,4-difluoropiperidin-1-yl)-6-methoxy-N-(1H-pyrrol-3-yl)-7-(3-(pyrrolidin-1-yl)propoxy)quinazolin-4-amine;

2-(4,4-difluoropiperidin-1-yl)-6-methoxy-N-(1H-pyrazol-3-yl)-7-(3-(pyrrolidin-1-yl)propoxy)quinazolin-4-amine;

N-(2-(4,4-difluoropiperidin-1-yl)-6-methoxy-7-(3-(pyrrolidin-1-yl)propoxy)quinazolin-4-yl)isoxazol-3-amine;

N-cyclopropyl-2-(4,4-difluoropiperidin-1-yl)-6-methoxy-7-(3-(pyrrolidin-1-yl)propoxy)quinazolin-4-amine;

N-(2-(4,4-difluoropiperidin-1-yl)-6-methoxy-7-(3-(pyrrolidin-1-yl)propoxy)quinazolin-4-yl)cyanamide;

N-(2-(4,4-difluoropiperidin-1-yl)-6-methoxy-7-(3-(pyrrolidin-1-yl)propoxy)quinazolin-4-yl)methanediamine;

(2-(4,4-difluoropiperidin-1-yl)-6-methoxy-7-(3-(pyrrolidin-1-yl)propoxy)quinazolin-4-yl)carbamic acid;

methyl (2-(4,4-difluoropiperidin-1-yl)-6-methoxy-7-(3-(pyrrolidin-1-yl)propoxy)quinazolin-4-yl)carbamate;

((2-(4,4-difluoropiperidin-1-yl)-6-methoxy-7-(3-(pyrrolidin-1-yl)propoxy)quinazolin-4-yl)amino)methanol;

((2-(4,4-difluoropiperidin-1-yl)-6-methoxy-7-(3-(pyrrolidin-1-yl)propoxy)quinazolin-4-yl)amino)methyl acetate;

2-(4,4-difluoropiperidin-1-yl)-6-methoxy-N-(((3-methylazetidin-3-yl)oxy)methyl)-7-(3-(pyrrolidin-1-yl)propoxy)quinazolin-4-amine;

(R)-2-(cyclopropylamino)-2-((2-(4,4-difluoropiperidin-1-yl)-6-methoxy-7-(3-(pyrrolidin-1-yl)propoxy)quinazolin-4-yl)amino)propan-1-ol;

(R)-2-((2-(4,4-difluoropiperidin-1-yl)-6-methoxy-7-(3-(pyrrolidin-1-yl)propoxy)quinazolin-4-yl)amino)-3-methylbutan-2-ol;

2-(4,4-difluoropiperidin-1-yl)-6-methoxy-7-(3-(pyrrolidin-1-yl)propoxy)-N—((S)-1-(((R)-1,1,1-trifluoropropan-2-yl)oxy)ethyl)quinazolin-4-amine;

2-(4,4-difluoropiperidin-1-yl)-N-isobutyl-6-methoxy-7-(3-(pyrrolidin-1-yl)propoxy)quinazolin-4-amine;

(R)-2-(4,4-difluoropiperidin-1-yl)-6-methoxy-N-(2-(4-methoxypiperidin-1-yl)propyl)-7-(3-(pyrrolidin-1-yl)propoxy)quinazolin-4-amine;

(S)-1-cyclobutyl-N-(2-(4,4-difluoropiperidin-1-yl)-6-methoxy-7-(3-(pyrrolidin-1-yl)propoxy)quinazolin-4-yl)-N',N'-dimethylmethanediamine;

(R)-1-cyclopropyl-N-(2-(4,4-difluoropiperidin-1-yl)-6-methoxy-7-(3-(pyrrolidin-1-yl)propoxy)quinazolin-4-yl)methanediamine;

2-(4,4-difluoropiperidin-1-yl)-N-((isopropylthio)methyl)-6-methoxy-7-(3-(pyrrolidin-1-yl)propoxy)quinazolin-4-amine;

(R)—N-((2,2-difluoro-1-methylcyclopropyl)methyl)-2-(4,4-difluoropiperidin-1-yl)-6-methoxy-7-(3-(pyrrolidin-1-yl)propoxy)quinazolin-4-amine;

2-(4,4-difluoropiperidin-1-yl)-N-(1H-indol-3-yl)-6-methoxy-7-(3-(pyrrolidin-1-yl)propoxy)quinazolin-4-amine;

(3S,4R)-4-(((R)-1-((2-(4,4-difluoropiperidin-1-yl)-6-methoxy-7-(3-(pyrrolidin-1-yl)propoxy)quinazolin-4-yl)amino)ethyl)amino)tetrahydrofuran-3-ol;

(R)-2-(4,4-difluoropiperidin-1-yl)-N-(3-isopentyltetrahydro-2H-pyran-3-yl)-6-methoxy-7-(3-(pyrrolidin-1-yl)propoxy)quinazolin-4-amine;

1-(2-(4,4-difluoropiperidin-1-yl)-6-methoxy-7-(3-(pyrrolidin-1-yl)propoxy)quinazolin-4-yl)piperidin-3-amine;

4-((6-methoxy-2-(pyrrolidin-1-yl)-7-(3-(pyrrolidin-1-yl)propoxy)quinazolin-4-yl)amino)tetrahydro-2H-thiopyran 1,1-dioxide;

4-((2-(azetidin-1-yl)-6-methoxy-7-(3-(pyrrolidin-1-yl)propoxy)quinazolin-4-yl)amino)tetrahydro-2H-thiopyran 1,1-dioxide;

4-((6-methoxy-2-(1H-pyrazol-1-yl)-7-(3-(pyrrolidin-1-yl)propoxy)quinazolin-4-yl)amino)tetrahydro-2H-thiopyran 1,1-dioxide;

4-((2-(1H-imidazol-1-yl)-6-methoxy-7-(3-(pyrrolidin-1-yl)propoxy)quinazolin-4-yl)amino)tetrahydro-2H-thiopyran 1,1-dioxide;

4-((6-methoxy-7-(3-(pyrrolidin-1-yl)propoxy)-2-(1H-1,2,4-triazol-1-yl)quinazolin-4-yl)amino)tetrahydro-2H-thiopyran 1,1-dioxide;

4-((2-(1H-indol-1-yl)-6-methoxy-7-(3-(pyrrolidin-1-yl)propoxy)quinazolin-4-yl)amino)tetrahydro-2H-thiopyran 1,1-dioxide;

4-((2-(1H-benzo[d]imidazol-1-yl)-6-methoxy-7-(3-(pyrrolidin-1-yl)propoxy)quinazolin-4-yl)amino)tetrahydro-2H-thiopyran 1,1-dioxide;

4-((6-methoxy-2-(5-methylfuran-2-yl)-7-(3-(pyrrolidin-1-yl)propoxy)quinazolin-4-yl)amino)tetrahydro-2H-thiopyran 1,1-dioxide;

4-((6-methoxy-2-(5-methyl-1H-pyrrol-2-yl)-7-(3-(pyrrolidin-1-yl)propoxy)quinazolin-4-yl)amino)tetrahydro-2H-thiopyran 1,1-dioxide;

4-((6-methoxy-2-(5-methyloxazol-2-yl)-7-(3-(pyrrolidin-1-yl)propoxy)quinazolin-4-yl)amino)tetrahydro-2H-thiopyran 1,1-dioxide;

4-((6-methoxy-2-(2-methyloxazol-5-yl)-7-(3-(pyrrolidin-1-yl)propoxy)quinazolin-4-yl)amino)tetrahydro-2H-thiopyran 1,1-dioxide;

4-((6-methoxy-2-(5-methylthiazol-2-yl)-7-(3-(pyrrolidin-1-yl)propoxy)quinazolin-4-yl)amino)tetrahydro-2H-thiopyran 1,1-dioxide;

4-((6-methoxy-2-(2-methylthiazol-5-yl)-7-(3-(pyrrolidin-1-yl)propoxy)quinazolin-4-yl)amino)tetrahydro-2H-thiopyran 1,1-dioxide;

4-((2-cyclopentyl-6-methoxy-7-(3-(pyrrolidin-1-yl)propoxy)quinazolin-4-yl)amino)tetrahydro-2H-thiopyran 1,1-dioxide;

4-((2-ethyl-6-methoxy-7-(3-(pyrrolidin-1-yl)propoxy)quinazolin-4-yl)amino)tetrahydro-2H-thiopyran 1,1-dioxide;

4-((2-amino-6-methoxy-7-(3-(pyrrolidin-1-yl)propoxy)quinazolin-4-yl)amino)tetrahydro-2H-thiopyran 1,1-dioxide;

4-((6-methoxy-2-(methylamino)-7-(3-(pyrrolidin-1-yl)propoxy)quinazolin-4-yl)amino)tetrahydro-2H-thiopyran 1,1-dioxide;

4-((2-(dimethylamino)-6-methoxy-7-(3-(pyrrolidin-1-yl)propoxy)quinazolin-4-yl)amino)tetrahydro-2H-thiopyran 1,1-dioxide;

4-((6-methoxy-2-(piperazin-1-yl)-7-(3-(pyrrolidin-1-yl)propoxy)quinazolin-4-yl)amino)tetrahydro-2H-thiopyran 1,1-dioxide;

4-((2-cyclopropyl-6-methoxy-7-(3-(pyrrolidin-1-yl)propoxy)quinazolin-4-yl)amino)tetrahydro-2H-thiopyran 1,1-dioxide;

4-((2-(isopropylamino)-6-methoxy-7-(3-(pyrrolidin-1-yl)propoxy)quinazolin-4-yl)amino)tetrahydro-2H-thiopyran 1,1-dioxide;

4-((6-methoxy-2-((methoxymethyl)amino)-7-(3-(pyrrolidin-1-yl)propoxy)quinazolin-4-yl)amino)tetrahydro-2H-thiopyran 1,1-dioxide;

4-((6-methoxy-2-morpholino-7-(3-(pyrrolidin-1-yl)propoxy)quinazolin-4-yl)amino)tetrahydro-2H-thiopyran 1,1-dioxide;

4-(4-((1,1-dioxidotetrahydro-2H-thiopyran-4-yl)amino)-6-methoxy-7-(3-(pyrrolidin-1-yl)propoxy)quinazolin-2-yl)thiomorpholine 1,1-dioxide;

4-((2-ethoxy-6-methoxy-7-(3-(pyrrolidin-1-yl)propoxy)quinazolin-4-yl)amino)tetrahydro-2H-thiopyran 1,1-dioxide;

4-((2-(isopropylthio)-6-methoxy-7-(3-(pyrrolidin-1-yl)propoxy)quinazolin-4-yl)amino)tetrahydro-2H-thiopyran 1,1-dioxide;

4-((6-methoxy-7-(3-(pyrrolidin-1-yl)propoxy)-2-(tetrahydropyrimidin-1(2H)-yl)quinazolin-4-yl)amino)tetrahydro-2H-thiopyran 1,1-dioxide;

4-((6-methoxy-2-(piperidin-3-yl)-7-(3-(pyrrolidin-1-yl)propoxy)quinazolin-4-yl)amino)tetrahydro-2H-thiopyran 1,1-dioxide;

4-((6-methoxy-2-(4-methylpiperazin-1-yl)-7-(3-(pyrrolidin-1-yl)propoxy)quinazolin-4-yl)amino)tetrahydro-2H-thiopyran 1,1-dioxide;

4-((6-methoxy-2-(4-methyl-1,4-diazepan-1-yl)-7-(3-(pyrrolidin-1-yl)propoxy)quinazolin-4-yl)amino)tetrahydro-2H-thiopyran 1,1-dioxide;

4-((2-chloro-6-methoxy-7-(3-(pyrrolidin-1-yl)propoxy)quinazolin-4-yl)amino)tetrahydro-2H-thiopyran 1,1-dioxide;

4-((7-(benzyloxy)-2-chloro-6-methoxyquinazolin-4-yl)amino)tetrahydro-2H-thiopyran 1,1-dioxide;

2-chloro-N-(1-isopropylpiperidin-4-yl)-6-methoxy-7-(3-(pyrrolidin-1-yl)propoxy)quinazolin-4-amine;

2-chloro-6-methoxy-N-(oxetan-3-yl)-7-(3-(pyrrolidin-1-yl)propoxy)quinazolin-4-amine;

2-chloro-6-methoxy-7-(3-(pyrrolidin-1-yl)propoxy)-N-(tetrahydro-2H-pyran-4-yl)quinazolin-4-amine;

6-methoxy-2-(pyrrolidin-1-yl)-7-(3-(pyrrolidin-1-yl)propoxy)-N-(tetrahydro-2H-pyran-3-yl)quinazolin-4-amine;

7-(3-(dimethylamino)propoxy)-6-methoxy-2-(pyrrolidin-1-yl)-N-(tetrahydro-2H-pyran-3-yl)quinazolin-4-amine;

6-methoxy-7-(3-(piperidin-1-yl)propoxy)-2-(pyrrolidin-1-yl)-N-(tetrahydro-2H-pyran-3-yl)quinazolin-4-amine;

7-(3-(piperidin-1-yl)propoxy)-2-(pyrrolidin-1-yl)-N-(tetrahydro-2H-pyran-3-yl)quinazolin-4-amine;

6-fluoro-7-(3-(piperidin-1-yl)propoxy)-2-(pyrrolidin-1-yl)-N-(tetrahydro-2H-pyran-3-yl)quinazolin-4-amine;

6-methoxy-2-(4-methyl-1,4-diazepan-1-yl)-7-(3-(pyrrolidin-1-yl)propoxy)-N-(tetrahydro-2H-pyran-3-yl)quinazolin-4-amine;

6-fluoro-7-(3-(piperidin-1-yl)propoxy)-2-(1H-pyrazol-1-yl)-N-(tetrahydro-2H-pyran-3-yl)quinazolin-4-amine;

6-methoxy-7-(3-(pyrrolidin-1-yl)propoxy)-N-(tetrahydro-2H-pyran-3-yl)-2-(1H-1,2,4-triazol-1-yl)quinazolin-4-amine;

2-(1H-indol-3-yl)-6-methoxy-7-(3-(pyrrolidin-1-yl)propoxy)-N-(tetrahydro-2H-pyran-3-yl)quinazolin-4-amine;

6-methoxy-2-(5-methylfuran-2-yl)-7-(3-(pyrrolidin-1-yl)propoxy)-N-(tetrahydro-2H-pyran-3-yl)quinazolin-4-amine;

6-methoxy-2-(5-methyloxazol-2-yl)-7-(3-(pyrrolidin-1-yl)propoxy)-N-(tetrahydro-2H-pyran-3-yl)quinazolin-4-amine;

6-methoxy-2-(5-methylthiazol-2-yl)-7-(3-(pyrrolidin-1-yl)propoxy)-N-(tetrahydro-2H-pyran-3-yl)quinazolin-4-amine;

2-ethynyl-6-methoxy-7-(3-(pyrrolidin-1-yl)propoxy)-N-(tetrahydro-2H-pyran-3-yl)quinazolin-4-amine;

2-(1H-imidazol-1-yl)-6-methoxy-N-(pyridin-4-yl)-7-(3-(pyrrolidin-1-yl)propoxy)quinazolin-4-amine;

2-(1H-imidazol-1-yl)-6-methoxy-7-(3-(pyrrolidin-1-yl)propoxy)-N-(tetrahydro-2H-pyran-4-yl)quinazolin-4-amine;
(S)-6-methoxy-N2,N2-dimethyl-7-(3-(pyrrolidin-1-yl)propoxy)-N4-(tetrahydro-2H-pyran-3-yl)quinazoline-2,4-diamine;
4-((7-(benzyloxy)-2-(4,4-difluoropiperidin-1-yl)-6-methoxyquinazolin-4-yl)amino)tetrahydro-2H-thiopyran 1,1-dioxide;
3-((6-methoxy-2-(pyrrolidin-1-yl)-7-(3-(pyrrolidin-1-yl)propoxy)quinazolin-4-yl)amino)tetrahydro-2H-thiopyran 1,1-dioxide;
3-((2-(azetidin-1-yl)-7-(3-(dimethylamino)propoxy)-6-methoxyquinazolin-4-yl)amino)tetrahydro-2H-thiopyran 1,1-dioxide;
3-((6-methoxy-7-(3-(piperidin-1-yl)propoxy)-2-(pyrrolidin-1-yl)quinazolin-4-yl)amino)tetrahydro-2H-thiopyran 1,1-dioxide;
3-((7-(3-(piperidin-1-yl)propoxy)-2-(pyrrolidin-1-yl)quinazolin-4-yl)amino)tetrahydro-2H-thiopyran 1,1-dioxide;
3-((6-fluoro-7-(3-(piperidin-1-yl)propoxy)-2-(pyrrolidin-1-yl)quinazolin-4-yl)amino)tetrahydro-2H-thiopyran 1,1-dioxide;
3-((6-methoxy-2-(4-methyl-1,4-diazepan-1-yl)-7-(3-(pyrrolidin-1-yl)propoxy)quinazolin-4-yl)amino)tetrahydro-2H-thiopyran 1,1-dioxide;
3-((6-fluoro-2-(1H-imidazol-1-yl)-7-(3-(piperidin-1-yl)propoxy)quinazolin-4-yl)amino)tetrahydro-2H-thiopyran 1,1-dioxide;
3-((2-(1H-indol-1-yl)-6-methoxy-7-(3-(pyrrolidin-1-yl)propoxy)quinazolin-4-yl)amino)tetrahydro-2H-thiopyran 1,1-dioxide;
3-((2-cyclopentyl-6-methoxy-7-(3-(pyrrolidin-1-yl)propoxy)quinazolin-4-yl)amino)tetrahydro-2H-thiopyran 1,1-dioxide;
3-((6-methoxy-2-(5-methyl-1H-pyrrol-2-yl)-7-(3-(pyrrolidin-1-yl)propoxy)quinazolin-4-yl)amino)tetrahydro-2H-thiopyran 1,1-dioxide;
3-((6-methoxy-2-(2-methyloxazol-5-yl)-7-(3-(pyrrolidin-1-yl)propoxy)quinazolin-4-yl)amino)tetrahydro-2H-thiopyran 1,1-dioxide;
3-((6-methoxy-2-(2-methylthiazol-5-yl)-7-(3-(pyrrolidin-1-yl)propoxy)quinazolin-4-yl)amino)tetrahydro-2H-thiopyran 1,1-dioxide;
4-((1,1-dioxidotetrahydro-2H-thiopyran-3-yl)amino)-6-methoxy-7-(3-(pyrrolidin-1-yl)propoxy)quinazoline-2-carbonitrile;
6,7-dimethoxy-2-(pyrrolidin-1-yl)-N-(tetrahydro-2H-pyran-3-yl)quinazolin-4-amine;
3-((6,7-dimethoxy-2-(pyrrolidin-1-yl)quinazolin-4-yl)amino)tetrahydro-2H-thiopyran 1,1-dioxide;
1-(6,7-dimethoxy-2-(pyrrolidin-1-yl)quinazolin-4-yl)piperidin-3-amine;
1-(6,7-dimethoxy-2-(pyrrolidin-1-yl)quinazolin-4-yl)piperidin-3-ol;
3-((2-(4,4-difluoropiperidin-1-yl)-7-hydroxy-6-methoxyquinazolin-4-yl)amino)tetrahydro-2H-thiopyran 1,1-dioxide;
2-(1H-imidazol-1-yl)-N-(1-isopropylpiperidin-4-yl)-6-methoxy-7-(3-(pyrrolidin-1-yl)propoxy)quinazolin-4-amine;
N-(1-isopropylpiperidin-4-yl)-6-methoxy-2-(1H-pyrazol-1-yl)-7-(3-(pyrrolidin-1-yl)propoxy)quinazolin-4-amine;
(S)-6-methoxy-N-(piperidin-3-yl)-2-(pyrrolidin-1-yl)-7-(3-(pyrrolidin-1-yl)propoxy)quinazolin-4-amine;
(R)-6-methoxy-N-(piperidin-3-yl)-2-(pyrrolidin-1-yl)-7-(3-(pyrrolidin-1-yl)propoxy)quinazolin-4-amine;
1-(6-methoxy-2-(pyrrolidin-1-yl)-7-(3-(pyrrolidin-1-yl)propoxy)quinazolin-4-yl)piperidin-3-amine;
N-(1-(6-methoxy-2-(pyrrolidin-1-yl)-7-(3-(pyrrolidin-1-yl)propoxy)quinazolin-4-yl)piperidin-3-yl)acetamide;
1-(2-(pyrrolidin-1-yl)-7-(3-(pyrrolidin-1-yl)propoxy)quinazolin-4-yl)piperidin-3-amine;
1-(6-fluoro-2-(pyrrolidin-1-yl)-7-(3-(pyrrolidin-1-yl)propoxy)quinazolin-4-yl)piperidin-3-amine;
6-methoxy-2-(pyrrolidin-1-yl)-7-(3-(pyrrolidin-1-yl)propoxy)-N-(tetrahydro-2H-pyran-4-yl)quinazolin-4-amine;
6-methoxy-N-(piperazin-1-ylmethyl)-2-(pyrrolidin-1-yl)-7-(3-(pyrrolidin-1-yl)propoxy)quinazolin-4-amine;
1-(6-fluoro-2-(1H-imidazol-1-yl)-7-(3-(pyrrolidin-1-yl)propoxy)quinazolin-4-yl)piperidin-3-amine;
1-(6-methoxy-2-(4-methyl-1,4-diazepan-1-yl)-7-(3-(pyrrolidin-1-yl)propoxy)quinazolin-4-yl)piperidin-3-amine;
1-(6-methoxy-7-(3-(pyrrolidin-1-yl)propoxy)-2-(1H-1,2,4-triazol-1-yl)quinazolin-4-yl)piperidin-3-amine;
1-(6-fluoro-2-(1H-pyrazol-1-yl)-7-(3-(pyrrolidin-1-yl)propoxy)quinazolin-4-yl)piperidin-3-amine;
2-(1H-indol-1-yl)-6-methoxy-4-(piperidin-1-yl)-7-(3-(pyrrolidin-1-yl)propoxy)quinazoline;
2-(1H-indol-3-yl)-6-methoxy-4-(piperidin-1-yl)-7-(3-(pyrrolidin-1-yl)propoxy)quinazoline;
1-(2-cyclopentyl-6-methoxy-7-(3-(pyrrolidin-1-yl)propoxy)quinazolin-4-yl)piperidin-3-amine;
6-methoxy-2-(piperidin-1-yl)-7-(3-(pyrrolidin-1-yl)propoxy)-N-(tetrahydro-2H-pyran-4-yl)quinazolin-4-amine;
2-(azetidin-1-yl)-6-methoxy-7-(3-(pyrrolidin-1-yl)propoxy)-N-(tetrahydro-2H-pyran-4-yl)quinazolin-4-amine;
6-methoxy-2-(1H-pyrazol-1-yl)-7-(3-(pyrrolidin-1-yl)propoxy)-N-(tetrahydro-2H-pyran-4-yl)quinazolin-4-amine;
2-(1H-imidazol-1-yl)-6-methoxy-7-(3-(pyrrolidin-1-yl)propoxy)-N-(tetrahydro-2H-pyran-4-yl)quinazolin-4-amine;
6-methoxy-7-(3-(pyrrolidin-1-yl)propoxy)-N-(tetrahydro-2H-pyran-4-yl)-2-(1H-1,2,4-triazol-1-yl)quinazolin-4-amine;
2-(1H-indol-1-yl)-6-methoxy-7-(3-(pyrrolidin-1-yl)propoxy)-N-(tetrahydro-2H-pyran-4-yl)quinazolin-4-amine;
2-(1H-benzo[d]imidazol-1-yl)-6-methoxy-7-(3-(pyrrolidin-1-yl)propoxy)-N-(tetrahydro-2H-pyran-4-yl)quinazolin-4-amine;
6-methoxy-2-(5-methylfuran-2-yl)-7-(3-(pyrrolidin-1-yl)propoxy)-N-(tetrahydro-2H-pyran-4-yl)quinazolin-4-amine;
6-methoxy-2-(5-methyl-1H-pyrrol-2-yl)-7-(3-(pyrrolidin-1-yl)propoxy)-N-(tetrahydro-2H-pyran-4-yl)quinazolin-4-amine;
6-methoxy-2-(5-methyloxazol-2-yl)-7-(3-(pyrrolidin-1-yl)propoxy)-N-(tetrahydro-2H-pyran-4-yl)quinazolin-4-amine;
6-methoxy-2-(2-methyloxazol-5-yl)-7-(3-(pyrrolidin-1-yl)propoxy)-N-(tetrahydro-2H-pyran-4-yl)quinazolin-4-amine;
6-methoxy-2-(5-methylthiazol-2-yl)-7-(3-(pyrrolidin-1-yl)propoxy)-N-(tetrahydro-2H-pyran-4-yl)quinazolin-4-amine;
6-methoxy-2-(2-methylthiazol-5-yl)-7-(3-(pyrrolidin-1-yl)propoxy)-N-(tetrahydro-2H-pyran-4-yl)quinazolin-4-amine;

2-cyclopentyl-6-methoxy-7-(3-(pyrrolidin-1-yl)propoxy)-N-(tetrahydro-2H-pyran-4-yl)quinazolin-4-amine;
2-ethyl-6-methoxy-7-(3-(pyrrolidin-1-yl)propoxy)-N-(tetrahydro-2H-pyran-4-yl)quinazolin-4-amine;
6-methoxy-7-(3-(pyrrolidin-1-yl)propoxy)-N4-(tetrahydro-2H-pyran-4-yl)quinazoline-2,4-diamine;
6-methoxy-N2-methyl-7-(3-(pyrrolidin-1-yl)propoxy)-N4-(tetrahydro-2H-pyran-4-yl)quinazoline-2,4-diamine;
6-methoxy-N2,N2-dimethyl-7-(3-(pyrrolidin-1-yl)propoxy)-N4-(tetrahydro-2H-pyran-4-yl)quinazoline-2,4-diamine;
6-methoxy-2-(piperazin-1-yl)-7-(3-(pyrrolidin-1-yl)propoxy)-N-(tetrahydro-2H-pyran-4-yl)quinazolin-4-amine;
2-cyclopropyl-6-methoxy-7-(3-(pyrrolidin-1-yl)propoxy)-N-(tetrahydro-2H-pyran-4-yl)quinazolin-4-amine;
N2-isopropyl-6-methoxy-7-(3-(pyrrolidin-1-yl)propoxy)-N4-(tetrahydro-2H-pyran-4-yl)quinazoline-2,4-diamine;
6-methoxy-N2-(2-methoxyethyl)-7-(3-(pyrrolidin-1-yl)propoxy)-N4-(tetrahydro-2H-pyran-4-yl)quinazoline-2,4-diamine;
6-methoxy-2-morpholino-7-(3-(pyrrolidin-1-yl)propoxy)-N-(tetrahydro-2H-pyran-4-yl)quinazolin-4-amine;
4-(6-methoxy-7-(3-(pyrrolidin-1-yl)propoxy)-4-((tetrahydro-2H-pyran-4-yl)amino)quinazolin-2-yl)thiomorpholine 1,1-dioxide;
2-ethoxy-6-methoxy-7-(3-(pyrrolidin-1-yl)propoxy)-N-(tetrahydro-2H-pyran-4-yl)quinazolin-4-amine;
2-(isopropylthio)-6-methoxy-7-(3-(pyrrolidin-1-yl)propoxy)-N-(tetrahydro-2H-pyran-4-yl)quinazolin-4-amine;
N-(6-methoxy-7-(3-(pyrrolidin-1-yl)propoxy)-4-((tetrahydro-2H-pyran-4-yl)amino)quinazolin-2-yl)cyclopropanecarboxamide;
6-methoxy-7-(3-(pyrrolidin-1-yl)propoxy)-N-(tetrahydro-2H-pyran-4-yl)-2-(tetrahydropyrimidin-1(2H)-yl)quinazolin-4-amine;
6-methoxy-2-(piperidin-3-yl)-7-(3-(pyrrolidin-1-yl)propoxy)-N-(tetrahydro-2H-pyran-4-yl)quinazolin-4-amine;
6-methoxy-N-(piperazin-1-ylmethyl)-2-(piperidin-1-yl)-7-(3-(pyrrolidin-1-yl)propoxy)quinazolin-4-amine;
2-(azetidin-1-yl)-6-methoxy-N-(piperazin-1-ylmethyl)-7-(3-(pyrrolidin-1-yl)propoxy)quinazolin-4-amine;
6-methoxy-N-(piperazin-1-ylmethyl)-2-(1H-pyrazol-1-yl)-7-(3-(pyrrolidin-1-yl)propoxy)quinazolin-4-amine;
2-(1H-imidazol-1-yl)-6-methoxy-N-(piperazin-1-ylmethyl)-7-(3-(pyrrolidin-1-yl)propoxy)quinazolin-4-amine;
2-(1H-indol-1-yl)-6-methoxy-N-(piperazin-1-ylmethyl)-7-(3-(pyrrolidin-1-yl)propoxy)quinazolin-4-amine;
6-methoxy-N-(piperazin-1-ylmethyl)-7-(3-(pyrrolidin-1-yl)propoxy)-2-(1H-1,2,4-triazol-1-yl)quinazolin-4-amine;
2-(1H-benzo[d]imidazol-1-yl)-6-methoxy-N-(piperazin-1-ylmethyl)-7-(3-(pyrrolidin-1-yl)propoxy)quinazolin-4-amine;
6-methoxy-2-(5-methylfuran-2-yl)-N-(piperazin-1-ylmethyl)-7-(3-(pyrrolidin-1-yl)propoxy)quinazolin-4-amine;
6-methoxy-2-(5-methyl-1H-pyrrol-2-yl)-N-(piperazin-1-ylmethyl)-7-(3-(pyrrolidin-1-yl)propoxy)quinazolin-4-amine;
6-methoxy-2-(5-methyloxazol-2-yl)-N-(piperazin-1-ylmethyl)-7-(3-(pyrrolidin-1-yl)propoxy)quinazolin-4-amine;
6-methoxy-2-(2-methyloxazol-5-yl)-N-(piperazin-1-ylmethyl)-7-(3-(pyrrolidin-1-yl)propoxy)quinazolin-4-amine;
6-methoxy-2-(5-methylthiazol-2-yl)-N-(piperazin-1-ylmethyl)-7-(3-(pyrrolidin-1-yl)propoxy)quinazolin-4-amine;
6-methoxy-2-(2-methylthiazol-5-yl)-N-(piperazin-1-ylmethyl)-7-(3-(pyrrolidin-1-yl)propoxy)quinazolin-4-amine;
2-cyclopentyl-6-methoxy-N-(piperazin-1-ylmethyl)-7-(3-(pyrrolidin-1-yl)propoxy)quinazolin-4-amine;
2-ethyl-6-methoxy-N-(piperazin-1-ylmethyl)-7-(3-(pyrrolidin-1-yl)propoxy)quinazolin-4-amine;
6-methoxy-N4-(piperazin-1-ylmethyl)-7-(3-(pyrrolidin-1-yl)propoxy)quinazoline-2,4-diamine;
6-methoxy-N2-methyl-N4-(piperazin-1-ylmethyl)-7-(3-(pyrrolidin-1-yl)propoxy)quinazoline-2,4-diamine;
6-methoxy-N2,N2-dimethyl-N4-(piperazin-1-ylmethyl)-7-(3-(pyrrolidin-1-yl)propoxy)quinazoline-2,4-diamine;
6-methoxy-2-morpholino-N-(piperazin-1-ylmethyl)-7-(3-(pyrrolidin-1-yl)propoxy)quinazolin-4-amine;
2-cyclopropyl-6-methoxy-N-(piperazin-1-ylmethyl)-7-(3-(pyrrolidin-1-yl)propoxy)quinazolin-4-amine;
N2-isopropyl-6-methoxy-N4-(piperazin-1-ylmethyl)-7-(3-(pyrrolidin-1-yl)propoxy)quinazoline-2,4-diamine;
6-methoxy-N2-(2-methoxyethyl)-N4-(piperazin-1-ylmethyl)-7-(3-(pyrrolidin-1-yl)propoxy)quinazoline-2,4-diamine;
6-methoxy-2-morpholino-N-(piperazin-1-ylmethyl)-7-(3-(pyrrolidin-1-yl)propoxy)quinazolin-4-amine;
4-(6-methoxy-4-((piperazin-1-ylmethyl)amino)-7-(3-(pyrrolidin-1-yl)propoxy)quinazolin-2-yl)thiomorpholine 1,1-dioxide;
1-(6-methoxy-7-(3-(piperidin-1-yl)propoxy)-2-(pyrrolidin-1-yl)quinazolin-4-yl)piperidin-3-ol;
1-(6-methoxy-7-(3-(piperidin-1-yl)propoxy)-2-(pyrrolidin-1-yl)quinazolin-4-yl)piperidin-3-amine;
1-(7-(3-(dimethylamino)propoxy)-6-methoxy-2-(pyrrolidin-1-yl)quinazolin-4-yl)piperidin-3-amine;
1-(2-(azetidin-1-yl)-7-(3-(dimethylamino)propoxy)-6-methoxyquinazolin-4-yl)piperidin-3-amine;
2-(azetidin-1-yl)-N-(1-isopropylpiperidin-4-yl)-6-methoxy-7-(3-(pyrrolidin-1-yl)propoxy)quinazolin-4-amine;
4-((4-(dimethylamino)cyclohexyl)amino)-6-methoxy-7-(3-(pyrrolidin-1-yl)propoxy)quinazoline-2-carbonitrile;
6-methoxy-2-(4-methylpiperazin-1-yl)-7-(3-(pyrrolidin-1-yl)propoxy)-N-(tetrahydro-2H-pyran-4-yl)quinazolin-4-amine;
6-methoxy-2-(4-methyl-1,4-diazepan-1-yl)-7-(3-(pyrrolidin-1-yl)propoxy)-N-(tetrahydro-2H-pyran-4-yl)quinazolin-4-amine;
4-((2-(4,4-difluoropiperidin-1-yl)-7-hydroxy-6-methoxyquinazolin-4-yl)amino)tetrahydro-2H-thiopyran 1,1-dioxide;
4-((2-(4,4-difluoropiperidin-1-yl)-6-methoxy-7-(3-(pyrrolidin-1-yl)prop-1-yn-1-yl)quinazolin-4-yl)amino)tetrahydro-2H-thiopyran 1,1-dioxide;
6-methoxy-2-(pyrrolidin-1-yl)-7-(3-(pyrrolidin-1-yl)prop-1-yn-1-yl)-N-(tetrahydro-2H-pyran-3-yl)quinazolin-4-amine;
6-methoxy-2-(pyrrolidin-1-yl)-7-(3-(pyrrolidin-1-yl)prop-1-yn-1-yl)-N-(tetrahydro-2H-pyran-4-yl)quinazolin-4-amine;
3-((6-methoxy-2-(pyrrolidin-1-yl)-7-(3-(pyrrolidin-1-yl)prop-1-yn-1-yl)quinazolin-4-yl)amino)tetrahydro-2H-thiopyran 1,1-dioxide;
1-(6-methoxy-2-(pyrrolidin-1-yl)-7-(3-(pyrrolidin-1-yl)prop-1-yn-1-yl)quinazolin-4-yl)piperidin-3-amine;
1-(6-methoxy-2-(pyrrolidin-1-yl)-7-(3-(pyrrolidin-1-yl)prop-1-yn-1-yl)quinazolin-4-yl)piperidin-3-ol;

4-((6-methoxy-2-(pyrrolidin-1-yl)-7-(3-(pyrrolidin-1-yl)prop-1-yn-1-yl)quinazolin-4-yl)amino)tetrahydro-2H-thiopyran 1,1-dioxide;

6-methoxy-2-(pyrrolidin-1-yl)-7-(3-(pyrrolidin-1-yl)prop-1-yn-1-yl)-N-(tetrahydro-2H-pyran-4-yl)quinazolin-4-amine;

6-methoxy-N-(piperazin-1-ylmethyl)-2-(pyrrolidin-1-yl)-7-(3-(pyrrolidin-1-yl)prop-1-yn-1-yl)quinazolin-4-amine;

6-methoxy-N-(pyridin-3-yl)-2-(pyrrolidin-1-yl)-7-(3-(pyrrolidin-1-yl)prop-1-yn-1-yl)quinazolin-4-amine;

N-(2-isopropoxyethyl)-6-methoxy-2-(pyrrolidin-1-yl)-7-(3-(pyrrolidin-1-yl)prop-1-yn-1-yl)quinazolin-4-amine;

4-((6-methoxy-2-(pyrrolidin-1-yl)-7-(3-(pyrrolidin-1-yl)prop-1-yn-1-yl)quinazolin-4-yl)amino)tetrahydro-2H-thiopyran 1,1-dioxide;

6-methoxy-N-(piperazin-1-ylmethyl)-2-(pyrrolidin-1-yl)-7-(3-(pyrrolidin-1-yl)prop-1-yn-1-yl)quinazolin-4-amine;

6-methoxy-N-(morpholinomethyl)-2-(pyrrolidin-1-yl)-7-(3-(pyrrolidin-1-yl)prop-1-yn-1-yl)quinazolin-4-amine;

N-(3-isopropoxypropyl)-6-methoxy-2-(pyrrolidin-1-yl)-7-(3-(pyrrolidin-1-yl)prop-1-yn-1-yl)quinazolin-4-amine;

(2S)—N2-(6-methoxy-2-(pyrrolidin-1-yl)-7-(3-(pyrrolidin-1-yl)prop-1-yn-1-yl)quinazolin-4-yl)-N1-((tetrahydrofuran-2-yl)methyl)propane-1,2-diamine;

N-isopropyl-6-methoxy-2-(pyrrolidin-1-yl)-7-(3-(pyrrolidin-1-yl)prop-1-yn-1-yl)quinazolin-4-amine;

N-(2-(azetidin-3-yloxy)ethyl)-6-methoxy-2-(pyrrolidin-1-yl)-7-(3-(pyrrolidin-1-yl)prop-1-yn-1-yl)quinazolin-4-amine;

2-(4-((6-methoxy-2-(pyrrolidin-1-yl)-7-(3-(pyrrolidin-1-yl)prop-1-yn-1-yl)quinazolin-4-yl)amino)piperidin-1-yl)acetic acid;

6-methoxy-N-(2-methoxyethyl)-2-(pyrrolidin-1-yl)-7-(3-(pyrrolidin-1-yl)prop-1-yn-1-yl)quinazolin-4-amine;

6-methoxy-N-(pyridin-2-yl)-2-(pyrrolidin-1-yl)-7-(3-(pyrrolidin-1-yl)prop-1-yn-1-yl)quinazolin-4-amine;

6-methoxy-N-(pyridin-3-yl)-2-(pyrrolidin-1-yl)-7-(3-(pyrrolidin-1-yl)prop-1-yn-1-yl)quinazolin-4-amine;

6-methoxy-N-(pyridin-4-yl)-2-(pyrrolidin-1-yl)-7-(3-(pyrrolidin-1-yl)prop-1-yn-1-yl)quinazolin-4-amine;

N-((aminooxy)carbonyl)-6-methoxy-2-(pyrrolidin-1-yl)-7-(3-(pyrrolidin-1-yl)prop-1-yn-1-yl)quinazolin-4-amine;

N-(6-methoxy-2-(pyrrolidin-1-yl)-7-(3-(pyrrolidin-1-yl)prop-1-yn-1-yl)quinazolin-4-yl)cyclopropanecarboxamide;

4-(2-((6-methoxy-2-(pyrrolidin-1-yl)-7-(3-(pyrrolidin-1-yl)prop-1-yn-1-yl)quinazolin-4-yl)amino)propyl)cyclohexan-1-ol;

(R)-2-((2-((6-methoxy-2-(pyrrolidin-1-yl)-7-(3-(pyrrolidin-1-yl)prop-1-yn-1-yl)quinazolin-4-yl)amino)propyl)amino)ethan-1-ol;

((2R,5R)-4-(((6-methoxy-2-(pyrrolidin-1-yl)-7-(3-(pyrrolidin-1-yl)prop-1-yn-1-yl)quinazolin-4-yl)amino)methyl)-5-methylmorpholin-2-yl)methanol;

N-cyclopentyl-6-methoxy-2-(pyrrolidin-1-yl)-7-(3-(pyrrolidin-1-yl)prop-1-yn-1-yl)quinazolin-4-amine;

1-(4-((6-methoxy-2-(pyrrolidin-1-yl)-7-(3-(pyrrolidin-1-yl)prop-1-yn-1-yl)quinazolin-4-yl)amino)piperidin-1-yl)ethan-1-one;

6-methoxy-N-methyl-2-(pyrrolidin-1-yl)-7-(3-(pyrrolidin-1-yl)prop-1-yn-1-yl)quinazolin-4-amine;

2-((6-methoxy-2-(pyrrolidin-1-yl)-7-(3-(pyrrolidin-1-yl)prop-1-yn-1-yl)quinazolin-4-yl)amino)acetonitrile;

N-(3,5-difluorophenyl)-6-methoxy-2-(pyrrolidin-1-yl)-7-(3-(pyrrolidin-1-yl)prop-1-yn-1-yl)quinazolin-4-amine;

(1S,2S)-1-(dimethylamino)-2-((6-methoxy-2-(pyrrolidin-1-yl)-7-(3-(pyrrolidin-1-yl)prop-1-yn-1-yl)quinazolin-4-yl)amino)propan-1-ol;

(S)-2,2,2-trifluoro-1-((6-methoxy-2-(pyrrolidin-1-yl)-7-(3-(pyrrolidin-1-yl)prop-1-yn-1-yl)quinazolin-4-yl)amino)ethan-1-ol;

6-methoxy-N-(pyridin-2-ylmethyl)-2-(pyrrolidin-1-yl)-7-(3-(pyrrolidin-1-yl)prop-1-yn-1-yl)quinazolin-4-amine;

6-methoxy-N-(pyridin-3-ylmethyl)-2-(pyrrolidin-1-yl)-7-(3-(pyrrolidin-1-yl)prop-1-yn-1-yl)quinazolin-4-amine;

6-methoxy-N-(pyridin-4-ylmethyl)-2-(pyrrolidin-1-yl)-7-(3-(pyrrolidin-1-yl)prop-1-yn-1-yl)quinazolin-4-amine;

(S)-6-methoxy-N-(piperidin-2-yl)-2-(pyrrolidin-1-yl)-7-(3-(pyrrolidin-1-yl)prop-1-yn-1-yl)quinazolin-4-amine;

(S)-2-isopropoxy-N-(6-methoxy-2-(pyrrolidin-1-yl)-7-(3-(pyrrolidin-1-yl)prop-1-yn-1-yl)quinazolin-4-yl)-N'-methylethane-1,1-diamine;

6-methoxy-2-(pyrrolidin-1-yl)-7-(3-(pyrrolidin-1-yl)prop-1-yn-1-yl)-N-(thiophen-2-yl)quinazolin-4-amine;

N-(furan-2-yl)-6-methoxy-2-(pyrrolidin-1-yl)-7-(3-(pyrrolidin-1-yl)prop-1-yn-1-yl)quinazolin-4-amine;

6-methoxy-N-(1H-pyrrol-2-yl)-2-(pyrrolidin-1-yl)-7-(3-(pyrrolidin-1-yl)prop-1-yn-1-yl)quinazolin-4-amine;

6-methoxy-N-(1H-pyrrol-3-yl)-2-(pyrrolidin-1-yl)-7-(3-(pyrrolidin-1-yl)prop-1-yn-1-yl)quinazolin-4-amine;

6-methoxy-N-(1H-pyrazol-3-yl)-2-(pyrrolidin-1-yl)-7-(3-(pyrrolidin-1-yl)prop-1-yn-1-yl)quinazolin-4-amine;

N-(6-methoxy-2-(pyrrolidin-1-yl)-7-(3-(pyrrolidin-1-yl)prop-1-yn-1-yl)quinazolin-4-yl)isoxazol-3-amine;

N-(6-methoxy-2-(pyrrolidin-1-yl)-7-(3-(pyrrolidin-1-yl)prop-1-yn-1-yl)quinazolin-4-yl)isoxazol-3-amine;

N-(6-methoxy-2-(pyrrolidin-1-yl)-7-(3-(pyrrolidin-1-yl)prop-1-yn-1-yl)quinazolin-4-yl)oxazol-5-amine;

N-(6-methoxy-2-(pyrrolidin-1-yl)-7-(3-(pyrrolidin-1-yl)prop-1-yn-1-yl)quinazolin-4-yl)thiazol-5-amine;

6-methoxy-N-(1H-pyrrol-3-yl)-2-(pyrrolidin-1-yl)-7-(3-(pyrrolidin-1-yl)prop-1-yn-1-yl)quinazolin-4-amine;

N-cyclopropyl-6-methoxy-2-(pyrrolidin-1-yl)-7-(3-(pyrrolidin-1-yl)prop-1-yn-1-yl)quinazolin-4-amine;

6-methoxy-2-(pyrrolidin-1-yl)-7-(3-(pyrrolidin-1-yl)prop-1-yn-1-yl)-N-(trifluoromethyl)quinazolin-4-amine;

N-(6-methoxy-2-(pyrrolidin-1-yl)-7-(3-(pyrrolidin-1-yl)prop-1-yn-1-yl)quinazolin-4-yl)cyanamide;

6-methoxy-N-(oxetan-3-yl)-2-(pyrrolidin-1-yl)-7-(3-(pyrrolidin-1-yl)prop-1-yn-1-yl)quinazolin-4-amine;

N-benzyl-6-methoxy-2-(pyrrolidin-1-yl)-7-(3-(pyrrolidin-1-yl)prop-1-yn-1-yl)quinazolin-4-amine;

4-((2-(4,4-difluoropiperidin-1-yl)-6-methoxy-7-(3-(pyrrolidin-1-yl)prop-1-yn-1-yl)quinazolin-4-yl)amino)tetrahydro-2H-thiopyran 1,1-dioxide;

4-((6-methoxy-2-morpholino-7-(3-(pyrrolidin-1-yl)prop-1-yn-1-yl)quinazolin-4-yl)amino)tetrahydro-2H-thiopyran 1,1-dioxide;

4-((2-(azetidin-1-yl)-6-methoxy-7-(3-(pyrrolidin-1-yl)prop-1-yn-1-yl)quinazolin-4-yl)amino)tetrahydro-2H-thiopyran 1,1-dioxide;

4-((6-methoxy-2-(4-methyl-1,4-diazepan-1-yl)-7-(3-(pyrrolidin-1-yl)prop-1-yn-1-yl)quinazolin-4-yl)amino)tetrahydro-2H-thiopyran 1,1-dioxide;

4-((2-cyclopentyl-6-methoxy-7-(3-(pyrrolidin-1-yl)prop-1-yn-1-yl)quinazolin-4-yl)amino)tetrahydro-2H-thiopyran 1,1-dioxide;

4-((2-cyclopropyl-6-methoxy-7-(3-(pyrrolidin-1-yl)prop-1-yn-1-yl)quinazolin-4-yl)amino)tetrahydro-2H-thiopyran 1,1-dioxide;

4-((2-(dimethylamino)-6-methoxy-7-(3-(pyrrolidin-1-yl)
prop-1-yn-1-yl)quinazolin-4-yl)amino)tetrahydro-2H-
thiopyran 1,1-dioxide;

4-((6-methoxy-2-(4-methylpiperazin-1-yl)-7-(3-(pyrrolidin-
1-yl)prop-1-yn-1-yl)quinazolin-4-yl)amino)tetrahydro-
2H-thiopyran 1,1-dioxide;

4-((2-(1,4-diazepan-1-yl)-6-methoxy-7-(3-(pyrrolidin-1-yl)
prop-1-yn-1-yl)quinazolin-4-yl)amino)tetrahydro-2H-
thiopyran 1,1-dioxide;

2-(4,4-difluoropiperidin-1-yl)-6-methoxy-7-(3-(pyrrolidin-
1-yl)prop-1-yn-1-yl)-N-(tetrahydro-2H-pyran-4-yl)qui-
nazolin-4-amine;

6-methoxy-2-morpholino-7-(3-(pyrrolidin-1-yl)prop-1-yn-
1-yl)-N-(tetrahydro-2H-pyran-4-yl)quinazolin-4-amine;

2-(azetidin-1-yl)-6-methoxy-7-(3-(pyrrolidin-1-yl)prop-1-
yn-1-yl)-N-(tetrahydro-2H-pyran-4-yl)quinazolin-4-
amine;

6-methoxy-2-(4-methyl-1,4-diazepan-1-yl)-7-(3-(pyrroli-
din-1-yl)prop-1-yn-1-yl)-N-(tetrahydro-2H-pyran-4-yl)
quinazolin-4-amine;

2-cyclopentyl-6-methoxy-7-(3-(pyrrolidin-1-yl)prop-1-yn-
1-yl)-N-(tetrahydro-2H-pyran-4-yl)quinazolin-4-amine;

2-cyclopropyl-6-methoxy-7-(3-(pyrrolidin-1-yl)prop-1-yn-
1-yl)-N-(tetrahydro-2H-pyran-4-yl)quinazolin-4-amine;

6-methoxy-N2,N2-dimethyl-7-(3-(pyrrolidin-1-yl)prop-1-
yn-1-yl)-N4-(tetrahydro-2H-pyran-4-yl)quinazoline-2,4-
diamine;

6-methoxy-2-(4-methylpiperazin-1-yl)-7-(3-(pyrrolidin-1-
yl)prop-1-yn-1-yl)-N-(tetrahydro-2H-pyran-4-yl)qui-
nazolin-4-amine;

2-(1,4-diazepan-1-yl)-6-methoxy-7-(3-(pyrrolidin-1-yl)
prop-1-yn-1-yl)-N-(tetrahydro-2H-pyran-4-yl)quinazo-
lin-4-amine;

2-(4,4-difluoropiperidin-1-yl)-6-methoxy-N-(piperidin-4-
yl)-7-(3-(pyrrolidin-1-yl)prop-1-yn-1-yl)quinazolin-4-
amine;

2-(4,4-difluoropiperidin-1-yl)-6-methoxy-N-(methoxym-
ethyl)-7-(3-(pyrrolidin-1-yl)prop-1-yn-1-yl)quinazolin-4-
amine;

2-(4,4-difluoropiperidin-1-yl)-6-methoxy-N-(oxetan-3-yl)-
7-(3-(pyrrolidin-1-yl)prop-1-yn-1-yl)quinazolin-4-amine;

2-(4,4-difluoropiperidin-1-yl)-6-methoxy-N-(piperidin-4-
ylmethyl)-7-(3-(pyrrolidin-1-yl)prop-1-yn-1-yl)quinazo-
lin-4-amine;

2-(4,4-difluoropiperidin-1-yl)-6-methoxy-N-((1-methylpip-
eridin-4-yl)methyl)-7-(3-(pyrrolidin-1-yl)prop-1-yn-1-yl)
quinazolin-4-amine;

2-(4,4-difluoropiperidin-1-yl)-6-methoxy-N-(piperazin-1-
ylmethyl)-7-(3-(pyrrolidin-1-yl)prop-1-yn-1-yl)quinazo-
lin-4-amine;

2-(4,4-difluoropiperidin-1-yl)-6-methoxy-N-(morpholi-
nomethyl)-7-(3-(pyrrolidin-1-yl)prop-1-yn-1-yl)quinazo-
lin-4-amine;

2-(4,4-difluoropiperidin-1-yl)-6-methoxy-N-(pyridin-4-yl)-
7-(3-(pyrrolidin-1-yl)prop-1-yn-1-yl)quinazolin-4-amine;

2-(4,4-difluoropiperidin-1-yl)-6-methoxy-N-(pyridin-3-yl)-
7-(3-(pyrrolidin-1-yl)prop-1-yn-1-yl)quinazolin-4-amine;

2-(4,4-difluoropiperidin-1-yl)-6-methoxy-N-(pyridin-2-yl)-
7-(3-(pyrrolidin-1-yl)prop-1-yn-1-yl)quinazolin-4-amine;

N-cyclopentyl-2-(4,4-difluoropiperidin-1-yl)-6-methoxy-7-
(3-(pyrrolidin-1-yl)prop-1-yn-1-yl)quinazolin-4-amine;

2-(4,4-difluoropiperidin-1-yl)-6-methoxy-N-(5-methyl-
furan-2-yl)-7-(3-(pyrrolidin-1-yl)prop-1-yn-1-yl)qui-
nazolin-4-amine;

N-(2-(4,4-difluoropiperidin-1-yl)-6-methoxy-7-(3-(pyrroli-
din-1-yl)prop-1-yn-1-yl)quinazolin-4-yl)-2-methyloxa-
zol-5-amine;

N-(2-(4,4-difluoropiperidin-1-yl)-6-methoxy-7-(3-(pyrroli-
din-1-yl)prop-1-yn-1-yl)quinazolin-4-yl)-2-methylthi-
azol-5-amine;

2-(4,4-difluoropiperidin-1-yl)-6-methoxy-N-(5-methyl-1H-
pyrazol-3-yl)-7-(3-(pyrrolidin-1-yl)prop-1-yn-1-yl)qui-
nazolin-4-amine;

2-((2-(4,4-difluoropiperidin-1-yl)-6-methoxy-7-(3-(pyrroli-
din-1-yl)prop-1-yn-1-yl)quinazolin-4-yl)amino)acet-
amide;

2-(4,4-difluoropiperidin-1-yl)-6-methoxy-N-(2-methoxy-
ethyl)-7-(3-(pyrrolidin-1-yl)prop-1-yn-1-yl)quinazolin-4-
amine;

N-cyclopropyl-2-(4,4-difluoropiperidin-1-yl)-6-methoxy-7-
(3-(pyrrolidin-1-yl)prop-1-yn-1-yl)quinazolin-4-amine;

N-cyclobutyl-2-(4,4-difluoropiperidin-1-yl)-6-methoxy-7-
(3-(pyrrolidin-1-yl)prop-1-yn-1-yl)quinazolin-4-amine;

2-(4,4-difluoropiperidin-1-yl)-6-methoxy-N-(oxetan-3-yl)-
7-(3-(pyrrolidin-1-yl)prop-1-yn-1-yl)quinazolin-4-amine;

2-(4,4-difluoropiperidin-1-yl)-6-methoxy-7-(3-(pyrrolidin-
1-yl)prop-1-yn-1-yl)-N-(trifluoromethyl)quinazolin-4-
amine;

N-(2-(4,4-difluoropiperidin-1-yl)-6-methoxy-7-(3-(pyrroli-
din-1-yl)prop-1-yn-1-yl)quinazolin-4-yl)cyclopropan-
ecarboxamide;

N-(3,5-difluorophenyl)-2-(4,4-difluoropiperidin-1-yl)-6-
methoxy-7-(3-(pyrrolidin-1-yl)prop-1-yn-1-yl)quinazo-
lin-4-amine;

2-(4,4-difluoropiperidin-1-yl)-6-methoxy-N-(piperidin-4-
yl)-7-(3-(pyrrolidin-1-yl)prop-1-yn-1-yl)quinazolin-4-
amine;

2-(4,4-difluoropiperidin-1-yl)-6-methoxy-N-(piperidin-3-
yl)-7-(3-(pyrrolidin-1-yl)prop-1-yn-1-yl)quinazolin-4-
amine;

2-(4,4-difluoropiperidin-1-yl)-6-methoxy-N-(piperidin-2-
yl)-7-(3-(pyrrolidin-1-yl)prop-1-yn-1-yl)quinazolin-4-
amine;

2-(4,4-difluoropiperidin-1-yl)-6-methoxy-7-(3-(pyrrolidin-
1-yl)prop-1-yn-1-yl)-N-(pyrrolidin-3-yl)quinazolin-4-
amine;

2-(4,4-difluoropiperidin-1-yl)-6-methoxy-7-(3-(pyrrolidin-
1-yl)prop-1-yn-1-yl)-N-(pyrrolidin-2-yl)quinazolin-4-
amine;

2-(4,4-difluoropiperidin-1-yl)-6-methoxy-7-(3-(pyrrolidin-
1-yl)prop-1-yn-1-yl)-N-(tetrahydrofuran-3-yl)quinazolin-
4-amine;

3-((2-(4,4-difluoropiperidin-1-yl)-6-methoxy-7-(3-(pyrroli-
din-1-yl)prop-1-yn-1-yl)quinazolin-4-yl)amino)tetrahy-
drothiophene 1,1-dioxide;

2-((2-(4,4-difluoropiperidin-1-yl)-6-methoxy-7-(3-(pyrroli-
din-1-yl)prop-1-yn-1-yl)quinazolin-4-yl)amino)tetrahy-
drothiophene 1,1-dioxide;

N-(2-(4,4-difluoropiperidin-1-yl)-6-methoxy-7-(3-(pyrroli-
din-1-yl)prop-1-yn-1-yl)quinazolin-4-yl)methanesulfona-
mide;

1-(2-(4,4-difluoropiperidin-1-yl)-6-methoxy-7-(3-(pyrroli-
din-1-yl)prop-1-yn-1-yl)quinazolin-4-yl)-3-methylurea;

1-(2-(4,4-difluoropiperidin-1-yl)-6-methoxy-7-(3-(pyrroli-
din-1-yl)prop-1-yn-1-yl)quinazolin-4-yl)piperidin-2-
amine;

1-(2-(4,4-difluoropiperidin-1-yl)-6-methoxy-7-(3-(pyrroli-
din-1-yl)prop-1-yn-1-yl)quinazolin-4-yl)piperidin-3-
amine;

2-(4,4-difluoropiperidin-1-yl)-N-(1-isopropylpiperidin-4-
yl)-6-methoxy-7-(3-(pyrrolidin-1-yl)propoxy)quinazolin-
4-amine;

2-cyclohexyl-N-(1-isopropylpiperidin-4-yl)-6-methoxy-7-
(3-(pyrrolidin-1-yl)propoxy)quinazolin-4-amine;

N-(1-cyclohexylpiperidin-4-yl)-2-(4-isopropyl-1,4-diazepan-1-yl)-6-methoxy-7-(3-(piperidin-1-yl)propoxy)quinazolin-4-amine;

N-(1-isopropylpiperidin-4-yl)-6-methoxy-2-(4-methyl-1,4-diazepan-1-yl)-7-(3-(piperidin-1-yl)propoxy)quinazolin-4-amine;

N-(1-isopropylpiperidin-4-yl)-6-methoxy-2-morpholino-7-(3-(pyrrolidin-1-yl)propoxy)quinazolin-4-amine;

4-(4-((1-cyclopropylpiperidin-4-yl)amino)-6-methoxy-7-(3-(pyrrolidin-1-yl)propoxy)quinazolin-2-yl)thiomorpholine 1,1-dioxide;

N-(1-benzylpiperidin-4-yl)-2-(4-isopropyl-1,4-diazepan-1-yl)-6,7-dimethoxyquinazolin-4-amine;

6-methoxy-2-(4-methyl-1,4-diazepan-1-yl)-N-(1-methylpiperidin-4-yl)-7-(3-(pyrrolidin-1-yl)prop-1-yn-1-yl)quinazolin-4-amine;

7-((5-aminopentyl)oxy)-N4-(1-(5-aminopentyl)piperidin-4-yl)-N2-(3-(dimethylamino)propyl)-6-methoxyquinazoline-2,4-diamine;

N2-hexyl-6,7-dimethoxy-N4-(1-methylpiperidin-4-yl)quinazoline-2,4-diamine;

2-(4-(cyclohexylmethyl)-1,4-diazepan-1-yl)-N-(1-isopropylpiperidin-4-yl)-6-methoxy-7-(3-(pyrrolidin-1-yl)propoxy)quinazolin-4-amine;

N-(1-isopropylpiperidin-4-yl)-6-methoxy-2-(4-phenyl-1,4-diazepan-1-yl)-7-(3-(pyrrolidin-1-yl)propoxy)quinazolin-4-amine;

2-(4-benzyl-1,4-diazepan-1-yl)-N-(1-isopropylpiperidin-4-yl)-6-methoxy-7-(3-(pyrrolidin-1-yl)propoxy)quinazolin-4-amine;

N-(1-isopropylpiperidin-4-yl)-6-methoxy-2-(piperidin-1-yl)-7-(3-(pyrrolidin-1-yl)propoxy)quinazolin-4-amine;

2-(azepan-1-yl)-N-(1-isopropylpiperidin-4-yl)-6-methoxy-7-(3-(pyrrolidin-1-yl)propoxy)quinazolin-4-amine;

N-(1-isopropylpiperidin-4-yl)-6-methoxy-7-(3-(pyrrolidin-1-yl)propoxy)-2-(tetrahydro-2H-pyran-4-yl)quinazolin-4-amine;

N-(1-isopropylpiperidin-4-yl)-6-methoxy-2-morpholino-7-(3-(pyrrolidin-1-yl)propoxy)quinazolin-4-amine;

4-(4-((1-cyclopropylpiperidin-4-yl)amino)-6-methoxy-7-(3-(pyrrolidin-1-yl)propoxy)quinazolin-2-yl)thiomorpholine 1,1-dioxide;

N-(1-isopropylpiperidin-4-yl)-6-methoxy-7-(3-(pyrrolidin-1-yl)propoxy)-2-(3,3,4,4-tetrafluoropyrrolidin-1-yl)quinazolin-4-amine;

2-cyclohexyl-N-(1-isopropylpiperidin-4-yl)-6-methoxy-7-(3-(pyrrolidin-1-yl)propoxy)quinazolin-4-amine;

7-(3-(4,4-difluoropiperidin-1-yl)propoxy)-N-(1-isopropylpiperidin-4-yl)-6-methoxy-2-(tetrahydro-2H-pyran-4-yl)quinazolin-4-amine;

2-(azepan-1-yl)-N-(1-isopropylpiperidin-4-yl)-6-methoxy-7-(3-(piperidin-1-yl)propoxy)quinazolin-4-amine;

N-(1-isopropylpiperidin-4-yl)-6-methoxy-2-(4-methyl-1,4-diazepan-1-yl)-7-(3-(piperidin-1-yl)propoxy)quinazolin-4-amine;

2-(4-isopropyl-1,4-diazepan-1-yl)-N-(1-isopropylpiperidin-4-yl)-6-methoxy-7-(3-(piperidin-1-yl)propoxy)quinazolin-4-amine;

N-(1-cyclopropylpiperidin-4-yl)-2-(4,4-difluoropiperidin-1-yl)-6-methoxy-7-(3-(pyrrolidin-1-yl)propoxy)quinazolin-4-amine;

4-(4-((1-isopropylpiperidin-4-yl)amino)-6-methoxy-7-(3-(pyrrolidin-1-yl)propoxy)quinazolin-2-yl)thiomorpholine 1,1-dioxide;

N-(1-(cyclohexylmethyl)piperidin-4-yl)-2-(4-isopropyl-1,4-diazepan-1-yl)-6-methoxy-7-(3-(piperidin-1-yl)propoxy)quinazolin-4-amine;

N-(1-cyclohexylpiperidin-4-yl)-2-(4-isopropyl-1,4-diazepan-1-yl)-6-methoxy-7-(3-(piperidin-1-yl)propoxy)quinazolin-4-amine;

N-(1-cyclohexylpiperidin-4-yl)-6-methoxy-2-(4-methyl-1,4-diazepan-1-yl)-7-(3-(piperidin-1-yl)propoxy)quinazolin-4-amine;

6-methoxy-2-(4-methyl-1,4-diazepan-1-yl)-N-(1-methylpiperidin-4-yl)-7-(3-(piperidin-1-yl)propoxy)quinazolin-4-amine;

6-methoxy-2-(4-methyl-1,4-diazepan-1-yl)-N-(1-methylpiperidin-4-yl)-7-(3-morpholinopropoxy)quinazolin-4-amine;

6-methoxy-2-(4-methyl-1,4-diazepan-1-yl)-N-(1-methylpiperidin-4-yl)-7-(3-(pyrrolidin-1-yl)propoxy)quinazolin-4-amine;

7-(2-(dimethylamino)ethoxy)-6-methoxy-2-(4-methyl-1,4-diazepan-1-yl)-N-(1-methylpiperidin-4-yl)quinazolin-4-amine;

7-(3-(dimethylamino)propoxy)-6-methoxy-2-(4-methyl-1,4-diazepan-1-yl)-N-(1-methylpiperidin-4-yl)quinazolin-4-amine;

6-methoxy-2-(4-methyl-1,4-diazepan-1-yl)-N-(1-methylpiperidin-4-yl)-7-(3-(pyrrolidin-1-yl)propoxy)quinazolin-4-amine;

7-(4-(dimethylamino)butoxy)-6-methoxy-2-(4-methyl-1,4-diazepan-1-yl)-N-(1-methylpiperidin-4-yl)quinazolin-4-amine;

7-((5-(dimethylamino)pentyl)oxy)-6-methoxy-2-(4-methyl-1,4-diazepan-1-yl)-N-(1-methylpiperidin-4-yl)quinazolin-4-amine;

7-((6-(dimethylamino)hexyl)oxy)-6-methoxy-2-(4-methyl-1,4-diazepan-1-yl)-N-(1-methylpiperidin-4-yl)quinazolin-4-amine;

1-(6,7-dimethoxy-2-(pyrrolidin-1-yl)quinazolin-4-yl)piperidin-2-amine;

1-(6-methoxy-2-(4-methyl-1,4-diazepan-1-yl)-7-(3-(pyrrolidin-1-yl)propoxy)quinazolin-4-yl)piperidin-2-amine;

1-(6-methoxy-2-(pyrrolidin-1-yl)-7-(3-(pyrrolidin-1-yl)propoxy)quinazolin-4-yl)piperidin-2-amine;

1-(6-methoxy-2-(pyrrolidin-1-yl)-7-(3-(pyrrolidin-1-yl)prop-1-yn-1-yl)quinazolin-4-yl)piperidin-2-amine;

1-(2-(1H-imidazol-1-yl)-6-methoxy-7-(3-(pyrrolidin-1-yl)propoxy)quinazolin-4-yl)piperidin-2-amine;

1-(2-(4,4-difluoropiperidin-1-yl)-6-methoxy-7-(3-(pyrrolidin-1-yl)propoxy)quinazolin-4-yl)piperidin-2-amine;

1-(6-methoxy-7-(3-(piperidin-1-yl)propoxy)-2-(pyrrolidin-1-yl)quinazolin-4-yl)piperidin-2-amine;

1-(2-(azetidin-1-yl)-7-(3-(dimethylamino)propoxy)-6-methoxyquinazolin-4-yl)piperidin-2-amine;

1-(6-methoxy-2-(pyrrolidin-1-yl)-7-(3-(pyrrolidin-1-yl)propoxy)quinazolin-4-yl)piperidin-2-ol;

1-(6-methoxy-7-(3-(piperidin-1-yl)propoxy)-2-(pyrrolidin-1-yl)quinazolin-4-yl)piperidin-2-ol;

1-(6,7-dimethoxy-2-(pyrrolidin-1-yl)quinazolin-4-yl)piperidin-2-ol;

1-(6-methoxy-2-(4-methyl-1,4-diazepan-1-yl)-7-(3-(pyrrolidin-1-yl)propoxy)quinazolin-4-yl)piperidin-2-ol;

1-(6-methoxy-2-(1H-pyrazol-1-yl)-7-(3-(pyrrolidin-1-yl)propoxy)quinazolin-4-yl)piperidin-2-ol;

1-(6-methoxy-2-(pyrrolidin-1-yl)-7-(3-(pyrrolidin-1-yl)prop-1-yn-1-yl)quinazolin-4-yl)piperidin-2-ol;

1-(2-(4,4-difluoropiperidin-1-yl)-6-methoxy-7-(3-(pyrrolidin-1-yl)propoxy)quinazolin-4-yl)piperidin-2-ol;

1-(2-(azetidin-1-yl)-7-(3-(dimethylamino)propoxy)-6-methoxyquinazolin-4-yl)piperidin-2-ol;

2-((2-(4,4-difluoropiperidin-1-yl)-6-methoxy-7-(3-(pyrrolidin-1-yl)propoxy)quinazolin-4-yl)amino)acetamide;

2-(4,4-difluoropiperidin-1-yl)-N-(1-isopropylpiperidin-4-yl)-6-methoxy-7-(3-(pyrrolidin-1-yl)propoxy)quinazolin-4-amine;
2-cyclohexyl-N-(1-isopropylpiperidin-4-yl)-6-methoxy-7-(3-(piperidin-1-yl)propoxy)quinazolin-4-amine;
2-cyclohexyl-7-(2-(2-(dimethylamino)ethoxy)ethoxy)-N-(1-isopropylpiperidin-4-yl)-6-methoxyquinazolin-4-amine;
2-cyclohexyl-7-(3-(4,4-difluoropiperidin-1-yl)propoxy)-N-(1-isopropylpiperidin-4-yl)-6-methoxyquinazolin-4-amine;
N-(1-isopropylpiperidin-4-yl)-6-methoxy-2-(4-methyl-1,4-diazepan-1-yl)-7-(3-(pyrrolidin-1-yl)propoxy)quinazolin-4-amine;
2-(4-ethyl-1,4-diazepan-1-yl)-N-(1-isopropylpiperidin-4-yl)-6-methoxy-7-(3-(pyrrolidin-1-yl)propoxy)quinazolin-4-amine;
2-(4-isopropyl-1,4-diazepan-1-yl)-N-(1-isopropylpiperidin-4-yl)-6-methoxy-7-(3-(pyrrolidin-1-yl)propoxy)quinazolin-4-amine;
2-(4-cyclohexyl-1,4-diazepan-1-yl)-N-(1-isopropylpiperidin-4-yl)-6-methoxy-7-(3-(pyrrolidin-1-yl)propoxy)quinazolin-4-amine;
6-methoxy-2-(4-methyl-1,4-diazepan-1-yl)-7-(3-(methylamino)propoxy)-N-(1-methylpiperidin-4-yl)quinazolin-4-amine;
7-(3-(diethylamino)propoxy)-6-methoxy-2-(4-methyl-1,4-diazepan-1-yl)-N-(1-methylpiperidin-4-yl)quinazolin-4-amine;
6-methoxy-7-(3-(methyl(propyl)amino)propoxy)-2-(4-methyl-1,4-diazepan-1-yl)-N-(1-methylpiperidin-4-yl)quinazolin-4-amine;
6-methoxy-2-(4-methyl-1,4-diazepan-1-yl)-7-((5-methylhexyl)oxy)-N-(1-methylpiperidin-4-yl)quinazolin-4-amine;
6-methoxy-7-(4-methoxybutoxy)-2-(4-methyl-1,4-diazepan-1-yl)-N-(1-methylpiperidin-4-yl)quinazolin-4-amine;
tert-butyl (4-((6-methoxy-2-(4-methyl-1,4-diazepan-1-yl)-4-((1-methylpiperidin-4-yl)amino)quinazolin-7-yl)oxy)butyl)carbamate;
7-(4-aminobutoxy)-6-methoxy-2-(4-methyl-1,4-diazepan-1-yl)-N-(1-methylpiperidin-4-yl)quinazolin-4-amine;
5-((6-methoxy-2-(4-methyl-1,4-diazepan-1-yl)-4-((1-methylpiperidin-4-yl)amino)quinazolin-7-yl)oxy)pentanamide;
7-(2-(2-(dimethylamino)ethoxy)ethoxy)-6-methoxy-2-(4-methyl-1,4-diazepan-1-yl)-N-(1-methylpiperidin-4-yl)quinazolin-4-amine;
6-methoxy-2-(4-methyl-1,4-diazepan-1-yl)-N-(1-methylpiperidin-4-yl)-7-(2-(2-(pyrrolidin-1-yl)ethoxy)ethoxy)quinazolin-4-amine;
N1-(2-((6-methoxy-2-(4-methyl-1,4-diazepan-1-yl)-4-((1-methylpiperidin-4-yl)amino)quinazolin-7-yl)oxy)ethyl)-N1,N2,N2-trimethylethane-1,2-diamine;
6-methoxy-2-(4-methyl-1,4-diazepan-1-yl)-N-(1-methylpiperidin-4-yl)-7-(piperidin-3-ylmethoxy)quinazolin-4-amine;
2-(4-ethyl-1,4-diazepan-1-yl)-N-(1-isopropylpiperidin-4-yl)-6-methoxy-7-(3-(piperidin-1-yl)propoxy)quinazolin-4-amine; and
4-(4-((1-cyclopropylpiperidin-4-yl)amino)-6-methoxy-7-(3-(pyrrolidin-1-yl)propoxy)quinazolin-2-yl)thiomorpholine 1,1-dioxide.

In some embodiments, Formula (I) does not include one or more of the following compounds: 2-(4,4-difluoropiperidin-1-yl)-N-(1-isopropylpiperidin-4-yl)-6-methoxy-7-(3-(pyrrolidin-1-yl)propoxy)quinazolin-4-amine; 2-cyclohexyl-N-(1-isopropylpiperidin-4-yl)-6-methoxy-7-(3-(pyrrolidin-1-yl)propoxy)quinazolin-4-amine; N-(1-cyclohexylpiperidin-4-yl)-2-(4-isopropyl-1,4-diazepan-1-yl)-6-methoxy-7-(3-(piperidin-1-yl)propoxy)quinazolin-4-amine; N-(1-isopropylpiperidin-4-yl)-6-methoxy-2-(4-methyl-1,4-diazepan-1-yl)-7-(3-(piperidin-1-yl)propoxy)quinazolin-4-amine; N-(1-isopropylpiperidin-4-yl)-6-methoxy-2-morpholino-7-(3-(pyrrolidin-1-yl)propoxy)quinazolin-4-amine; 4-(4-((1-cyclopropylpiperidin-4-yl)amino)-6-methoxy-7-(3-(pyrrolidin-1-yl)propoxy)quinazolin-2-yl)thiomorpholine 1,1-dioxide; 2-cyclohexyl-N-(1-isopropylpiperidin-4-yl)-7-methoxy-8-(3-(pyrrolidin-1-yl)propoxy)-3H-benzo[e][1,4]diazepin-5-amine; 6-methoxy-2-(5-methylfuran-2-yl)-N-((1-methylpiperidin-4-yl)methyl)-7-(3-(pyrrolidin-1-yl)propoxy)quinolin-4-amine; 5'-methoxy-6'-(3-(pyrrolidin-1-yl)propoxy)spiro[cyclobutane-1,3 '-indol]-2'-amine; N-(1-benzylpiperidin-4-yl)-2-(4-isopropyl-1,4-diazepan-1-yl)-6,7-dimethoxyquinazolin-4-amine; 6-methoxy-2-(4-methyl-1,4-diazepan-1-yl)-N-(1-methylpiperidin-4-yl)-7-(3-(pyrrolidin-1-yl)prop-1-yn-1-yl)quinazolin-4-amine; 7-((5-aminopentyl)oxy)-N4-(1-(5-aminopentyl)piperidin-4-yl)-N2-(3-(dimethylamino)propyl)-6-methoxyquinazoline-2,4-diamine; 6-methoxy-2-(5-methylfuran-2-yl)-N-(1-methylpiperidin-4-yl)-7-(3-(pyrrolidin-1-yl)propoxy)quinolin-4-amine; 6-methoxy-2-(5-methyl-1H-pyrrol-2-yl)-N-(1-methylpiperidin-4-yl)-7-(3-(pyrrolidin-1-yl)propoxy)quinolin-4-amine; N2-hexyl-6,7-dimethoxy-N4-(1-methylpiperidin-4-yl)quinazoline-2,4-diamine; 2-(4-(cyclohexylmethyl)-1,4-diazepan-1-yl)-N-(1-isopropylpiperidin-4-yl)-6-methoxy-7-(3-(pyrrolidin-1-yl)propoxy)quinazolin-4-amine; N-(1-isopropylpiperidin-4-yl)-6-methoxy-2-(4-phenyl-1,4-diazepan-1-yl)-7-(3-(pyrrolidin-1-yl)propoxy)quinazolin-4-amine; 2-(4-benzyl-1,4-diazepan-1-yl)-N-(1-isopropylpiperidin-4-yl)-6-methoxy-7-(3-(pyrrolidin-1-yl)propoxy)quinazolin-4-amine; N-(1-isopropylpiperidin-4-yl)-6-methoxy-2-(piperidin-1-yl)-7-(3-(pyrrolidin-1-yl)propoxy)quinazolin-4-amine; 2-(azepan-1-yl)-N-(1-isopropylpiperidin-4-yl)-6-methoxy-7-(3-(pyrrolidin-1-yl)propoxy)quinazolin-4-amine; N-(1-isopropylpiperidin-4-yl)-6-methoxy-7-(3-(pyrrolidin-1-yl)propoxy)-2-(tetrahydro-2H-pyran-4-yl)quinazolin-4-amine; N-(1-isopropylpiperidin-4-yl)-6-methoxy-2-morpholino-7-(3-(pyrrolidin-1-yl)propoxy)quinazolin-4-amine; 4-(4-((1-cyclopropylpiperidin-4-yl)amino)-6-methoxy-7-(3-(pyrrolidin-1-yl)propoxy)quinazolin-2-yl)thiomorpholine 1,1-dioxide; N-(1-isopropylpiperidin-4-yl)-6-methoxy-7-(3-(pyrrolidin-1-yl)propoxy)-2-(3,3,4,4-tetrafluoropyrrolidin-1-yl)quinazolin-4-amine; 2-cyclohexyl-N-(1-isopropylpiperidin-4-yl)-6-methoxy-7-(3-(pyrrolidin-1-yl)propoxy)quinazolin-4-amine; 7-(3-(4,4-difluoropiperidin-1-yl)propoxy)-N-(1-isopropylpiperidin-4-yl)-6-methoxy-2-(tetrahydro-2H-pyran-4-yl)quinazolin-4-amine; 2-(azepan-1-yl)-N-(1-isopropylpiperidin-4-yl)-6-methoxy-7-(3-(piperidin-1-yl)propoxy)quinazolin-4-amine; N-(1-isopropylpiperidin-4-yl)-6-methoxy-2-(4-methyl-1,4-diazepan-1-yl)-7-(3-(piperidin-1-yl)propoxy)quinazolin-4-amine; 2-(4-isopropyl-1,4-diazepan-1-yl)-N-(1-isopropylpiperidin-4-yl)-6-methoxy-7-(3-(piperidin-1-yl)propoxy)quinazolin-4-amine; N-(1-cyclopropylpiperidin-4-yl)-2-(4,4-difluoropiperidin-1-yl)-6-methoxy-7-(3-(pyrrolidin-1-yl)propoxy)quinazolin-4-amine; 4-(4-((1-isopropylpiperidin-4-yl)amino)-6-methoxy-7-(3-(pyrrolidin-1-yl)propoxy)quinazolin-2-yl)thiomorpholine 1,1-dioxide; N-(1-(cyclohexylmethyl)piperidin-4-yl)-2-(4-isopropyl-1,4- diazepan-1-yl)-6-methoxy-7-(3-(piperidin-1-yl)propoxy)quinazolin-4-amine; N-(1-cyclohexylpiperidin-4-yl)-2-(4-isopropyl-1,4-diazepan-1-yl)-6-methoxy-7-(3-(piperidin-1-yl)propoxy)quinazolin-4-amine; N-(1-cyclohexylpiperidin-4-yl)-6-methoxy-2-(4-methyl-1,4-diazepan-1-yl)-7-(3-(piperidin-1-yl)propoxy)quinazolin-4-amine; 6-methoxy-2-(4-methyl-1,4-diazepan-1-yl)-N-(1-methylpiperidin-4-yl)-7-(3-(piperidin-1-yl)propoxy)quinazolin-4-amine; 6-methoxy-2-(4-methyl-1,4-diazepan-1-yl)-N-(1-methylpiperidin-4-yl)-7-(3-morpholinopropoxy)quinazolin-4-amine; 6-methoxy-2-(4-methyl-1,4-diazepan-1-yl)-N-(1-methylpiperidin-4-yl)-7-(3-(pyrrolidin-1-yl)propoxy)quinazolin-4-amine; 7-(2-(dimethylamino)ethoxy)-6-methoxy-2-(4-methyl-1,4-diazepan-1-yl)-N-(1-methylpiperidin-4-yl)quinazolin-4-amine; 7-(3-(dimethylamino)propoxy)-6-methoxy-2-(4-methyl-1,4-diazepan-1-yl)-N-(1-methylpiperidin-4-yl)quinazolin-4-amine; 6-methoxy-2-(4-methyl-1,4-diazepan-1-yl)-N-(1-methylpiperidin-4-yl)-7-(3-(pyrrolidin-1-yl)propoxy)quinazolin-4-amine; 7-(4-(dimethylamino)butoxy)-6-methoxy-2-(4-methyl-1,4-diazepan-1-yl)-N-(1-methylpiperidin-4-yl)quinazolin-4-amine; 7-((5-(dimethylamino)pentyl)oxy)-6-methoxy-2-(4-methyl-1,4-diazepan-1-yl)-N-(1-methylpiperidin-4-yl)quinazolin-4-amine; 7-((6-(dimethylamino)hexyl)oxy)-6-methoxy-2-(4-methyl-1,4-diazepan-1-yl)-N-(1-methylpiperidin-4-yl)quinazolin-4-amine; 2-(4,4-difluoropiperidin-1-yl)-N-(1-isopropylpiperidin-4-yl)-6-methoxy-7-(3-(pyrrolidin-1-yl)propoxy)quinazolin-4-amine; 2-cyclohexyl-N-(1-isopropylpiperidin-4-yl)-6-methoxy-7-(3-(piperidin-1-yl)propoxy)quinazolin-4-amine; 2-cyclohexyl-7-(2-(2-(dimethylamino)ethoxy)ethoxy)-N-(1-isopropylpiperidin-4-yl)-6-methoxyquinazolin-4-amine; 2-cyclohexyl-7-(3-(4,4-difluoropiperidin-1-yl)propoxy)-N-(1-isopropylpiperidin-4-yl)-6-methoxyquinazolin-4-amine; N-(1-isopropylpiperidin-4-yl)-6-methoxy-2-(4-methyl-1,4-diazepan-1-yl)-7-(3-(pyrrolidin-1-yl)propoxy)quinazolin-4-amine; 2-(4-ethyl-1,4-diazepan-1-yl)-N-(1-isopropylpiperidin-4-yl)-6-methoxy-7-(3-(pyrrolidin-1-yl)propoxy)quinazolin-4-amine; 2-(4-isopropyl-1,4-diazepan-1-yl)-N-(1-isopropylpiperidin-4-yl)-6-methoxy-7-(3-(pyrrolidin-1-yl)propoxy)quinazolin-4-amine; 2-(4-cyclohexyl-1,4-diazepan-1-yl)-N-(1-isopropylpiperidin-4-yl)-6-methoxy-7-(3-(pyrrolidin-1-yl)propoxy)quinazolin-4-amine; 6-methoxy-2-(4-methyl-1,4-diazepan-1-yl)-7-(3-(methylamino)propoxy)-N-(1-methylpiperidin-4-yl)quinazolin-4-amine; 7-(3-(diethylamino)propoxy)-6-methoxy-2-(4-methyl-1,4-diazepan-1-yl)-N-(1-methylpiperidin-4-yl)quinazolin-4-amine; 6-methoxy-7-(3-(methyl(propyl)amino)propoxy)-2-(4-methyl-1,4-diazepan-1-yl)-N-(1-methylpiperidin-4-yl)quinazolin-4-amine; 6-methoxy-2-(4-methyl-1,4-diazepan-1-yl)-7-((5-methylhexyl)oxy)-N-(1-methylpiperidin-4-yl)quinazolin-4-amine; 6-methoxy-7-(4-methoxybutoxy)-2-(4-methyl-1,4-diazepan-1-yl)-N-(1-methylpiperidin-4-yl)quinazolin-4-amine; tert-butyl (4-((6-methoxy-2-(4-methyl-1,4-diazepan-1-yl)-4-((1-methylpiperidin-4-yl)amino)quinazolin-7-yl)oxy)butyl)carbamate; 7-(4-aminobutoxy)-6-methoxy-2-(4-methyl-1,4-diazepan-1-yl)-N-(1-methylpiperidin-4-yl)quinazolin-4-amine; 5-((6-methoxy-2-(4-methyl-1,4-diazepan-1-yl)-4-((1-methylpiperidin-4-yl)amino)quinazolin-7-yl)oxy)pentanamide; 7-(2-(2-(dimethylamino)ethoxy)ethoxy)-6-methoxy-2-(4-methyl-1,4-diazepan-1-yl)-N-(1-methylpiperidin-4-yl)quinazolin-4-amine; 6-methoxy-2-(4-methyl-1,4-diazepan-1-yl)-N-(1-methylpiperidin-4-yl)-7-(2-(2-(pyrrolidin-1-yl)ethoxy)ethoxy)quinazolin-4-amine; N1-(2-((6-methoxy-2-(4-methyl-1,4-diazepan-1-yl)-4-((1-methylpiperidin-4-yl)amino)quinazolin-7-yl)oxy)ethyl)-N1,N2,N2-trimethylethane-1,2-diamine; 6-methoxy-2-(4-methyl-1,4-diazepan-1-yl)-N-(1-methylpiperidin-4-yl)-7-(piperidin-3-ylmethoxy)quinazolin-4-amine; 2-(4-ethyl-1,4-diazepan-1-yl)-N-(1-isopropylpiperidin-4-yl)-6-methoxy-7-(3-(piperidin-1-yl)propoxy)quinazolin-4-amine; 4-(4-((1-cyclopropylpiperidin-4-yl)amino)-6-methoxy-7-(3-(pyrrolidin-1-yl)propoxy)quinazolin-2-yl)thiomorpholine 1,1-dioxide; and/or the compound of Formula (I) lacks the particular combination of 2-, 4-, 6- and 7-quinazolinyl substituents of any of the forgoing compounds in this paragraph. To demonstrate an instance where Formula (I) lacks the particular combination of 2-, 4-, 6- and 7-quinazolinyl substituents of structures provided in this paragraph, 2-(4-ethyl-1,4-diazepan-1-yl)-N-(1-isopropylpiperidin-4-yl)-6-methoxy-7-(3-(piperidin-1-yl)propoxy)quinazolin-4-amine is used for illustration. To illustrate, in several embodiments, where the 4-position substituent is N-(1-isopropylpiperidin-4-yl)-amine, a structure of Formula (I) may lack one or more of (4-ethyl-1,4-diazepan-1-yl) at the 2-position, methoxy at the 6-position, and/or (3-(piperidin-1-yl)propoxy) at the 7-position. As further illustration, in several embodiments, where the 2-position substituent is (4-ethyl-1,4-diazepan-1-yl), a structure of Formula (I) may lack one or more of N-(1-isopropylpiperidin-4-yl)-amine at the 4-position, methoxy at the 6-position, and/or (3-(piperidin-1-yl)propoxy) at the 7-position. As further illustration, in several embodiments, where the 6-position substituent is methoxy, a structure of Formula (I) may lack one or more of N-(1-isopropylpiperidin-4-yl)-amine at the 4-position, (4-ethyl-1,4-diazepan-1-yl) at the 2-position, and/or (3-(piperidin-1-yl)propoxy) at the 7-position. Finally, in several embodiments, where the 7-position substituent is (3-(piperidin-1-yl)propoxy), a structure of Formula (I) may lack one or more of N-(1-isopropylpiperidin-4-yl)-amine at the 4-position, (4-ethyl-1,4-diazepan-1-yl) at the 2-position, and/or methoxy at the 6-position.

Compounds of Formula (Ia)

Several embodiments pertain to quinazolinyl compounds having the structure of Formula (Ia) (or a stereoisomer, tautomer or pharmaceutically acceptable salt thereof):

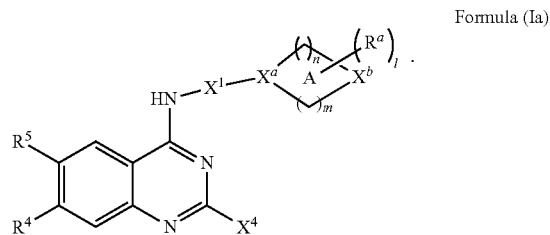

Formula (Ia)

In several embodiments, the variable groups of Formula (Ia) are as disclosed elsewhere herein. For example, in several embodiments, the variables for Formula (Ia) are as disclosed elsewhere herein for Formula (Ia) or as disclosed elsewhere herein for any other formula having variables shared with those in Formula (Ia) (e.g., Formula (I), etc.). In several embodiments, the variables of the "A" ring are as disclosed elsewhere herein. In several embodiments, ring "A" is a cycloalkyl ring or a heterocyclyl ring. In several embodiments, $X^a$ is selected from the group consisting of CH and N. In several embodiments, m is independently an integer selected from 0, 1, 2, and 3. In several embodiments, n is independently an integer selected from 0, 1, 2, and 3. In several embodiments, $X^b$ is selected from the group consisting of $CH_2$, $NR^b$, O, and $SO_2$. In several embodiments, $R^a$ is optionally present and can be provided at any position of the "A" ring by replacing one or more —H of any carbon or nitrogen atom present within the "A" ring.

In several embodiments, $R^a$ is selected from the group consisting of amino, —OH, and optionally substituted $C_1$-$C_6$ alkyl. The optional substituents may be selected from substituents as disclosed elsewhere herein.

In several embodiments, $R^b$ is selected from the group consisting of hydrogen, optionally substituted $C_1$-$C_6$ alkyl, and C-carboxy. The optional substituents may be selected from substituents as disclosed elsewhere herein.

In several embodiments, n is 1 and m is 3.

In several embodiments, $X^b$ is O or $SO_2$.

In several embodiments, the structure of Formula (I) is represented by a structure of Formula Ia. For example, in several embodiments, $X^3$ of Formula (I) may be represented by the following:

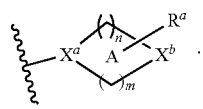

Compounds of Formula (Ib)

Several embodiments pertain to quinazolinyl compounds having the structure of Formula (Ib) (or a stereoisomer, tautomer or pharmaceutically acceptable salt thereof):

Formula (Ib)

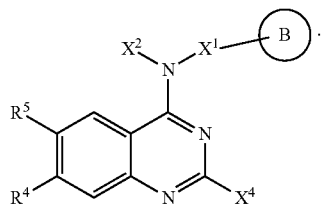

In several embodiments, the variable groups of Formula (Ib) are as disclosed elsewhere herein. For example, in several embodiments, the variables for Formula (Ib) are as disclosed elsewhere herein for Formula (Ib) or as disclosed elsewhere herein for any other formula having variables shared with those in Formula (Ib) (e.g., Formula (I), etc.).

In several embodiments, $X^3$ is represented by ring "B".

In several embodiments, the "B" ring is an unsaturated ring selected from the group consisting of optionally substituted cyclopentenyl, optionally substituted phenyl, optionally substituted furyl, optionally substituted thienyl, optionally substituted pyrrolyl, optionally substituted oxazolyl, optionally substituted thiazolyl, optionally substituted imidazolyl, optionally substituted benzimidazolyl, optionally substituted pyrazolyl, optionally substituted isoxazolyl, optionally substituted triazolyl, optionally substituted pyridinyl, optionally substituted pyridazinyl, optionally substituted pyrimidinyl, optionally substituted pyrazinyl, optionally substituted indolyl, optionally substituted isoindolyl, and optionally substituted benzothienyl.

In several embodiments, the "B" ring is selected from any of the following:

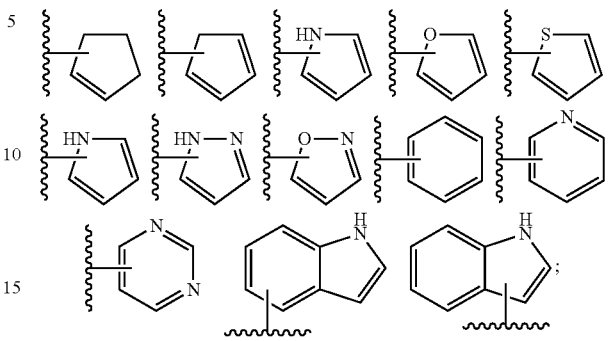

any one of which may be optionally substituted by replacing one or more —H atoms of any carbon or nitrogen atom present on the "B" ring.

In several embodiments, the optional substitutions of the "B" ring are selected from one or more amino, —OH, optionally substituted $C_1$-$C_6$ alkyl, and halogen. In several embodiments, the optional substituents may be selected from substituents as disclosed elsewhere herein.

In several embodiments, the structure of Formula (I) is represented by a structure of Formula (Ib). For example, in several embodiments, $X^3$ of Formula (I) may be represented by the following:

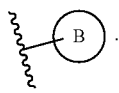

Compounds of Formula (Ic)

Several embodiments pertain to quinazolinyl compounds having the structure of Formula (Ic) (or a stereoisomer, tautomer or pharmaceutically acceptable salt thereof):

Formula (Ic)

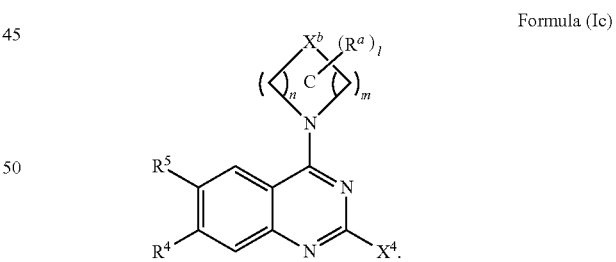

In several embodiments, the variable groups of Formula (Ic) are as disclosed elsewhere herein. For example, in several embodiments, the variables for Formula (Ic) are as disclosed elsewhere herein for Formula (Ic) or as disclosed elsewhere herein for any other formula having variables shared with those in Formula (Ic) (e.g., Formula (I), etc.).

In several embodiments, m is independently an integer selected from 0, 1, 2, and 3.

In several embodiments, n is independently an integer selected from 0, 1, 2, and 3.

In several embodiments, $X^b$ is selected from the group consisting of $CH_2$, $NR^b$, O, and $SO_2$.

In several embodiments, $R^a$ is optionally present and can be provided at any position of the "C" ring by replacing one or more —H of any carbon or nitrogen atom present within the "C" ring.

In several embodiments, $R^a$ is selected from the group consisting of amino, N-amido, —OH, optionally substituted $C_1$-$C_6$ alkyl. In several embodiments, the optional substituents may be selected from substituents as disclosed elsewhere herein.

In several embodiments, $R^b$ is selected from $C_1$-$C_6$ alkyl and C-carboxy.

In several embodiments, the structure of Formula (I) is represented by a structure of Formula (Ic). For example, in several embodiments, $X^2$—N—$X^1$—$X^3$ of Formula (I) may be represented by the following:

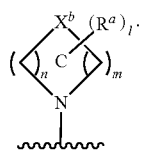

Compounds of Formula (Id)

Several embodiments pertain to quinazolinyl compounds having the structure of Formula (Id) (or a stereoisomer, tautomer or pharmaceutically acceptable salt thereof):

Formula (Id)

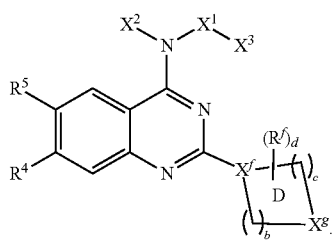

In several embodiments, the variable groups of Formula (Id) are as disclosed elsewhere herein. For example, in several embodiments, the variables for Formula (Id) are as disclosed elsewhere herein for Formula (Id) or as disclosed elsewhere herein for any other formula having variables shared with those in Formula (Id) (e.g., Formula (I), etc.).

In several embodiments, wherein ring "D" is a cycloalkyl ring or a heterocyclyl ring. In several embodiments, $X^f$ is selected from the group consisting of CH and N. In several embodiments, b is independently an integer selected from 0, 1, 2, 3, or 4. In several embodiments, c is independently an integer selected from 0, 1, 2, 3, or 4. In several embodiments, $X^g$ is selected from the group consisting of $CH_2$, $NR^h$, O, and $SO_2$. In several embodiments, $R^f$ is optionally present and each instance can be provided at any position of the "D" ring by replacing one or more —H of any carbon or nitrogen atom present within the "D" ring. In several embodiments, d is an integer selected from 0, 1, 2, 3, or 4.

In several embodiments, $R^f$ is selected from the group consisting of halogen, amino, —OH, optionally substituted $C_1$-$C_6$ alkyl. In several embodiments, the optional substituents may be selected from substituents as disclosed elsewhere herein.

In several embodiments, $R^h$ is selected from the group consisting of hydrogen, optionally substituted $C_1$-$C_6$ alkyl, and C-carboxy. In several embodiments, the optional substituents may be selected from substituents as disclosed elsewhere herein.

In several embodiments, n is 1 and m is 2. In several embodiments, n is 1 and m is 3. In several embodiments, n is 2 and m is 2. In several embodiments, n is 0.

In several embodiments, the structure of Formula (I) is represented by a structure of Formula (Id). For example, in several embodiments, $X^4$ of Formula (I) may be represented by the following:

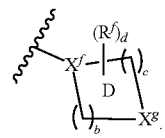

Compounds of Formula (Ie)

Several embodiments pertain to quinazolinyl compounds having the structure of Formula (Ie) (or a stereoisomer, tautomer or pharmaceutically acceptable salt thereof):

Formula (Ie)

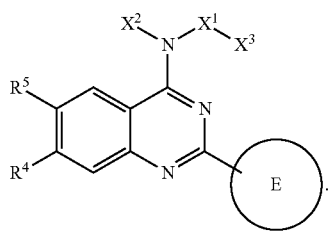

In several embodiments, the variable groups of Formula (Ie) are as disclosed elsewhere herein. For example, in several embodiments, the variables for Formula (Ie) are as disclosed elsewhere herein for Formula (Ie) or as disclosed elsewhere herein for any other formula having variables shared with those in Formula (Ie) (e.g., Formula (I), etc.).

In several embodiments, $X^4$ is represented by ring "E". In several embodiments, the "E" ring is an unsaturated ring selected from the group consisting of optionally substituted cyclopentenyl, optionally substituted phenyl, optionally substituted furyl, optionally substituted thienyl, optionally substituted pyrrolyl, optionally substituted oxazolyl, optionally substituted thiazolyl, optionally substituted imidazolyl, optionally substituted benzimidazolyl, optionally substituted pyrazolyl, optionally substituted isoxazolyl, optionally substituted triazolyl, optionally substituted pyridinyl, optionally substituted pyridazinyl, optionally substituted pyrimidinyl, optionally substituted pyrazinyl, optionally substituted indolyl, optionally substituted isoindolyl, and optionally substituted benzothienyl.

In several embodiments, the "E" ring is selected from any of the following:

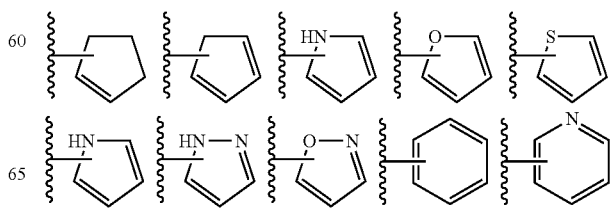

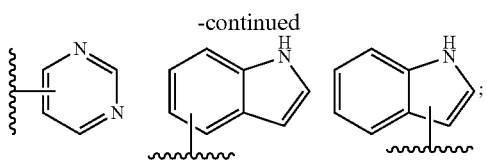

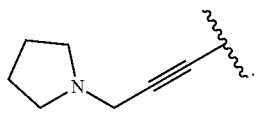

Compounds of Formula (Ig)

Several embodiments pertain to quinazolinyl compounds having the structure of Formula (Ig) (or a stereoisomer, tautomer or pharmaceutically acceptable salt thereof):

Formula (Ig)

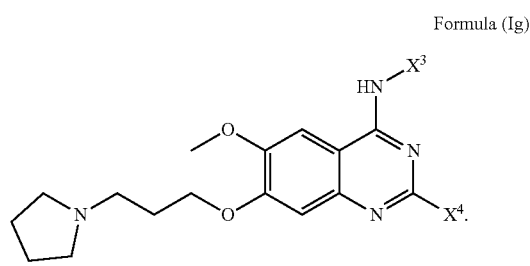

any one of which may be optionally substituted by replacing one or more —H atoms of any carbon or nitrogen atom present on the "E" ring. In several embodiments, when the E ring comprises one or more optional substitutions, the one or more optional substitutions may be independently selected from the group consisting of $C_1$-$C_3$ alkyl, halo, cyano, hydroxy, and $C_1$-$C_3$ alkoxy. In several embodiments, the optional substitutions of the "E" ring are selected from one or more of amino, —OH, optionally substituted $C_1$-$C_6$ alkyl, and halogen. In several embodiments, the optional substituents may be selected from substituents as disclosed elsewhere herein.

In several embodiments, the structure of Formula (I) is represented by a structure of Formula (Ie). For example, in several embodiments, $X^4$ of Formula (I) may be represented by the following:

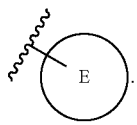

Compounds of Formula (If)

Several embodiments pertain to quinazolinyl compounds having the structure of Formula (If) (or a stereoisomer, tautomer or pharmaceutically acceptable salt thereof):

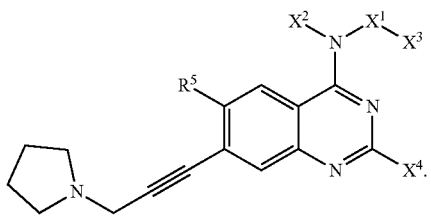

In several embodiments, the variable groups of Formula (If) are as disclosed elsewhere herein. For example, in several embodiments, the variables for Formula (If) are as disclosed elsewhere herein for Formula (If) or as disclosed elsewhere herein for any other formula having variables shared with those in Formula (If) (e.g., Formula (I)). In several embodiment, the pyrrolidinyl ring is optionally substituted. In several embodiments, when the pyrrolidinyl ring comprises one or more optional substitutions, the one or more optional substitutions may be independently selected from the group consisting of $C_1$-$C_3$ alkyl, halo, cyano, hydroxy, and $C_1$-$C_3$ alkoxy. In several embodiments, the structure of Formula (I) is represented by a structure of Formula (If). For example, in several embodiments, $R^4$ of Formula (I) may be represented by the following:

In several embodiments, the variable groups of Formula (Ig) are as disclosed elsewhere herein. For example, in several embodiments, the variables for Formula (Ig) are as disclosed elsewhere herein for Formula (Ig) or as disclosed elsewhere herein for any other formula having variables shared with those in Formula (Ig) (e.g., Formula (I), etc.). In several embodiment, the pyrrolidinyl ring is optionally substituted. In several embodiments, when the pyrrolidinyl ring comprises one or more optional substitutions, the one or more optional substitutions may be independently selected from the group consisting of $C_1$-$C_3$ alkyl, halo, cyano, hydroxy, and $C_1$-$C_3$ alkoxy.

In several embodiments, $X^3$ is as disclosed elsewhere herein. In several embodiments, $X^3$ is selected from the group consisting of optionally substituted 2-10 membered heteroalkyl, optionally substituted 3-10 membered heterocyclyl, or optionally substituted 5-10 membered heteroaryl. In several embodiments, $X^4$ is —CN or —$NR^2R^3$.

In several embodiments, the structure of Formula (I) is represented by a structure of Formula (Ig). For example, in several embodiments, $R^4$ of Formula (I) may be represented by the following:

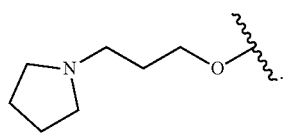 [SMILES: *OCCCN1CCCC1]

Compounds of Formula (Ih)

Several embodiments pertain to quinazolinyl compounds having the structure of Formula (Ih) (or a stereoisomer, tautomer or pharmaceutically acceptable salt thereof):

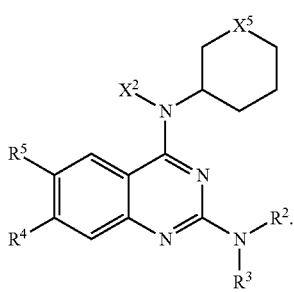

Formula (Ih)

In several embodiments, the variable groups of Formula (Ih) are as disclosed elsewhere herein. For example, in several embodiments, the variables for Formula (Ih) are as disclosed elsewhere herein for Formula (Ih) or as disclosed elsewhere herein for any other formula having variables shared with those in Formula (Ih) (e.g., Formula (I) etc.). In several embodiments, $X^5$ is oxygen or sulfonyl.

In several embodiments, the structure of Formula (I) is represented by a structure of Formula (If). For example, in several embodiments, $X^3$ of Formula (I) may be represented by the following:

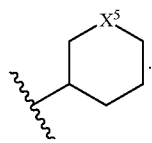

Compounds of Formula (Ij)

Several embodiments pertain to quinazolinyl compounds having the structure of Formula (Ij) (or a stereoisomer, tautomer or pharmaceutically acceptable salt thereof):

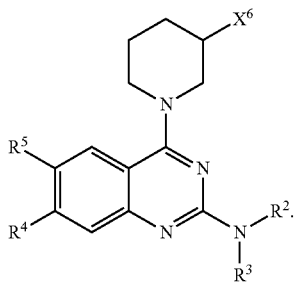

In several embodiments, the variable groups of Formula (Ih) are as disclosed elsewhere herein. For example, in several embodiments, the variables for Formula (Ih) are as disclosed elsewhere herein for Formula (Ih) or as disclosed elsewhere herein for any other formula having variables shared with those in Formula (Ih) (e.g., Formula (I)).

In several embodiments, $X^6$ is selected from the group consisting of hydrogen, —NH$_2$, —OH, and N-amide.

In several embodiments, the structure of Formula (I) is represented by a structure of Formula (Ij). For example, in several embodiments, $X^2$—N—$X^1$—$X^3$ of Formula (I) may be represented by the following:

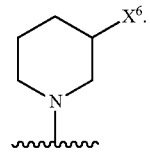

Compounds of Formula (Ik)

Several embodiments pertain to quinazolinyl compounds having the structure of Formula (Ik) (or a stereoisomer, tautomer or pharmaceutically acceptable salt thereof):

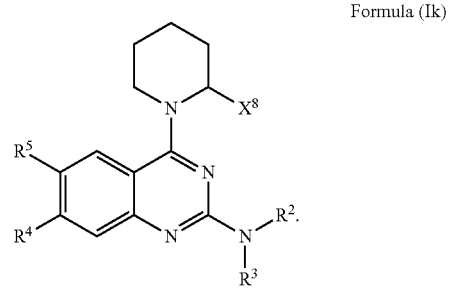

Formula (Ik)

In several embodiments, the variable groups of Formula (Ik) are as disclosed elsewhere herein. For example, in several embodiments, the variables for Formula (Ik) are as disclosed elsewhere herein for Formula (Ik) or as disclosed elsewhere herein for any other formula having variables shared with those in Formula (Ik). In several embodiments, $X^8$ is selected from the group consisting of hydrogen, —NH$_2$, —OH, and N-amide.

In several embodiments, the structure of Formula (I) is represented by a structure of Formula (Ik). For example, in several embodiments, $X^2$—N—$X^1$—$X^3$ of Formula (I) may be represented by the following:

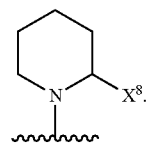

Compounds of Formula (II)

Several embodiments pertain to quinazolinyl compounds having the structure of Formula (II) (or a stereoisomer, tautomer or pharmaceutically acceptable salt thereof):

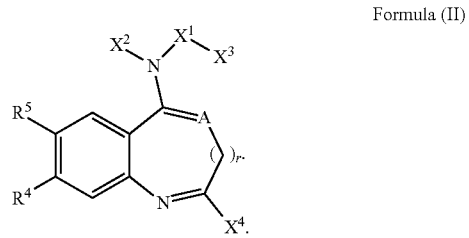

Formula (II)

In several embodiments, the variable groups of Formula (II) are as disclosed elsewhere herein. For example, in several embodiments, the variables for Formula (II) are as disclosed elsewhere herein for Formula (II) or as disclosed elsewhere herein for any other formula having variables shared with those in Formula (II) (e.g., Formula (I), etc.). In several embodiments, r is an integer equal to 0 or 1. In several embodiments, A is selected from the group consisting of N, CH, or $CH_2$. In several embodiments, $X^3$ is optionally substituted. In several embodiments, when $X^3$ is comprises one or more optional substitutions, the one or more optional substitutions may be independently selected from the group consisting of $C_1$-$C_3$ alkyl, halo, cyano, hydroxy, $C_1$-$C_3$ alkoxy, and 3 to 6 membered carbocyclyl.

The compound of Formula (II) may be selected from

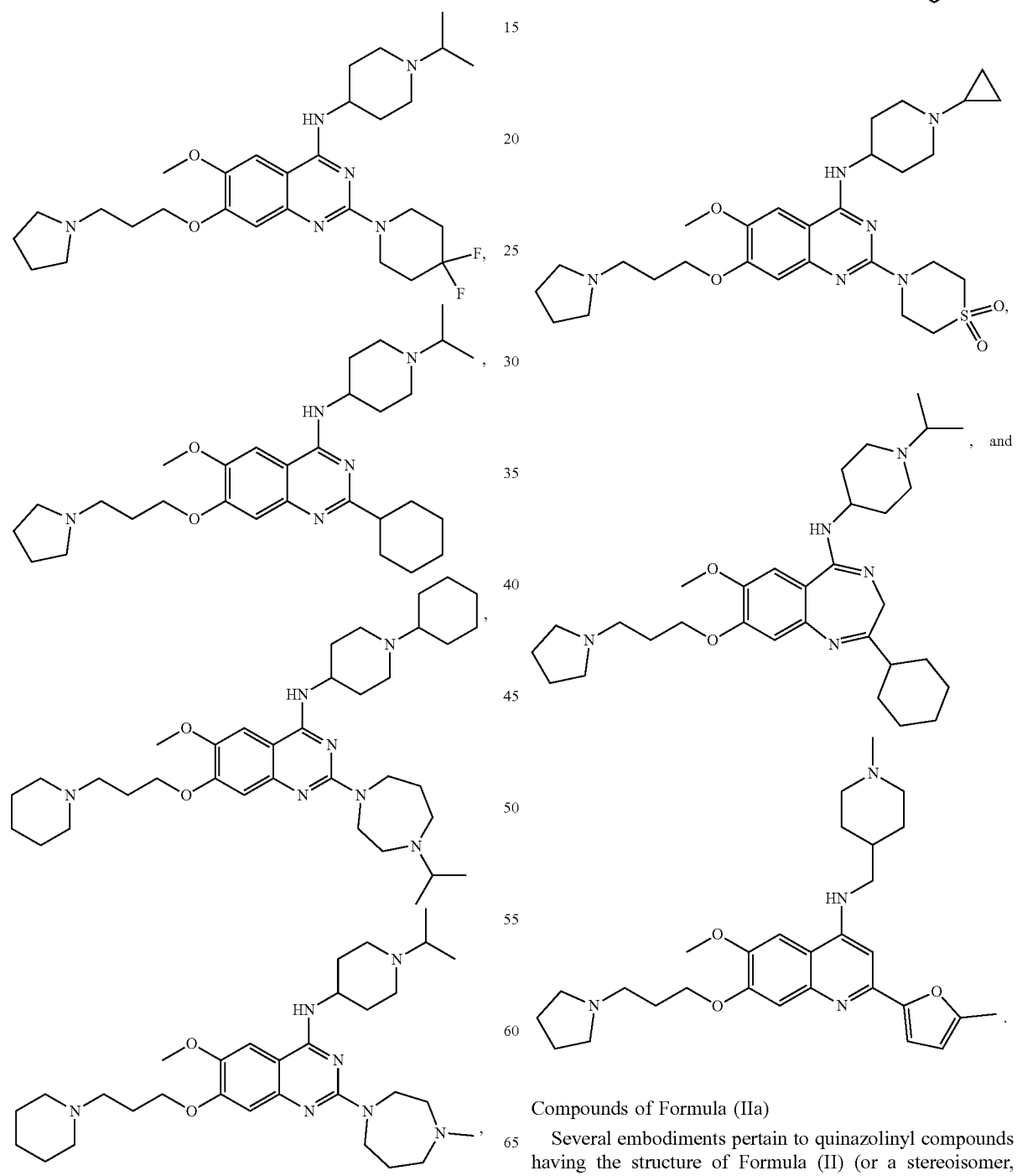

Compounds of Formula (IIa)

Several embodiments pertain to quinazolinyl compounds having the structure of Formula (II) (or a stereoisomer, tautomer or pharmaceutically acceptable salt thereof):

Formula (IIa)

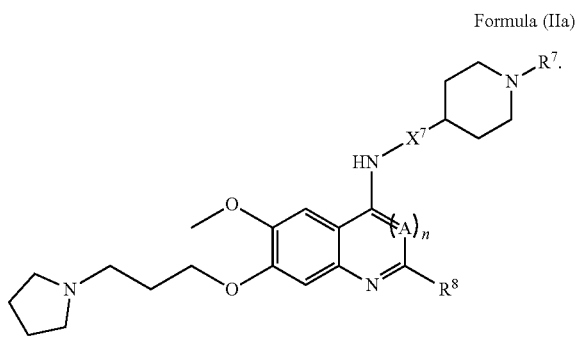

In several embodiments, the variable groups of Formula (IIa) are as disclosed elsewhere herein. For example, in several embodiments, the variables for Formula (IIa) are as disclosed elsewhere herein for Formula (IIa) or as disclosed elsewhere herein for any other formula having variables shared with those in Formula (IIa). In several embodiments, $X^7$ is $CH_2$ or a covalent bond. In several embodiments, $R^7$ is $C_1$-$C_6$ alkyl or 3-6 membered carbocyclyl. In several embodiments, $R^8$ is selected from the group consisting of cyclohexyl, 5-6 membered heteroaryl optionally substituted with methyl, or 5-7 membered heterocyclyl optionally substituted with fluoro, oxo, or $C_1$-$C_6$ alkyl. In several embodiments, A is selected from the group consisting of N, CH, or $CH_2$. In several embodiments, n is independently an integer selected from 0, 1, and 2.

Additional Compounds

In several embodiments, the compound may be

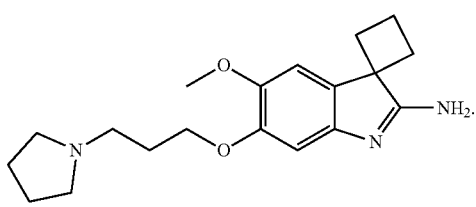 [SMILES: COc1cc2c(cc1OCCCN1CCCC1)N=C(N)C21CCC1]

Several embodiments relate to a pharmaceutical composition comprising a therapeutically effective amount of a compound as described herein and a pharmaceutically acceptable excipient.

Methods of Treating

Several embodiments relate to treating a subject using a compound or pharmaceutical composition as described herein. In several embodiments, the compound is a compound of Formula (I), (Ia), (Ib), (Ic), (Id), (Ie), (If), (Ig), (Ih), (Ij), (Ik), (II), (IIa).

In several embodiments, a method of treating a subject having a gastrointestinal and/or an autoimmune disorder is provided. In several embodiments, the method comprises acquiring knowledge of a gastrointestinal and/or an autoimmune disorder in said subject. In several embodiments, the method comprises administering to the subject (e.g., one having a gastrointestinal and/or an autoimmune disorder) an effective amount of a compound as disclosed herein.

Several embodiments relate to treating a gastrointestinal and/or an autoimmune disorder, comprising administering to a subject in need thereof a compound or pharmaceutical composition as described herein.

In several embodiments, the autoimmune disorder is selected from the group consisting of inflammatory bowel disease (IBD), Ulcerative Colitis, Crohn's disease, systemic lupus erythematosus, psoriasis, rheumatoid arthritis, type 1 diabetes, multiple sclerosis, celiac disease, Graft versus host disease (GVHD), Sjogren syndrome, Graves' Disease, Hashimoto's Thyroiditis, Autoimmune Hepatitis, Behcet's Disease, atopic dermatitis, Castleman disease, Allergic Rhinitis, Eczema, Dressler's Syndrome, Eosinophilic esophagitis, Fibromyalgia, Guillain-Barre Syndrome, Juvenile arthritis, Kawasaki disease, Mooren's ulcer, mixed connective tissue disease, Parry Romberg syndrome, primary biliary cirrhosis, primary sclerosing cholangitis, psoriatic arthritis, sarcoidosis, scleroderma, undifferentiated connective tissue disease, uveitis, vasculitis and vitiligo. In several embodiments, to have a therapeutic potential in ulcerative colitis and Crohn's disease it is important to be effective in both induction of healing and suppression of inflammation. In several embodiments, surprisingly, the compounds and compositions disclosed herein induce healing and/or suppress inflammation in the gastrointestinal tract (e.g., in the small or large intestine). In several embodiments, the compounds or compositions reduce markers for inflammation, inflammatory bowel disease (IBD), Ulcerative Colitis, and/or Crohn's disease, including one or more of Ccl2, Ccl3, Ccl7, Ccl9, Csf3, Csf3r, Cxcl1, Cxcl2, Cxcl3, Cxcl5, Il1a, Il1b, Il1r2, Il11, Il13ra2, Il6, Mmp3, Osm, Osmr, Ptgs2, Stc1, and/or Tnfrsf11b.

Several embodiments relate to a method of treating G9a-mediated inflammation, the method comprising administering a compound or pharmaceutical composition as disclosed herein to a patient in need of treatment. Several embodiments relate to a method of inhibiting the G9a protein, the method comprising administering a compound or pharmaceutical composition as disclosed herein to a patient in need of treatment.

Several embodiments relate to a method of reducing inflammation by reducing the level of pro-inflammatory cytokines (e.g., CXCL2, CXCL3, S100A8.9, IL6) family and/or metalloproteinases (MMP3, MMP13), the method comprising administering a compound or pharmaceutical composition as disclosed herein to a patient in need of treatment.

Several embodiments, as disclosed elsewhere herein, pertain to treating a gastrointestinal and/or an autoimmune disease (e.g., IBD, ulcerative colitis, Crohn's disease, etc.) and/or inflammation. In several embodiments, the method involves administering a compound (e.g., in an effective amount) or composition as disclosed herein to a patient. In several embodiments, the compound induces T regulatory cells production and/or activity. In several embodiments, the compound does not substantially affect IL17 protein levels.

In several embodiments, a method of ameliorating and/or treating disruptive effects of the combined exposure of intestinal epithelial cells to TNFα and/or IFNγ is provided, the method comprising administering a compound or pharmaceutical composition as disclosed herein to a patient in need of treatment. In several embodiments, a method of decreasing levels of electrical resistance in intestinal epithelial cells is provided, the method comprising administering a compound or pharmaceutical composition as disclosed herein to a patient in need of treatment. In several embodiments, a method of reversed cytokine induced barrier damage in the intestine (e.g., in intestinal epithelial cells) is provided, the method comprising administering a compound or pharmaceutical composition as disclosed herein to a patient in need of treatment.

Several embodiments relate to a method of improving gut health, the method comprising administering a compound or pharmaceutical composition as disclosed herein to a patient in need of treatment. In several embodiments, the microbiome of the gut is improved (e.g., intestine, including the small or large intestine). In several embodiments, levels of beneficial bacteria are increased and levels of harmful bacteria are decreased. In several embodiments, administering a compound or pharmaceutical composition as disclosed herein results in one or more of a decrease of the Firmicutes phylum (e.g., *Megasphaera massiliensis*, etc.), an increase of Bacteroidetes (e.g., one or more of *Bacteroides* (B) *caecimuris, B. sartorii, B. thetaiotaomicron, Duncaniella muris, Bacteroides mediterraneensis, Prevotella copri*, etc.), an increase of Proteobacteria (e.g., etc.), and an increase of Verrucomicrobia phyla (e.g., *Akkermansia muciniphila*, etc.). In several embodiments, administering a compound or pharmaceutical composition as disclosed herein results in one or more of an increase of the Firmicutes phylum (e.g., *Megasphaera massiliensis*, etc.). In several embodiments, a compound that results in an increase of the Proteobacteria (e.g., *Sutterella wadsworthensis*, etc.) is predicted to be a potential candidate. In several embodiments, administration of a compound as disclosed herein induces a greater abundance of bacteria associated with anti-inflammatory effects.

In several embodiments, a method for diagnosing the likelihood a drug candidate is effective for the treatment of inflammatory bowel disease (IBD), Ulcerative Colitis, and/or Crohn's disease is provided. In several embodiments, the method involves testing a panel of bacteria and predicting the efficacy of that drug candidate. In several embodiments, a drug that results in levels of beneficial bacteria that are increased and/or levels of harmful bacteria that are decreased is predicted to be potential candidates for treatment of IBD, Ulcerative Colitis, and/or Crohn's disease. In several embodiments, a compound that results in one or more of a decrease of the Firmicutes phylum (e.g., *Megasphaera massiliensis*, etc.), an increase (e.g., enrichment) of Bacteroidetes (e.g., one or more of *Bacteroides* (B) *caecimuris, B. sartorii, B. thetaiotaomicron, Duncaniella muris, Bacteroides mediterraneensis, Prevotella copri*, etc.), an increase of Proteobacteria (e.g., *Sutterella wadsworthensis*, etc.), and/or an increase of Verrucomicrobia phyla (e.g., *Akkermansia muciniphila*, etc.) is predicted to be a potential drug candidate. In several embodiments, a compound that results in an increase of the Firmicutes phylum (e.g., *Megasphaera massiliensis*, etc.) is predicted to be a potential candidate. In several embodiments, the diagnostic test is provided in a kit. In several embodiments, the kit includes instructions for use. In several embodiments, the kit comprises culture medium.

Several embodiments relate to a method of reducing infiltration of the lamina propria by CD4+ T cells, neutrophils, and/or macrophages (and/or other proinflammatory cells), the method comprising administering a compound or pharmaceutical composition as disclosed herein to a patient in need of treatment. Several embodiments relate to a method of reducing infiltration of the lamina propria with CD4+ T cells, neutrophils, and/or macrophages in a patient suffering from an inflammatory disease, comprising administering a compound or pharmaceutical composition as disclosed herein to a patient in need of treatment. In several embodiments, the inflammatory disease IBD, Crohn's disease, or colitis. Several embodiments relate to a method of reducing the severity and/or eliminating diarrhea, weight loss, and rectal prolapse associated with a gastrointestinal disorder (e.g., Crohn's disease, IBD, etc.), the method comprising administering a compound or pharmaceutical composition as disclosed herein to a patient in need of treatment.

In several embodiments, a method of treating a subject having a cancer is provided. In several embodiments, the method comprises acquiring knowledge of a presence of cancer in said subject. In several embodiments, the method comprises administering to the subject an effective amount of a compound as disclosed herein.

Several embodiments relate to a method of treating a cancer, comprising administering to a subject in need thereof a compound as described herein, or a pharmaceutical composition as described herein.

In several embodiments, the cancer is selected from the group consisting of colorectal (e.g., colon or rectal), gastric, stomach, esophageal, liver, pancreatic, breast, prostate, bladder, renal, ovarian, lung, melanoma, and multiple myeloma. In several embodiments, the compound causes activation and/or upregulation of genes active in inducing a tumor reduction response, including p53 signaling pathway genes (e.g., KEGG), HDAC deacetylate histones associated genes (e.g., REAC), TF Factor genes (e.g., p53 and/or p63). In several embodiments, the compound causes inhibition and/or downregulation of genes associated with increased cancer growth, including cell cycle genes (KEGG), genes associated with DNA replication (KEGG), E2F-1 genes, and/or and E2F-4 genes. In several embodiments, genes implicated and/or down regulated by a compound as disclosed herein may include one or more of CCNE2, E2F2, CCNA2, BUB1, CDC25C, CDKN2C, CCNB2, ORC1, PLK1, CDC20, TTK, ESPL1, CDK1, BUB1B, CDC45, MAD2L1, E2F1, CCNB1, MCM5, CDC6, PKMYT1, ORC6, MCM6, MCM7, MCM2, MCM4, RBL1, CDC25A, SKP2, MCM3, CDC7, WEE1, PTTG1, CHEK2, DBF4, CHEK1, and/or SMC1A. In several embodiments, genes implicated and/or down regulated by a compound as disclosed herein may include one or more of TP5313, ZMAT3, SERPINE1, CDKN1A, MDM2, PMAIP1, RRM2B, FAS, SERPINB5, SESN2, GADD45A, SESN1, CD82, THBS1, and/or CCND1.

In several embodiments, the compounds as disclosed herein have surprisingly and/or beneficially improved efficacy and/or pharmaceutical properties. In several embodiments, a compound as disclosed herein has unexpectedly improved permeability as measured using PAMPA testing. In several embodiments, a compound as disclosed herein has a permeability (in $P_e$) of equal to or greater than about: $1\times10^{-8}$, $2.5\times10^{-8}$, $5\times10^{-8}$, $7.5\times10^{-8}$, $1\times10^{-7}$, $5\times10^{-7}$, $1\times10^{-6}$, $5\times10^{-6}$, $1\times10^{-5}$, or ranges including and/or spanning the aforementioned values.

In several embodiments, the half-life of a compound as disclosed herein in a subject is equal to or at least about: 45 minutes, 55 minutes, 60 minutes, 2 hours, 3 hours, 5 hours, or ranges including and/or spanning the aforementioned values.

In several embodiments, the inhibition of cytochrome P450 is low for compound or pharmaceutical composition as disclosed herein to a patient in need of treatment.

Administration and Pharmaceutical Compositions

In several embodiments, the compounds are administered at a therapeutically effective dosage. In several embodiments, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarily, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

In several embodiments, the oral formulation comprises dimethylacetamide (DMA). In several embodiments, the oral formulation comprises DMA in an amount (in wt %) of equal or less than about: 1%, 5%, 7.5%, 10%, 15%, or ranges including and/or spanning the aforementioned values. In several embodiments, the oral formulation comprises propylene glycol (PG). In several embodiments, the oral formulation comprises PG in an amount (in wt %) of equal or less than about: 10%, 20%, 25%, 30%, 35%, or ranges including and/or spanning the aforementioned values. In several embodiments, the oral formulation comprises polyethylene glycol (PEG). In several embodiments, the oral formulation comprises PEG in an amount (in wt %) of equal or less than about: 15%, 25%, 30%, 35%, 40%, or ranges including and/or spanning the aforementioned values. In several embodiments, the oral formulation comprises water. In several embodiments, the oral formulation comprises water in an amount (in wt %) of equal or less than about: 15%, 25%, 30%, 35%, 40%, or ranges including and/or spanning the aforementioned values.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives (e.g., active pharmaceutical agents). In some embodiments, the composition may comprise one or more quinazolinyl compounds as disclosed elsewhere herein.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

The compounds and compositions described herein, if desired, may be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compounds and compositions described herein are formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01 to 99.99 wt % of a compound of the present technology based on the total formulation, with the balance being one or more suitable pharmaceutical excipients. Preferably, the compound is present at a level of about 1 to 80 wt %. Representative pharmaceutical formulations are described below.

The compounds and compositions described herein may be administered orally, intraperitoneally (i.p), intravenous (i.v.) and as an enema.

The pharmaceutical compositions described herein may take the form of solutions, suspensions, emulsion, tablets, pills, capsules, powders, patches, gels, creams, ointments, sustained-release formulations. The pharmaceutical compositions described herein may further comprise pharmaceutical excipients including, but not limited to, wetting agents, emulsifying agents, and pH adjusting agents.

In several embodiments, intravenous formulations of the compounds described herein comprise water, saline solutions, aqueous dextrose and glycerol solutions as carriers.

In several embodiments, parenteral formulations of the compounds described herein may be suspensions prepared as oily injection suspensions or aqueous injection suspensions. For oily suspension injections, suitable lipophilic solvents or vehicles may be used, including fatty oils such as sesame oil, or synthetic fatty acids, esters such as ethyl oleate, triglycerides or liposomes.

In several embodiments, for transmucosal or transdermal formulations, penetrants (such as PEG) appropriate to the barrier to be permeated may be used.

In several embodiments, oral formulations of the compounds described herein may be formulated readily by combining the active compounds with pharmaceutically acceptable carriers and excipients. Such carriers enable the compounds of the present disclosure to be formulated as tablets, pills, capsules, liquids, gels, syrups, slurries, suspensions, and the like, for oral ingestion by a subject. Pharmacological preparations for oral use may be made using a solid excipient, optionally grinding the resulting mixture, and processing the mixture of granules, after adding suitable auxiliaries if desired, to obtain tablets. Suitable excipients are, in particular, fillers such as sugars, including lactose, sucrose, mannitol, or sorbitol; cellulose preparations such as, for example, maize starch, wheat starch, rice starch, potato starch, gelatin, methyl cellulose, hydroxypropylmethyl-cellulose and sodium carboxymethylcellulose.

In several embodiments, an enteric coating of could be used to prevent exposure of the compounds of the present disclosure to the gastric environment.

In several embodiments, pharmaceutical compositions of the compounds described herein that may be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally stabilizers.

Several embodiments comprise the compounds described herein encapsulated in soft capsules, in which the active compounds may be dissolved or suspended in suitable liquids, such as fatty oils, liquid paraffin, or liquid polyethylene glycols. In addition, stabilizers could be added.

In several embodiments, the dosage of a composition to be administered would depend on several factors including the subject being treated, the stage of the autoimmune disease, the route of administration, and the judgment of the prescribing clinician.

Intermediates for Synthesizing Quinazolinyl Compounds and Methods of Preparation Several embodiments pertain to methods of making quinazolinyl compounds and intermediates for making quinazolinyl compounds.

In several embodiments, the quinazolinyl compounds may be prepared in general by a two consecutive displacement synthetic (e.g., halogen displacement reactions). A first displacement is provided in the reaction scheme below (where an intermediate may have a structure as shown in Formula (IIIa) or (IIIb):

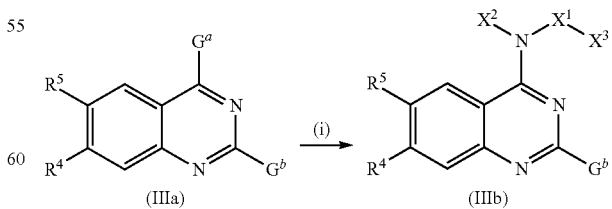

where $G^a$ is a substitutable group such as a halogen (e.g., Cl), where $G^b$ is a substitutable group such as a halogen (e.g., Cl), and the remainder of the variables are as provided elsewhere herein. In several embodiments, the conditions include providing an amine (e.g., HN(X²)X¹X³). In several embodiments, reaction (i) is performed under basic conditions (e.g., in the presence of an organic base such as diisopropylethylamine (DIPEA), triethylamine (TEA), etc.). In several embodiments, reaction (i) is performed in the presence of NaH. In several embodiments, reaction (i) is performed at room temperature. In several embodiments, reaction (i) is performed at elevated temperature. In several embodiments, reaction (i) is performed at a temperature of equal to or greater than about: 20° C., 30° C., 40° C., 50° C., 60° C., 70° C., 80° C., or ranges including or spanning the aforementioned values. In several embodiments, the HN(X²)X¹X³ is present in a stoichiometric equal amount or in excess (1-5 eq.). In several embodiments, the base is present in a stoichiometric equal amount or in excess (1-10 eq.). In several embodiments, a polar solvent is used (e.g., DMF, THF, MeOH, EtOH, iPrOH, 2-BuOH or combination).

In several embodiments, the second displacement is provided in the reaction scheme below: an intermediate may have a structure as shown in Formula (Ma) below:

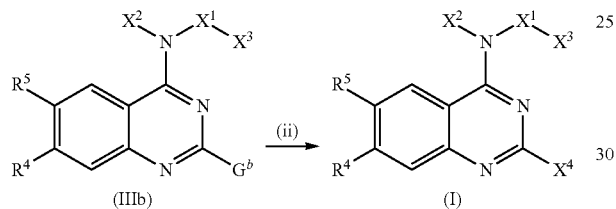

where the variables are as provided elsewhere herein. In several embodiments, the conditions include providing H—X⁴. In several embodiments, reaction (ii) is performed under basic conditions (e.g., in the presence of an organic base such as DIPEA, TEA, etc.). In several embodiments, reaction (ii) is performed in the presence of NaH. In several embodiments, reaction (ii) is performed at room temperature. In several embodiments, reaction (ii) is performed at elevated temperature. In several embodiments, reaction (i) is performed at a temperature of equal to or greater than about: 20° C., 30° C., 40° C., 50° C., 60° C., 70° C., 80° C., 100° C., 120° C., 140° C., or ranges including or spanning the aforementioned values. In several embodiments, the H—X⁴ is present in a stoichiometric equal amount or in excess (1-20 eq.). In several embodiments, the base is present in a stoichiometric equal amount or in excess (1-10 eq.). In several embodiments, a polar solvent is used (e.g., DMF, THF, MeOH, EtOH, iPrOH, 2-BuOH or combination). Alternatively, reaction (ii) may be performed in the presence of K₂CO₃ or Cs₂CO₃ (2-3 eq.), BINAP or Xantphos (0.1-0.4 eq.), Pd(OAc)₂, or Pd(PPh₃)₄ (0.1-0.25 eq.) at elevated temperature (e.g., 20° C., 30° C., 40° C., 50° C., 60° C., 70° C., 80° C., 100° C., 120° C., 140° C., or ranges including or spanning the aforementioned values).

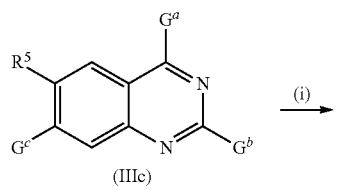

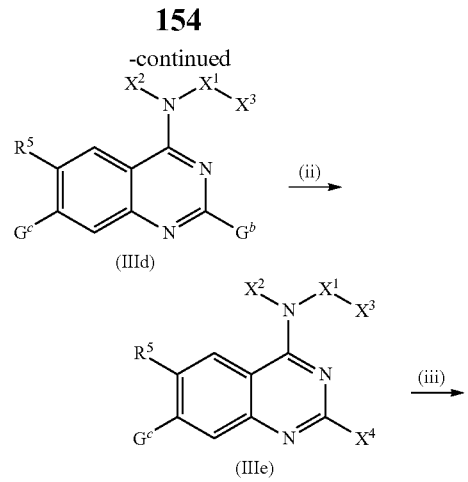

where $G^c$ is an alcohol protecting group (such as an OBz group) and the remaining variables are as provided elsewhere herein. In several embodiments, the structure of Formula (IIId) is the following structure:

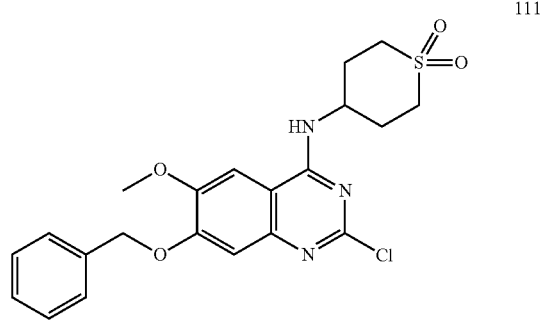 [SMILES: COc1cc2c(NC3CCS(=O)(=O)CC3)nc(Cl)nc2cc1OCc1ccccc1]

In several embodiments, the compound of Formula (IIIe) is deprotected to reveal the hydroxyl group at position 7 of the quinazolinyl ring using (as shown in Formula (IIIf)) using deprotecting conditions (such as hydrogenation conditions). In several embodiments, the deprotection is performed using a metal catalyst (e.g., Pd/c) in the presence of hydrogen and solvent (e.g., MeOH, EtOH, THF or dioxane). In several embodiments, the reaction is performed at room temperature. In several embodiments, the structure of Formula (IIIe) is the following structure:

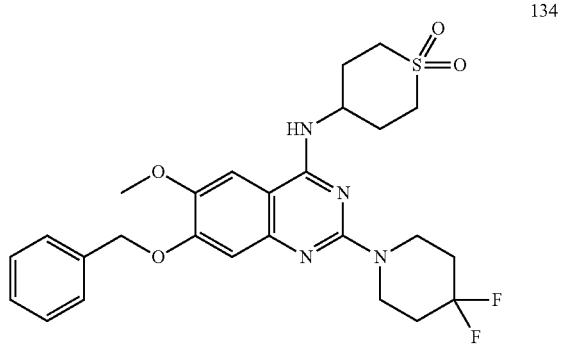 [SMILES: COc1cc2c(NC3CCS(=O)(=O)CC3)nc(N3CCC(F)(F)CC3)nc2cc1OCc1ccccc1]

In several embodiments, as shown in the following scheme, the hydroxyl group is converted to a leaving group.

In several embodiments, the leaving group (OLg) is a triflate (OTf⁻), a tosylate (OTs⁻), a mesylate (OMs⁻), or the like.

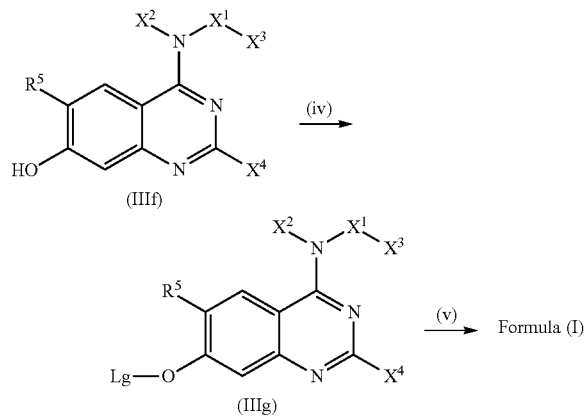

where the variables are as provided elsewhere herein (and OLg is OTf, OTs, OMs, etc.). In several embodiments, reaction (iv) is performed in the presence of a N-phenylbis sulfonamide (e.g., PhN(Tf)$_2$), a base (e.g., K$_2$CO$_3$), and solvent (e.g., THF) at room temperature. In several embodiments, the leaving group is removed in reaction (v) in the presence of H—R$_4$ (1-3 eq.), a metal catalyst (e.g., Pd(PPh$_3$)Cl$_2$ (0.1-0.25 eq.), CuI (1-2 eq.), Cs$_2$CO$_3$), and solvent (e.g., MeCN). Alternatively, the leaving group is removed in reaction (v) in the presence of boronic acid, H—R$_4$ (1-3 eq.), a metal catalyst (e.g., Pd(PPh$_3$)$_4$ (0.1-0.25 eq.)), and CsF$_2$, LiCl, and CuI, in the presence of solvent (e.g., THF). In several embodiments, reaction (v) is performed at a temperature of equal to or greater than about: 50° C., 60° C., 70° C., 80° C., 100° C., or ranges including or spanning the aforementioned values.

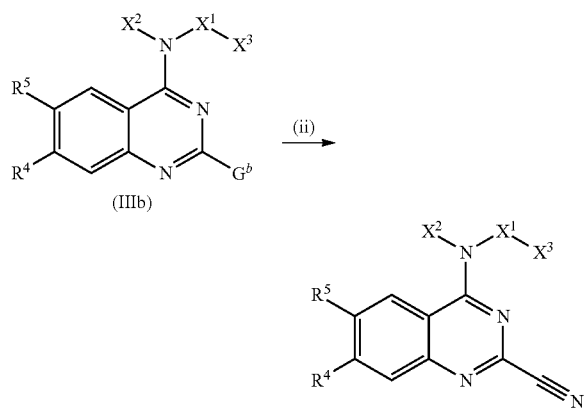

To prepare a compound where X$^4$ is nitrile, 1,4-diazabi-cyclo[2.2.2]octane (DABCO) may be used in the presence of NaCN and solvent (e.g., DMSO). In several embodiments, reaction (ii) is performed at a temperature of equal to or greater than about: 50° C., 60° C., 70° C., 80° C., 100° C., or ranges including or spanning the aforementioned values.

As will be readily understood by a person of ordinary skill in the art, in several embodiments, intermediate compounds are provided, such as those of formula (IIIa), (IIIb), (IIIc), (IIId), (IIIf), and (IIIg). In several embodiments, the intermediate compound is the following Formula (IIIg):

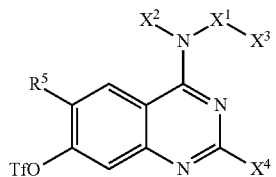

where —OLg is —OTf. In several embodiments, the structure of Formula (IIIg) is represented by the following:

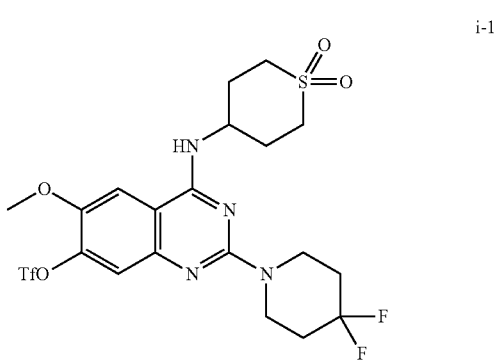 [SMILES: COc1cc2c(NC3CCS(=O)(=O)CC3)nc(N3CCC(F)(F)CC3)nc2cc1OS(=O)(=O)C(F)(F)F]

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, N.Y. (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

If the compounds of the present technology contain one or more chiral centers, such compounds can be prepared or isolated as pure stereoisomers, i.e., as individual enantiomers or d(l) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

It will be apparent to the skilled artisan that methods for preparing precursors and functionality related to the compounds claimed herein are generally described in the literature. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like. All the intermediate compounds of the present disclosure were used without further purification unless otherwise specified.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

Trademarks used herein are examples only and reflect illustrative materials used at the time of the present disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the present disclosure.

EXAMPLES

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. Changes therein and other uses which are encompassed within the spirit of the disclosure as defined by the scope of the claims will occur to those skilled in the art.

General Procedures

The following abbreviations have the indicated meanings:
ACN=Acetonitrile
DCM=dichloromethane
DIEA=N,N-Diisopropylethylamine
DIPEA=N,N-Diisopropylethylamine
DMF=N,N-dimethylformamide
DMP=Dess Martin Periodinane
DNs=dinitrosulfonyl
ESBL=extended-spectrum β-lactamase
EtOAc=ethyl acetate
EA=ethyl acetate
FCC=Flash Column Chromatography
HATU=2-(7-aza-1H-benzotriazole-1-yl)-1,1,3,3-tetramethyluronium hexafluorophosphate
MeCN=acetonitrile
NMR=nuclear magnetic resonance
PE=Petroleum Ether
Prep=preparatory
Py=pyridine
Sat.=saturated aqueous
TBDMSCl=tert-butyldimethylsilyl chloride
TBS=tert-butyldimethylsilyl
TFA=trifluoroacetic acid
THF=tetrahydrofuran
TLC=thin layer chromatography
TrtCl=Trityl chloride
Trt=Trityl Several compounds of the formulae disclosed herein (e.g., Formula (I), etc.) are prepared as described below. All reactions were carried out under an atmosphere of argon. Reagents and solvents were used from commercial sources without additional purification. Hydrogenation reactions were run under a balloon. Microwave reactions were performed using a CEM Discover SP microwave synthesizer. Sample purification was conducted on a Buchi Pureflash with ELSD purification system using pre-packed commercially available silica gel columns. Thin layer chromatography (TLC) was performed on aluminium plates using Merck Kiesegel 60 F254 (230-400 mesh) fluorescent treated silwhich were visualized under ultraviolet light (254 nm), or by staining with potassium permanganate or ninhydrin solution as appropriate. All Nuclear Magnetic Resonance (NMR) spectra were acquired on a Bruker Avance III HD 400 MHz NMR spectrometer; chemical shifts are reported in ppm (δ). HPLC/MS was performed on a Sciex 5500 Qtrap mass spectrometry coupled with Shidmazu Nexera X2 UHPLC using Phenomenex Luna C18 column (50×2.0 mm, 3 μm particle size) via following method: The gradient mobile phase A contains 0.1% formic acid in water and mobile phase B contains 0.1% formic acid in acetonitrile; A/B (95:5) from 0 to 0.9 minutes; to A/B (5:95) from 0.9 to 2.2 minutes; A/B (5:95) from 2.2 to 4.14 minutes; to A/B (95:5) from 4.14 to 4.20 minutes; A/B (95:5) from 4.2 to 6 minutes. The flow rate was 0.4 mL/min and the column temperature maintained at 35° C. and autosampler temperature at 4° C. Ion spray voltage, drying gas temperature, ion source gas 1, and ion source gas 2 settings were 4500V, 500° C., 35V, and 45V with ESI set in positive mode using full scan. All compound's purity was analyzed on an Agilent 1260 Infinity II Lab LC Series HPLC (1260 Quat pum, 1260 vial autosampler, ICC column oven, 1260 DAD WR detector). Samples were injected into Phenomenex Synergi Polar RP column (150×4.6 mm, 4 μm, 80 Å). The gradient mobile phase (A: water with 0.1% trifluoroacetic acid, B: acetonitrile with 0.1% trifluoroacetic acid; A/B (99:1) from 0 minute; to A/B (1:99) from 0 to 15 minutes; A/B (1:99) from 15 to 18 minutes; A/B (99:1) from 18 to 18.1 minutes; A/B (99:1) from 18.1 to 20 minutes) pumped at a flow rate of 1 mL/min. UV detector was set to 254 nm with column oven at 35° C. Injection volume was 10 μL, unless otherwise specified. All compounds that were evaluated in biological assays had ≥90% purity and animal studies had ≥95% purity.

pH Solubility

Saturated solutions of selected compounds were prepared at pH 1, 4, 6.5, and 7.4. The pH conditions selected are within the extremes of the normal physiological pH of the human gastrointestinal tract. Solubility testing of drug under different pH conditions was carried out by adding an excess amount of drug to each pH condition initiating with 1 mg/mL and then confirmed saturation by visual observation of undissolved material. The saturated solutions are continuously shaking at 6,000 rpm for 24 hours at room temperature. The saturated solutions were filtered through Millipore 0.22 um PVDF hydrophilic filters and subjected to HPLC to evaluate the solubility concentration of the test compound. Filtered saturated solutions were diluted with acetonitrile:water (50:50) within the calibration standard curve. A calibration curve of test compound contained seven (7) standards at concentrations 0.25, 0.5, 1.0, 5.0, 10, 25, 50 and 100 μg/mL were prepared in acetonitrile:water (50:50).

Compounds were measured in filtered saturated solution using an Agilent 1260 Infinity II Lab LC Series HPLC (1260 quat pump, 1260 vial autosampler, ICC column oven, 1260 DAD WR detector). The chromatographic separation was achieved by Phenomenex Synergi Polar RP column (150×4.6 mm, 4 μm, 80 Å). The mobile phase was gradient (A: water with 0.1% trifluoroacetic acid, B: acetonitrile with 0.1% trifluoroacetic acid; A/B (99:1) from 0 minute; to A/B (1:99) from 0 to 10 minutes; A/B (1:99) from 10 to 12 minutes; to A/B (99:1) from 12 to 12.1 minutes; A/B (99:1) from 12.1 to 13 minutes) pumped at a flow rate of 1 mL/min. The detection of the eluent was monitored at 254 nm. The column oven was set at 35° C. Injection volume was 10 μL, unless otherwise specified. Data acquisition and peak integrations were obtained by OpenLAB CDS Version 2.4 (Agilent) operating with Windows (Microsoft).

Formulation Stability 5 mg/mL of test compound was formulated with 10% Dimethylacetamide (DMA), 30% Propylene Glycol, 35% PEG-300, 25% water ($H_2O$). The formulation solution was stored at 4° C. and 25° C. The samples were retrieved at the following time points: 1 day, 3 days, 5 days, 7 days, 10 days and 14 days. The sample retrieved at each time point was examined visually observation of the physical state (texture and color) prior to sample preparation for analysis for physical stability. For chemical stability, the sample was diluted 1:250 dilution with acetonitrile (ACN) for potency analysis, and to 100 ug/mL final solution for impurity profile. The sample were prepared in triplication for potency analysis. The samples were then injected to HPLC for the determination of test compound concentration and its impurity profile. An Agilent 1260 Infinity II Lab LC Series HPLC system was used including 1260 Quat pump, 1260 vial autosampler, ICC column oven, and 1260 DAD WR detector. The chromatographic separation was achieved by a Phenomenex Synergi Polar RP column (150×4.6 mm, 4 μm, 80 Å). The flow rate was 1 mL/min and the detection was set at 254 nm. Injection volume was 10 uL, otherwise specified. The mobile phase consisted A, water with 0.1% trifluoroacetic acid and B, acetonitrile with 0.1% trifluoroacetic acid. For potency analysis, the gradient was A/B (99:1) from 0 minute; to A/B (1:99) from 0 to 10 minutes; A/B (1:99) from 10 to 12 minutes; to A/B (99:1) from 12 to 12.1 minutes; A/B (99:1) from 12.1 to 13 minutes. For impurity profile, the gradient was A/B (99:1) from 0 minute; to A/B (1:99) from 0 to 15 minutes; A/B (1:99) from 15 to 18 minutes; to A/B (99:1) from 18 to 18.1 minutes; A/B (99:1) from 18.1 to 20 minutes. Data acquisition and peak integrations were obtained by OpenLAB CDS Version 2.4 (Agilent) operating with Windows (Microsoft).

Microsome Stability

In each of the species (human, rat, mouse) of liver matrix to be tested, a working concentration of 2 μg/mL was prepared of each test article from the 0.5 mg/mL DMSO stock solution by adding 3 μL of 0.5 mg/mL test article stock solution to 747 μL of the 1 mg/mL liver matrix. Incubation was performed at 37±2° C. with gentle, continuous mixing in shaking water bath in 2.0 mL-well capacity 96-Deepwell plates (96-DWP). Samples were retrieved in duplicate at the following time points: 0, 5, 10, 15, 30 and 60 minutes. The final mixture contained 1 μg/mL of drug and 0.5 mg/mL of liver matrix. First, 50 μL of test articles in liver matrix was added to the 96-DWP and pre-warmed the mixture in the 96-DWP for 2 minutes in the 37° C. water bath. The enzymatic reaction was started by the addition of 50 μL of the corresponding 2× NADPH regenerating system (NRS) cofactor solution to all sample wells and stopped by the addition of 300 μL of stop solution (acetonitrile containing 10 ng/mL Tolbutamide as an internal standard (I.Std.). The samples were agitated for 10 minutes and then centrifuged for 20 minutes at 4500 rpm. 25 μL of supernatant was diluted with 475 μL acetonitrile containing I. Std. into a new 96-DWPs for LC-MS/MS analysis.

All samples were analyzed by electrospray ionization (ESI) liquid chromatograph/mass spectrometry (LC/MS) system utilizing Sciex 5500 quadropule ion trap (Qtrap) mass spectrometry with Shidmazu Nexera X2 UHPLC. The LC-MS/MS instrument monitored each of the test compound in the study based of their respective mass-to-charge (m/z) transitions and MS parameters. Chromatographic separation was achieved on Phenomenex Luna C18 column (50×2.0 mm, 3 μm particle size) by using a gradient elution: mobile phase A contains 0.1% formic acid in water and mobile phase B contains 0.1% formic acid in acetonitrile; A/B (99:1) from 0 to 1 minutes; to A/B (1:99) from 1 to 4 minutes; A/B (1:99) from 4 to 8 minutes; to A/B (99:1) from 8 to 8.20 minutes; A/B (99:1) from 8.2 to 9 minutes. The flow rate was 0.4 mL/min and the column temperature was maintained at 35° C. and autosampler temperature at 4° C. For detection, the electrospray ionization operated in the positive mode using multiple reaction monitoring (MRM).

Data acquisition, peak integrations or m/z (mass-to-charge ratio of non-blank peaks) were obtained by Analyst® Version 1.7.1 (Sciex) operating with Windows® (Microsoft). Half-life calculations were generated and calculated by Graphpad Prism® software. The half-life of test compound was calculated based on the first-order reaction kinetics. The data was transformed to linear regression (y=log(y) where "y" axis represents the % compound remaining at any given time with respect to time 0 minutes; "x" axis represents time in minutes) in order to calculate the half-life.

Compound/API Stability

Shelf life testing is part of the development and maintenance of drugs. Active pharmaceutical ingredients (APIs) might be sensitive to the effects of heat, light and oxygen. API stability testing provides evidences of how the quality of an API/drug varies with time under the influence of a variety of environmental factors such as temperature, humidity and light. The following procedure was used to test API stability.

The API in a power form was accurately weighed out 25 individual containers containing 15 mg+2 mg of API and randomly divided the samples into 4 groups. Each group was stored under one of the following temperatures: −20° C., 4° C., 25° C. with 60% relative humidity, or 40° C. with 75% relative humidity. The samples were retrieved at the following time points: 1 month, 2 months, 3 months, 6 months, 9 months and 12 months. At each time point, visual observation of the physical state (texture and color) of the samples was examined and recorded prior to preparation for analysis for physical stability. For each sample, the API was reconstituted in its original container by adding the appropriate volume of DMSO to result in a stock solution of 4.0 mg/mL. 25 µL of the 4.0 mg/ml sample stock solution was diluted with 975 µL of acetonitrile for a final concentration of 100 µg/mL of API. The sample solution was injected into HPLC for the determination of potency and impurity profile. A calibration curve of test compound contained seven (5) standards at concentrations 1.0, 5.0, 10, 25, 50 and 100 µg/mL were prepared in acetonitrile.

An Agilent 1260 Infinity II Lab LC Series HPLC system was used including 1260 Quat pump, 1260 vial autosampler, ICC column oven, and 1260 DAD WR detector. The chromatographic separation was achieved by a Phenomenex Synergi Polar RP column (150×4.6 mm, 4 µm, 80 Å). The flow rate was 1 mL/min and the detection was set at 254 nm. Injection volume was 10 uL, otherwise specified. The mobile phase consisted A, water with 0.1% trifluoroacetic acid and B, acetonitrile with 0.1% trifluoroacetic acid. For potency analysis, the gradient was A/B (99:1) from 0 minute; to A/B (1:99) from 0 to 10 minutes; A/B (1:99) from 10 to 12 minutes; to A/B (99:1) from 12 to 12.1 minutes; A/B (99:1) from 12.1 to 13 minutes. For impurity profile, the gradient was A/B (99:1) from 0 minute; to A/B (1:99) from 0 to 15 minutes; A/B (1:99) from 15 to 18 minutes; to A/B (99:1) from 18 to 18.1 minutes; A/B (99:1) from 18.1 to 20 minutes. Data acquisition and peak integrations were obtained by OpenLAB CDS Version 2.4 (Agilent) operating with Windows (Microsoft). The impurity profile was determined by the relative percent peak area of each peak detected.

PAMPA Assay

Parallel artificial membrane permeability (PAMPA) assay is a non-cell based assay designed to predict in vivo biological membrane permeability of drugs in early stage of drug discovery. The 96-well Corning Gentest Pre-coated PAMPA Plate System (catalog no. 353015) was used to perform the assay. The Corning Gentest Pre-coated PAMPA plate system was designed by 96-well insert system with a 0.45 µm PVDF (polyvinylidene fluoride) filter plate which has been pre-coated with structured tri-layers of phospholipids (lipid/oil/lipid) and a matched receiver microplate.

Donor solutions of test compounds (300 µL, 20 µM in PBS/MeOH 90:10) were added to each well of the donor plate. 200 µL of PBS/MeOH 90:10 was added to each well of the acceptor plate. The acceptor plate was coupled with the donor plate and incubated for 5 hours at room temperature (RT) without agitation. In each plate, compounds were tested in triplicate. At the end of the incubation, drug concentration in the initial donor solution, acceptor and the donor wells were determined using LC/MS/MS. A five (5) points standard curve from 0.1 to 1000 nM for each test compound were prepared. Analyte samples were diluted to within standard curve concentration with ACN/H$_2$O 50:50 prior analysis.

All samples were analyzed by electrospray ionization (ESI) liquid chromatograph/mass spectrometry (LC/MS) system utilizing Sciex 5500 quadropule ion trap (Qtrap) mass spectrometry with Shidmazu Nexera X2 UHPLC. The LC-MS/MS instrument monitored each of the test compound in the study based of their respective mass-to-charge (m/z) transitions and MS parameters. Chromatographic separation was achieved on Phenomenex Luna C18 column (50×2.0 mm, 3 µm particle size) by using a gradient elution: mobile phase A contains 0.1% formic acid in water and mobile phase B contains 0.1% formic acid in acetonitrile; A/B (99:1) from 0 to 1 minutes; to A/B (1:99) from 1 to 4 minutes; A/B (1:99) from 4 to 8 minutes; to A/B (99:1) from 8 to 8.20 minutes; A/B (99:1) from 8.2 to 9 minutes. The flow rate was 0.4 mL/min and the column temperature was maintained at 35° C. and autosampler temperature at 4° C. For detection, the electrospray ionization operated in the positive mode using multiple reaction monitoring (MRM).

Data acquisition, and peak integrations were obtained by Analyst® Version 1.7.1 (Sciex) operating with Windows® (Microsoft). The standard curve regressions and sample concentrations were generated and calculated by Analyst®. Concentrations in the sample solutions were determined based on the measured peak area ratios from the response of the analyte to the internal standard with reference to the standard calibration curve. All sample calculations were calculated using a linear regression with $1/x^2$ weighting (where x is the concentration of given calibration standard level).

Permeability of the test compounds was calculated using the following formula:

$$\text{Permeability(cm/s)}: P_e = \{-\ln[1 - C_A(t)/C_{equilibrium}]\}/[A*(1/V_D + 1/V_A)*t]$$

Where:

A=filter area=0.3 cm$^3$ $V_A$=acceptor well volume (0.2 mL)

$V_D$=donor well volume (0.2 mL), t=incubation time=5 hours=18000 seconds, $C_A(t)$=compound concentration in acceptor well at time t (nM), $C_D(t)$=compound concentration in donor well at time t (nM), and $C_{equilibrium}=[C_D(t)*V_D+C_A(t)*V_A]/(V_D+V_A)$ Modeling of Compounds All claimed structures were generated by computational molecular docking using the available software SeeSAR v.10. The published crystal structure data of compound UNC-0638 bounded to G9a protein (3RJW-UNC0638) was download from The Protein Data Bank (https://www.resb.org/) and affinity binding was estimated. The built-in function "inspirator" was used to generate new compounds with good affinity that are within the claims.

CYP-Direct Inhibition of Test Compounds in Human Cytochrome P450 Assay

Many drugs inhibit cytochrome P450 enzymes to cause clinically significant changes in the pharmacokinetics of other drugs. In vitro cytochrome P450 inhibition, can provide crucial information in evaluating potential clinical drug-drug interactions and is useful for focusing in vivo tests to areas of concern. The cytochrome P450 inhibition assay was developed by preparing a working cocktail solution consisting of six probe substrates 10 μM ethoxy-resorufin (CYP1A2), 100 μM rosiglitazone (CYP2C8), 50 μM diclofenac (CYP2C9), 300 μM S-mephenytoin (CYP2C19), 50 μM dextromethorphan (CYP2D6), and 20 μM midazolam (CYP3A4). A mixture solution consists of 140 uL of 0.286 mg/mL of pooled human liver microsome working solution and 20 uL working solutions of test articles, standard control inhibitors, or positive control placebo and 20 uL of substrate cocktail mixture working solution was prepared. The mixture solution was pre-warm in a gentle shaking bath at 37±2° C. for 5 minutes. The enzymatic reaction started by adding 20 uL of NRS working solution to the mixture solution and incubated for 10 minutes at 37±2° C. To stop the reaction, an addition of 400 μL cold stop solution (acetonitrile containing 50 ng/mL Tolbutamide as an internal standard (I.Std.) was added to the mixture solution. The final concentration of test article, inhibitors, substrates, and cofactors are noted in Table 0.1 below. Two individual samples were prepared for each test compound. The extracted samples were vortexed and then centrifuged at 4500 rpm for 7 minutes using Eppendorf Centrifuge 5910R. 200 uL of supernatant was diluting with 200 uL of 50% Methanol into 96-DW plate for LC/MS/MS analysis

TABLE 0.1

Final concentration of test compound, inhibitors, substrates, and cofactor

|  | Component | Final Conc. |
|---|---|---|
| Substrate | Ethoxy-resorufin | 1 μM |
|  | Rosiglitazone | 10 μM |
|  | Diclofenac | 5 μM |
|  | S-mephenytoin | 30 μM |
|  | Dextromethorphan | 5 μM |
|  | Midazolam | 2 μM |
| Inhibitors | a-Naphtoflavone | 3 μM |
|  | Quercetin | 3 μM |
|  | Sulfaphenazole | 3 μM |
|  | (+)-N-3-benzylnivanol | 3 μM |
|  | Quinidine | 3 μM |
|  | Ketoconazole | 3 μM |
| Cofactors | NRS Solution A | 0.4X |
|  | NRS Solution B | 0.4X |
|  | Human liver microsomes | 0.2 mg/mL |
| Test compounds | Conc. 1 | 0.78 μM |
|  | Conc. 2 | 1.56 μM |
|  | Conc. 3 | 3.12 μM |
|  | Conc. 4 | 6.25 μM |
|  | Conc. 5 | 12.5 μM |
|  | Conc. 6 | 25 μM |
|  | Conc. 7 | 50 μM |
|  | Conc. 8 | 100 μM |

All samples were analyzed by electrospray ionization (ESI) liquid chromatograph/mass spectrometry (LC/MS) system utilizing Sciex 5500 quadropule ion trap (Qtrap) mass spectrometry with Shidmazu Nexera X2 UHPLC. The LC-MS/MS instrument monitored each of the metabolites of the substrate based on their respective mass-to-charge (m/z) transitions and MS parameters. Chromatographic separation was achieved on Phenomenex Luna C18 column (50×2.0 mm, 3 μm particle size) by using a gradient elution: mobile phase A contains 0.1% formic acid in water and mobile phase B contains 0.1% formic acid in acetonitrile; A/B (95:5) from 0 to 1 minutes; to A/B (15:85) from 1 to 2.4 minutes; to A/B (10:90) from 2.4 to 4 minutes; to A/B (95:5) from 4 to 4.1 minutes; A/B (95:5) from 4.1 to 6 minutes. The flow rate was 0.4 mL/min and the column temperature was maintained at 35° C. and autosampler temperature at 4° C. For detection, the electrospray ionization operated in the positive mode using multiple reaction monitoring (MRM).

Data acquisition, and peak integrations were obtained by Analyst® Version 1.7.1 (Sciex) operating with Windows® (Microsoft). Concentration-response plots are used to determine the effects of an inhibitor on an enzymatic reaction. A typical concentration-response plot provides fractional activity (Y axis) is plotted as a function of log inhibitor concentration (X axis). The data are fitted using a standard Sigmoidal dose-response equation which is also called a three-parameter logistic equation. The concentration of compound that results in 50% inhibition of maximal activity is termed as the $IC_{50}$ (inhibitor concentration yielding 50% inhibition). $IC_{50}$ value is calculated using Prism GraphPad software, version 9. IC50 values were obtained only when the data fit in the curve, and if the % inhibition was less than 50% at 100 μM, then IC50 will be >100.

Example 1

Synthesis of 4-((2-(4,4-difluoropiperidin-1-yl)-6-methoxy-7-(3-(pyrrolidin-1-yl)propoxy)quinazolin-4-yl)amino)tetrahydro-2H-thiopyran 1,1-dioxide (Compound 1)

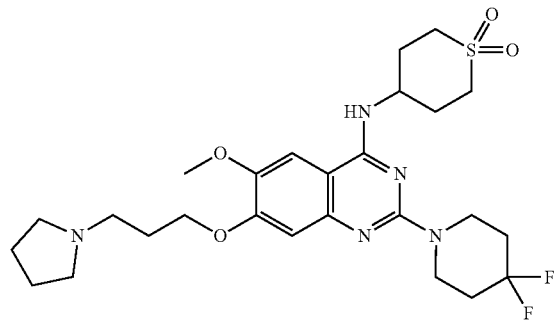 [SMILES: COc1cc2c(NC3CCS(=O)(=O)CC3)nc(N3CCC(F)(F)CC3)nc2cc1OCCCN1CCCC1]

Preparation: To a solution of commercially available 2,4-dichloro-6-methoxy-7-(3-(pyrrolidine-1-yl)propoxy) quinazoline (0.15 g, 0.42 mmol) and 4-aminotetrahydro-2H-thiopyran (0.94 g, 0.63 mmol) in anhydrous DMF (2 mL) was added DIPEA (0.44 mL, 2.53 mmol). The sealed tube was heated to 50° C. under argon atmosphere. The reaction was monitored by TLC with dichloromethane and LCMS of 469.1. Upon completion after 3 days, the cooled reaction mixtures were quenched with sat. NaHCO₃ and extracted with 8:2 dichloromethane/isopropanol mixtures (5×50 mL). The combined organic layers were dried over anhydrous Na₂SO₄, filtered, and concentrated in vacuo. The crude was dissolved in 2-butanol (2 ml) with adding DIPEA (0.44 mL, 2.53 mmol) and 4,4-difluoropiperidine hydrochloride (0.33 g, 2.11 mmol) then the sealed tube was heated to 90° C. for 3 days. The cooled mixtures were extracted with dichloromethane/isopropanol (8:2) mixtures washing with sat.

NaHCO$_3$ and with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 4-((2-(4,4-difluoropiperidin-1-yl)-6-methoxy-7-(3-(pyrrolidin-1-yl)propoxy)quinazolin-4-yl)amino)tetrahydro-2H-thiopyran 1,1-dioxide (0.14 g, 60%) as a beige solid. $^1$H NMR (400 MHz, CDCl$_3$): δ 6.91 (s, 1H), 6.69 (s, 1H), 5.11 (d, 1H, J=8.0 Hz), 4.42 (m, 1H), 4.17 (t, 2H, J=8.0 Hz), 3.95 (m, 4H), 3.92 (s, 3H), 3.17 (m, 4H), 2.61 (t, 2H, J=8.0 Hz), 2.55-2.47 (m, 6H), 2.32 (m, 2H), 2.09 (m, 2H), 1.99 (m, 4H), 1.76 (m, 4H). MS (ESI): Calcd. for C$_{26}$H$_{37}$F$_2$N$_5$O$_4$S: 553, found 554 (M+H)$^+$.

Example 2

Synthesis of 2-(4,4-difluoropiperidin-1-yl)-6-methoxy-7-(3-(pyrrolidin-1-yl)propoxy)-N-(tetrahydro-2H-pyran-4-yl)quinazolin-4-amine (Compound 2)

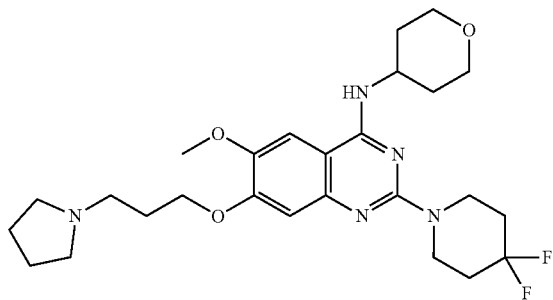

Preparation: To a solution of commercially available 2,4-dichloro-6-methoxy-7-(3-(pyrrolidine-1-yl)propoxy)quinazoline (0.15 g, 0.42 mmol) and 4-aminotetrahydro-2H-thiopyran (0.64 g, 0.63 mmol) in anhydrous DMF (2 mL) was added DIPEA (0.44 mL, 2.53 mmol). The sealed tube was heated to 50° C. under argon atmosphere. The reaction was monitored by TLC with dichloromethane and HPLC/MS of 421.1. Upon completion after 3 days, the cooled reaction was quenched with sat. NaHCO$_3$ and extracted with 8:2 dichloromethane/isopropanol mixtures (3×50 mL). The combined organic layers were dried over anhydrous Na$_2$SO$_4$, filtered, and concentrated in vacuo. The crude was dissolved in 2-butanol (2 ml) with adding DIPEA (0.44 mL, 2.53 mmol) and 4,4-difluoropiperidine hydrochloride (0.33 g, 2.11 mmol) then the sealed tube was heated to 90° C. for 3 days. The cooled mixtures were quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia (8:2) to give 2-(4,4-difluoropiperidin-1-yl)-6-methoxy-7-(3-(pyrrolidin-1-yl)propoxy)-N-(tetrahydro-2H-pyran-4-yl)quinazolin-4-amine (0.12 g, 57%) as a beige solid. $^1$H NMR (400 MHz, CDCl$_3$): δ 6.90 (s, 1H), 6.69 (s, 1H), 4.96 (d, 1H, J=8.0 Hz), 4.31 (m, 1H), 4.17 (m, 2H), 4.04 (m, 2H), 3.96 (m, 4H), 3.91 (s, 3H), 3.56 (ddd, 2H, J=12.0, 12.0, 4.0 Hz), 2.61 (m, 2H), 2.50 (m, 4H), 2.09 (m, 3H), 2.04-1.94 (m, 4H), 1.76 (m, 4H), 1.62 (m, 3H). MS (ESI): Calcd. for C$_{26}$H$_{37}$F$_2$N$_5$O$_3$: 505, found 506 (M+H)$^+$.

Example 3

Synthesis of 2-(4,4-difluoropiperidin-1-yl)-6-methoxy-N-(1-(2-methoxyethyl)piperidin-4-yl)-7-(3-(pyrrolidin-1-yl)propoxy)quinazolin-4-amine (Compound 3)

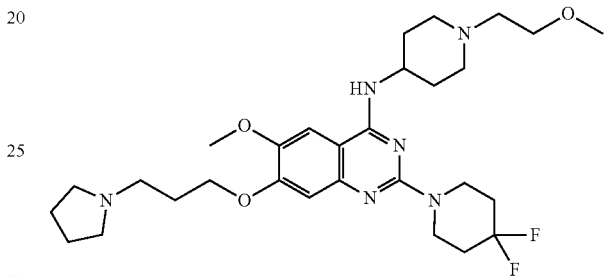

Preparation: To a solution of commercially available 2,4-dichloro-6-methoxy-7-(3-(pyrrolidine-1-yl)propoxy)quinazoline (0.15 g, 0.42 mmol) and 1-(2-methoxyethyl)piperidin-4-amine (0.10 g, 0.63 mmol) in anhydrous DMF (2 mL) was added DIPEA (0.44 mL, 2.53 mmol). The sealed tube was heat to 50° C. under argon atmosphere. The reaction was monitored by TLC with dichloromethane and HPLC/MS of 478.2. Upon completion after 3 days, the cooled reaction was quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The crude was dissolved in 2-butanol (2 ml) with adding DIPEA (0.44 mL, 2.53 mmol) and 4,4-difluoropiperidine hydrochloride (0.33 g, 2.11 mmol) then the sealed tube was heated to 90° C. for 3 days. The cooled mixtures were quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia (8:2) to give 2-(4,4-difluoropiperidin-1-yl)-6-methoxy-N-(1-(2-methoxyethyl)piperidin-4-yl)-7-(3-(pyrrolidin-1-yl)propoxy)quinazolin-4-amine (0.11 g, 48%) as a beige solid. $^1$H NMR (400 MHz, CDCl$_3$): δ 6.88 (s, 1H), 6.68 (s, 1H), 4.96 (d, 1H, J=8.0 Hz), 4.16 (t, 2H, J=8.0 Hz), 4.10 (m, 1H), 3.96 (m, 4H), 3.84 (s, 3H), 3.53 (m, 2H), 3.36 (s, 3H), 2.97 (m, 2H), 2.70 (m, 2H), 2.61 (m, 4H), 2.22 (m, 2H), 2.13 (m, 4H), 1.98 (m, 5H), 1.81 (m, 4H), 1.65 (m, 2H). MS (ESI): Calcd. for C$_{29}$H$_{44}$F$_2$N$_6$O$_3$: 562, found 563 (M+H)$^+$.

Example 4

Synthesis of 2-(4,4-difluoropiperidin-1-yl)-6-methoxy-N-(2-methoxyethyl)-7-(3-(pyrrolidin-1-yl)propoxy)quinazolin-4-amine (Compound 4)

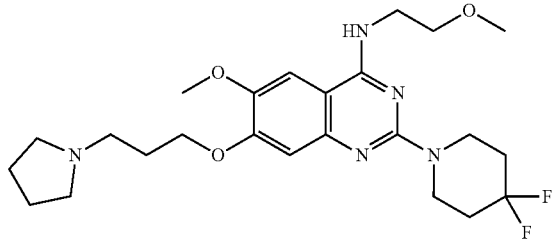 [SMILES: COCCNc1nc(N2CCC(F)(F)CC2)nc2cc(OCCCN3CCCC3)c(OC)cc12]

Preparation: To a solution of commercially available 2,4-dichloro-6-methoxy-7-(3-(pyrrolidine-1-yl)propoxy)quinazoline (0.15 g, 0.42 mmol) and 2-methoxyethylamine (0.05 g, 0.63 mmol) in anhydrous DMF (2 mL) was added DIPEA (0.44 mL, 2.53 mmol). The sealed tube was heated to 50° C. under argon atmosphere. The reaction was monitored by TLC with dichloromethane and HPLC/MS of 394.3. Upon completion after 3 days, the cooled reaction was quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The crude was dissolved in 2-butanol (2 ml) with adding DIPEA (0.44 mL, 2.53 mmol) and 4,4-difluoropiperidine hydrochloride (0.33 g, 2.11 mmol) then the sealed tube was heated to 90° C. for 3 days. The cooled mixtures were quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 2-(4,4-difluoropiperidin-1-yl)-6-methoxy-N-(2-methoxyethyl)-7-(3-(pyrrolidin-1-yl)propoxy)quinazolin-4-amine (0.113 g, 56%) as a beige solid. $^1$H NMR (400 MHz, CDCl$_3$): δ 6.89 (s, 1H), 6.74 (s, 1H), 5.55 (t, 1H, J=8.0 Hz), 4.16 (m, 2H), 3.97 (m, 4H), 3.89 (s, 3H), 3.77 (dd, 2H, J=12.0, 4.0 Hz), 3.64 (t, 2H, J=4.0 Hz), 3.40 (s, 3H), 2.62 (t, 2H, J=8.0 Hz), 2.51 (m, 4H), 2.10 (p, 2H, J=8.0 Hz), 1.97 (m, 4H), 1.77 (m, 4H). MS (ESI): Calcd. for C$_{24}$H$_{35}$F$_2$N$_5$O$_3$: 479, found 480 (M+H)$^+$.

Example 5

Synthesis of 2-(4,4-difluoropiperidin-1-yl)-6-methoxy-N-((1-methylpiperidin-4-yl)methyl)-7-(3-(pyrrolidin-1-yl)propoxy)quinazolin-4-amine (Compound 5)

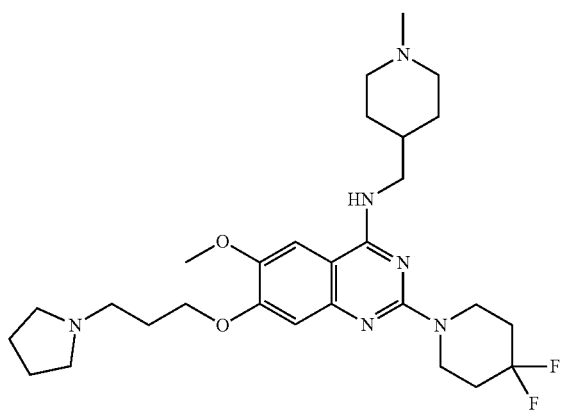 [SMILES: COc1cc2c(NCC3CCN(C)CC3)nc(N3CCC(F)(F)CC3)nc2cc1OCCCN1CCCC1]

Preparation: To a solution of commercially available 2,4-dichloro-6-methoxy-7-(3-(pyrrolidine-1-yl)propoxy)quinazoline (0.15 g, 0.42 mmol) and (1-methyl-4-piperidinyl)methanamine (0.08 g, 0.63 mmol) in anhydrous DMF (2 mL) was added DIPEA (0.44 mL, 2.53 mmol). The sealed tube was heated to 50° C. under argon atmosphere. The reaction was monitored by TLC with dichloromethane and HPLC/MS of 448.2. Upon completion after 3 days, the cooled reaction was quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The crude was dissolved in 2-butanol (2 ml) with adding DIPEA (0.44 mL, 2.53 mmol) and 4,4-difluoropiperidine hydrochloride (0.33 g, 2.11 mmol) then the sealed tube was heated to 90° C. for 3 days. The cooled mixtures were quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 2-(4,4-difluoropiperidin-1-yl)-6-methoxy-N-((1-methylpiperidin-4-yl)methyl)-7-(3-(pyrrolidin-1-yl)propoxy)quinazolin-4-amine (0.09 g, 41%) as a beige solid. $^1$H NMR (400 MHz, CDCl$_3$): δ 6.89 (s, 1H), 6.69 (s, 1H), 5.26 (dd, 1H, J=8.0, 4.0 Hz), 4.16 (dd, 2H, J=8.0, 4.0 Hz), 3.97 (m, 4H), 3.90 (s, 3H), 3.50 (dd, 2H, J=8.0. 4.0 Hz), 2.86 (m, 2H), 2.61 (dd, 2H, J=8.0, 4.0 Hz), 2.50 (m, 4H), 2.26 (s, 3H), 2.09 (p, 2H, J=8.0 Hz), 1.98 (m, 4H), 1.89 (m, 3H), 1.75 (m, 6H), 1.39 (ddd, 2H, J=12.0, 12.0, 4.0 Hz). MS (ESI): Calcd. for C$_{28}$H$_{42}$F$_2$N$_6$O$_2$: 532, found 533 (M+H)$^+$.

Example 6

Synthesis of (R)-6-methoxy-N-(piperidin-3-yl)-2-(pyrrolidin-1-yl)-7-(3-(pyrrolidin-1-yl)propoxy)quinazolin-4-amine (Compound 159)

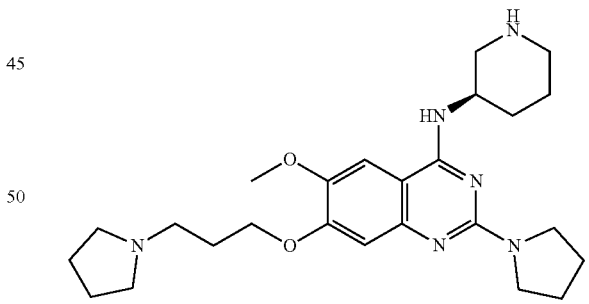

Preparation: To a solution of commercially available 2,4-dichloro-6-methoxy-7-(3-(pyrrolidine-1-yl)propoxy)quinazoline (0.10 g, 0.28 mmol) and (R)-1-boc-3-aminopiperidine (0.08 g, 0.42 mmol) in anhydrous 1:1 DMF/2-butanol (2 mL) was added DIPEA (0.88 mL, 3.36 mmol). The sealed tube was heated to 50° C. under argon atmosphere. The reaction was monitored by TLC with dichloromethane. Upon completion after 2 days (HPLC/MS=520), then excess pyrrolidine (3.43 g, 48.25 mmol) was added and heated to 90° C. for 3 days. The cooled mixtures were quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo.

The crude (LCMS=555.2) was hydrolyzed with 40% trifluoromethyl acetic acid in dichloromethane (5 mL) for 20 h. Then the mixtures were neutralized with 1N aq. NaOH and extracted with 8:2 dichloromethane/isopropanol mixtures (3×25 mL). The combined organic layers were dried over anhydrous Na$_2$SO$_4$, filtered, and concentrated in vacou. The residue was purified by Buchi Pureflash chromatography over silica gel cartridge (12 g) with 8:2 CH$_2$Cl$_2$:MeOH w/2% 7N ammonia to give (R)-6-methoxy-N-(piperidin-3-yl)-2-(pyrrolidin-1-yl)-7-(3-(pyrrolidin-1-yl)propoxy)quinazolin-4-amine (0.33 g, 48%) as beige solid. $^1$H NMR (400 MHz, CDCl$_3$): δ 6.9 (s, 1H), 6.75 (s, 1H), 5.44 (d, 1H, J=4.0 Hz), 4.31 (m, 1H), 4.15 (dd, 2H, J=8.0 Hz, 4.0 Hz), 3.90 (s, 3H), 3.61 (m, 4H), 3.27 (dd, 1H, J=8.0, 2.0 Hz), 2.86 (m, 1H), 2.75 (m, 1H), 2.70 (dd, 1H, J=12.0, 4.0 Hz), 2.60 (t, 2H, J=8.0 Hz), 2.49 (m, 4H), 2.08 (p, 2H, J=8.0 Hz), 1.92 (m, 5H), 1.76 (m, 7H), 1.56 (m, 1H). MS (ESI): Calcd. for C$_{25}$H$_{38}$N$_6$O$_2$: 454, found 455 (M+H)$^+$.

Example 7

Synthesis of 2-(4((2-(4,4-difluoropiperidin-1-yl)-6-methoxy-7-(3-(pyrrolidin-1-yl)propoxy)quinazolin-4-yl)amino)piperidin-1-yl)acetic acid (Compound 6)

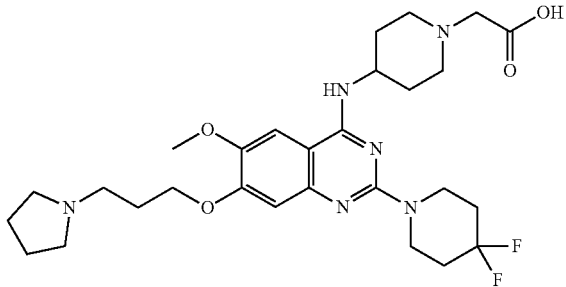 [SMILES: COc1cc2c(NC3CCN(CC(=O)O)CC3)nc(N3CCC(F)(F)CC3)nc2cc1OCCCN1CCCC1]

Preparation: To a solution of commercially available 2,4-dichloro-6-methoxy-7-(3-(pyrrolidine-1-yl)propoxy) quinazoline (0.10 g, 0.28 mmol) and (4-aminopiperidin-1-yl)acetic acid hydrochloride (0.08 g, 0.42 mmol) in anhydrous DMF (2 mL) was added DIPEA (0.29 mL, 0.21 mmol). The sealed tube was heated to 50° C. under argon atmosphere. The reaction was monitored by TLC with dichloromethane and HPLC/MS of 478.2. Upon completion after 3 days, the precipitate intermediate was collected by filtration washing with isopropanol and dried under vacuum. The crude was suspended in isopropanol (2 ml) with DIPEA (0.44 mL, 2.53 mmol) and 4,4-difluoropiperidine hydrochloride (0.33 g, 2.11 mmol) then the sealed tube was microwaved at 150° C. for 90 min. The precipitate was collected by filtration washing with cold acetonitrile and dried under vacuum to give 2-(4-((2-(4,4-difluoropiperidin-1-yl)-6-methoxy-7-(3-(pyrrolidin-1-yl)propoxy)quinazolin-4-yl) amino)piperidin-1-yl)acetic acid (0.05 g, 48%) as a beige solid. $^1$H NMR (400 MHz, DMSO-d): δ (poor solubility issue to obtain a clear spectrum). MS (ESI): Calcd. for C$_{28}$H$_{440}$F$_2$N$_6$O$_4$: 562, found 563 (M+H)$^+$.

Example 8

Synthesis of 2-chloro-N-(1-isopropylpiperidin-4-yl)-6-methoxy-7-(3-(pyrrolidin-1-yl)propoxy)quinazolin-4-amine (Compound 113)

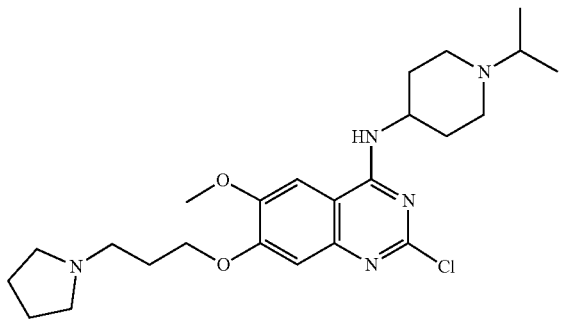 [SMILES: COc1cc2c(NC3CCN(C(C)C)CC3)nc(Cl)nc2cc1OCCCN1CCCC1]

Preparation: To a solution of commercially available 2,4-dichloro-6-methoxy-7-(3-(pyrrolidine-1-yl)propoxy) quinazoline (0.50 g, 1.40 mmol) and 4-amino-1-isopropylpiperidine (0.30 g, 2.11 mmol) in anhydrous 1:1 DMF/2-butanol (7 mL) was added DIPEA (0.73 mL, 4.21 mmol). The sealed tube was heated to 50° C. for 3 days under argon atmosphere. The cooled reaction was quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 2-chloro-N-(1-isopropylpiperidin-4-yl)-6-methoxy-7-(3-(pyrrolidin-1-yl)propoxy)quinazolin-4-amine (0.43 g, 67%) as a yellow solid. $^1$H NMR (400 MHz, CDCl$_3$): δ 7.10 (s, 1H), 6.75 (s, 1H), 5.30 (d, 1H, J=8.0 Hz), 4.21 (m, 1H), 4.15 (t, 2H, J=4.0 Hz), 3.94 (s, 3H), 2.87 (m, 2H), 2.76 (septet, 1H, J=8.0 Hz), 2.60 (t, 2H, J=8.0 Hz), 2.49 (m, 4H), 2.37 (dt, 2H, J=12.0, 4.0 Hz), 2.15 (m 2H), 2.08 (p, 2H, J=8.0 Hz), 1.76 (m, 4H), 1.56 (dq, 2H, J=8.0, 4.0 Hz), 1.05 (s, 3H), 1.03 (s, 3H). MS (ESI): Calcd. for C$_{24}$H$_{36}$ClN$_5$O$_2$: 462, found 463 (M+H)$^+$.

Example 9

Synthesis of 2-(azetidin-1-yl)-N-(1-isopropylpiperidin-4-yl)-6-methoxy-7-(3-(pyrrolidin-1-yl)propoxy) quinazolin-4-amine, (Compound 234)

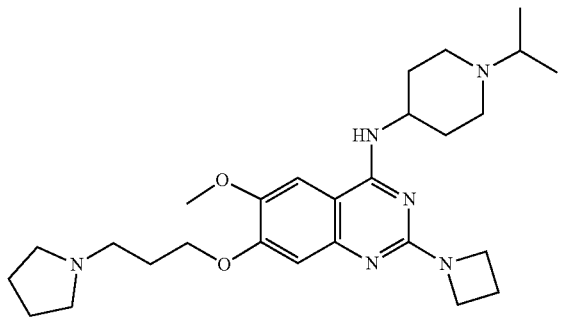 [SMILES: COc1cc2c(NC3CCN(C(C)C)CC3)nc(N3CCC3)nc2cc1OCCCN1CCCC1]

Preparation: To a solution of 2-chloro-N-(1-isopropylpiperidin-4-yl)-6-methoxy-7-(3-(pyrrolidin-1-yl)propoxy)quinazolin-4-amine (0.08 g, 0.16 mmol) and azetidine hydrochloride (0.08 g, 0.81 mmol) in anhydrous 1:1 DMF/2-butanol (7 mL) was added DIPEA (0.22 mL, 1.30 mmol). The sealed tube was heated to 90° C. for 2 days under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 2-(azetidin-1-yl)-N-(1-isopropylpiperidin-4-yl)-6-methoxy-7-(3-(pyrrolidin-1-yl)propoxy)quinazolin-4-amine (0.03 g, 44%) as an off-white solid. $^1$H NMR (400 MHz, CDCl$_3$): δ 6.93 (s, 1H), 6.68 (s, 1H), 4.94 (d, 1H, J=8.0 Hz), 4.15-4.10 (m, 7H), 3.89 (s, 3H), 2.89 (m, 2H), 2.77 (septet, 1H, J=8.0 Hz), 2.6 (m, 2H), 2.51 (m, 4H), 2.35-2.24 (m, 4H), 2.16 (m 2H), 2.10 (m, 2H), 1.76 (m, 4H), 1.55 (m, 2H), 1.06 (s, 3H), 1.05 (s, 3H). MS (ESI): Calcd. for C$_{27}$H$_{42}$N$_6$O$_2$: 482, found 483 (M+H)$^+$.

Example 10

Synthesis of (5)-6-methoxy-N-(piperidin-3-yl)-2-(pyrrolidin-1-yl)-7-(3-(pyrrolidin-1-yl)propoxy)quinazolin-4-amine (Compound 158)

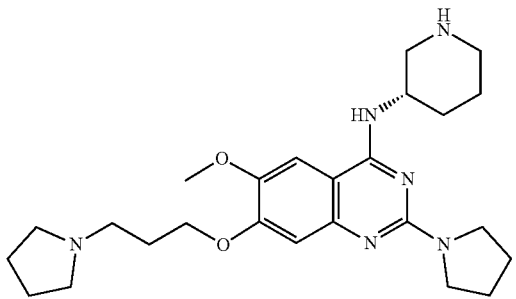 [SMILES: COc1cc2c(N[C@H]3CCCNC3)nc(N3CCCC3)nc2cc1OCCCN1CCCC1]

Preparation: To a solution of commercially available 2,4-dichloro-6-methoxy-7-(3-(pyrrolidine-1-yl)propoxy)quinazoline (0.25 g, 0.70 mmol) and (5)-1-boc-3-aminopiperidine (0.21 g, 1.05 mmol) in anhydrous DMF (5 mL) was added DIPEA (0.36 mL, 2.10 mmol). The sealed tube was heated to 50° C. under argon atmosphere. The reaction was monitored by TLC with dichloromethane. Upon completion after 2 days (HPLC/MS=520), then excess pyrrolidine (3.43 g, 48.25 mmol) was added and heated to 90° C. for 3 days. The cooled mixtures were quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo.

The crude (LCMS=555.2) was hydrolyzed with 40% trifluoromethyl acetic acid in dichloromethane (5 mL) for 20 h. Then the mixtures were neutralized with 1N aq. NaOH and extracted with 8:2 dichloromethane/isopropanol mixtures (3×50 mL). The combined organic layers were dried over anhydrous Na$_2$SO$_4$, filtered, and concentrated in vacou. The residue was purified by Buchi Pureflash chromatography over silica gel cartridge (12 g) with 8:2 CH$_2$Cl$_2$:MeOH w/2% 7N ammonia to give (S)-6-methoxy-N-(piperidin-3-yl)-2-(pyrrolidin-1-yl)-7-(3-(pyrrolidin-1-yl)propoxy)quinazolin-4-amine (0.16 g, 50%) as beige solid. $^1$H NMR (400 MHz, CDCl$_3$): δ 6.9 (s, 1H), 6.76 (s, 1H), 5.45 (d, 1H, J=4.0 Hz), 4.30 (m, 1H), 4.15 (dd, 2H, J=8.0 Hz, 4.0 Hz), 3.89 (s, 3H), 3.60 (m, 4H), 3.26 (dd, 1H, J=8.0, 2.0 Hz), 2.86 (m, 1H), 2.78 (m, 1H), 2.70 (dd, 1H, J=12.0, 4.0 Hz), 2.60 (t, 2H, J=8.0 Hz), 2.49 (m, 4H), 2.08 (p, 2H, J=8.0 Hz), 1.92 (m, 5H), 1.75 (m, 7H), 1.56 (m, 1H). MS (ESI): Calcd. for C$_{25}$H$_{38}$N$_6$O$_2$: 454, found 455 (M+H)$^+$.

Example 11

Synthesis of N-(1-isopropylpiperidin-4-yl)-6-methoxy-2-(1H-pyrazol-1-yl)-7-(3-(pyrrolidin-1-yl)propoxy)quinazolin-4-amine (Compound 157)

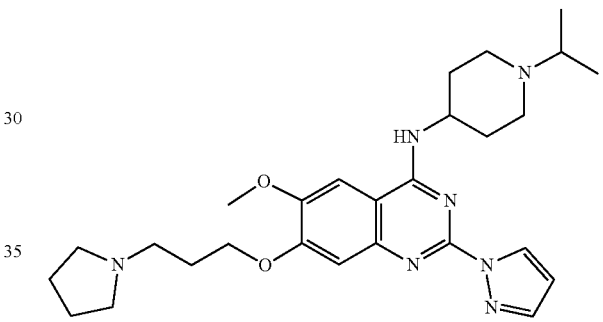

Preparation: To a solution of 2-chloro-N-(1-isopropylpiperidin-4-yl)-6-methoxy-7-(3-(pyrrolidin-1-yl)propoxy)quinazolin-4-amine (0.08 g, 0.16 mmol), potassium carbonate (0.11 g, 0.81 mmol), and pyrazole (0.22 g, 3.25 mmol) in anhydrous acetonitrile (3 mL). The sealed tube was microwaved at 160° C. for 3 hours under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 9:1 CH$_2$Cl$_2$:MeOH w/2% 7N ammonia to give N-(1-isopropylpiperidin-4-yl)-6-methoxy-2-(1H-pyrazol-1-yl)-7-(3-(pyrrolidin-1-yl)propoxy)quinazolin-4-amine (0.07 g, 85%) as a yellow solid. $^1$H NMR (400 MHz, CDCl$_3$): δ 8.56 (dd, 1H, J=4.0, 2.0 Hz), 7.77 (dd, 1H, J=2.0, 2.0 Hz), 7.34 (s, 1H), 6.83 (s, 1H), 6.42 (dd, 1H, J=4.0, 2.0 Hz), 5.40 (d, 1H, J=8.0 Hz), 4.24 (m, 1H), 4.15 (m, 2H), 3.94 (s, 3H), 2.92 (dd, 2H, J=12.0, 8.0 Hz), 2.78 (septet, 1H, J=8.0 Hz), 2.61 (dd, 2H, J=8.0, 8.0 Hz), 2.50 (m, 4H), 2.37 (dt, 2H, J=12.0, 4.0 Hz), 2.22 (m, 2H), 2.08 (p, 2H, J=8.0 Hz), 1.76 (m, 4H), 1.61 (dq, 2H, J=8.0, 4.0 Hz), 1.07 (s, 3H), 1.06 (s, 3H). MS (ESI): Calcd. for C$_{27}$H$_{39}$N$_7$O$_2$: 493, found 494 (M+H)$^+$.

Example 12

Synthesis of 2-(1H-imidazol-1-yl)-N-(1-isopropylpiperidin-4-yl)-6-methoxy-7-(3-(pyrrolidin-1-yl)propoxy)quinazolin-4-amine (Compound 156)

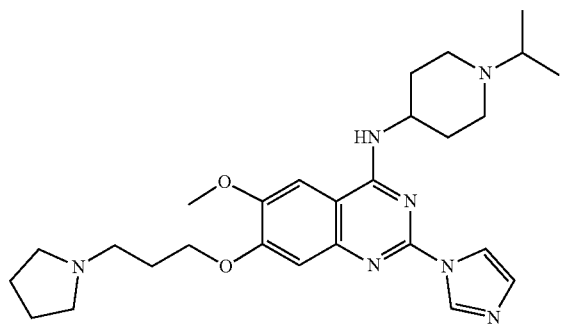 [SMILES: COc1cc2c(NC3CCN(C(C)C)CC3)nc(-n3ccnc3)nc2cc1OCCCN1CCCC1]

Preparation: To a solution of 2-chloro-N-(1-isopropylpiperidin-4-yl)-6-methoxy-7-(3-(pyrrolidin-1-yl)propoxy)quinazolin-4-amine (0.08 g, 0.16 mmol), potassium carbonate (0.11 g, 0.81 mmol), and imidazole (0.22 g, 3.25 mmol) in anhydrous acetonitrile (3 mL). The sealed tube was microwaved at 160° C. for 3 hours under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 9:1 CH$_2$Cl$_2$:MeOH w/2% 7N ammonia (8:2) to give 2-(1H-imidazol-1-yl)-N-(1-isopropylpiperidin-4-yl)-6-methoxy-7-(3-(pyrrolidin-1-yl)propoxy)quinazolin-4-amine (0.07 g, 86%) as a yellow solid. $^1$H NMR (400 MHz, CDCl$_3$): δ 8.61 (dd, 1H, J=4.0, 2.0 Hz), 7.90 (dd, 1H, J=4.0, 2.0 Hz), 7.16 (s, 1H), 7.12 (dd, 1H, J=4.0, 2.0 Hz), 6.81 (s, 1H), 5.39 (d, 1H, J=8.0 Hz), 4.23 (t, 2H, J=8.0 Hz), 4.19 (m, 1H), 3.96 (s, 3H), 2.94 (m, 2H), 2.79 (septet, 1H, J=8.0 Hz), 2.64 (dd, 2H, J=8.0, 4.0 Hz), 2.52 (m, 4H), 2.37 (dt, 2H, J=8.0, 2.0 Hz), 2.21 (m, 2H), 2.12 (p, 2H, J=8.0 Hz), 1.78 (m, 4H), 1.62 (dq, 2H, J=12.0, 4.0 Hz), 1.08 (s, 3H), 1.07 (s, 3H). MS (ESI): Calcd. for C$_{27}$H$_{39}$N$_7$O$_2$: 493, found 494 (M+H)$^+$.

Example 13

Synthesis of 2-(4,4-difluoropiperidin-1-yl)-6-methoxy-N-(pyridin-4-yl)-7-(3-(pyrrolidin-1-yl)propoxy)quinazolin-4-amine (Compound 7)

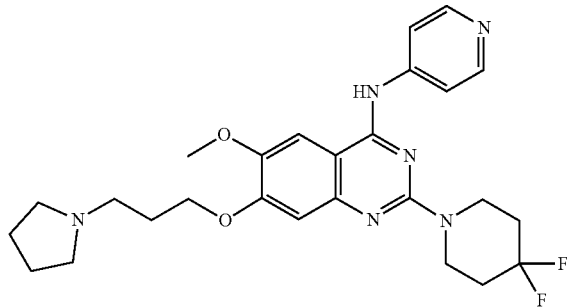 [SMILES: COc1cc2c(Nc3ccncc3)nc(N3CCC(F)(F)CC3)nc2cc1OCCCN1CCCC1]

Preparation: To a solution of commercially available 2,4-dichloro-6-methoxy-7-(3-(pyrrolidine-1-yl)propoxy)quinazoline (0.15 g, 0.42 mmol) and 4-aminopyridine (0.04 g, 0.46 mmol) in anhydrous THF (3 mL) was added excess 60% sodium hydride (0.11, 2.73 mmol). The mixtures were stirred for 30 min under an argon balloon. The tube was then sealed and heated to 50° C. under argon atmosphere. The reaction was monitored by TLC with dichloromethane and HPLC/MS of 414. Upon completion after 20 hours, the cooled reaction was quenched with sat. NH$_4$Cl (2 mL) and followed by sat. NaHCO$_3$ (50 mL). The mixtures were then extracted with 8:2 dichloromethane/isopropanol mixtures (3×50 mL) and washed once with brine. The combined organic layers were dried over anhydrous Na$_2$SO$_4$, filtered, and concentrated in vacuo. The crude was dissolved in 1:1 THF/2-butanol (4 ml) with adding DIPEA (0.44 mL, 2.53 mmol) and 4,4-difluoropiperidine hydrochloride (0.33 g, 2.11 mmol) then the sealed tube was heated to 110° C. for 3 days. The cooled mixtures were quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 9:1 CH$_2$Cl$_2$:MeOH w/2% 7N ammonia to give 2-(4,4-difluoropiperidin-1-yl)-6-methoxy-N-(pyridin-4-yl)-7-(3-(pyrrolidin-1-yl)propoxy)quinazolin-4-amine (0.10 g, 50%) as a light yellow solid. $^1$H NMR (400 MHz, CDCl$_3$): δ 8.51 (dd, 1H, J=4.0, 1.0 Hz), 7.60 (dd, 1H, J=8.0, 1.0 Hz), 7.20 (s, 1H), 6.97 (s, 1H), 6.88 (s, 1H), 4.20 (t, 2H, J=8.0 Hz), 4.01 (m, 4H), 3.94 (s, 3H), 2.67 (m, 2H), 2.56 (m, 4H), 2.13 (septet, 1H, J=8.0 Hz), 2.03 (m, 5H), 1.79 (m, 4H). MS (ESI): Calcd. for C$_{26}$H$_{32}$F$_2$N$_6$O$_2$: 498, found 499 (M+H)$^+$.

Example 14

Synthesis of 4-((1-isopropylpiperidin-4-yl)amino)-6-methoxy-7-(3-(pyrrolidin-1-yl)propoxy)quinazoline-2-carbonitrile (Compound 235)

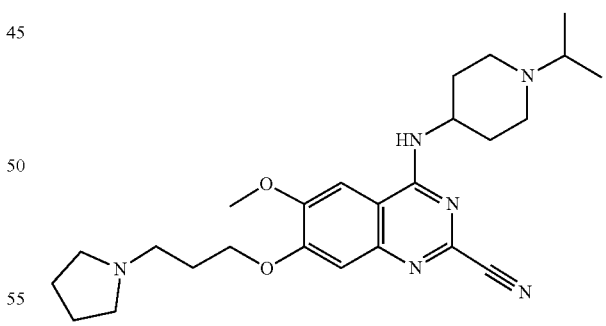

Preparation: To a solution of 2-chloro-N-(1-isopropylpiperidin-4-yl)-6-methoxy-7-(3-(pyrrolidin-1-yl)propoxy)quinazolin-4-amine (0.10 g, 0.22 mmol), and 1,4-diazobicyclo[2.2.2]octane (0.03 g, 0.22 mmol) in anhydrous dimethylsulfoxide (1.5 mL). The mixtures were stirred for 2 hours at room temperature and then added sodium cyanide (0.01 g, 0.23 mmol). The sealed tube was heat to 120° C. for 4 days under argon atmosphere. The cooled reaction was quenched with brine (50 mL) and extracted with 8:2 dichloromethane/isopropanol mixtures (3×50 mL). The combined organic layers were dried over anhydrous Na₂SO₄, filtered, and concentrated in vacuo. The residue was purified by Buchi Pureflash chromatography over silica gel cartridge (12 g) with 8:2 CH₂Cl₂:MeOH w/2% 7N ammonia (8:2) to give 4-((1-isopropylpiperidin-4-yl)amino)-6-methoxy-7-(3-(pyrrolidin-1-yl)propoxy)quinazoline-2-carbonitrile (0.07 g, 71%) as a beige solid. ¹H NMR (400 MHz, CDCl₃): δ 7.18 (s, 1H), 7.08 (s, 1H), 6.25 (d, 1H, J=8.0 Hz), 4.41 (m, 1H), 4.20 (t, 2H, J=8.0 Hz), 4.01 (s, 3H), 3.21 (d, 2H, J=12.0 Hz), 3.14 (septet, 1H, J=8.0 Hz), 2.74 (m, 2H), 2.70-2.62 (m, 6H), 2.28-2.10 (m, 6H), 1.83 (m, 4H), 1.27 (s, 3H), 1.25 (s, 3H). MS (ESI): Calcd. for C₂₅H₃₆N₆O₂: 452, found 453 (M+H)⁺.

Example 15

Synthesis of 2-(4,4-difluoropiperidin-1-yl)-6-methoxy-N-(piperidin-4-yl)-7-(3-(pyrrolidin-1-yl)propoxy)quinazolin-4-amine (Compound 8)

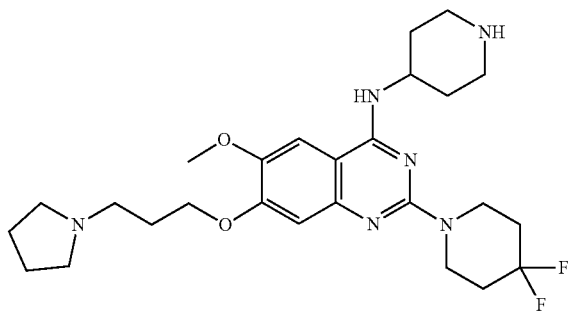 [SMILES: COc1cc2c(NC3CCNCC3)nc(N3CCC(F)(F)CC3)nc2cc1OCCCN1CCCC1]

Preparation: To a solution of commercially available 2,4-dichloro-6-methoxy-7-(3-(pyrrolidine-1-yl)propoxy)quinazoline (0.15 g, 0.42 mmol) and 1-boc-4-aminopiperidine (0.13 g, 0.63 mmol) in anhydrous DMF (2 mL) was added DIPEA (0.44 mL, 2.53 mmol). The sealed tube was heated to 50° C. under argon atmosphere. The reaction was monitored by TLC with dichloromethane. Upon completion after 3 days (HPLC/MS=520.2), then excess pyrrolidine (3.43 g, 48.25 mmol) was added and heated to 90° C. for 3 days. The cooled mixtures were quenched with sat. NaHCO₃ and extracted with 8:2 dichloromethane/isopropanol mixtures (3×50 mL) then washed once with brine. The combined organic layers were dried over anhydrous Na₂SO₄, filtered, and concentrated in vacuo.

The crude (HPLC/MS=605.2) was hydrolyzed with 40% trifluoromethyl acetic acid in dichloromethane (2.5 mL) for 20 h. Then the mixtures were neutralized with 10N aq. NaOH and sat. sodium bicarbonate in ice-bath, then was extracted with 8:2 dichloromethane/isopropanol mixtures (3×50 mL). The combined organic layers were dried over anhydrous Na₂SO₄, filtered, and concentrated in vacou. The residue was purified by Buchi Pureflash chromatography over silica gel cartridge (12 g) with 8:2 CH₂Cl₂:MeOH w/2% 7N ammonia to give 2-(4,4-difluoropiperidin-1-yl)-6-methoxy-N-(piperidin-4-yl)-7-(3-(pyrrolidin-1-yl)propoxy)quinazolin-4-amine (0.10 g, 48%) as beige solid. ¹H NMR (400 MHz, CDCl₃): δ 6.89 (s, 1H), 6.69 (s, 1H), 4.99 (d, 1H, J=8.0 Hz), 4.16 (t, 2H, J=8.0 Hz), 3.96 (m, 4H), 3.91 (s, 3H), 3.15 (dt, 2H, J=12.0, 4.0 Hz), 2.77 (dd, 2H, J=12.0, 4.0 Hz), 2.63 (t, 2H, J=8.0 Hz), 2.53 (m, 4H), 2.12 (m, 4H), 1.98 (m, 5H), 1.77 (m, 5H), 1.47 (ddd, 2H, J=12.0, 12.0, 4.0 Hz). MS (ESI): Calcd. for C₂₆H₃₈F₂N₆O₂: 504, found 505 (M+H)⁺.

Example 16

Synthesis of 2-chloro-6-methoxy-7-(3-(pyrrolidin-1-yl)propoxy)-N-(tetrahydro-2H-pyran-4-yl)quinazolin-4-amine (Compound 115)

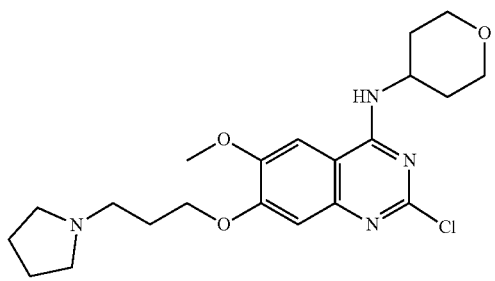 [SMILES: COc1cc2c(NC3CCOCC3)nc(Cl)nc2cc1OCCCN1CCCC1]

Preparation: To a solution of commercially available 2,4-dichloro-6-methoxy-7-(3-(pyrrolidine-1-yl)propoxy)quinazoline (1.50 g, 4.21 mmol) and tetrahydro-2H-pyran-4-amine (0.639 g, 6.32 mmol) in anhydrous DMF (12 mL) was added DIPEA (2.20 mL, 12.63 mmol). The sealed tube was heated to 50° C. for 10 days under argon atmosphere. The cooled reaction was quenched with sat. NaHCO₃ and extracted with 8:2 dichloromethane/isopropanol mixtures (3×50 mL) then washed once with brine. The combined organic layers were dried over anhydrous Na₂SO₄, filtered, and concentrated in vacuo. The residue was purified by Buchi Pureflash chromatography over silica gel cartridge (80 g) with 8:2 CH₂Cl₂:MeOH w/2% 7N ammonia to give 2-chloro-6-methoxy-7-(3-(pyrrolidin-1-yl)propoxy)-N-(tetrahydro-2H-pyran-4-yl)quinazolin-4-amine (1.08 g, 61%) as a yellow solid. ¹H NMR (400 MHz, CDCl₃): δ 7.10 (s, 1H), 6.81 (s, 1H), 5.42 (d, 1H, J=8.0 Hz), 4.46 (m, 1H), 4.14 (m, 2H), 4.02 (dd, 2H, J=12.0, 4.0 Hz), 3.95 (s, 3H), 3.58 (dt, 2H, J=12.0, 2.0 Hz), 2.63 (t, 2H, J=8.0 Hz), 2.51 (m, 4H), 2.10 (m, 4H), 1.76 (m, 4H), 1.62 (ddd, 2H, J=12.0, 12.0, 4.0 Hz). MS (ESI): Calcd. for C₂₁H₂₉ClN₄O₃: 420, found 421 (M+H)⁺.

Example 17

Synthesis of 2-((2-(4,4-difluoropiperidin-1-yl)-6-methoxy-7-(3-(pyrrolidin-1-yl)propoxy)quinazolin-4-yl)amino)acetamide (Compound 9)

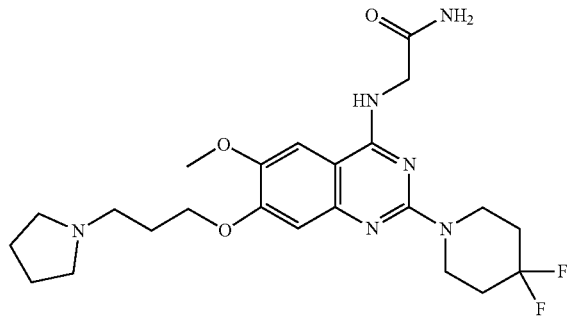 [SMILES: COc1cc2c(NCC(N)=O)nc(N3CCC(F)(F)CC3)nc2cc1OCCCN1CCCC1]

Preparation: To a solution of commercially available 2,4-dichloro-6-methoxy-7-(3-(pyrrolidine-1-yl)propoxy)quinazoline (0.20 g, 0.56 mmol) and glycinamide hydrochloride (0.93 g, 0.84 mmol) in anhydrous DMF (2 mL) was added DIPEA (0.59 mL, 3.36 mmol). The sealed tube was heated to 50° C. under argon atmosphere. The reaction was monitored by TLC with dichloromethane and HP/LCMS found 394.1. Upon completion after 3 days, the cooled reaction was extracted with 8:2 dichloromethane/isopropanol mixtures (4×50 mL) and washed with sat. sodium bicarbonate. The combined organic layers were dried over anhydrous $Na_2SO_4$, filtered, and concentrated in vacuo. The crude was dissolved in 2-butanol (1 ml) with DIPEA (1.18 mL, 6.72 mmol) and added 4,4-difluoropiperidine hydrochloride (1.03 mL, 12.35 mmol) then the sealed tube was heated to 90° C. for 4 days. The cooled mixtures were extracted with dichloromethane/isopropanol (8:2) mixtures washing with sat. $NaHCO_3$ and with brine. The combined organic layers were dried over anhydrous $Na_2SO_4$, filtered, and concentrated in vacuo. The residue was purified by Buchi Pureflash chromatography over silica gel cartridge (24 g) with 9:1 $CH_2Cl_2$:MeOH w/2% 7N ammonia to give 2-((2-(4,4-difluoropiperidin-1-yl)-6-methoxy-7-(3-(pyrrolidin-1-yl)propoxy)quinazolin-4-yl)amino)acetamide (0.13 g, 49%) as a light orange solid. $^1$H NMR (400 MHz, DMSO-d): δ 6.89 (s, 1H), 6.84 (s, 1H), 6.16 (s, 1H), 6.06 (bs, 1H), 5.54 (s, 1H), 4.21 (d, 2H, J=8.0 Hz), 4.17 (m, 2H), 3.96 (m, 4H), 3.89 (s, 3H), 2.70 (m, 2H), 2.60 (m, 4H), 2.13 (m, 2H), 1.96 (m, 4H), 1.81 (m, 4H). MS (ESI): Calcd. for $C_{23}H_{32}F_2N_6O_3$: 478, found 479 (M+H)$^+$.

Example 18

Synthesis of 2-(azetidin-1-yl)-6-methoxy-7-(3-(pyrrolidin-1-yl)propoxy)-N-(tetrahydro-2H-pyran-4-yl)quinazolin-4-amine (Compound 174)

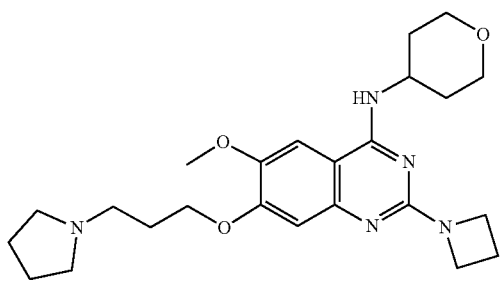 [SMILES: COc1cc2c(NC3CCOCC3)nc(N3CCC3)nc2cc1OCCCN1CCCC1]

Preparation: To a solution of 7-(3-(pyrrolidin-1-yl)propoxy)-N-(tetrahydro-2H-pyran-4-yl)quinazolin-4-amine (0.15 g, 0.36 mmol) and azetidine hydrochloride (0.33 g, 3.56 mmol) in anhydrous THF (2 mL) was added DIPEA (1.55 mL, 8.91 mmol). The sealed tube was heated to 90° C. for 7 days under argon atmosphere. The cooled reaction was quenched with sat. $NaHCO_3$ and extracted with 8:2 dichloromethane/isopropanol mixtures (3×25 mL) then washed once with brine. The combined organic layers were dried over anhydrous $Na_2SO_4$, filtered, and concentrated in vacuo. The residue was purified by Buchi Pureflash chromatography over silica gel cartridge (24 g) with 8:2 $CH_2Cl_2$:MeOH w/2% 7N ammonia to give 2-(azetidin-1-yl)-6-methoxy-7-(3-(pyrrolidin-1-yl)propoxy)-N-(tetrahydro-2H-pyran-4-yl)quinazolin-4-amine (0.04 g, 27%) as a white solid. $^1$H NMR (400 MHz, CDCl$_3$): δ 6.94 (s, 1H), 6.70 (s, 1H), 4.98 (d, 1H, J=8.0 Hz), 4.34 (m, 1H), 4.18-4.10 (m, 6H), 4.01 (m, 2H), 3.90 (s, 3H), 3.54 (dt, 2H, J=12.0, 0.2 Hz), 2.62 (t, 2H, J=8.0 Hz), 2.52 (m, 4H), 2.29 (m, 2H), 2.16-2.02 (m, 4H), 1.76 (m, 4H), 1.59 (ddd, 2H, J=8.0, 8.0, 4.0 Hz). MS (ESI): Calcd. for $C_{24}H_{35}N_5O_3$: 441, found 442 (M+H)$^+$.

Example 19

Synthesis of 6-methoxy-2-(pyrrolidin-1-yl)-7-(3-(pyrrolidin-1-yl)propoxy)-N-(tetrahydro-2H-pyran-4-yl)quinazolin-4-amine (Compound 164)

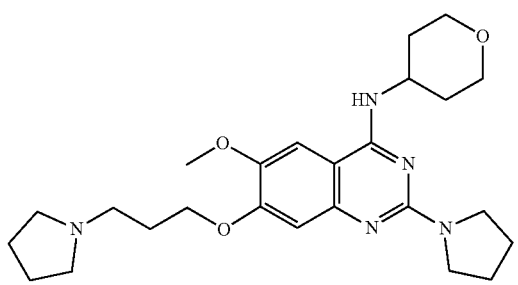 [SMILES: COc1cc2c(NC3CCOCC3)nc(N3CCCC3)nc2cc1OCCCN1CCCC1]

Preparation: To a solution of 7-(3-(pyrrolidin-1-yl)propoxy)-N-(tetrahydro-2H-pyran-4-yl)quinazolin-4-amine (0.15 g, 0.36 mmol) and pyrrolidine (0.20 g, 3.56 mmol) in anhydrous THF (2 mL) was added DIPEA (0.09 mL, 0.53 mmol). The sealed tube was heated to 90° C. for 3 days under argon atmosphere. The cooled reaction was quenched with sat. $NaHCO_3$ and extracted with 8:2 dichloromethane/isopropanol mixtures (3×25 mL) then washed once with brine. The combined organic layers were dried over anhydrous $Na_2SO_4$, filtered, and concentrated in vacuo. The residue was purified by Buchi Pureflash chromatography over silica gel cartridge (24 g) with 8:2 $CH_2Cl_2$:MeOH w/2% 7N ammonia to give 6-methoxy-2-(pyrrolidin-1-yl)-7-(3-(pyrrolidin-1-yl)propoxy)-N-(tetrahydro-2H-pyran-4-yl)quinazolin-4-amine (0.15 g, 89%) as a beige solid. $^1$H NMR (400 MHz, CDCl$_3$): δ 7.21 (s, 1H), 6.88 (s, 1H), 5.56 (d, 1H, J 8.0 Hz), 4.34 (m, 1H), 4.15 (m, 2H), 4.01 (m, 2H), 3.90 (s, 3H), 3.65 (m, 4H), 3.54 (dt, 2H, J=12.0, 0.2 Hz), 2.72 (m, 2H), 2.65 (m, 4H), 2.12 (m, 4H), 1.96 (m, 4H), 1.82 (m, 4H), 1.68 (ddd, 2H, J=8.0, 8.0, 4.0 Hz). MS (ESI): Calcd. for $C_{25}H_{37}N_5O_3$: 455, found 456 (M+H)$^+$.

Example 20

Synthesis of 6-methoxy-2-morpholino-7-(3-(pyrrolidin-1-yl)propoxy)-N-(tetrahydro-2H-pyran-4-yl)quinazolin-4-amine (Compound 195)

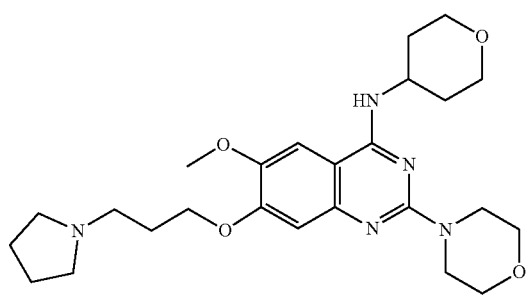 [SMILES: COc1cc2c(NC3CCOCC3)nc(N3CCOCC3)nc2cc1OCCCN1CCCC1]

Preparation: To a solution of 7-(3-(pyrrolidin-1-yl)propoxy)-N-(tetrahydro-2H-pyran-4-yl)quinazolin-4-amine (0.15 g, 0.36 mmol) and morpholine (0.10 g, 1.78 mmol) in anhydrous THF (2 mL) was added DIPEA (0.09 mL, 0.53 mmol). The sealed tube was heated to 90° C. for 3 days under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 6-methoxy-2-morpholino-7-(3-(pyrrolidin-1-yl)propoxy)-N-(tetrahydro-2H-pyran-4-yl)quinazolin-4-amine (0.16 g, 96%) as a beige solid. $^1$H NMR (400 MHz, CDCl$_3$): δ 6.90 (s, 1H), 6.70 (s, 1H), 4.99 (d, 1H, J=8.0 Hz), 4.32 (m, 1H), 4.15 (m, 2H), 4.02 (m, 2H), 3.91 (s, 3H), 3.77 (s, 4H), 3.55 (dt, 2H, J=8.0, 2.0 Hz), 2.66 (m, 2H), 2.56 (m, 4H), 2.11 (m, 4H), 1.79 (m, 4H), 1.62 (ddd, 2H, J=8.0, 8.0, 4.0 Hz). MS (ESI): Calcd. for C$_{25}$H$_{37}$N$_5$O$_4$: 471, found 472 (M+H)$^+$.

Example 21

Synthesis of 6-methoxy-2-(4-methylpiperazin-1-yl)-7-(3-(pyrrolidin-1-yl)propoxy)-N-(tetrahydro-2H-pyran-4-yl)quinazolin-4-amine (Compound 236)

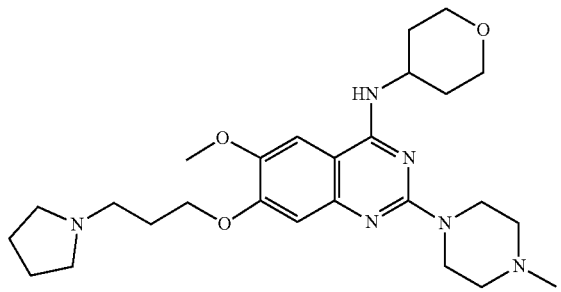 [SMILES: COc1cc2c(NC3CCOCC3)nc(N3CCN(C)CC3)nc2cc1OCCCN1CCCC1]

Preparation: To a solution of 7-(3-(pyrrolidin-1-yl)propoxy)-N-(tetrahydro-2H-pyran-4-yl)quinazolin-4-amine (0.10 g, 0.24 mmol) and 1-methylpiperazine (0.07 g, 1.19 mmol) in anhydrous THF (1.5 mL) was added DIPEA (0.09 mL, 0.53 mmol). The sealed tube was heated to 90° C. for 3 days under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 6-methoxy-2-(4-methylpiperazin-1-yl)-7-(3-(pyrrolidin-1-yl)propoxy)-N-(tetrahydro-2H-pyran-4-yl)quinazolin-4-amine (0.11 g, 97%) as an off-white solid. $^1$H NMR (400 MHz, CDCl$_3$): δ 6.89 (s, 1H), 6.68 (s, 1H), 4.94 (d, 1H, J=4.0 Hz), 4.32 (m, 1H), 4.15 (t, 2H, J=8.0 Hz), 4.03 (m, 2H), 3.90 (s, 3H), 3.83 (m, 4H), 3.56 (dt, 2H, J=12.0, 2.0 Hz), 2.63 (t, 2H, J=8.0 Hz), 2.53 (m, 4H), 2.47 (m, 4H), 2.33 (s, 3H), 2.15-2.05 (m, 4H), 1.77 (m, 4H), 1.61 (ddd, 2H, J=8.0, 8.0, 4.0 Hz). MS (ESI): Calcd. for C$_{26}$H$_{40}$N$_6$O$_3$: 484, found 485 (M+H)$^+$.

Example 22

Synthesis of 6-methoxy-2-(4-methyl-1,4-diazepan-1-yl)-7-(3-(pyrrolidin-1-yl)propoxy)-N-(tetrahydro-2H-pyran-4-yl)quinazolin-4-amine (Compound 237)

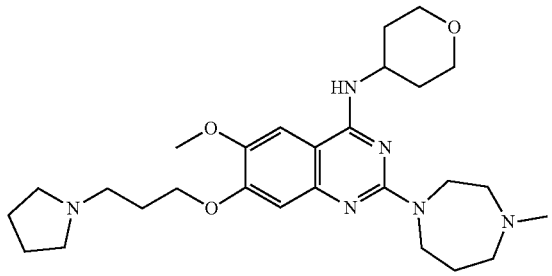 [SMILES: COc1cc2c(NC3CCOCC3)nc(N3CCCN(C)CC3)nc2cc1OCCCN1CCCC1]

Preparation: To a solution of 7-(3-(pyrrolidin-1-yl)propoxy)-N-(tetrahydro-2H-pyran-4-yl)quinazolin-4-amine (0.10 g, 0.24 mmol) and 1-methylhomopiperazine (0.07 g, 1.19 mmol) in anhydrous THF (1.5 mL) was added DIPEA (0.09 mL, 0.53 mmol). The sealed tube was heated to 90° C. for 3 days under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 9:1 CH$_2$Cl$_2$:MeOH w/2% 7N ammonia to give 6-methoxy-2-(4-methyl-1,4-diazepan-1-yl)-7-(3-(pyrrolidin-1-yl)propoxy)-N-(tetrahydro-2H-pyran-4-yl)quinazolin-4-amine (0.12 g, 99%) as an-off white solid. $^1$H NMR (400 MHz, CDCl$_3$): δ 6.88 (s, 1H), 6.68 (s, 1H), 4.91 (d, 1H, J=8.0 Hz), 4.29 (m, 1H), 4.15 (m, 2H), 4.03 (m, 2H), 3.95 (m, 2H), 3.90 (s, 3H), 3.85 (t, 2H, J=8.0 Hz), 3.55 (dt, J=12.0, 4.0 Hz), 2.68 (t, 2H, J=4.0 Hz), 2.62 (t, 2H, J=8.0 Hz), 2.51 (m, 4H), 2.35 (s, 3H), 2.15-2.05 (m, 4H), 1.99 (m, 2), 1.77 (m, 4H), 1.61 (ddd, 2H, J=8.0, 8.0, 4.0 Hz). MS (ESI): Calcd. for C$_{27}$H$_{42}$N$_6$O$_3$: 498, found 499 (M+H)$^+$.

Example 24

Synthesis of 4-(6-methoxy-7-(3-(pyrrolidin-1-yl)propoxy)-4-((tetrahydro-2H-pyran-4-yl)amino)quinazolin-2-yl)thiomorpholine 1,1-dioxide (Compound 196)

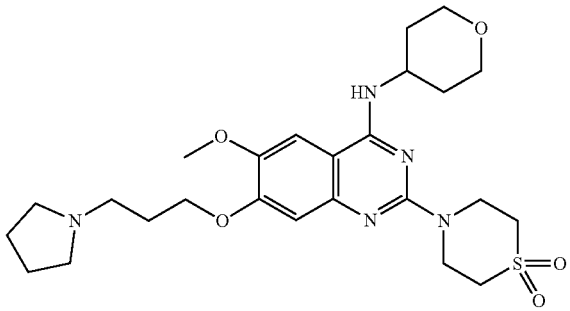 [SMILES: COc1cc2c(NC3CCOCC3)nc(N3CCS(=O)(=O)CC3)nc2cc1OCCCN1CCCC1]

Preparation: To a solution of 7-(3-(pyrrolidin-1-yl)propoxy)-N-(tetrahydro-2H-pyran-4-yl)quinazolin-4-amine (0.15 g, 0.36 mmol) and thiomorpholine 1,1-dioxide (0.24 g, 1.78 mmol) in anhydrous THF (3 mL) was added DIPEA (0.12 mL, 0.71 mmol). The sealed tube was heated to 90° C. for 10 days under argon atmosphere. The precipitate was collected by filtration to give 4-(6-methoxy-7-(3-(pyrrolidin-1-yl)propoxy)-4-((tetrahydro-2H-pyran-4-yl)amino)quinazolin-2-yl)thiomorpholine 1,1-dioxide (0.11 g, 61%) as a white solid. $^1$H NMR (400 MHz, CDCl$_3$): δ 6.92 (s, 1H), 6.87 (s, 1H), 5.48 (bs, 1H), 4.36 (m, 4H), 4.27 (m, 1H), 4.17 (m, 2H), 4.04 (m, 4H), 3.92 (s, 3H), 3.54 (m, 3H), 3.26 (m, 3H), 3.05 (m, 5H), 2.45 (m, 2H), 2.13 (m, 4H), 2.06 (m, 3H), 1.70 (ddd, 2H, J=8.0, 8.0, 4.0 Hz). MS (ESI): Calcd. for C$_{25}$H$_{37}$N$_5$O$_5$S: 519, found 520 (M+H)$^+$.

Example 25

Synthesis of 4-((2-chloro-6-methoxy-7-(3-(pyrrolidin-1-yl)propoxy)quinazolin-4-yl)amino)tetrahydro-2H-thiopyran 1,1-dioxide (Compound 111)

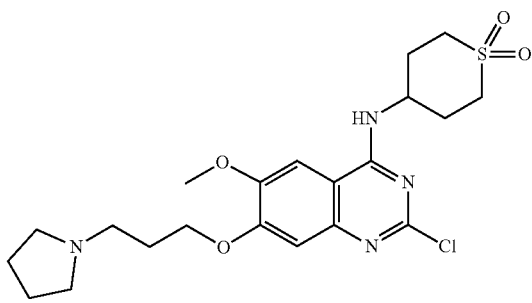 [SMILES: COc1cc2c(NC3CCS(=O)(=O)CC3)nc(Cl)nc2cc1OCCCN1CCCC1]

Preparation: To a solution of commercially available 2,4-dichloro-6-methoxy-7-(3-(pyrrolidine-1-yl)propoxy)quinazoline (2.03 g, 5.69 mmol) and 4-aminotetrahydro-2H-thiopyran (1.27 g, 8.54 mmol) in anhydrous 3:1 DMF/isopropanol (20 mL) was added DIPEA (1.98 mL, 11.39 mmol). The sealed tube was heated to 50° C. for 6 days under argon atmosphere. The cooled reaction was concentrated in vacuo. The residue was dried load onto silica (15 g) and purified by Buchi Pureflash chromatography over silica gel cartridge (80 g) with 9:1 CH$_2$Cl$_2$:MeOH w/2% 7N ammonia to give 4-((2-chloro-6-methoxy-7-(3-(pyrrolidin-1-yl)propoxy)quinazolin-4-yl)amino)tetrahydro-2H-thiopyran 1,1-dioxide (1.93 g, 72%) as a beige solid. $^1$H NMR (400 MHz, CDCl$_3$): δ 7.07 (s, 1H), 6.99 (s, 1H), 6.27 (d, 1H, J=8.0 Hz), 4.65 (m, 1H), 4.15 (t, 2H, J=8.0 Hz), 3.95 (s, 3H), 3.29 (m, 3H), 3.16 (m, 2H), 2.90 (m, 1H), 2.70 (t, 2H, J=8.0 Hz), 2.62 (m, 4H), 2.48 (m, 2H), 2.37 (m, 4H), 2.19 (m, 1H), 2.14 (p, 2H, J=8.0 Hz), 1.99 (m, 1H), 1.81 (m, 4H). MS (ESI): Calcd. for C$_{21}$H$_{29}$ClN$_4$O$_4$S: 469, found 469 (M)$^+$, 471 (M+2H)$^+$.

Example 26

Synthesis of 4-((6-methoxy-2-(pyrrolidin-1-yl)-7-(3-(pyrrolidin-1-yl)propoxy)quinazolin-4-yl)amino)tetrahydro-2H-thiopyran 1,1-dioxide (Compound 80)

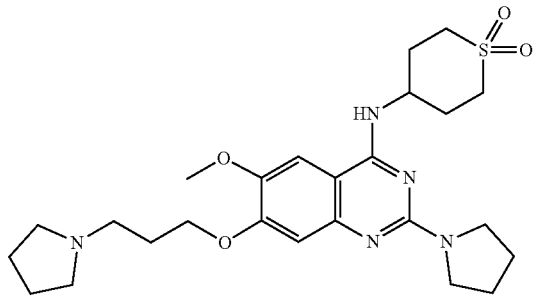 [SMILES: COc1cc2c(NC3CCS(=O)(=O)CC3)nc(N3CCCC3)nc2cc1OCCCN1CCCC1]

Preparation: To a solution of 4-((2-chloro-6-methoxy-7-(3-(pyrrolidin-1-yl)propoxy)quinazolin-4-yl)amino)tetrahydro-2H-thiopyran 1,1-dioxide (0.15 g, 0.32 mmol) and pyrrolidine (0.11 g, 1.60 mmol) in anhydrous THF (2 mL) was added DIPEA (0.08 mL, 0.48 mmol). The sealed tube was heated to 90° C. for 5 days under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 4-((6-methoxy-2-(pyrrolidin-1-yl)-7-(3-(pyrrolidin-1-yl)propoxy)quinazolin-4-yl)amino)tetrahydro-2H-thiopyran 1,1-dioxide (0.15 g, 89%) as an off-white solid. $^1$H NMR (400 MHz, CDCl$_3$): δ 6.92 (s, 1H), 6.71 (s, 1H), 5.08 (d, 1H, J=8.0 Hz), 4.44 (m, 1H), 4.14 (t, 2H, J=8.0 Hz), 3.90 (s, 3H), 3.59 (m, 4H), 3.15 (m, 4H), 2.61 (t, 2H, J=8.0 Hz), 2.53 (m, 2H), 2.51 (m, 4H), 2.28 (m, 2H), 2.08 (p, 2H, J=8.0 Hz), 1.95 (m, 4H), 1.76 (m, 4H). MS (ESI): Calcd. for C$_{25}$H$_{37}$N$_5$O$_4$S: 503, found 504 (M+H)$^+$.

Example 27

Synthesis of 4-((6-methoxy-2-morpholino-7-(3-(pyrrolidin-1-yl)propoxy)quinazolin-4-yl)amino)tetrahydro-2H-thiopyran 1,1-dioxide (Compound 102)

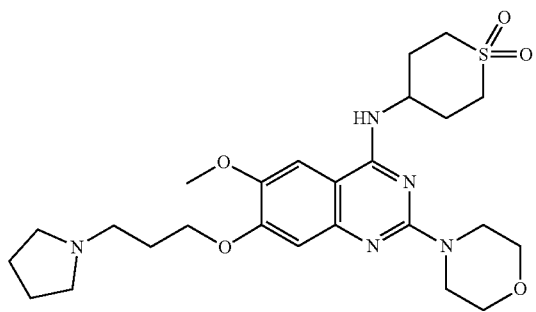 [SMILES: COc1cc2c(NC3CCS(=O)(=O)CC3)nc(N3CCOCC3)nc2cc1OCCCN1CCCC1]

Preparation: To a solution of 4-((2-chloro-6-methoxy-7-(3-(pyrrolidin-1-yl)propoxy)quinazolin-4-yl)amino)tetrahydro-2H-thiopyran 1,1-dioxide (0.15 g, 0.32 mmol) and morpholine (0.14 g, 1.60 mmol) in anhydrous THF (2 mL) was added DIPEA (0.08 mL, 0.48 mmol). The sealed tube was heated to 90° C. for 5 days under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 4-((6-methoxy-2-morpholino-7-(3-(pyrrolidin-1-yl)propoxy)quinazolin-4-yl)amino)tetrahydro-2H-thiopyran 1,1-dioxide (0.13 g, 80%) as an off-white solid. $^1$H NMR (400 MHz, CDCl$_3$): δ 6.90 (s, 1H), 6.71 (s, 1H), 5.15 (d, 1H, J=8.0 Hz), 4.43 (m, 1H), 4.16 (t, 2H, J=8.0 Hz), 3.91 (s. 3H), 3.77 (bs, 8H), 3.16 (dd, 4H, J=8.0, 4.0 Hz), 2.66 (t, 2H, J=8.0 Hz), 2.56 (m, 4H), 2.52 (m, 2H), 2.31 (m, 2H), 2.12 (p, 2H, J=8.0 Hz), 1.79 (m, 4H). MS (ESI): Calcd. for C$_{25}$H$_{37}$N$_5$O$_5$S: 519, found 520 (M+H)$^+$.

Example 28

Synthesis of 4-((6-methoxy-2-(4-methylpiperazin-1-yl)-7-(3-(pyrrolidin-1-yl)propoxy)quinazolin-4-yl)amino)tetrahydro-2H-thiopyran 1,1-dioxide (Compound 109)

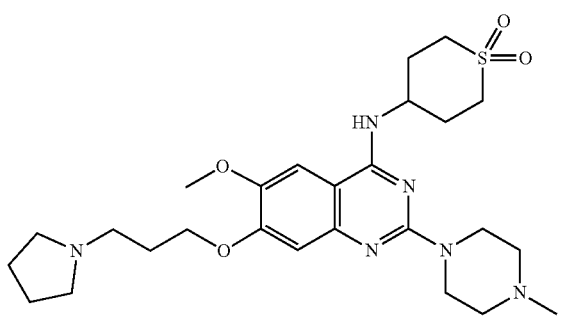 [SMILES: COc1cc2c(NC3CCS(=O)(=O)CC3)nc(N3CCN(C)CC3)nc2cc1OCCCN1CCCC1]

Preparation: To a solution of 4-((2-chloro-6-methoxy-7-(3-(pyrrolidin-1-yl)propoxy)quinazolin-4-yl)amino)tetrahydro-2H-thiopyran 1,1-dioxide (0.10 g, 0.21 mmol) and 1-methylpiperazine (0.11 g, 1.07 mmol) in anhydrous THF (2 mL) was added DIPEA (0.06 mL, 0.32 mmol). The sealed tube was heated to 90° C. for 5 days under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia to give 4-((6-methoxy-2-(4-methylpiperazin-1-yl)-7-(3-(pyrrolidin-1-yl)propoxy)quinazolin-4-yl)amino)tetrahydro-2H-thiopyran 1,1-dioxide (0.09 g, 81%) as an off-white solid. $^1$H NMR (400 MHz, CDCl$_3$): δ 6.90 (s, 1H), 6.69 (s, 1H), 5.07 (d, 1H, J=8.0 Hz), 4.43 (m, 1H), 4.15 (t, 2H, J=8.0 Hz), 3.91 (s, 3H), 3.82 (m, 4H), 3.16 (m, 4H), 2.63 (t, 2H, J=8.0 Hz), 2.33 (s, 3H), 2.27 (m, 3H), 2.10 (p, 2H, J=8.0 Hz), 1.94 (bs, 1H), 1.77 (m, 4H). MS (ESI): Calcd. for C$_{26}$H$_{40}$N$_6$O$_4$S: 532, found 533 (M+H)$^+$.

Example 29

Synthesis of 4-(4-((1,1-dioxidotetrahydro-2H-thiopyran-4-yl)amino)-6-methoxy-7-(3-(pyrrolidin-1-yl)propoxy)quinazolin-2-yl)thiomorpholine 1,1-dioxide (Compound 103)

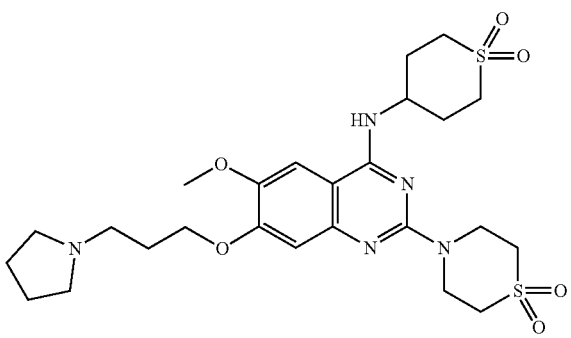 [SMILES: COc1cc2c(NC3CCS(=O)(=O)CC3)nc(N3CCS(=O)(=O)CC3)nc2cc1OCCCN1CCCC1]

Preparation: To a solution of 4-((2-chloro-6-methoxy-7-(3-(pyrrolidin-1-yl)propoxy)quinazolin-4-yl)amino)tetrahydro-2H-thiopyran 1,1-dioxide (0.15 g, 0.32 mmol) and thiomorpholine 1,1-dioxide (0.22 g, 1.60 mmol) in anhydrous THF (2 mL) was added DIPEA (0.11 mL, 0.64 mmol). The sealed tube was heated to 90° C. for 12 days under argon atmosphere. The reaction was cooled reaction and the precipitate product was collected by filtration washing with cold THF to give 4-(4-((1,1-dioxidotetrahydro-2H-thiopyran-4-yl)amino)-6-methoxy-7-(3-(pyrrolidin-1-yl)propoxy)quinazolin-2-yl)thiomorpholine 1,1-dioxide (0.09 g, 81%) as beige solid. $^1$H NMR (400 MHz, CDCl$_3$/DMSO-d mixture): δ 6.88 (s, 1H), 6.71 (s, 1H), 5.12 (d, 1H, J=8.0 Hz), 4.38 (m 1H), 4.15 (t, 2H, J=8.0 Hz), 3.93 (m, 2H), 3.90 (s, 1H), 3.84 (t, 2H, J=8.0 Hz), 3.16 (m, 3H), 2.67 (m 2H), 2.60 (t, 2H, J=8.0 Hz), 2.55 (m, 2H) 2.48 (m 4H), 2.35 (s, 3H), 2.28 (m, 1H), 2.08 (p, 2H, J=8.0 Hz), 1.98 (m, 4H), 1.76 (m, 4H). MS (ESI): Calcd. for C$_{25}$H$_{37}$N$_5$O$_6$S$_2$: 567, found 568 (M+H)$^+$.

Example 30

Synthesis of 4-((6-methoxy-2-(4-methyl-1,4-diazepan-1-yl)-7-(3-(pyrrolidin-1-yl)propoxy)quinazolin-4-yl)amino)tetrahydro-2H-thiopyran 1,1-dioxide (Compound 110)

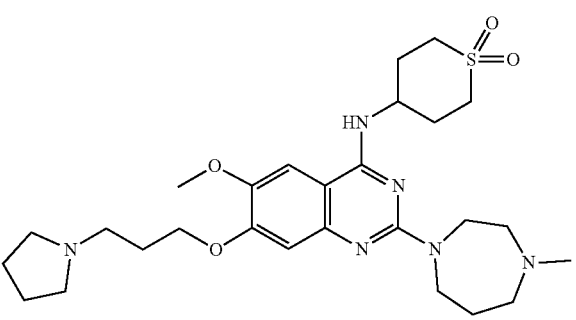 [SMILES: COc1cc2c(NC3CCS(=O)(=O)CC3)nc(N3CCCN(C)CC3)nc2cc1OCCCN1CCCC1]

Preparation: To a solution of 4-((2-chloro-6-methoxy-7-(3-(pyrrolidin-1-yl)propoxy)quinazolin-4-yl)amino)tetrahydro-2H-thiopyran 1,1-dioxide (0.10 g, 0.21 mmol) and 1-methylhomopiperazine (0.12 g, 1.07 mmol) in anhydrous THF (2 mL) was added DIPEA (0.05 mL, 0.32 mmol). The sealed tube was heated to 90° C. for 5 days under argon atmosphere. The cooled reaction was quenched with sat. NaHCO$_3$ and extracted with 8:2 dichloromethane/isopropanol mixtures (3×25 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 9:1 CH$_2$Cl$_2$:MeOH w/2% 7N ammonia to give 4-((6-methoxy-2-(4-methyl-1,4-diazepan-1-yl)-7-(3-(pyrrolidin-1-yl)propoxy)quinazolin-4-yl)amino) tetrahydro-2H-thiopyran 1,1-dioxide (0.12 g, 99%) as an off-white solid. $^1$H NMR (400 MHz, CDCl$_3$): δ 6.89 (s, 1H), 6.68 (s, 1H), 5.02 (d, 1H, J=8.0 Hz), 4.38 (m, 1H), 4.16 (t, 2H, J=8.0 Hz), 3.94 (m, 2H), 3.90 (s, 3H), 3.84 (t, 2H, J=8.0 Hz), 3.16 (m, 4H) 2.69 (m, 2H), 2.63 (t, 2H, J=8.0 Hz), 2.59-2.45 (m, 8H), 2.36 (s, 3H), 2.28 (m, 2H), 2.10 (p, 2H, J=8.0 Hz), 1.99 (m, 3H), 1.77 (m, 4H). MS (ESI): Calcd. for C$_{27}$H$_{42}$N$_6$O$_4$S: 546, found 547 (M+H)$^+$.

Example 31

4-((7-(benzyloxy)-2-chloro-6-methoxyquinazolin-4-yl)amino)tetrahydro-2H-thiopyran 1,1-dioxide (Compound-133)

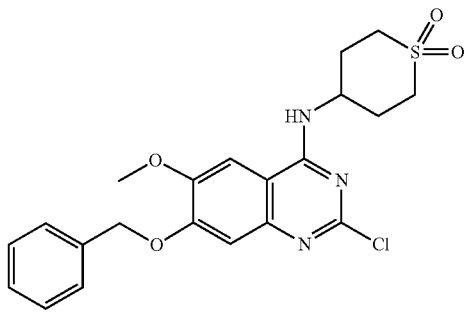 [SMILES: COc1cc2c(NC3CCS(=O)(=O)CC3)nc(Cl)nc2cc1OCc1ccccc1]

Preparation: To a solution of commercially available 7-(benzyloxy)-2,4-dichloro-6-methoxyquinazoline (2.00 g, 5.97 mmol) and 4-aminotetrahydro-2H-thiopyran (1.34 g, 8.95 mmol) in anhydrous DMF (15 mL) was added DIPEA (2.60 mL, 14.92 mmol). The sealed tube was heated to 50° C. for 6 days under argon atmosphere. The cooled reaction was concentrated in vacuo. The crude solid was suspended and sonicated in minimum amount of methanol and the precipitate was collected by filtration to give 4-((7-(benzyloxy)-2-chloro-6-methoxyquinazolin-4-yl)amino)tetrahydro-2H-thiopyran 1,1-dioxide (2.67 g, 100%) as a white solid. $^1$H NMR (400 MHz, DMSO-d): δ 8.07 (d, 1H, J=8.0 Hz), 7.65 (s, 1H), 7.48 (d, 2H, J=4.0 Hz), 7.41 (dd, 2H, J=4.0, 4.0 Hz), 7.36 (d, 1H, J=4.0 Hz), 7.18 (s, 1H), 4.53 (m, 1H), 3.90 (s, 3H), 3.45 (td, 2H, J=12.0, 4.0 Hz), 3.12 (d, 2H, J=8.0 Hz), 2.25-2.10 (m, 4H). MS (ESI): Calcd. for C$_{21}$H$_{22}$ClN$_3$O$_4$S: 447, found 448 (M+H)$^+$.

Example 32

4-((7-(benzyloxy)-2-(4,4-difluoropiperidin-1-yl)-6-methoxyquinazolin-4-yl)amino)tetrahydro-2H-thiopyran 1,1-dioxide, (Compound-134)

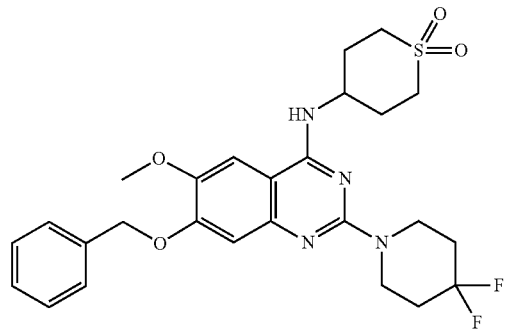 [SMILES: COc1cc2c(NC3CCS(=O)(=O)CC3)nc(N3CCC(F)(F)CC3)nc2cc1OCc1ccccc1]

Preparation: To a suspension of 4-((7-(benzyloxy)-2-chloro-6-methoxyquinazolin-4-yl)amino)tetrahydro-2H-thiopyran 1,1-dioxide (1.30 g, 2.90 mmol) and DIPEA (0.44 mL, 2.53 mmol) in anhydrous 2-butanol (20 mL) was added 4,4-difluoropiperidine hydrochloride (2.29 g, 14.51 mmol). The sealed tube was stirred and heated to 90° C. under argon atmosphere. Upon completion after 5 days, the cooled reaction mixtures were quenched with sat. NaHCO$_3$ and extracted with 8:2 dichloromethane/isopropanol mixtures (3×50 mL). The combined organic layers were dried over anhydrous Na$_2$SO$_4$, filtered, and concentrated in vacuo. The crude solid was suspended and sonicated in minimum amount of dichloromethane and the precipitated product was collected by filtration to give 4-((7-(benzyloxy)-2-(4,4-difluoropiperidin-1-yl)-6-methoxyquinazolin-4-yl)amino)tetrahydro-2H-thiopyran 1,1-dioxide (1.35 g, 87%) as a white solid. $^1$H NMR (400 MHz, DMSO-d): δ 7.52 (d, 1H, J=8.0 Hz), 7.51 (s, 1H), 7.52 (d, 2H, J=8.0 Hz), 7.40 (m, 2H), 7.34 (m 1H), 6.87 (s, 1H), 5.18 (s, 2H), 4.48 (m, 1H), 3.91 (m, 4H), 3.83 (s, 3H), 3.43 (td, 2H, J=12.0, 4.0 Hz), 3.14 (d, 2H, J=12.0 Hz), 2.25 (m, 2H), 2.13 (m, 2H), 1.95 (m, 4H). MS (ESI): Calcd. for C$_{26}$H$_{30}$F$_2$N$_4$O$_4$S: 532, found 533 (M+H)$^+$.

Example 33

4-((2-(4,4-difluoropiperidin-1-yl)-7-hydroxy-6-methoxyquinazolin-4-yl)amino)tetrahydro-2H-thiopyran 1,1-dioxide, (Compound-238)

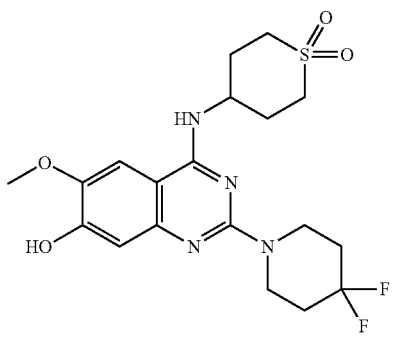 [SMILES: COc1cc2c(NC3CCS(=O)(=O)CC3)nc(N3CCC(F)(F)CC3)nc2cc1O]

Preparation: To a suspension of 4-((7-(benzyloxy)-2-(4,4-difluoropiperidin-1-yl)-6-methoxyquinazolin-4-yl)amino)tetrahydro-2H-thiopyran 1,1-dioxide (1.10 g, 2.90 mmol) in absolute ethanol (120 mL) was bubbled under argon atmosphere for 20 min was added 10% palladium over carbon (0.22 g, 0.21 mmol). Then the mixtures were bubbled with hydrogen gas via a needle into the solution for 15 min. The reaction was stirred and kept under a hydrogen balloon over the weekend. After completion, the mixture was diluted with THF (300 mL) and filter through a pad of celite. The solvent was concentrated to a solid. The crude solid was then suspended and sonicated in minimum amount of methanol and the precipitated product was collected by filtration to give 4-((2-(4,4-difluoropiperidin-1-yl)-7-hydroxy-6-methoxyquinazolin-4-yl)amino)tetrahydro-2H-thiopyran 1,1-dioxide (1.35 g, 87%) as a white solid. $^1$H NMR (400 MHz, DMSO-d): δ 9.77 (s, 1H), 7.42 (m, 2H), 6.65 (s, 1H), 4.47 (m, 1H), 3.87 (m, 4H), 3.82 (s, 3H), 3.41 (td, 2H, J=12.0, 4.0 Hz), 3.14 (m, 2H), 2.25 (m, 2H), 2.12 (m, 2H), 1.94 (m, 4H). MS (ESI): Calcd. for $C_{19}H_{24}F_2N_4O_4S$: 442, found 443 (M+H)$^+$.

Example 34

2-(4,4-difluoropiperidin-1-yl)-4-((1,1-dioxidotetrahydro-2H-thiopyran-4-yl)amino)-6-methoxyquinazolin-7-yl trifluoromethanesulfonate, (Compound-i-1)

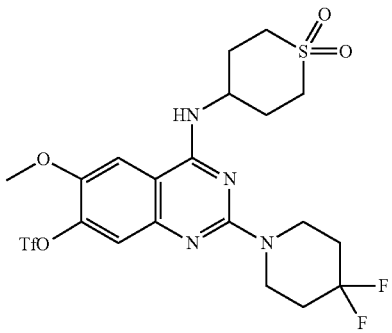 [SMILES: COc1cc2c(NC3CCS(=O)(=O)CC3)nc(N3CCC(F)(F)CC3)nc2cc1OS(=O)(=O)C(F)(F)F]

Preparation: To a suspension of 4-((2-(4,4-difluoropiperidin-1-yl)-7-hydroxy-6-methoxyquinazolin-4-yl)amino)tetrahydro-2H-thiopyran 1,1-dioxide (0.45 g, 1.02 mmol) in anhydrous THF (20 mL) under argon atmosphere was added potassium carbonate (0.28 g, 2.05 mmol) and N-phenyl-bis(trifluoromethanesulfonimide (0.48 g, 1.33 mmol). The reaction was stirred for 24 hr. After completion, the reaction was quenched with sat. NaHCO$_3$ and extracted with 8:2 dichloromethane/isopropanol mixtures (5×50 mL) then washed once with brine. The combined organic layers were dried over anhydrous Na$_2$SO$_4$, filtered, and concentrated in vacuo. The residue was solid loaded onto silica (5 g) and purified by Buchi Pureflash chromatography over silica gel cartridge (80 g) with 95:5 CH$_2$Cl$_2$:MeOH w/2% 7N ammonia to give 2-(4,4-difluoropiperidin-1-yl)-4-((1,1-dioxidotetrahydro-2H-thiopyran-4-yl)amino)-6-methoxyquinazolin-7-yl trifluoromethanesulfonate (0.56 g, 95%) as a white solid. $^1$H NMR (400 MHz, DMSO-d): δ 7.88 (d, 1H, J=12.0 Hz), 7.83 (s, 1H), 7.32 (s, 1H), 4.53 (m, 1H), 3.96 (s, 3H), 3.92 (m, 4H), 3.45 (td, 2H, J=12.0, 4.0 Hz), 3.16 (d, 2H, J=12.0 Hz), 2.27 (m, 2H), 2.14 (m, 4H), 1.97 (m, 4H). MS (ESI): Calcd. for $C_{20}H_{23}F_2N_4O_6S_2$: 574, found 574 (M)$^+$.

Example 35

4-((2-(4,4-difluoropiperidin-1-yl)-6-methoxy-7-(3-(pyrrolidin-1-yl)prop-1-yn-1-yl)quinazolin-4-yl)amino)tetrahydro-2H-thiopyran 1,1-dioxide (Compound 248)

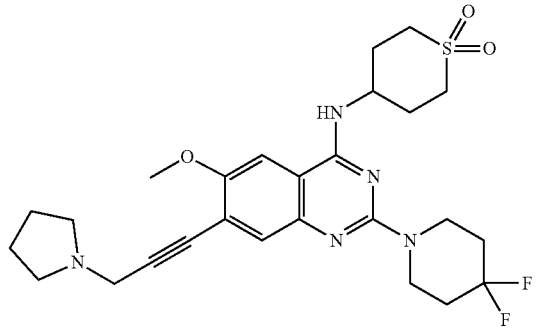 [SMILES: COc1cc2c(NC3CCS(=O)(=O)CC3)nc(N3CCC(F)(F)CC3)nc2cc1C#CCN1CCCC1]

Preparation: To a pressure vessel charged with 1-(prop-2-yn-1-yl)pyrrolidine hydrochloride (355 mg, 2.44 mmol), cesium carbonate (1.36 g, 4.18 mmol), and anhydrous acetonitrile (5 mL) under argon stirred for 5 min. Then, 2-(4,4-difluoropiperidin-1-yl)-4-((1,1-dioxidotetrahydro-2H-thiopyran-4-yl)amino)-6-methoxyquinazolin-7-yl trifluoromethanesulfonate (200 mg, 0.35 mmol) and copper(I) iodide (7.96 mg, 0.042 mmol) was added. The mixtures were bubbled with argon for 15 min, prior to the addition of bis(triphenylphosphine)palladium(II) chloride (24.43 mg, 0.035 mmol) and the sealed vessel was heated to 80° C. for 4 hours. Upon completion, the cooled reaction mixtures were filtered through a pad of celite washing thoroughly with acetonitrile. The solvent was concentrated in vacuo and dried loaded onto silica (3.5 g). It was then purified by Buchi Pureflash chromatography over silica gel cartridge (40 g) with 95:5 CH$_2$Cl$_2$:MeOH w/2% 7N ammonia to give 4-((2-(4,4-difluoropiperidin-1-yl)-6-methoxy-7-(3-(pyrrolidin-1-yl)prop-1-yn-1-yl)quinazolin-4-yl)amino)tetrahydro-2H-thiopyran 1,1-dioxide (1.35 g, 87%) as a light yellow solid. $^1$H NMR (400 MHz, DMSO-d): δ 7.76 (d, 1H, J=8.0 Hz), 7.51 (s, 1H), 7.31 (s, 1H), 4.51 (m, 1H), 3.90 (m, 4H), 3.86 (s, 3H), 3.44 (td, 2H, J=12.0, 4.0 Hz), 3.15 (d, 2H, J=12.0 Hz), 2.60 (m, 4H), 2.26 (m, 2H), 2.14 (m, 2H), 1.96 (m, 4H), 1.73 (m, 4H). MS (ESI): Calcd. for $C_{26}H_{33}F_2N_5O_3S$: 533, found 534 (M+H)$^+$.

Example 36

2-chloro-6-methoxy-N-(oxetan-3-yl)-7-(3-(pyrrolidin-1-yl)propoxy)quinazolin-4-amine, (Compound-114)

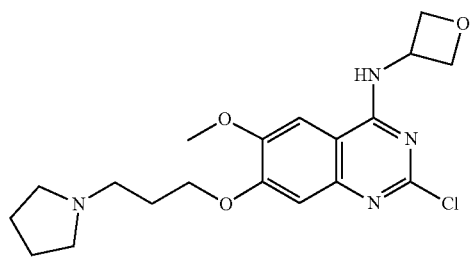 [SMILES: COc1cc2c(NC3COC3)nc(Cl)nc2cc1OCCCN1CCCC1]

Preparation: To a solution of commercially available 2,4-dichloro-6-methoxy-7-(3-(pyrrolidine-1-yl)propoxy)quinazoline (2.00 g, 5.61 mmol) and 3-oxetanamine (0.62 g, 8.42 mmol) in anhydrous DMF (15 mL) was added DIPEA (2.93 mL, 16.84 mmol). The sealed tube was heated to 50° C. for 3 days under argon atmosphere. The cooled reaction was quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (80 g) with 95:5 CH$_2$Cl$_2$:MeOH w/2% 7N ammonia to give 2-chloro-6-methoxy-N-(oxetan-3-yl)-7-(3-(pyrrolidin-1-yl)propoxy)quinazolin-4-amine (1.37 g, 62%) as a beige solid. $^1$H NMR (400 MHz, CDCl$_3$-d): δ 7.10 (s, 1H), 6.92 (s, 1H), 6.25 (d, 1H, J=8.0 Hz), 5.38 (m, 1H), 5.10 (t, 2H, J=8.0 Hz), 4.65 (t, 2H, J=4.0 Hz), 4.14 (t, 2H, J=4.0 Hz), 3.95 (s, 3H), 2.61 (dd, 2H, J=8.0 Hz), 2.50 (m, 4H), 2.08 (m, 2H), 1.76 (m, 4H). MS (ESI): Calcd. for C$_{19}$H$_{25}$ClN$_4$O$_3$: 392, found 393 (M+H)$^+$.

Example 37

2-(4,4-difluoropiperidin-1-yl)-6-methoxy-N-(oxetan-3-yl)-7-(3-(pyrrolidin-1-yl)propoxy)quinazolin-4-amine, (Compound 11)

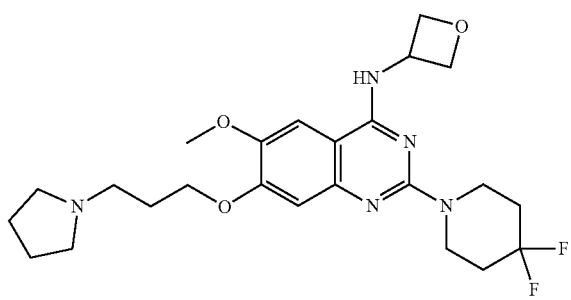 [SMILES: COc1cc2c(NC3COC3)nc(N3CCC(F)(F)CC3)nc2cc1OCCCN1CCCC1]

Preparation: To a solution of 2-chloro-6-methoxy-N-(oxetan-3-yl)-7-(3-(pyrrolidin-1-yl)propoxy)quinazolin-4-amine (0.20 g, 0.51 mmol) and 4,4-difluoropiperidine (0.31 g, 2.55 mmol) in anhydrous THF (8 mL) was added DIPEA (0.33 g, 2.55 mmol). The sealed tube was heat to 90° C. under argon atmosphere for 8 days. The cooled mixtures were quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (40 g) with 9:1 CH$_2$Cl$_2$:MeOH w/2% 7N ammonia to give 2-(4,4-difluoropiperidin-1-yl)-6-methoxy-N-(oxetan-3-yl)-7-(3-(pyrrolidin-1-yl)propoxy)quinazolin-4-amine (0.30 g, 42%) an off-white solid. $^1$H NMR (400 MHz, CDCl$_3$): δ 6.91 (s, 1H), 6.89 (s, 1H), 5.96 (bs, 1H), 5.24 (m, 1H), 5.02 (t, 2H, J=8.0 Hz), 4.72 (t, 2H, J=4.0 Hz), 4.15 (t, 2H, J=8.0 Hz), 3.94 (m, 4H), 3.92 (s, 3H), 2.86 (m, 2H), 2.81 (m, 4H), 2.23 (m, 2H), 1.97 (m, 4H), 1.90 (m, 4H). MS (ESI): Calcd. for C$_{24}$H$_{33}$F$_2$N$_5$O: 477, found 478 (M+H)$^+$.

Example 38

2-(1H-imidazol-1-yl)-6-methoxy-N-(pyridin-4-yl)-7-(3-(pyrrolidin-1-yl)propoxy)quinazolin-4-amine, (Compound-130)

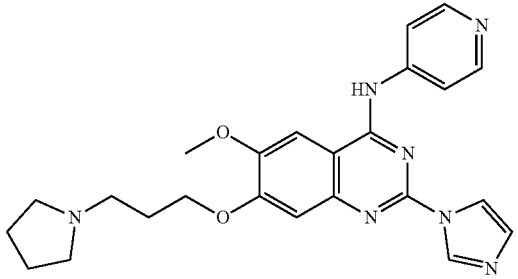 [SMILES: COc1cc2c(Nc3ccncc3)nc(-n3ccnc3)nc2cc1OCCCN1CCCC1]

Preparation: To a solution of commercially available 2,4-dichloro-6-methoxy-7-(3-(pyrrolidine-1-yl)propoxy)quinazoline (0.25 g, 0.70 mmol) and 4-aminopyridine (0.07 g, 0.77 mmol) in anhydrous THF (5 mL) was added excess 60% sodium hydride (0.04, 0.91 mmol). The mixtures were stirred for 30 min under an argon balloon. The tube was then sealed and heated to 50° C. under argon atmosphere. The reaction was monitored by TLC with dichloromethane and HPLC/MS of 414. Upon completion after 20 hours, the cooled reaction was quenched with sat. NH$_4$Cl (2 mL) and followed by sat. NaHCO$_3$ (50 mL). The mixtures were then extracted with 8:2 dichloromethane/isopropanol mixtures (3×50 mL) and washed once with brine. The combined organic layers were dried over anhydrous Na$_2$SO$_4$, filtered, and concentrated in vacuo. The crude was dissolved in anhydrous acetonitrile (5 ml) followed by adding K$_2$CO$_3$ (0.48 g, 1.76 mmol) and imidazole (0.96 g, 14.04 mmol) then the sealed tube was microwave at 160° C. for 5 hours. The cooled mixtures were quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (40 g) with 9:1 CH$_2$Cl$_2$:MeOH w/2% 7N ammonia to give 2-(1H-imidazol-1-yl)-6-methoxy-N-(pyridin-4-yl)-7-(3-(pyrrolidin-1-yl)propoxy)quinazolin-4-amine (0.05 g, 16%) as a yellow solid. $^1$H NMR (400 MHz, DMSO-d): δ 10.04 (s, 1H), 8.60 (dd, 2H, J=4.0, 1.0 Hz), 8.54 (s, 1H), 7.92 (m, 4H), 7.24 (s, 1H), 7.15 (s, 1H), 4.23 (t, 2H, J=8.0 Hz), 3.99 (s. 3H), 2.59 (t, 2H, J=8.0 Hz), 2.47 (m, 4H), 1.99 (p, 2H, J=8.0 Hz), 1.71 (m, 4H). MS (ESI): Calcd. for C$_{24}$H$_{27}$F$_2$N$_7$O$_2$: 445, found 446 (M+H)$^+$.

Example 39

2-(1H-imidazol-1-yl)-6-methoxy-7-(3-(pyrrolidin-1-yl)propoxy)-N-(tetrahydro-2H-pyran-4-yl)quinazolin-4-amine (Compound 131)

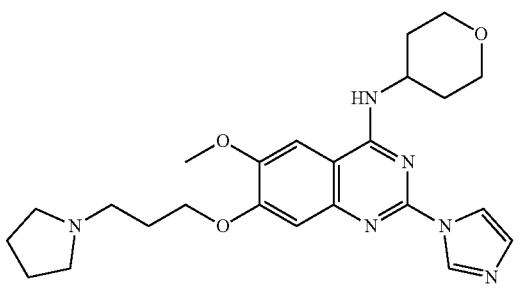 [SMILES: COc1cc2c(NC3CCOCC3)nc(-n3ccnc3)nc2cc1OCCCN1CCCC1]

Preparation: To a solution of commercially available 2,4-dichloro-6-methoxy-7-(3-(pyrrolidine-1-yl)propoxy) quinazoline (0.30 g, 0.84 mmol) and 4-aminotetrahydro-2H-thiopyran (0.09 g, 0.93 mmol) in anhydrous DMF (2 mL) was added potassium carbonate (0.23 g, 1.68 mmol). The sealed tube was heated to 50° C. under argon atmosphere. The reaction was monitored by TLC with dichloromethane and HPLC/MS of 421.1. Upon completion, the cooled reaction was quenched with brine and extracted with 8:2 dichloromethane/isopropanol mixtures (3×50 mL). The combined organic layers were dried over anhydrous $Na_2SO_4$, filtered, and concentrated in vacuo. The crude was dissolved in acetonitrile (3.5 ml) with added potassium carbonate (0.23 g, 1.68 mmol) and imidazole (0.46 g, 6.74 mmol) then the sealed tube was microwave at 160° C. for 5 hours. The cooled mixtures were quenched with sat. $NaHCO_3$ and extracted with 8:2 dichloromethane/isopropanol mixtures (3×50 mL) then washed once with brine. The combined organic layers were dried over anhydrous $Na_2SO_4$, filtered, and concentrated in vacuo. The residue was purified by Buchi Pureflash chromatography over silica gel cartridge (40 g) with 8:2 $CH_2Cl_2$:MeOH w/2% 7N ammonia (8:2) to give 2-(1H-imidazol-1-yl)-6-methoxy-7-(3-(pyrrolidin-1-yl)propoxy)-N-(tetrahydro-2H-pyran-4-yl)quinazolin-4-amine (0.20 g, 53%) as a beige solid. $^1$H NMR (400 MHz, CDCl$_3$): δ 8.56 (t, 1H, J=1.2 Hz), 8.02 (d, 1H, J=7.2 Hz), 7.92 (t, 1H, J=1.2 Hz), 7.68 (s, 1H), 7.09 (s, 1H), 7.07 (t, 1H, J=1.2 Hz), 4.48 (m, 1H), 4.16 (t, 2H, J=6.8 Hz), 3.95 (dd, 2H, J=10.8, 3.2 Hz), 3.91 (s, 3H), 3.54 (tt, 2H, J=12.0, 2.0 Hz), 2.53 (t, 2H, J=7.2 Hz), 2.44 (m, 4H), 1.96 (m, 4H), 1.68 (m, 6H). MS (ESI): Calcd. for $C_{24}H_{32}N_6O_3$: 452, found 453 (M+H)$^+$.

Example 40

(R)-2-(4,4-difluoropiperidin-1-yl)-6-methoxy-7-(3-(pyrrolidin-1-yl)propoxy)-N-(tetrahydro-2H-pyran-3-yl)quinazolin-4-amine (Compound 12)

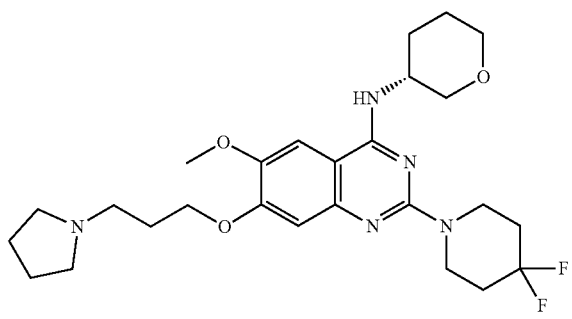

Preparation: To a solution of commercially available 2,4-dichloro-6-methoxy-7-(3-(pyrrolidine-1-yl)propoxy) quinazoline (0.25 g, 0.70 mmol) and (R)-tetrahydro-2H-pyran-3-amine hydrochloride (0.145 g, 0.11 mmol) in anhydrous DMF (6 mL) was added DIPEA (0.37 mL, 2.11 mmol). The sealed tube was heated to 50° C. under argon atmosphere. The reaction was monitored by TLC with dichloromethane and HPLC/MS of 421.2. Upon completion after 3 days, the cooled reaction was quenched with sat. $NaHCO_3$ and extracted with 8:2 dichloromethane/isopropanol mixtures (3×50 mL). The combined organic layers were dried over anhydrous $Na_2SO_4$, filtered, and concentrated in vacuo. The crude was dissolved in 2-butanol (6 ml) with adding DIPEA (0.73 mL, 4.21 mmol) and 4,4-difluoropiperidine hydrochloride (0.44 g, 2.81 mmol) then the sealed tube was heated to 90° C. for 3 days. The cooled mixtures were quenched with sat. $NaHCO_3$ and extracted with 8:2 dichloromethane/isopropanol mixtures (3×50 mL) then washed once with brine. The combined organic layers were dried over anhydrous $Na_2SO_4$, filtered, and concentrated in vacuo. The residue was purified by Buchi Pureflash chromatography over silica gel cartridge (24 g) with 8:2 $CH_2Cl_2$: MeOH w/2% 7N ammonia (8:2) to give (R)-2-(4,4-difluoropiperidin-1-yl)-6-methoxy-7-(3-(pyrrolidin-1-yl)propoxy)-N-(tetrahydro-2H-pyran-3-yl)quinazolin-4-amine (0.20 g, 57%) as an off-white solid. $^1$H NMR (400 MHz, DMSO-d$_6$): δ 7.47 (s, 1H), 7.30 (d, 1H, J=7.2 Hz), 6.75 (s, 1H), 4.20 (m, 1H), 4.07 (t, 2H, J=6.4 Hz), 3.99 (dd, 1H, J=10.4, 4.0 Hz), 3.87 (m, 4H), 3.82 (s, 3H), 3.80 (1H, partially mask under 3.82), 3.35 (1H, partially mask under water peak), 3.17 (t, 1H, J=10.0 Hz), 2.52 (t, 2H, J=7.2 Hz), 2.43 (m, 4H), 2.05-1.85 (m, 7H), 1.76-1.64 (m, 7H). MS (ESI): Calcd. for $C_{26}H_{37}F_2N_5O_3$: 505, found 506 (M+H)$^+$.

Example 41

(S)-2-(4,4-difluoropiperidin-1-yl)-6-methoxy-7-(3-(pyrrolidin-1-yl)propoxy)-N-(tetrahydro-2H-pyran-3-yl)quinazolin-4-amine (Compound 13) & (S)-6-methoxy-N2,N2-dimethyl-7-(3-(pyrrolidin-1-yl)propoxy)-N4-(tetrahydro-2H-pyran-3-yl)quinazoline-2,4-diamine (Compound 132)

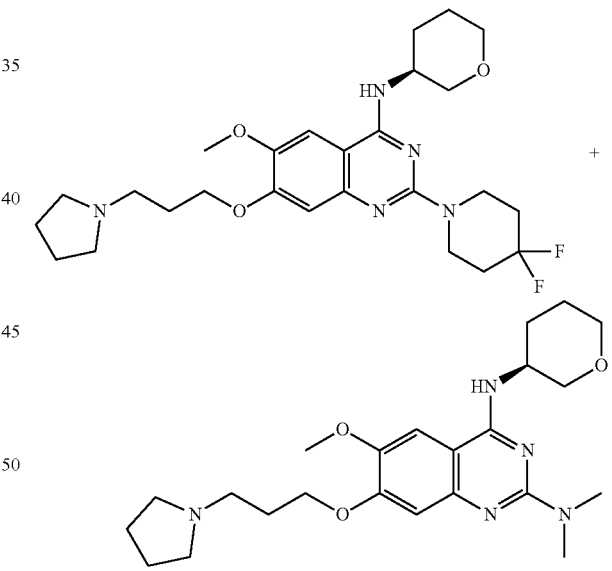

Preparation: To a solution of commercially available 2,4-dichloro-6-methoxy-7-(3-(pyrrolidine-1-yl)propoxy) quinazoline (0.25 g, 0.70 mmol) and (S)-tetrahydro-2H-pyran-3-amine hydrochloride (0.145 g, 0.11 mmol) in anhydrous DMF (6 mL) was added DIPEA (0.37 mL, 2.11 mmol). The sealed tube was heated to 50° C. under argon atmosphere. The reaction was monitored by TLC with dichloromethane and HPLC/MS of 421.2. Upon completion after 3 days, the cooled reaction was quenched with sat. $NaHCO_3$ and extracted with 8:2 dichloromethane/isopropanol mixtures (3×50 mL). The combined organic layers were dried over anhydrous $Na_2SO_4$, filtered, and concentrated in vacuo. The crude was dissolved in DMF (6 ml) with adding DIPEA (0.73 mL, 4.21 mmol) and 4,4-difluoropiperidine hydrochloride (0.44 g, 2.81 mmol) then the sealed tube was heated to 90° C. for 3 days. The cooled mixtures were quenched with sat. NaHCO$_3$ and extracted with 8:2 dichloromethane/isopropanol mixtures (3×50 mL) then washed once with brine. The combined organic layers were dried over anhydrous Na$_2$SO$_4$, filtered, and concentrated in vacuo. The residue was purified by Buchi Pureflash chromatography over silica gel cartridge (24 g) with 8:2 CH$_2$Cl$_2$:MeOH w/2% 7N ammonia (8:2) to give two products. (S)-2-(4,4-difluoropiperidin-1-yl)-6-methoxy-7-(3-(pyrrolidin-1-yl)propoxy)-N-(tetrahydro-2H-pyran-3-yl)quinazolin-4-amine (0.09 g, 25%) as an off-white solid $^1$H NMR (400 MHz, DMSO-d$_6$): δ 7.47 (s, 1H), 7.30 (d, 1H, J=7.2 Hz), 6.75 (s, 1H), 4.20 (m, 1H), 4.07 (t, 2H, J=6.4 Hz), 3.99 (dd, 1H, J=10.4, 4.0 Hz), 3.87 (m, 4H), 3.82 (s, 3H), 3.80 (1H, partially mask under 3.82), 3.35 (1H, partially mask under water peak), 3.17 (t, 1H, J=10.0 Hz), 2.52 (t, 2H, J=7.2 Hz), 2.43 (m, 4H), 2.05-1.85 (m, 7H), 1.76-1.64 (m, 7H). MS (ESI): Calcd. for C$_{26}$H$_{37}$F$_2$N$_5$O$_3$: 505, found 506 (M+H)$^+$.

And (S)-6-methoxy-N2,N2-dimethyl-7-(3-(pyrrolidin-1-yl)propoxy)-N4-(tetrahydro-2H-pyran-3-yl)quinazoline-2,4-diamine as an off-white solid (0.12 g, 40%). $^1$H NMR (400 MHz, DMSO-d$_6$): δ 7.43 (s, 1H), 7.16 (d, 1H, J=7.2 Hz), 6.70 (s, 1H), 4.22 (m, 1H), 4.06 (t, 2H, J=6.4 Hz), 4.01 (dd, 1H, J=12.0, 4.4 Hz), 3.82 (m, 1H), 3.81 (s, 3H), 3.30 (1H, partially mask under water), 3.17 (t, 1H, J=10.0 Hz), 3.09 (s, 6H), 2.23 (t, 2H, J=7.2 Hz), 2.44 (m, 4H), 2.04 (d, 1H, J=10.8 Hz), 1.91 (m, 2H), 1.76-1.64 (m, 7H). MS (ESI): Calcd. for C$_{23}$H$_{35}$N$_5$O$_3$: 429, found 430 (M+H)$^+$.

The remainder of the compounds disclosed herein may be synthesized using methods similar to those used for the preceding compounds.

Example 42

Testing of Compounds

In this experiment, the effects of Compounds 1 and 2 (prepared in Examples 1 and 2) as compared with Compound 400 on transepithelial resistance (TEER) of CaCo-2 cells was evaluated.

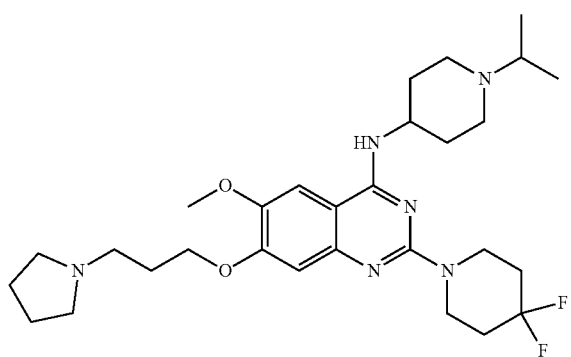

Compound 400

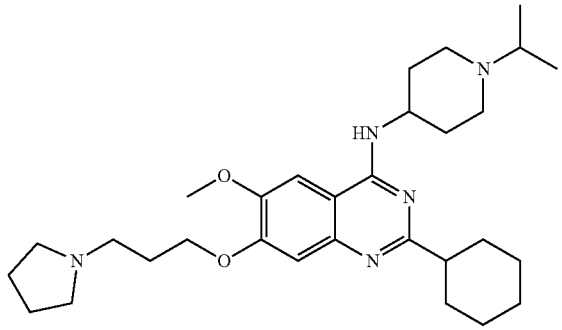

Compound 401

Figure 2:
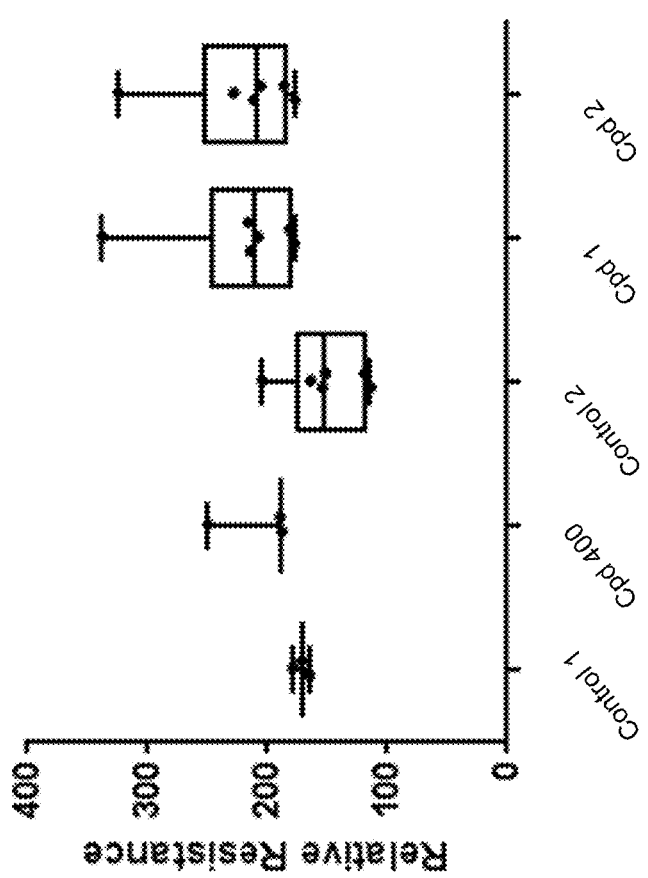
FIG. 2 is a chart showing the relative transepithelial resistance of CaCo-2 cells after 24 hours of exposure to selected conditions.

The intestinal epithelial barrier plays a central role in the pathophysiology of multiple chronic inflammatory and autoimmune diseases. Intestinal epithelial cells provide a physical barrier that interacts with immune cells and protects internal cavities from mucosal bacterial and antigen intrusion. Intestinal inflammation during IBD is associated with disruption of this barrier and cytokines like TNFα play important roles. Here, CaCo-2 intestinal epithelial cells were exposed to TNFα and IFNγ (20 ng/ml and 200 ng/ml, respectively) to induce epithelial barrier disruption and then treated them with Compound 1 and Compound 2. Both Compound 1 and Compound 2 ameliorated the disruptive effects of the combined exposure of CaCo-2 intestinal epithelial cells to TNFα and IFNγ (FIG. 1, p<0.01) after 24 hrs of treatment. Both compounds reversed the effects to levels of electrical resistance that resembled the levels of the vehicle CaCo-2 cells. FIG. 2 depicts the differences in the responses between the Compound 400 vs Compound 1 and Compound 2 with their respective controls also shown to account for the fact that the observations were made in two different experiments. In contrast to Compound 400, both Compound 1 and Compound 2 reversed cytokine induced barrier damage significantly compared to their control groups (FIG. 2).

Figure 3:
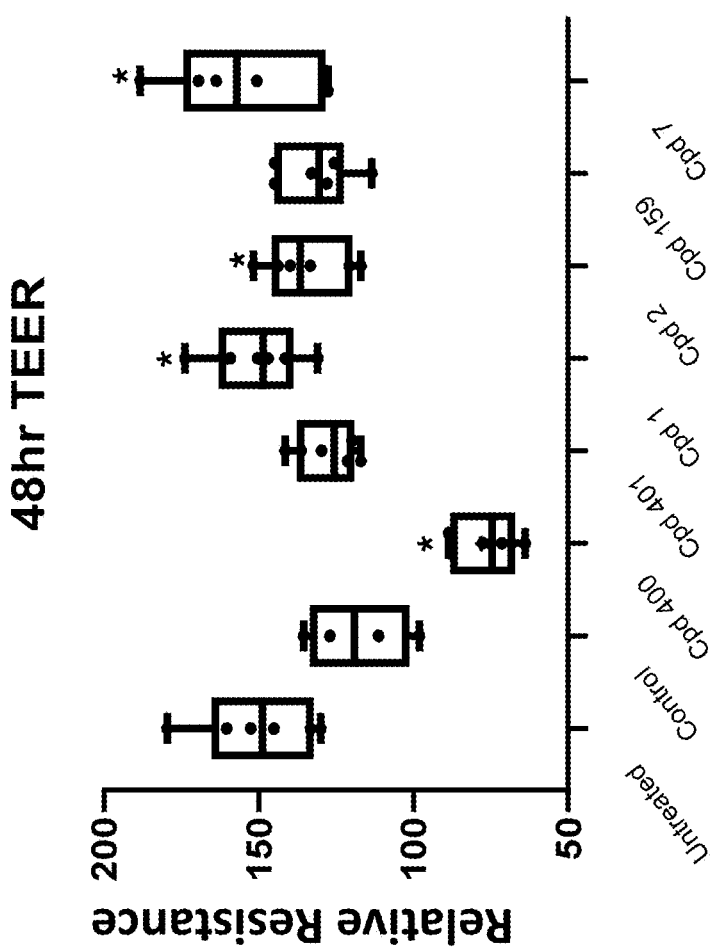
FIG. 3 is a chart showing the relative transepithelial resistance of CaCo-2 cells after 48 hours of exposure to selected conditions.

Next, CaCo-2 intestinal epithelial cells were exposed to TNFα and IFNγ (10 ng/ml and 100 ng/ml, respectively) to induce epithelial barrier disruption and then treated them with selected compounds (1 μM, FIG. 3 and epithelial barrier resistance was measured relative to untreated baseline measurements at 0 hours and baseline unseeded (empty of cells) well resistance. Compound 1, Compound 2, and Compound 7 (as provided in Example 13) recovered epithelial barrier resistance levels back to those of untreated cells after 48 hrs of treatment. In contrast Compound 401 failed to restore barrier damage compared to control (FIG. 3). Interestingly, Compound 400 increased intestinal permeability, which potentially could worsen the disease state.

Example 43

In Vivo Testing

Figure 4B:
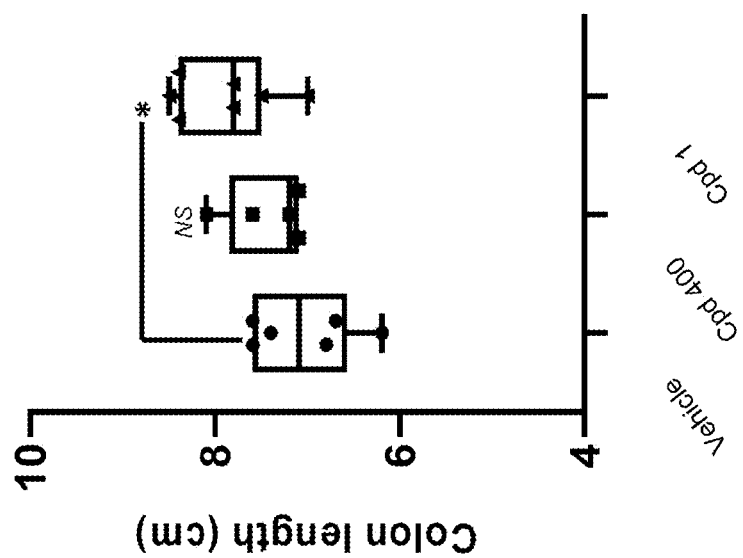
FIG. 4B is a chart showing that colon lengths of mice after exposure to selected conditions.
Figure 4A:
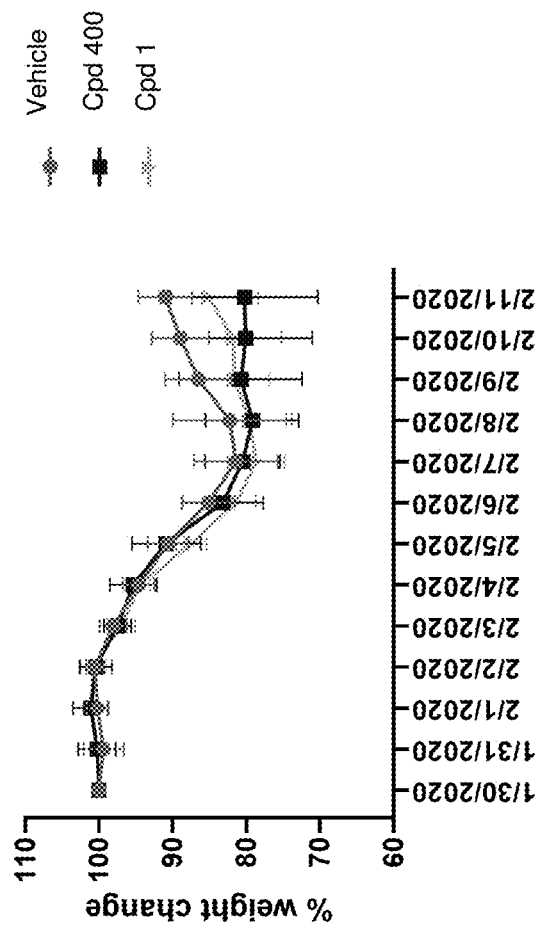
FIG. 4A is a graph showing the percent weight change in mice after treatment with selected compounds.

To determine the effects of selected compounds on the outcome of colitis C57BL/6 mice received daily oral doses of Compound 400 and Compound 1 (50 mg/kg) that were determined by our MTD studies to not cause any effects in weight change in these animals. Dextran sodium sulfate (DSS) was added to the water 24 hrs after compound administration and weight was measured daily. The results demonstrated that Compound 1 resulted in increased weight, while Compound 400 failed to increase DSS-induced weight loss (FIG. 4A). Furthermore, when mice were sacrificed at d12 after DSS induction, colon length was increased only in mice that received Compound 1 and not in mice that received Compound 400 compared to vehicle treated controls and Compound 400 treated mice (FIG. 4B; p<0.01 vs control).

Example 44

In Vivo Testing—Weight Loss

Compound 1 and Compound 2 were administered daily via oral gavage to mice (n=8/group) with DSS colitis as described above. Both Compound 1 and Compound 2 showed significant protection against colitis induced weight loss after d11 (FIG. 5A). Also, both compounds significantly prevented colitis-induced weight loss (FIG. 5B, p<0.05) and colon length shortening (FIG. 5C, p<0.01) compared to vehicle treated control mice as measured on d12 of the study.

Example 45

HT-29 Colorectal Cancer Cell Testing

Figure 6:
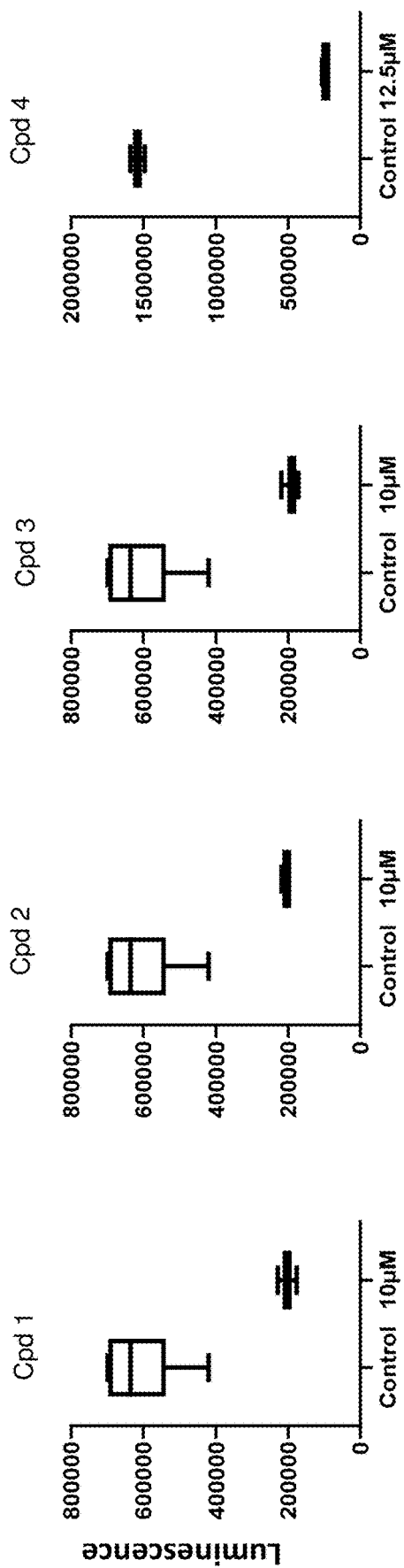
FIG. 6 shows four charts depicting the suppressive effect of four compounds on the growth of HT-29 colorectal cancer cells.

To determine the anti-cancer properties of Compounds 1-4, HT-29 colorectal cancer cells were plated at a density of 1,000 cells in 100 µl (McCoy's 5a+10% FBS) per well in 96 well plates. Equal volume of 2× RealTime-Glo™ reagent (2 µl of MT Cell Viability Substrate 1,000×, and 2 µl of NanoLuc® Enzyme 1,000×, per 1 ml of media, Promega) was added to each well and cells were incubated at 37° C. Luminescence was evaluated at 72 h. As shown in FIG. 6, Compounds 1, 2, 3, and 4 all showed potent anti-cancer activity by suppressing the growth of HT-29 colorectal cancer cells.

PG(mouse, oral)=22 g/kg, PEG300(rat, oral)=27.5 g/kg] are well described in the Handbook of Pharmaceutical Excipients. All compounds are tested in microgram-scale with visual stability for 7 days as shown in below table prior to preparing the actual test articles in milligram scale. Since these compounds have high solubility in lower pH as described in the solubility study section, the intervenous delivery is performed with 100% phosphate buffer solution of pH 6.5 allowing up to 7 mg/mL concentration. The formulated test articles can be store at 4° C. Prior to dosing, it should be warmed and vortexed for about 1 min to make a homogenous solution. If needed, filter through 0.2 µM syringe filter to maintain clean and sterile. The structure of Compound 402 is:

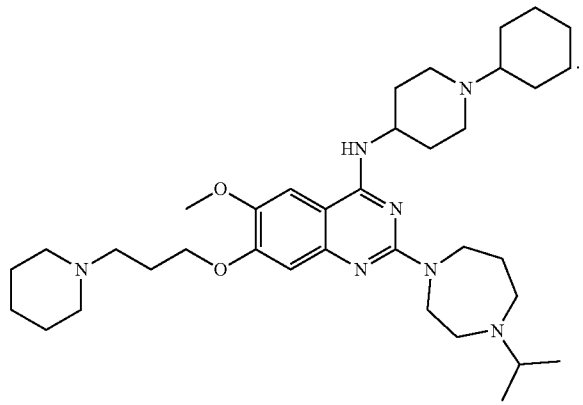 [SMILES: COc1cc2c(NC3CCN(C4CCCCC4)CC3)nc(N3CCCN(C(C)C)CC3)nc2cc1OCCCN1CCCCC1]

TABLE 46.1

Formulations of selected compounds at 25° C..

| Compound | Drug (mg) | [Conc.] mg/mL | DMA | PG | PEG 300 | Water | Appearance 30 min | 1 h | 5 h | 24 h | 7 d |
|---|---|---|---|---|---|---|---|---|---|---|---|
| 400 | 1 | 10 | 10 µL | 30 µL | 35 µL | 25 µL | clear | clear | clear | clear | clear |
| 401 | 1.1 | 11 | 10 µL | 30 µL | 35 µL | 25 µL | clear | clear | clear | clear | clear |
| 402 | 1 | 10 | 10 µL | 30 µL | 35 µL | 25 µL | clear | clear | clear | clear | clear |
| 1 | 1.1 | 11 | 10 µL | 30 µL | 35 µL | 25 µL | clear | clear | clear | clear | clear |
| 2 | 1 | 10 | 10 µL | 30 µL | 35 µL | 25 µL | clear | clear | clear | clear | clear |

Example 46

Formulation Preparation and Testing

All formulations were conducted with FDA approved excipients and with high purity material such as USP grade quality. Formulation stability of test articles are performed using HPLC purity method described within analytical section. This formula may be used for oral administration of the compounds described herein; 10% dimethylacetamide (DMA), 30% propylene glycol (PG), 35% polyethylene glycol 300 (PEG 300), 25% distilled water, up to on average of 14 mg/mL concentration in this following order of addition with the practitioner applying gentle warming, sonication, or vortex as necessary to complete the dissolution of the test articles. The safety application of these excipients and their $LD_{50}$ [DMA(rat, oral)=4.93 g/kg, Example 47

Solubility Testing

Solubility is the ability of a drug to dissolve in an aqueous solution under different pH conditions. It is defined as the amount of substance that passes into solution to achieve a saturated solution at a constant temperature and pressure. The purpose of this study was to determine the solubility of selected compounds under different pH conditions and determine whether an oral solution is feasible or a suspension would be better to support the drug formulation process for pre-clinical studies. The pH conditions selected were within the extremes of the normal physiological pH of the human gastrointestinal tract, such as pH 1, pH 4, pH 6.5, and pH 7.4.

Table 47.1 shows the results of these experiments. The solubilities of all four selected test compounds were pH dependent. The solubilities of compounds 1 and 2 were 40-fold higher than the solubility of compound 201 under pH 7.4. This determined that an oral solution might be feasible for compounds 1 and 2.

TABLE 47.1

Solubility-pH Profile of Selected Compounds

| Compound | pH 1 | pH 4 | pH 6.5 | pH 7.4 |
|---|---|---|---|---|
| Compound 400 | 22.8 | 13.2 | 7.51 | 0.011 |
| Compound 1 | n/a | 11.6 | 6.05 | 0.424 |
| Compound 2 | n/a | n/a | 27.5 | 0.449 |
| Compound 11 | n/a | 4.45 | 3.18 | 0.245 | n/a: data not available

Example 48

Stability Testing

Physical and chemical stability of dosing formulation lead to the investigation of potential impurities upon storage at various temperatures. The stability results can be used to assess the appropriate storage conditions and shelf life of a formulation, and can provide important information for drug formulation development, nonclinical, and clinical studies, especially on-going efficacy studies. The dosing formulation in these experiments contained 5 mg/mL test compound 1, with 10% Dimethylacetamide (DMA), 30% Propylene Glycol, 35% PEG-300, 25% water ($H_2O$). The dosing formulation was stored at 4° C. and 25° C. The samples were retrieved at the following time points: 1 day and 3 days. The dosing formulation was diluted and analyzed for potency and impurity profile using reverse phase high pressure liquid chromatography. The impurity profile was described as the relative percent peak area of each peak detected.

No difference in physical stability was observed within 3 days at either temperature (Table 48.1). As shown in Tables 48.2 and 48.3, compared to Time 0, there was <2% change in drug potency after 3 days at 4° C. and 10% at 25° C. The relative higher potency of 3 days at 25° C. could be attributed to particle sedimentation or inhomogeneous solution. All samples had <0.16% change in overall purity. No significant increase was observed in the major degradation or impurity peaks throughout the stability. Thus, it is recommended to sonicate and heat the solution prior dosing.

TABLE 48.1

Physical Stability of Compound 1 in Dosing Formulation

| Time (Days) | Observation[a] | |
|---|---|---|
| | 4° C. | 25° C. |
| 0 | Clear solution | Clear solution |
| 1 | Clear solution | Clear solution |
| 3 | Clear solution | Clear solution |

[a]Visual observation of the physical state (texture and color) of the samples were recorded prior to preparation for analysis.

TABLE 48.2

Potency Stability of Compound 1 in Dosing Formulation

| | 4° C. | | 25° C. | |
|---|---|---|---|---|
| Time (Days) | Conc. (mg/mL) | Recovery (%)[a] | Conc. (mg/mL) | Recovery (%)[a] |
| 0 | 5.56 | 100.0 | 5.56 | 100.0 |
| 1 | 5.57 | 100.2 | 5.47 | 98.4 |
| 3 | 5.65 | 101.6 | 6.09 | 109.5 |

[a]Recovery (%) was calculated by comparing to the time zero.

TABLE 48.3

Impurity Profile of Compound 1 in Dosing Formulation

| Impurity Peak (RRT[b] to Compound 1) | Time (Days) | 4° C. | 25° C. |
|---|---|---|---|
| 0.978 | 0 | 0.14 | 0.14 |
| | 1 | 0.14 | 0.13 |
| | 3 | 0.31 | 0.30 |
| 1.00 (Compound 1) | 0 | 99.86 | 99.86 |
| | 1 | 99.86 | 99.87 |
| | 3 | 99.69 | 99.70 |

[b]RRT = relative retention time by comparing the retention time of impurity peak to the parent compound.

Example 49

Permeability Testing

The permeability of compounds was evaluated with the parallel artificial membrane permeation assay (PAMPA) as an in vivo model of passive diffusion across a porous filter coated with a lipid/oil/lipid tri-layer artificial membrane. PAMPA experiments are carried out during the early drug discovery phase to screen oral absorption potential of drug compounds to eliminate poor performers and structure modification of discovery compounds to improve their in vivo diffusion characteristics. The test compounds were tested in parallel with positive control, Diclofenac (published high permeability). Donor solutions of test compounds (300 µL, 20 µM in PBS/MeOH 90:10) were added to each well of the donor plate. 200 µL of PBS/MeOH 90:10 was added to each well of the acceptor plate. The acceptor plate was coupled with the donor plate and incubated for 5 hours at room temperature (RT) without agitation. In each plate, compounds were tested in triplicate. At the end of the incubation, drug concentration in the initial donor solution, acceptor and the donor wells were determined using LC/MS/MS. Permeability of test compounds was calculated based on the formula described in the General Procedures above. The PAMPA permeability classification criteria are categorized into three (3) classes with a high (Pe≥1.5×10−6 cm/s), intermediate (5.5×10−8<Pe<1.5×10−6 cm/s), and low (Pe<5.5×10−8 cm/s) permeability.

Overall, the tested compounds generally showed low permeability, indicating low oral absorption potential. Unexpectedly, Compounds 2 and 4 showed very high permeability indicating high oral absorption potential compared to other tested compounds. The structures of compounds 403 and 404 is as follows:

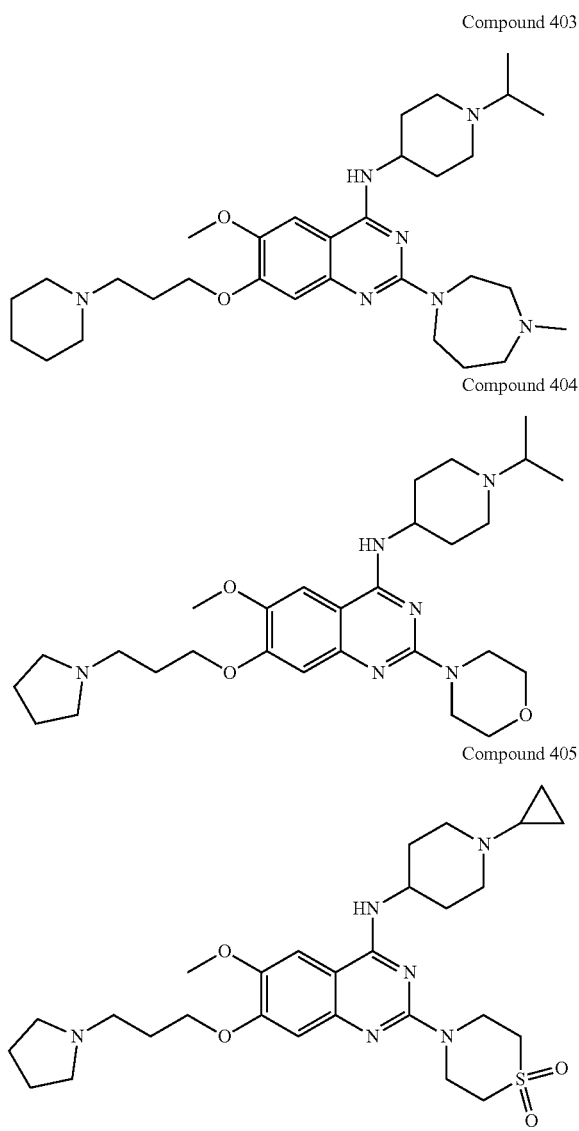

Compound 403

Compound 404

Compound 405

TABLE 49.1

| Compound | PAMPA Permeability Permeability, $P_e$ (cm/s) | Classification |
|---|---|---|
| Compound 400 | $1.78 \times 10^{-7}$ | Intermediate |
| Compound 404 | $6.24 \times 10^{-9}$ | Low |
| Compound 405 | $1.01 \times 10^{-7}$ | Intermediate |
| Compound 401 | $1.45 \times 10^{-7}$ | Intermediate |
| Compound 403 | $9.60 \times 10^{-9}$ | Low |
| Compound 402 | $9.71 \times 10^{-9}$ | Low |
| Compound 1 | $4.41 \times 10^{-8}$ | Low |
| Compound 2 | $6.38 \times 10^{-6}$ | High |
| Compound 3 | $4.51 \times 10^{-7}$ | Intermediate |
| Compound 4 | $1.77 \times 10^{-6}$ | High |
| Compound 5 | $6.49 \times 10^{-9}$ | Low |
| Compound 159 | $2.27 \times 10^{-8}$ | Low |
| Compound 234 | $2.85 \times 10^{-10}$ | Low |
| Compound 158 | $4.53 \times 10^{-9}$ | Low |
| Compound 157 | $5.55 \times 10^{-10}$ | Low |
| Compound 156 | $2.25 \times 10^{-9}$ | Low |
| Compound 7 | $5.84 \times 10^{-7}$ | Intermediate |
| Compound 235 | $4.60 \times 10^{-9}$ | Low |

TABLE 49.1-continued

| Compound | PAMPA Permeability Permeability, $P_e$ (cm/s) | Classification |
|---|---|---|
| Compound 8 | $1.73 \times 10^{-9}$ | Low |
| Compound 9 | $9.81 \times 10^{-9}$ | Low |
| Compound 174 | $7.54 \times 10^{-8}$ | Intermediate |
| Compound 164 | $4.76 \times 10^{-8}$ | Low |
| Compound 195 | $2.38 \times 10^{-7}$ | Intermediate |
| Compound 236 | $2.99 \times 10^{-8}$ | Low |
| Compound 237 | $4.31 \times 10^{-9}$ | Low |
| Compound 196 | $3.50 \times 10^{-8}$ | Low |
| Compound 80 | $2.98 \times 10^{-9}$ | Low |
| Compound 102 | $6.48 \times 10^{-10}$ | Low |
| Compound 109 | $4.75 \times 10^{-9}$ | Low |
| Compound 103 | $1.19 \times 10^{-8}$ | Low |
| Compound 110 | $6.76 \times 10^{-9}$ | Low |
| Compound 248 | $1.32 \times 10^{-6}$ | Intermediate |
| Compound 11 | $4.58 \times 10^{-7}$ | Intermediate |
| Compound 130 | $1.29 \times 10^{-8}$ | Low |

Several compounds showed low permeability indicating low oral absorption potential. Unexpectedly, compound 2 and 4 showed significantly higher permeability than compounds 400-405 indicating high oral absorption potential.

Example 50

In-Vitro Half-Life Determination in Human, Rat, and Mouse Liver Microsomes

A comparison of metabolic stability in time-course incubation experiments in varying species of liver can provide information of pharmacokinetic properties of drugs attributable to species-related differences in hepatic metabolism. The results of these experiments often assist in further applications such as assessing in vitro metabolite profiling and choosing relevant species for toxicology studies based on similarities relative to the metabolic stability to the human profile. For these experiments, the test compound was tested in parallel with a positive control, Dasatinab, in an enzymatic reaction solution of each species (human and rat) of liver microsomes containing a NADPH regenerating system (NRS). The final mixture contained 1 µg/mL of drug and 0.5 mg/mL of liver matrix. Incubations were performed at 37±2° C. with gentle, continuous mixing in shaking water bath in 96-Deep well plates. The stability of the test compound is monitored using fast, specific and sensitive LC/MS/MS analysis.

TABLE 50.1

Microsomal Stability Profile of Selected Compounds

| Compound | Metabolic Half-life (min)$^a$ | | |
|---|---|---|---|
| | Human | Rat | Mouse |
| Compound 400 | >60 | >60 | >60 |
| Compound 401 | >60 | 13.0 | 54.7 |
| Compound 402 | >60 | >60 | >60 |
| Compound 1 | >60 | >60 | >60 |
| Compound 2 | >60 | 49.7 | >60 |
| Compound 3 | >60 | >60 | >60 |
| Compound 4 | >60 | >60 | >60 |
| Compound 5 | >60 | >60 | >60 |
| Compound 159 | >60 | 33.3 | 39.3 |
| Compound 234 | >60 | >60 | >60 |
| Compound 158 | >60 | 33.0 | 38.2 |
| Compound 157 | >60 | >60 | >60 |
| Compound 156 | >60 | >60 | 59.3 |

TABLE 50.1-continued

Microsomal Stability Profile of Selected Compounds

| Compound | Metabolic Half-life (min)[a] | | |
|---|---|---|---|
| | Human | Rat | Mouse |
| Compound 7 | >60 | 37.0 | 43.6 |
| Compound 235 | >60 | >60 | >60 |
| Compound 8 | >60 | >60 | >60 |
| Compound 9 | >60 | >60 | >60 |
| Compound 174 | >60 | >60 | >60 |
| Compound 164 | >60 | >60 | >60 |
| Compound 195 | >60 | >60 | >60 |
| Compound 236 | >60 | >60 | 22.8 |
| Compound 237 | >60 | 22.0 | 26.4 |
| Compound 196 | >60 | >60 | >60 |
| Compound 80 | >60 | >60 | >60 |
| Compound 102 | >60 | >60 | >60 |
| Compound 109 | 20.5 | >60 | >60 |
| Compound 103 | >60 | >60 | >60 |
| Compound 110 | >60 | >60 | >60 |
| Compound 248 | 37.8 | 16.9 | >60 |
| Compound 11 | >60 | >60 | >60 |
| Compound 130 | >60 | >60 | 32.1 |

[a]Metabolic half-life was calculated by Graphpad Prism ® software based on first-order reaction kinetics.

As shown in Table 50.1, a species difference in metabolism was observed. Based on the in vitro metabolic stability, the half-life of all selected tested compounds is expected to be more than 60 minutes in any in vivo system of the above-stated species, except for compounds 401, 237, and 248 in rat species. The low metabolic stability in rat microsome of compounds except compounds 401, 237, and 248 in rat species indicates a high clearance and a reduced half-life when administered to rat for PK profiling.

Example 51

CYP-Direct Inhibition of G9a Inhibitors in Human Cytochrome P450

Cytochrome P450 inhibition of a drug is a key factor in determining pharmacokinetic drug-drug interactions. The objective of this study was to evaluate the inhibition potential of G9a inhibitors on six (6) major human cytochrome P450 enzymes, including CYP1A2, CYP2C8, CYP2C9, CYP2C19, CYP2D6, and CYP3A4. Inhibition was determined by using a substrate cocktail and analyzing the rate of specific metabolites formation. The cytochrome P450 inhibition assay was developed using a cocktail consisting of six (6) probe substrates ethoxy-resorufin (CYP1A2), rosiglitazone (CYP2C8), diclofenac (CYP2C9), S-mephenytoin (CYP2C19), dextromethorphan (CYP2D6), and midazolam (CYP3A4). The cocktail was incubated in human liver microsome with NADPH regenerating system (NRS) in a shaking bath at 37±2° C. The formation of specific metabolites was monitored by LC/MS/MS. Test compound was added to the cocktail-liver microsome mixture at varying concentrations and its effect on cytochrome P450 activity was determined by analyzing the rate of specific metabolite formation. The percent inhibition was calculated and plotted with reference to the concentration, and the $IC_{50}$ value for inhibition was derived by fitting the data with a using log(inhibitor) vs. normalized response with variable slope least squares fit by Graphpad Prism® software. $IC_{50}$ values were obtained only when the data fit in the curve, and if the % inhibition was less than 50% at 100 μM, then $IC_{50}$ will be >100 μM. The reliability of the inhibition assay was established by confirming the inhibition of known inhibitors on different P450 enzymes. The $IC_{50}$ is categorized into three classes with a high ($IC_{50}$<1 μM), medium (1<$IC_{50}$<10 μM), and low ($IC_{50}$>10 μM) risk potential.

Most of the tested compounds showed did not inhibit all six CYP450 isozymes: CYP1A2, CYP2C8, CYP2C9, CYP2C19, CYP2D6, and CYP3A4 with an $IC_{50}$ of more than 10 uM. G9a inhibitors are unlikely to cause clinically important pharmacokinetic interactions with drugs metabolized by cytochrome P450 enzymes.

TABLE 8

In-Vitro $IC_{50}$ Calculations of Selected Compounds

| Compound | $IC_{50}$ (μM) | | | | | |
|---|---|---|---|---|---|---|
| | CYP-1A2 | CYP-2C8 | CYP-2C9 | CYP-2C19 | CYP-2D6 | CYP-3A4 |
| Cpd 400 | >100 | >100 | >100 | >100 | 28.8 | >100 |
| Cpd 1 | >100 | 89.1 | >100 | >100 | 21.9 | >100 |
| Cpd 2 | >100 | 20.4 | >100 | >100 | 17.6 | >100 |
| Cpd 3 | >100 | >100 | >100 | >100 | 9.55 | >100 |
| Cpd 4 | >100 | 27.4 | >100 | 60.9 | 13.3 | >100 |
| Cpd 5 | >100 | >100 | >100 | >100 | >100 | >100 |
| Cpd 159 | >100 | >100 | >100 | >100 | 50.9 | >100 |
| Cpd 234 | >100 | >100 | >100 | >100 | 77.9 | >100 |
| Cpd 158 | >100 | >100 | >100 | >100 | 65.6 | >100 |
| Cpd 157 | >100 | >100 | >100 | >100 | 64.9 | >100 |
| Cpd 156 | >100 | >100 | >100 | >100 | 4.72 | >100 |
| Cpd 7 | >100 | 75.7 | >100 | 44.3 | 12.0 | >100 |
| Cpd 235 | >100 | >100 | >100 | >100 | >100 | >100 |
| Cpd 8 | >100 | >100 | >100 | >100 | >100 | >100 |
| Cpd 9 | >100 | >100 | >100 | >100 | >100 | >100 |
| Cpd 174 | 63.1 | >100 | >100 | >100 | 23.0 | >100 |
| Cpd 164 | >100 | 91.8 | >100 | >100 | 24.8 | >100 |
| Cpd 195 | >100 | >100 | >100 | >100 | >100 | >100 |
| Cpd 236 | >100 | >100 | >100 | >100 | >100 | >100 |
| Cpd 237 | >100 | 95.5 | >100 | >100 | 86.2 | >100 |
| Cpd 196 | >100 | >100 | >100 | >100 | 84.8 | >100 |
| Cpd 80 | >100 | 23.4 | >100 | >100 | 43.0 | >100 |
| Cpd 102 | >100 | 60.6 | >100 | >100 | 29.0 | >100 |
| Cpd 109 | >100 | >100 | >100 | >100 | >100 | >100 |
| Cpd 103 | >100 | >100 | >100 | >100 | >100 | >100 |
| Cpd 110 | >100 | >100 | >100 | >100 | >100 | >100 |
| Cpd 248 | >100 | 43.1 | >100 | >100 | 55.9 | >100 |
| Cpd 11 | >100 | 16.0 | >100 | >100 | 29.5 | >100 |
| Cpd 130 | 10.4 | 4.66 | 65.5 | 75.7 | 4.88 | 3.85 |

Example 52

Effectiveness of Selected Compounds on DSS Colitis

C57BL/6 mice (20-22 grams) were fed ad lib and assigned to 4 different groups (n=8/group). After a 72 hr acclimation period test groups received 25 mg/kg of test compounds PO (gavage) in vehicle daily. A control group received vehicle alone. After 24 hrs, mice were weighed and DSS was added to their drinking water. Mice were then treated with the test compounds and weighed daily and the DSS water was replenished every 72 hrs for 5 days, at which point, it was replaced by regular drinking water. Mice were sacrificed on day twelve and clinical scored was assessed. Intestinal tissue for and blood were also collected. Tissues were either flash frozen and kept in −80° C. for RNA and protein isolation or placed in 10% formalin solution for future histological analysis. Blood was spun at 5K rpm for 5 min and serum was collected and kept at −20° C. for multiplex cytokine analysis.

TABLE 52.1

Effect of Selected Compounds on DSS Colitis

| Compound # | TEER | DSS Efficacy | Clinical Score | Colon Length |
|---|---|---|---|---|
| 400 | − | − | − | − |
| 401 | − | − | − | − |
| 1 | + | + | + | + |
| 2 | + | ++ | ++ | ++ |
| 5 |   | + | + | + |

"−" indicates no statistically significant effect in the variable measured when compared with the control group
"+" indicates a statistically significant difference in the variable measured when compared with the control group
"++" indicates measurements that include multiple variables in the calculation of their differences when compared with the control group, and represents the presence of significant changes across all variable measurements The results from these experiments (Table 52.1) demonstrate a novel effect for compounds 1, 2, and 5 on the alleviation of the effects of DSS colitis compared to no effect observed for compounds 400 and 401. Interestingly, compound 2 had a very strong effect for all varied measurables of overall efficacy, clinical score (includes weight, bleeding, diarrhea, rectal prolapse), and colon length. This is in comparison with all other compounds including 400 and 401 that had no effect.

Example 53

Effectiveness of Selected Compounds on TNBS Colitis

C57BL/6 mice (20-22 grams) were fed ad lib and assigned to 4 different groups (n=8/group). After a 72 hr acclimation period the test group groups received 25 mg/kg of test compound PO (gavage) in vehicle daily. A control group received vehicle alone. After 24 hrs, mice were weighed and TNBS was injected intra-colonically using 5 cm of polyethylene (¼ inch) tubing. Mice were then treated with the test compounds and weighed daily for 4 days. Mice were sacrificed on day 4 and clinical score was assessed. Intestinal tissue for and blood were also collected. Tissues were either flash frozen and kept in −80° C. for RNA and protein isolation or placed in 10% formalin solution for future histological analysis. Blood was spun at 5K rpm for 5 min and serum was collected and kept at −20° C. for multiplex cytokine analysis.

The data for compound 2 in TNBS colitis reinforce our observations from the DSS colitis model that this compound is a strong inhibitor of colitis associated damage in the intestine and protects mice from disease associated adverse outcomes. Our data in this additional model of colitis are also strongly supported by positive outcomes in the histological scores of mice that receive compound 2 compared to vehicle treated controls.

TABLE 53.1

Effect of Selected Compounds on TNBS Colitis

| Compound # | TNBS Efficacy | Clinical Score | Histological Score | Colon Length |
|---|---|---|---|---|
| 2 | ++ | ++ | ++ | ++ |

"++" indicates measurements that include multiple variables in the calculation of their differences when compared with the control group, and represents the presence of significant changes across all variable measurements Example 54

HTC-116 and HT-29 Cell Viability Assays (Effects of Compounds on Cancer Cell Line Viability)

To determine the plating density for cell viability assays, for each cell line, cells were counted and diluted to final densities of 2.5, 5, 10 and 20 thousand per 100 μl of their respective growth media per well in 96 well plates. A Promega Real-Time-Glo cell viability kit was used to determine the optimal concentration for cell plating so that each cell line would be within the linear part of its growth curve after 72 hrs in culture. For the determination of test compound $IC_{50}$s different cancer cell lines were plated in 96 well plates in the pre-determined optimal density for each cell line. Test compounds were then added at different concentrations for the creation of six-point curve and cell density was determined using the Promega Real-Time-Glo cell viability kit after 24, 48, and 72 hrs in culture. Test compound 72 hr $IC_{50}$s were calculated using the AAT Bioquest $IC_{50}$ calculator.

TABLE 54.1

HCT-116 Data.

| Compound # | Cell line: HCT-116 |
|---|---|
| 402 | $5 < IC_{50} < 10*$ |
| 403 | $5 < IC_{50} < 10$ |
| 3 | $1 < IC_{50} < 5$ |
| 4 | $1 < IC_{50} < 5$ |
| 234 | $1 < IC_{50} < 5$ |
| 156 | $1 < IC_{50} < 5$ |
| 7 | $1 < IC_{50} < 5$ |
| 235 | $1 < IC_{50} < 5$ |
| 174 | $1 < IC_{50} < 5$ |
| 164 | $1 < IC_{50} < 5$ |

TABLE 54.2

HT-29 Data.

| Compound # | Cell line: HT-29 |
|---|---|
| 400 | $5 < IC_{50} < 10*$ |
| 403 | $5 < IC_{50} < 10*$ |
| 402 | $10 < IC_{50} < 20$ |
| 2 | $1 < IC_{50} < 5$ |
| 4 | $1 < IC_{50} < 5$ |
| 156 | $1 < IC_{50} < 5$ |
| 7 | $1 < IC_{50} < 5$ |

Data on the effects of compounds as disclosed herein on colon cancer cell viability demonstrate that several of the disclosed compounds exhibit significantly increase capability for cancer cell growth inhibition compared to compounds 400, 402, and 403 after 72 hrs of treatment. This observation suggests that these compounds are stronger pharmacological inhibitors for the future treatment of cancers, including colon cancer.

TABLE 54.3

5637 Cell Line Data.

| Compound # | Cell line: 5637 |
|---|---|
| 401 | $IC_{50} > 20$ |
| 2 | $10 < IC_{50} < 20$ |
| 3 | $5 < IC_{50} < 10$ |

TABLE 54.3-continued

5637 Cell Line Data.

| Compound # | Cell line: 5637 |
| --- | --- |
| 4 | $10 < IC_{50} < 20$ |
| 234 | $5 < IC_{50} < 10$ |
| 156 | $1 < IC_{50} < 5$ |
| 7 | $1 < IC_{50} < 5$ |
| 235 | $5 < IC_{50} < 10$ |
| 174 | $10 < IC_{50} < 20$ |
| 164 | $5 < IC_{50} < 10$ |

TABLE 54.4

J82 Cell Line Data.

| Compound # | Cell line: J82 |
| --- | --- |
| 400 | $5 < IC_{50} < 10$ |
| 401 | $10 < IC_{50} < 20$ |
| 7 | $1 < IC_{50} < 5$ |

The data on the effects of compounds as disclosed herein on bladder cancer cell viability demonstrate that several of our compounds exhibit significantly increase capability for cancer cell growth inhibition compared to compounds 400 and 401 after 72 hrs of treatment. This observation suggests that these compounds are stronger pharmacological inhibitors for the future treatment of cancers, including bladder cancer.

TABLE 54.5

A-498 Cell Line Data.

| Compound # | Cell line: A-498 |
| --- | --- |
| 400 | $10 < IC_{50} < 20$ |
| 401 | $IC_{50} > 20$ |
| 3 | $5 < IC_{50} < 10$ |
| 234 | $5 < IC_{50} < 10$ |
| 156 | $5 < IC_{50} < 10$ |
| 7 | $1 < IC_{50} < 5$ |
| 235 | $5 < IC_{50} < 10$ |

The data on the effects of compounds as disclosed herein on kidney cancer cell viability demonstrate that several of our compounds exhibit significantly increase capability for cancer cell growth inhibition compared to compounds 400 and 401 after 72 hrs of treatment. This observation suggests that these compounds are stronger pharmacological inhibitors for the future treatment of kidney cancer.

Example 55

Evaluation of Compound 2 Effect on the Gene Expression of TNBS-Induced Colitis in Mice Method: TNBS colitis: C57BL/6 mice (20-22 grams) were fed ad lib and assigned to 4 different groups (n=8/group). After a 72 hr acclimation period the test group groups received 25 mg/kg of test compound PO (gavage) in vehicle daily. A control group received vehicle alone. After 24 hrs, mice were weighed and TNBS was injected intra-colonically using 5 cm of polyethylene (¼ inch) tubing. Mice were then treated with the test compounds and weighed daily for 4 days. Mice were sacrificed on day 4 and clinical score was assessed. Intestinal tissue for and blood were also collected. Tissues were either flash frozen and kept in −80° C. for RNA and protein isolation or placed in 10% formalin solution for future histological analysis. Blood was spun at 5K rpm for 5 min and serum was collected and kept at −20° C. for multiplex cytokine analysis.

RNA Sequencing: RNA was extracted from mouse colon tissue at Athos Therapeutics and was sent at Zymo Research or the Technology Center for Genomics & Bioinformatics at UCLA for sequencing and partial bioinformatics analysis.

Libraries for RNA-Seq were prepared with KAPA Stranded mRNA-Seq Kit. The workflow consists of mRNA enrichment and fragmentation, first strand cDNA synthesis using random priming, followed by second strand synthesis converting cDNA:RNA hybrid to double-stranded cDNA (dscDNA), and incorporates dUTP into the second cDNA strand. cDNA generation is followed by end repair to generate blunt ends, A-tailing, adaptor ligation, and PCR amplification. Different adaptors were used for multiplexing samples in one lane. Sequencing was performed on NovaSeq6000 (SP) for a PE 2×150 run. Data quality checking was done on Illumina SAV. Data de-multiplexing was performed with Illumina Bcl2fastq v 2.19.1.403 software. The reads were mapped by STAR 2.27a [1] and read counts per gene were quantified using the mouse Ensembl Mus-musculus.GRCm38.97 GTF file. In Partek Flow (Partek® Flow® software, v7.0 Copyright©. 2019 Partek Inc., St. Louis, Mo., USA) read counts were normalized by CPM +1.0E-4.

Gene differential expression analysis and downstream gene enrichment analysis was performed at Athos Therapeutics. The DESeq2 R package was used for differential expression analysis. DESeq2 FDR cutoff: 0.05, DESeq2 Log 2FC cutoff: 1 (FC cutoff: 2). Gene enrichment analysis was performed using the Enrichr) (https://maayanlab.cloud/Enrichr/enrich) and gprofiler (https://biit.cs.ut.ee/gprofiler/gost) platforms.

Results: Compound 2 is a Potent Inhibitor of a Pro-Inflammatory Gene Signature.

Administration of the haptenating agent 2,4,6-trinitrobenzene sulfonic acid (TNBS) renders colonic proteins immunogenic to the host immune system and thereby initiates a mucosal immune response that drives colitis in mouse strains. TNBS administration C57BL/10 mice induces a transmural colitis mainly driven by a Th1-mediated immune response and characterized by infiltration of the lamina propria with CD4$^+$ T cells, neutrophils, and macrophages as well as development of severe diarrhea, weight loss, and rectal prolapse. As some of these characteristics resemble features of Crohn's disease, TNBS colitis has been widely used in the study of immunologic aspects relevant to this disease, including cytokine secretion patterns, mechanisms of oral tolerance, and effects of potential immunotherapies. It is now well established that cytokine responses are key elements that control the inflammatory mechanisms underlying IBD. Indeed, it was noted early on that interferon-g (IFN-γ) synthesis, in particular, is a characteristic feature of Crohn's disease that might be responsible for the inflammation observed in this disease. Thus, it was highly significant that inflammation in TNBS colitis was associated with elevated levels of IFN-γ.

Figure 7A:
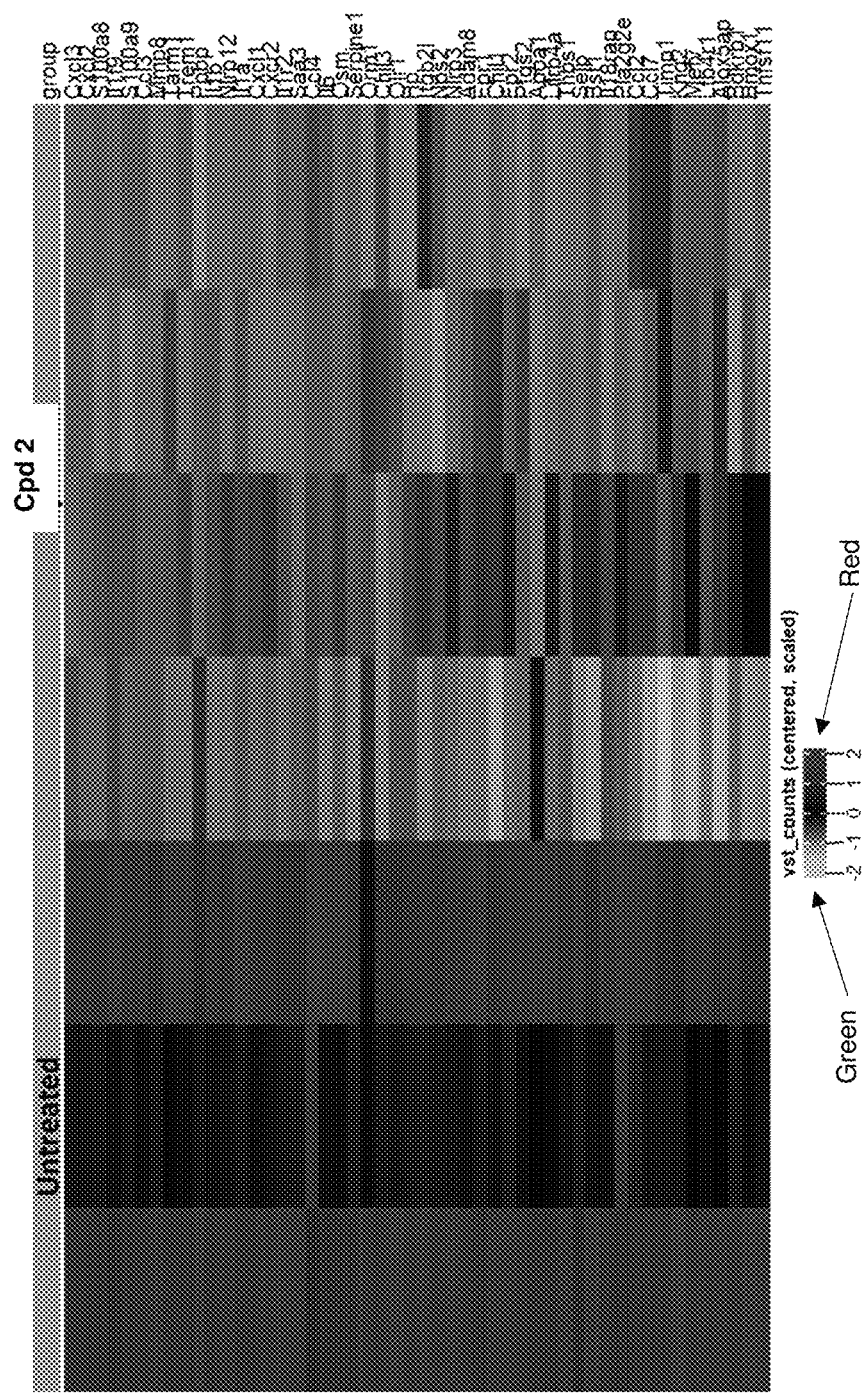
FIG. 7A provides information on colon tissue gene expression after administration with a compound as disclosed herein. Mice with TNBS-induced Colitis and Compound 2-treated showed significantly reduced expression of genes (>85 genes, for clarity 50 genes are depicted) related to inflammatory response.

Surprisingly as shown in FIG. 7A, mice with TNBS-induced Colitis and Compound 2-treated showed significantly reduced expression levels for many genes related to inflammatory response when compared to untreated mice. The fact that Compound 2 has the ability to block the expression of multiple key pro-inflammatory genes and not just one or two suggests its unique ability to have therapeutic potential in IBD and other inflammatory diseases, related to cpd400 or cpd401 that did not have any effect to suppress the inflammatory response or even other drugs targeting single inflammatory factors such as TNFA, IL1B, IL6 and others. FIG. 7A provides information on colon tissue gene expression. Mice with TNBS-induced Colitis and Compound 2-treated showed significantly reduced expression of genes (>85 genes, for clarity 50 genes are depicted) related to inflammatory response (gprofiler gene enrichment analysis, enriched Gene Ontology term: Biological Process: Inflammatory Response, p-adjusted=3.6E-32)

Compound 2 22-Gene Signature of Response

Figure 7B:
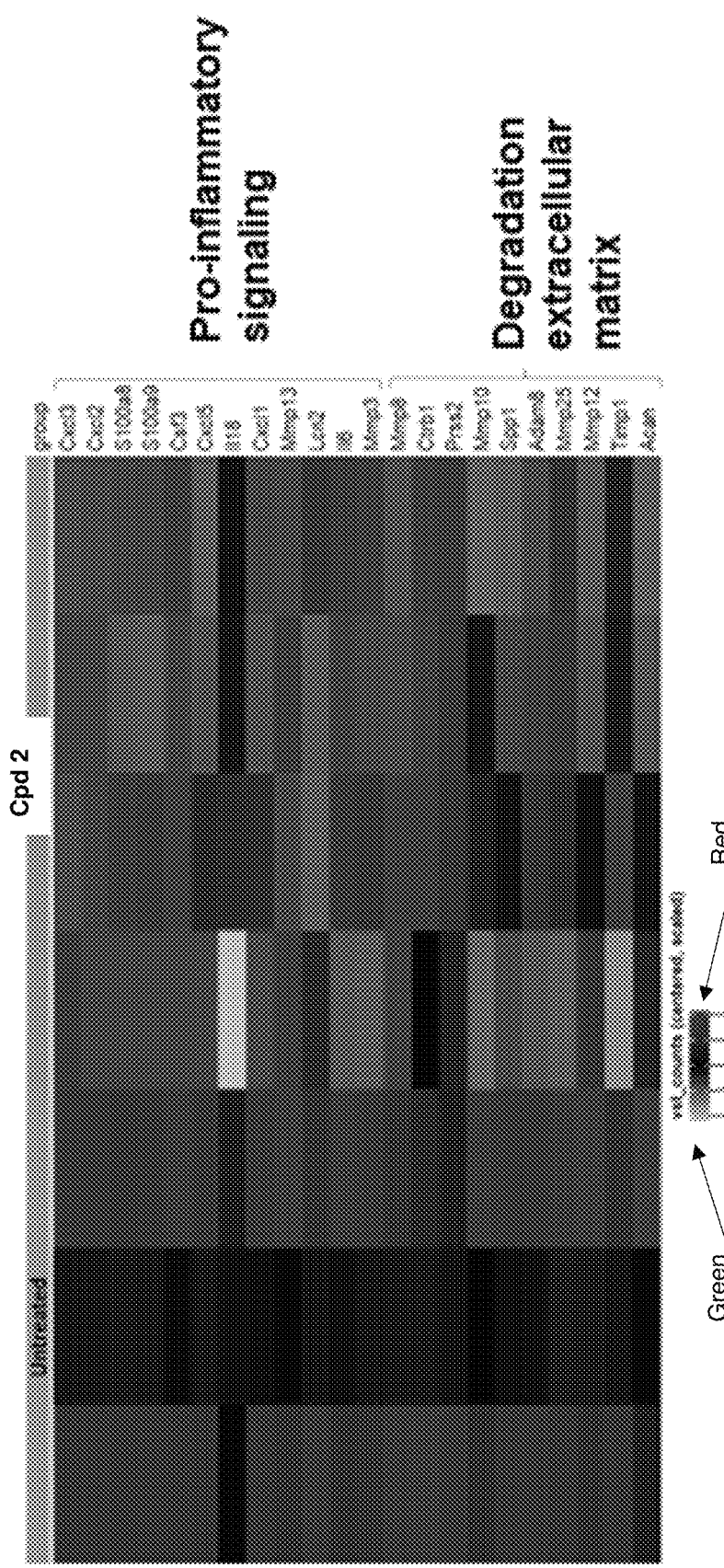
FIG. 7B. Compound 2 (or "cpd2") 22-gene signature of response: Mice with TNBS-induced Colitis and cpd2-treated showed significantly reduced expression of genes related to pro-inflammatory and degradation of extracellular matrix signaling pathways.

The pro-inflammatory cytokines (CXCL2, CXCL3, S100A8.9, IL6) family and metalloproteinases (MMP3, MMP13) play an essential role in the pathogenesis of IBD and other inflammatory diseases. Remarkably, as shown in FIG. 7B mice treated with Compound 2 showed significantly reduced expression of genes involved to these signaling pathways. Furthermore, a typical feature of IBD is tissue damage and alteration of the intestinal architecture due to chronic inflammation. Much of the tissue destruction is mediated by inflammatory leukocyte-derived and activated matrix metalloproteinases (MMPs), a family of zinc requiring proteolytic enzymes. Notably, as shown in FIG. 2, mice with TNBS-induced Colitis and Compound 2-treated showed significantly reduced expression of genes related to degradation of extracellular matrix. Taken together Compound 2 regulates a 22-gene signature related to both inflammatory and mucosal healing processes. FIG. 7B shows Compound 2 22-gene signature of response: Mice with TNBS-induced Colitis and cpd2-treated showed significantly reduced expression of genes related to pro-inflammatory and degradation of extracellular matrix signaling pathways.

Compound 2 Reverses a Gene Signature Related to Resistant to Anti-TNFA Agents

Clinical trials have shown that infliximab, a mouse/human chimeric monoclonal IgG1 antibody to tumor necrosis factor α (TNFα), is efficacious in the treatment of patients with refractory ulcerative colitis. Yet, ~40% of treated patients do not respond to infliximab. A recent study identified mucosal gene signatures predictive of response to infliximab in patients with ulcerative colitis. Responders to Infliximab showed reduced gene expression in numerous genes. Surprisingly, as shown in FIGS. 7C and 7D-H and Table 55.1, mice with TNBS-induced Colitis and cpd2-treated showed significantly reduced expression for several of these infliximab marker genes.

Figure 7C:
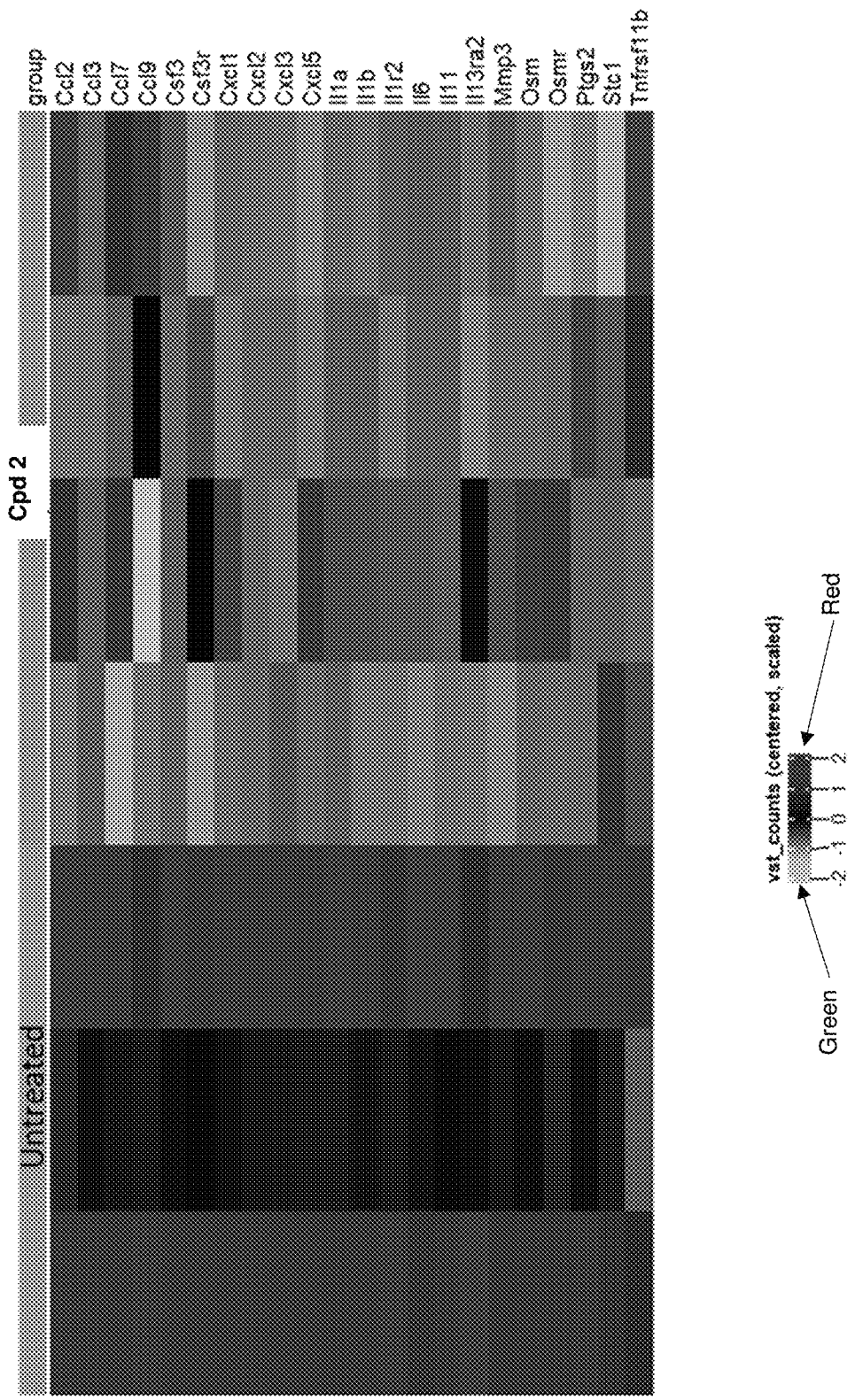
FIG. 7C. Colon tissue gene expression. Mice with TNBS-induced Colitis and cpd2-treated showed significantly reduced expression of marker genes for patients with untreated or refractory Ulcerative Colitis (marker genes for Infliximab response, a mouse/human chimeric monoclonal IgG1 antibody to tumor necrosis factor alpha (TNFa), were taken from a published study.

FIG. 7C provides colon tissue gene expression data. Mice with TNBS-induced Colitis and cpd2-treated showed significantly reduced expression of marker genes for patients with untreated or refractory Ulcerative Colitis (marker genes for Infliximab response, a mouse/human chimeric monoclonal IgG1 antibody to tumor necrosis factor alpha (TNFa), were taken from study: Arijs et al 2009 Gut 58:1612-1619. doi: 10.1136/gut.2009.178665).

FIGS. 7D-7G provide data for colon tissue gene expression. Mice with TNBS-induced Colitis and cpd2-treated showed significantly reduced expression of marker genes for patients with untreated or refractory Ulcerative Colitis (marker genes for Infliximab response, a mouse/human chimeric monoclonal IgG1 antibody to tumor necrosis factor alpha (TNFa), were taken from study: Arijs et al 2009 Gut 58:1612-1619. doi: 10.1136/gut.2009.178665).

Table 55.1 below shows colon tissue gene expression. Mice with TNBS-induced Colitis and cpd2-treated showed significantly reduced expression of marker genes for patients with untreated or refractory Ulcerative Colitis (marker genes for Infliximab response, a mouse/human chimeric monoclonal IgG1 antibody to tumor necrosis factor alpha (TNFa), were taken from study: Arijs et al 2009 Gut 58:1612-1619. doi: 10.1136/gut.2009.178665).

TABLE 55.1

|         | $Log_2FC$ | p-value  | p-adjusted |
|---------|-----------|----------|------------|
| Ccl2    | −2.71     | 1.66E−04 | 1.13E−02   |
| Ccl3    | −7.36     | 2.72E−08 | 1.84E−05   |
| Ccl7    | −2.73     | 2.37E−05 | 2.90E−03   |
| Ccl9    | −1.15     | 1.11E−03 | 3.86E−02   |
| Csf3    | −6.66     | 2.79E−08 | 1.84E−05   |
| Csf3r   | −3.19     | 3.99E−04 | 2.09E−02   |
| Cxcl1   | −6.03     | 1.86E−08 | 1.67E−05   |
| Cxcl2   | −8.30     | 5.98E−11 | 1.31E−07   |
| Cxcl3   | −10.19    | 1.53E−09 | 2.32E−06   |
| Cxcl5   | −6.57     | 2.91E−08 | 1.86E−05   |
| Il1a    | −6.05     | 5.56E−07 | 1.72E−04   |
| Il1b    | −6.17     | 2.77E−08 | 1.84E−05   |
| Il1r2   | −5.75     | 3.22E−10 | 6.35E−07   |
| Il11    | −4.05     | 5.12E−06 | 9.82E−04   |
| Il13ra2 | −2.38     | 9.28E−03 | 1.28E−01   |
| Il6     | −4.82     | 1.90E−07 | 7.09E−05   |
| Mmp3    | −4.47     | 1.73E−11 | 8.54E−08   |
| Osm     | −4.67     | 3.48E−08 | 2.02E−05   |
| Osmr    | −1.24     | 2.62E−04 | 1.55E−02   |
| Ptgs2   | −3.18     | 4.61E−07 | 1.45E−04   |
| Stc1    | −1.89     | 3.65E−05 | 3.87E−03   |
| Tnfrsf11b | −1.66   | 6.80E−03 | 1.08E−01   |

Tumor necrosis factor (TNF), a pro-inflammatory Th-1 cytokine, is chronically elevated, locally and systemically, in patients with IBD. Currently, one of the most effective therapies for treating refractory IBD is suppression of TNF function. Mice with deletion of the 3' regulatory element from the TNF transcript have increased, sustained production of TNF, resulting in CD-like inflammation and immune profile. Similarly, TNF has been shown to be pathogenic, both in a variety of mouse models of IBD and colitis associated colon cancer. It has also been shown that TNBS treated mice with ablation of the TNF gene (Tnf−/−mice) had less severe colonic inflammation than similarly treated wild type (WT) mice. Remarkably, as shown in FIG. 7H, mice with TNBS-induced Colitis and cpd2-treated showed significantly reduced expression of TNF.

Overall, the gene expression data using cpd2 in TNBS-induced colitis show that this compound is a strong inhibitor of inflammation and Colitis-associated damage in the intestine and promotes tissue healing.

Example 56

Evaluation of Compound 156 Effect on the Gene Expression of the Colon Cancer Cell Line HT-29

Methods: RNA was extracted from HTC colon cancer cells that has been treated or not with Compound 156 and was sent to the Technology Center for Genomics & Bioinformatics at UCLA for sequencing.

Library construction and sequencing methods: Libraries for RNA-Seq were prepared with TruSeq Stranded mRNA Library Prep Kit. The workflow consists of mRNA enrichment and fragmentation. Cleaved RNA fragments are copied into first strand cDNA using reverse transcriptase and random primers. Strand specificity is achieved by replacing dTTP with dUTP and followed by second strand cDNA synthesis using DNA Polymerase I and RNase H. cDNA generation is followed by A-tailing, adaptor ligation and PCR amplification. Different adaptors were used for multiplexing samples in one lane. Sequencing was performed on Illumina NovaSeq 6000 for PE 2×50 run. Data quality check was done on Illumina SAV. Demultiplexing was performed with Illumina Bcl2fastq v2.19.1.403 software.

Bioinformatics methods: The reads were mapped by STAR 2.27a to Human GRCh38 genome and read counts per gene were quantified using Ensembl Human GRCh38.98 GTF file. Gene differential expression analysis and downstream gene enrichment analysis was performed at Athos Therapeutics. The DESeq2 R package was used for differential expression analysis. DESeq2 FDR cutoff: 0.05, DESeq2 Log 2FC cutoff: 1 (FC cutoff: 2). Gene enrichment analysis was performed using the Enrichr (https://maayanlab.cloud/Enrichr/enrich) and gprofiler (https://biit.cs.ut.ee/gprofiler/gost) platforms.

Results: The p53 protein acts as a tumor suppressor in many tumor types. It induces growth arrest or apoptosis depending on the physiological circumstances and cell type. It is involved in the cell cycle regulation by negatively regulating cell division by controlling a set of genes required for this process. It is a transcriptional activator of p53-regulated genes. This results in three major outputs—cell cycle arrest, cellular senescence, or apoptosis.

Cell cycle progression is accomplished through a reproducible sequence of events. Cyclin-dependent kinases (CDKs) are key regulatory enzymes, which regulate the cell's progression through the phases of the cell cycle. Downstream targets of CDKs include transcription factor E2F. Precise activation and inactivation of CDKs at specific points in the cell cycle are required for orderly cell division.

Figure 8:
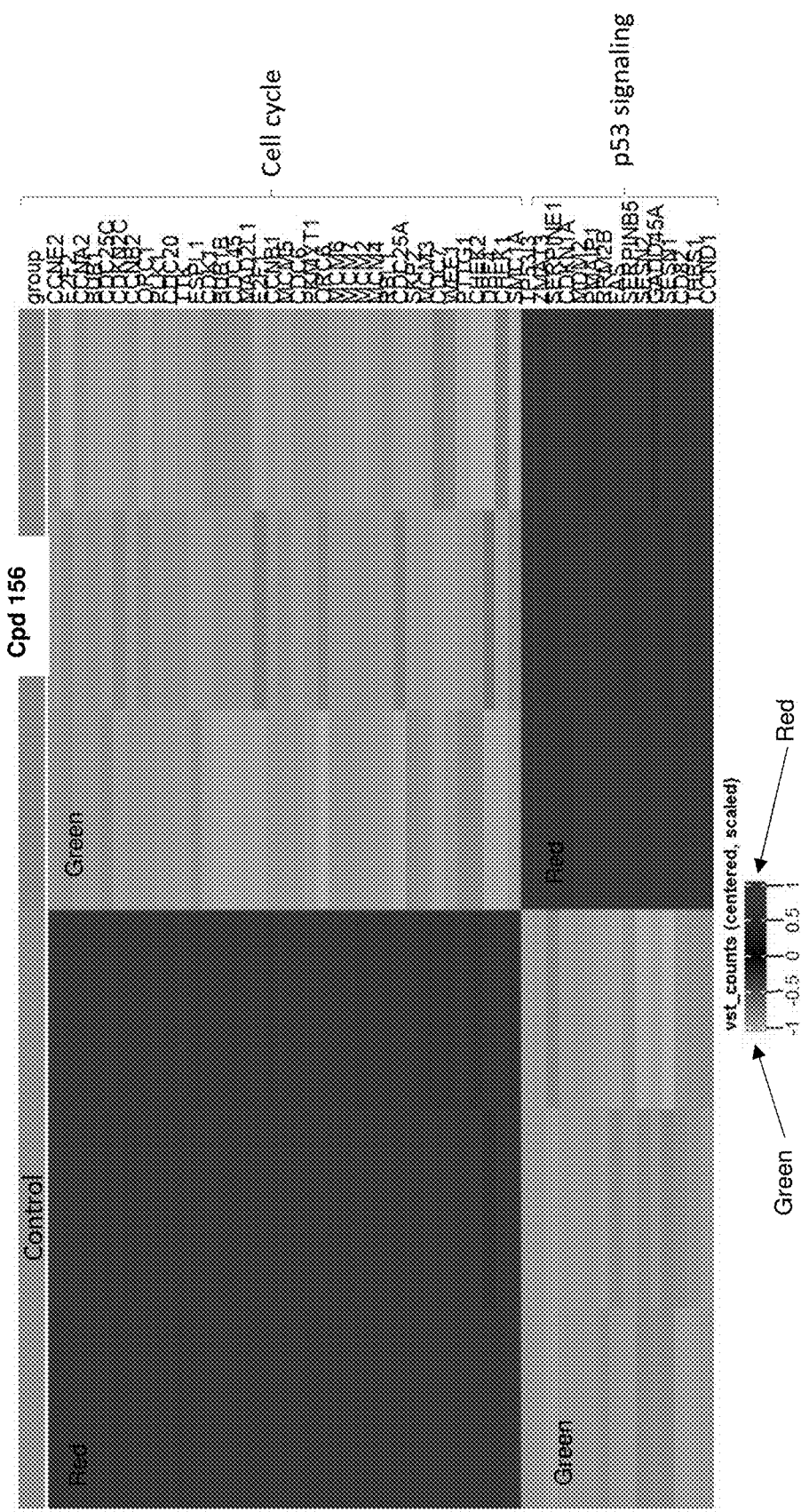
FIG. 8 provides colon cell line HCT gene expression data. Cells that were treated with cpd156 showed significantly reduced expression of genes implicated in the cell cycle pathway and significantly increased expression of genes related to the p53-signaling pathway.

Remarkably colon cancer cells that were treated with Compound 156 showed significant enrichment of genes involved in the p53-signaling and the cell cycle pathways (Table 56.1). As shown in FIG. 8, p-53 related genes were upregulated whereas genes related to cycle were downregulated. Additionally, multiple genes that are activated by p53 (>80, data not shown) were upregulated, whereas genes regulated by the transcription factors E2F-1 and E2F-4 were downregulated (>500 genes, data not shown).

These results show that Compound 156 exhibits a significant capability for cancer-cell growth inhibition.

TABLE 56.1.

Gene enrichment analysis. gprofiler gene enrichment analysis

| Prediction | Source | Term name | p-adj | Term coverage |
|---|---|---|---|---|
| Activation | KEGG | p53 signaling pathway | 9.1E−08 | 20.5 |
| Activation | REAC | HDAC deacetylate histones | 1.5E−06 | 17.0 |
| Activation | TF | Factor: p53 | 1.6E−06 | 4.9 |
| Activation | TF | Factor: p63 | 2.9E−06 | 3.9 |
| Inhibition | KEGG | Cell Cycle | 7.6E−21 | 29.8 |
| Inhibition | KEGG | DNA replication | 2.4E−20 | 61.1 |
| Inhibition | TF | Factor: E2F-1 | 7.1E−23 | 5.2 |
| Inhibition | TF | Factor: E2F-4 | 2.1E−22 | 5.7 |

FIG. 8. Colon cell line HCT gene expression. Cells that were treated with cpd156 showed significantly reduced expression of genes implicated in the cell cycle pathway and significantly increased expression of genes related to the p53-signaling pathway.

The genes of tables 56.2 and 56.3 are down-regulated by compounds as disclosed herein, including Compound 156:

TABLE 56.2.

List of genes implicated in the cell cycle pathway that showed reduced expression in the colon cell line HCT after treatment with cpd 156.

| Gene | Log2 Fold Change | p-adjusted |
|---|---|---|
| CCNE2 | −5.40892 | 1.91E−94 |
| E2F2 | −5.29589 | 2.71E−147 |
| CCNA2 | −5.16323 | 0 |
| BUB1 | −5.15684 | 0 |
| CDC25C | −5.14244 | 1.91E−107 |
| CDKN2C | −5.13985 | 4.64E−43 |
| CCNB2 | −5.04077 | 0 |
| ORC1 | −4.98677 | 1.28E−259 |
| PLK1 | −4.8821 | 0 |
| CDC20 | −4.82606 | 0 |
| TTK | −4.82397 | 0 |
| ESPL1 | −4.82095 | 0 |
| CDK1 | −4.77856 | 0 |
| BUB1B | −4.7094 | 0 |
| CDC45 | −4.67941 | 5.83E−196 |
| MAD2L1 | −4.38793 | 0 |
| E2F1 | −4.30926 | 1.23E−157 |
| CCNB1 | −4.23139 | 0 |
| MCM5 | −4.18256 | 0 |
| CDC6 | −4.12076 | 0 |
| PKMYT1 | −3.97132 | 1.08E−218 |
| ORC6 | −3.9103 | 2.62E−226 |
| MCM6 | −3.83429 | 0 |
| MCM7 | −3.81716 | 0 |
| MCM2 | −3.68599 | 0 |
| MCM4 | −3.34666 | 0 |
| RBL1 | −3.04321 | 1.01E−135 |
| CDC25A | −2.85783 | 2.04E−193 |
| SKP2 | −2.82263 | 2.40E−213 |
| MCM3 | −2.59891 | 0 |
| CDC7 | −2.49879 | 5.96E−156 |
| WEE1 | −2.39438 | 8.78E−189 |
| PTTG1 | −2.31714 | 1.16E−284 |
| CHEK2 | −2.18563 | 9.94E−124 |
| DBF4 | −2.53558 | 6.30E−89 |
| CHEK1 | −1.99422 | 8.19E−148 |
| SMC1A | −1.93397 | 6.29E−299 |

TABLE 56.3.

List of genes implicated in the p53 pathway that showed increased expression in the colon cell line HCT after treatment with cpd156.

| Genes | Log2 Fold Change | p-adjusted |
|---|---|---|
| TP53I3 | 3.870473 | 0 |
| ZMAT3 | 3.367294 | 0 |
| SERPINE1 | 3.23203 | 0 |
| CDKN1A | 3.189957 | 0 |
| MDM2 | 3.166013 | 0 |
| PMAIP1 | 3.102428 | 0 |
| RRM2B | 2.677773 | 0 |
| FAS | 2.667129 | 3.29E−285 |
| SERPINB5 | 2.470662 | 0 |
| SESN2 | 2.190084 | 3.79E−176 |
| GADD45A | 1.968929 | 5.78E−172 |
| SESN1 | 1.954867 | 3.32E−134 |
| CD82 | 1.878096 | 4.94E−75 |
| THBS1 | 1.87155 | 3.07E−125 |
| CCND1 | 1.791896 | 0 |

Example 57

Evaluation of Compound 1 and Compound 2 Effect on the Microbiome of DSS-Induced Colitis in Mice Methods DSS-induced colitis: C57BL/6 mice (20-22 grams) were fed ad lib and assigned to 4 different groups (n=8/group). After a 72 hr acclimation period test groups received 25 mg/kg of test compounds PO (gavage) in vehicle daily. A control group received vehicle alone. After 24 hrs, mice were weighed and DSS was added to their drinking water. Mice were then treated with the test compounds (Compound 1 or Compound 2) and weighed daily and the DSS water was replenished every 72 hrs for 5 days, at which point, it was replaced by regular drinking water. Mice were sacrificed on day twelve and clinical scored was assessed. Intestinal tissue and blood were also collected. Tissues were either flash frozen and kept in $-80°$ C. for RNA and protein isolation or placed in 10% formalin solution for future histological analysis. Blood was spun at 5K rpm for 5 min and serum was collected and kept at $-20°$ C. for multiplex cytokine analysis.

Shotgun Metagenomic Sequencing: Mouse colon tissue samples (treated with Compound 1 or Compound 2, and untreated) were processed and analyzed with the ZymoBIOMICS® Shotgun Metagenomic Sequencing Service (Zymo Research, Irvine, Calif.). DNA extraction was performed with ZymoBIOMICS®-96 MagBead DNA Kit (Zymo Research, Irvine, Calif.).

Library Preparation: Genomic DNA samples were profiled with shotgun metagenomic sequencing. Sequencing libraries were prepared with Nextera® DNA Flex Library Prep Kit (Illumina, San Diego, Calif.) with up to 100 ng DNA input following the manufacturer's protocol using internal dual-index 8 bp barcodes with Nextera® adapters (Illumina, San Diego, Calif.). All libraries were quantified with TapeStation® (Agilent Technologies, Santa Clara, Calif.) and then pooled in equal abundance. The final pool was quantified using qPCR.

Sequencing: The final library was sequenced on the NovaSeq® (Illumina, San Diego, Calif.) platform. The ZymoBIOMICS® Microbial Community DNA Standard (Zymo Research, Irvine, Calif.) was used as a positive control for each targeted library preparation. Negative controls (i.e. blank extraction control, blank library preparation control) were included to assess the level of bioburden carried by the wet-lab process.

Bioinformatics Analysis: Raw sequence reads were trimmed to remove low quality fractions and adapters with Trimmomatic-0.33 (Bolger 2014): quality trimming by sliding window with 6 bp window size and a quality cutoff of 20 and reads with size lower than 70 bp were removed. Antimicrobial resistance and virulence factor gene identification was performed with the DIAMOND sequence aligner (Buchfink 2015). Microbial composition was profiled with Centrifuge (Kim et al., 2016) using bacterial, viral, fungal, mouse, and human genome datasets. Strain-level abundance information was extracted from the Centrifuge outputs and further analyzed: a) to perform alpha- and beta-diversity analyses, b) to create microbial composition barplots with QIIME (Caporaso 2012), c) to create taxa abundance heatmaps with hierarchical clustering (based on Bray-Curtis dissimilarity), and d) for biomarker discovery with LEfSe (Segata 2011) with default settings (p>0.05 and LDA effect size>2).

Results

Figure 9:
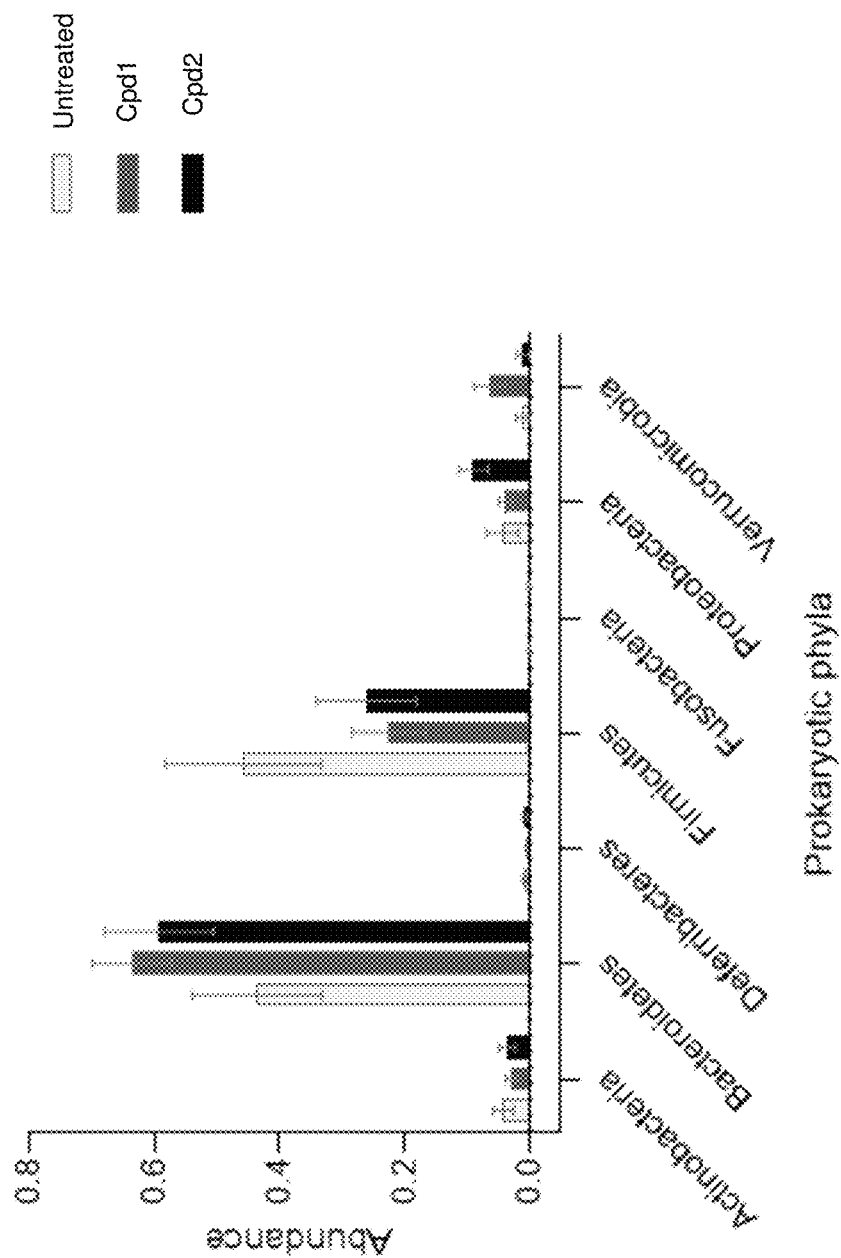
FIG. 9 provides results of a study on the microbiome of animals with induced colitis. The intestinal microbiome primarily include four phyla, Firmicutes, Bacteroidetes, Proteobacteria, and Actinobacteria. In inflammatory bowel disease (IBD) patients, the composition of the gut microbiota is altered compared to that of healthy individuals.

FIG. 9 provides results of the study. The gut microbiome plays a fundamental role in several aspects of host homeostasis: nutrition, immune development, metabolism, and defense against pathogens. Most intestinal bacteria belong to four phyla, Firmicutes, Bacteroidetes, Proteobacteria, and Actinobacteria (Jandhyala 2015). It is well known that in IBD patients, the composition of the gut microbiota is severely altered compared to that of healthy individuals.

Compound 1 and Compound 2 were evaluated for their effects on the microbial composition of DSS-induced colitis mice. As depicted in FIG. 9, DSS-induced colitis mice treated with Compound 1 or Compound 2 showed significant decrease of the Firmicutes phylum (Compound 1) and increase of the Bacteroidetes (Compound 1 and Compound 2), Proteobacteria (Compound 2), and Verrucomicrobia (Compound 1) phyla (multiple Mann-Whitney tests, p<0.05).

To determine the most divergent and potential microbial biomarker species, LeFSe analysis was performed. As shown in the FIG. 9, mice treated with Compound 1 showed enrichment in four Bacteroidetes (*Bacteroides* (B) *caecimuris, B. sartorii, B. thetaiotaomicron*, and *Duncaniella muris*) and one Verrucomicrobia (*Akkermansia muciniphila*) species. Surprisingly, one of them, *B. thetaiotaomicron*, is not only a prevalent species within the *Bacteroides* genus of the healthy human gut microbiota, but it also has anti-inflammatory properties, can increase mucosal barrier function and can limit pathogen invasion (Hooper 2004; Wrzosek 2013; Delly 2004). Treatment with *B. thetaiotaomicron* has been shown to induce protective effects in DSS and IL10K0 models of colitis in both mice and rats (Delday 2019). Additionally, the Verrucomicrobia enriched species *Akkermansia muciniphila* was found decreased in UC patients (Bajer 2017). Mice treated with Compound 2 showed enrichment in two Bacteroidetes (*Bacteroides mediterraneensis* and *Prevotella copri*), one Firmicutes (*Megasphaera massiliensis*), and one Proteobacteria (*Sutterella wadsworthensis*) species. Interestingly, in a panel of fifty gut bacterial strains that was screened for their ability to reduce pro-inflammatory IL-6 secretion in U373 glioblastoma astrocytoma cells *Megasphaera massiliensis* had the strongest capacity to reduce IL-6 secretion in vitro (Ahmed 2019). Additionally, although *Sutterella wadsworthensis* was previously found in patients with UC, experimental data did not confirm a connection between *S. wadsworthensis* and UC pathogenesis or other types of IBD (Mukhopadhya 2011).

| Compound | Phylum | Species | LDA score |
|---|---|---|---|
| Cpd 1 | Bacteroidetes | Bacteroidetes thetaiotamicron | 4.18 |
| | Baderoidetes | Bacteroidetes caecimaris | 3.17 |
| | Baderoidetes | Bacteroidetes sartorii. | 3.09 |
| | Baderoidetes | Duncaniella muris | 3.04 |
| | Verrucomicrobia | Akkemansia muciniphila | 3.75 |
| Cpd 2. | Bacteroidetes | Prevotella copri | 3.86 |
| | Bacteroidetes | Bacteroidetes mediterraneenis | 2.98 |
| | Firmicutes | Megaasphaera massiliensis | 3.0 |
| | Fimicutes | Megamonas funiformis | 3.0 |
| | Proteobacteria | Suterella wadsworthensis | 3.06 |
| Untreated | Firmkutes | Clostridium mediterraneense | 3.15 |

Overall, these data showed that treatment with Compound 1 and Compound 2, in induced colitis conditions, significantly altered the gut microbiome composition and shifted it towards eubiosis.

Example 58

Evaluation of Compounds to Induce Specific Differentiation of CD4+ T Cells Into CD25+ FoxP3+ T Regulatory Cells Naïve human CD4 T cells were cultured in DMEM supplemented with 10% heat-inactivated FBS, 2 mM glutamine, 100 U/ml penicillin, 100 µg/ml streptomycin and 25 mM Hepes. Human CD4 T cells were treated with anti-CD3 and anti-CD28 (100 ng/ml) together with small molecule compounds (500 nM) for 5 days. FoxP3 and CD4 positive cells were stained and imaged in a BD LSRII flow cytometer. The gated area represents the percentage $CD4^{high}FoxP3^{high}$ immune cell population. Furthermore, the same small molecule compounds were evaluated for their effects on IL17 protein levels in human CD4 T cells by using an ELISA assay (R&D systems, cat no. D1700).

TABLE 58.1.

| Compound | Tregs (%) |
| --- | --- |
| Untreated | 3.2 |
| cpd2 | 20.1 |
| Cpd400 | 4.7 |
| Cpd401 | 3.3 |

Cpd102, cpd400 and cpd401 were evaluated for their effects to induce differentiation of naïve human CD4 T cells into FoxP3+ Tregs, which has anti-inflammatory activity and therapeutic potential for autoimmune diseases, including ulcerative colitis, Crohn's Disease, Type 1 Diabetes, Systemic Lupus Erythematosus and Graft Versus Host Disease (GVHD). In the untreated state there 3.2% of the total CD4+ population were Tregs (baseline). Cpd401 did not have a significant effect on increasing the Treg cellular population and cpd400 had a small effect on increasing 1.46×-fold the number of Tregs. Unexpectedly, cpd2 had a large effect increasing substantially (6.28×-fold), which is a number of Treg cells that has therapeutic potential. Thus, although cpd2, cpd400 and cpd401 target G9A enzyme, only cpd2 showed a functional and robust increase on Treg cellular population.

Figure 10:
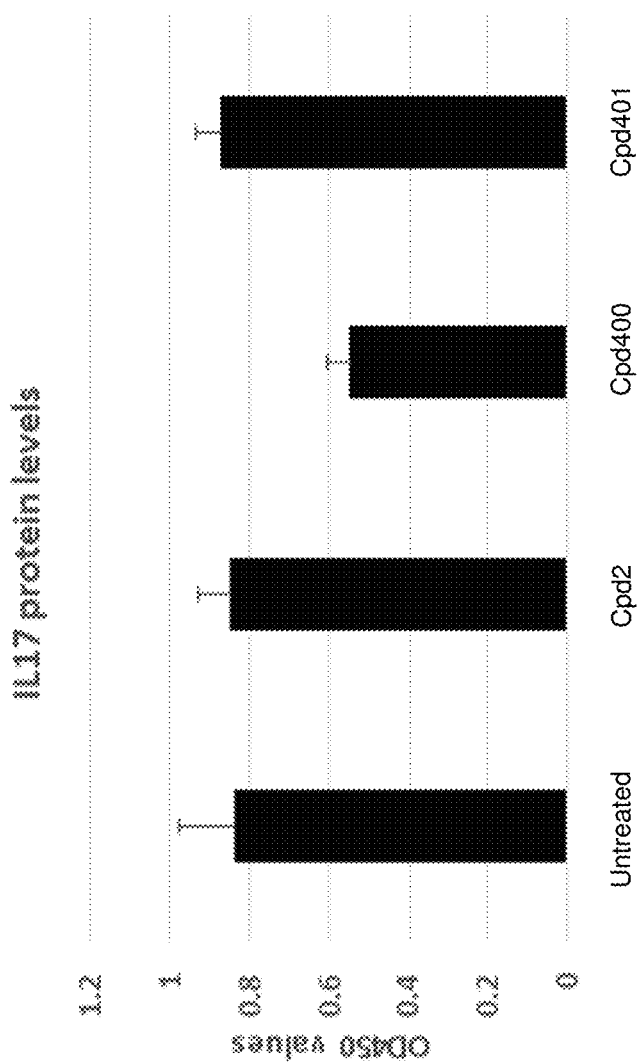
FIG. 10 provides the effects of Compound 2, Compound 400 and Compound 401 compounds on IL17 expression levels.

Furthermore, the effects of Cpd2, cpd400 and cpd401 compounds on IL17 expression levels was evaluated. IL17 is an interleukin that its suppression has shown to have adverse and not therapeutic effects on patients with ulcerative colitis and Crohn's disease, leading to disease exacerbation. As shown in FIG. 10, cpd2 and cpd401 do not have an effect on IL17 protein levels, while cpd400 significantly suppresses IL17 protein levels in CD4 T cells.

Taken together, Cpd2 is a compound that harbors unique properties of inducing substantially T regulatory cells without affecting the IL17 protein levels, a combination that shows cpd2 to have a therapeutic potential without side effects, which is not found in the cpd400 and cpd401 compounds.

Example 59

Prophetic Examples of Compounds Having Anti-Cancer Activities

The following compounds are evaluated for their ability to block cancer cell growth in colon (HT-29), liver (HepG2), pancreatic (MiaPaca-2) and bladder (5637) cancer cell lines. Specifically, the Promega Real-Time-Glo cell viability kit was used to determine the optimal concentration for cell plating so that each cell line would be within the linear part of its growth curve after 72 hrs in culture. For the determination of test compound $IC_{50}s$ different cancer cell lines are plated in 96 well plates in the pre-determined optimal density for each cell line. Test compounds are then added at different concentrations for the creation of six-point curve and cell density is determined using the Promega Real-Time-Glo cell viability kit after 24, 48, and 72 hrs in culture. Test compound 72 hr $IC_{50}s$ is calculated using the AAT Bioquest $IC_{50}$ calculator. Furthermore, the following scoring system is used:

TABLE 59.1.

| Com- | Cell lines | | | |
| --- | --- | --- | --- | --- |
| pound | HT-29 | HepG2 | MiaPaca-2 | 5637 |
| 14 | +++ | ++ | − | +++ |
| 16 | ++ | + | ++ | +++ |
| 18 | +++ | − | ++ | +++ |
| 20 | + | +++ | + | ++ |
| 21 | +++ | +++ | − | + |
| 25 | ++ | −_ | + | +++ |
| 27 | +++ | + | ++ | − |
| 30 | + | + | +++ | ++ |
| 39 | _− | ++ | +++ | _− |
| 49 | ++ | + | ++ | +++ |
| 51 | +++ | ++ | _− | + |
| 57 | ++ | + | +++ | ++ |
| 66 | + | +++ | + | − |
| 116 | − | ++ | +++ | +++ |
| 125 | ++ | + | +++ | ++ |
| 150 | − | +++ | + | − |
| 162 | − | + | +++ | + |
| 177 | ++ | +++ | + | − |
| 188 | +++ | ++ | + | +++ |
| 206 | + | ++ | +++ | + |
| 221 | ++ | − | ++ | + |
| 250 | +++ | − | +++ | ++ |
| 252 | + | ++ | + | + |
| 296 | ++ | + | − | +++ |
| 307 | +++ | ++ | + | + |
| 355 | +++ | + | + | + |
| 402 | − | ++ | ++ | − |
| 409 | + | +++ | ++ | − |
| 412 | ++ | + | ++ | +++ |

+++: $IC_{50}$: <1 uM
++: $IC_{50}$: 1-5 uM
+: $IC_{50}$: 5-10 uM
−: $IC_{50}$: >10 uM

Example 60

Prophetic Example Related to the Therapeutic Activity of Compounds Against Ulcerative Colitis & Crohn's Disease The following compounds are evaluated for their ability to induce gut mucosal healing (TEER assay) and suppress the inflammatory response in a DSS-induced colitis mouse model. To have a therapeutic potential in ulcerative colitis and Crohn's disease it is important to be effective in both mechanisms (induction of healing and suppression of inflammation).

DSS colitis mouse model: C57BL/6 mice (20-22 grains) are fed ad lib and assigned to different groups (n=8/group). After a 72 hr acclimation period test groups received 25 mg/kg of test compounds PO (gavage) in vehicle daily. A control group receives vehicle alone. After 24 h, mice are weighed and DSS is added to their drinking water. Mice are then treated with the test compounds and weighed daily and the DSS water is replenished every 72 liars for 5 days, at which point, it is replaced by regular drinking water. Mice are sacrificed on day twelve and clinical scored was assessed. Intestinal tissue for and blood are also collected. Tissues are either flash frozen and kept in −80° C. for RNA and protein isolation or placed in 10% formalin solution for future histological analysis.

TEER assay: CaCo-2 cells (ATCC) are plated on 24 trans-well plates (Fisher scientific) at a density of 105 cells/insert in growth medium (DMEM, 10% FBS, 0.01 mg/ml human transferrin). At confluence TEER is measured and TNFα along with compounds are added as described above. Compound-induced TEER is determined after correction with measurement prior to treatment. Thus, the effects of 21 compounds in a TEER colonic epithelial cellular assay and evaluated their effectiveness in a DSS-colitis mouse model is measured, using the following scoring system:

− on the table represents no statistical significance in any variable measured

+ on the table represent statistically significant differences in the variable measured ++ is for measurable that include multiple variables in the calculation of their differences and they represent the presence of significant changes across all variable measurements. Thus, they demonstrate more potent changes in the measurable outcome.

TABLE 60.1

| Compound | TEER | DSS Efficacy |
|---|---|---|
| 7 | − | − |
| 12 | ++ | ++ |
| 14 | + | ++ |
| 15 | ++ | + |
| 17 | + | + |
| 21 | − | + |
| 25 | + | + |
| 34 | − | − |
| 49 | − | − |
| 61 | + | + |
| 81 | + | ++ |
| 99 | ++ | ++ |
| 105 | + | + |
| 137 | + | + |
| 164 | ++ | ++ |
| 173 | ++ | ++ |
| 180 | ++ | ++ |
| 213 | + | + |
| 250 | ++ | ++ |
| 254 | + | + |
| 410 | − | + |

Example 61

Treatment of Ulcerative Colitis

Based on the inventor's clinical experience, the following results are projected using controlled studies.

Ulcerative colitis is an Inflammatory Bowel Disease (IBD) that causes inflammation and ulcers (sores) in your digestive tract and disruption of the colonic mucosal structure. Ulcerative colitis affects the innermost lining of your large intestine (colon) and rectum. A cohort of 60 patients with moderate to severe ulcerative colitis and colonic location of disease that are not responding to anti-TNFalpha biologics, between the ages of 25 and 60 years of age is identified by a gastroenterologist. All these patients have diarrhea, abdominal pain and cramping, rectal bleeding, urgency to defecate, inability to defecate despite urgency, weight loss, fatigue, and fever. A colonoscopy is performed to diagnose inflammation levels and to determine the extent of ulcer formation within the colon. This report establishes a patient baseline. The experimental group patients (n=20; "EXPT1") receive Compound 2 once a day orally. The experimental group patients (n=20; "EXPT2) receive Compound 400 once a day orally. The control group patients (n=20; "CONT") receive a placebo once a day orally. The study is conducted over a period of 12 weeks after which patient outcomes are measured by a gastroenterologist. Patients receiving the EXPT1 report substantial improvement in each symptom of ulcerative colitis as determined by improvement in standardized patient reported outcome questionnaire scores. An endoscopic examination of the colon of the patients also indicates mucosal healing and suppression of the pro-inflammatory markers in the patients in EXPT1, with colonic biopsies showing resolution of histologic inflammation. The number of systemic, circulating T regulatory immune (FoxP3+) cells were found to be 5-10-fold increased in the EXPT1 group of patients. Alternatively, patients in EXPT2 or the CONT group show no improvement in symptoms and/or an worsening in symptoms over the course of the study and no indications of mucosal or histologic healing. The differences between the EXPT2 and CONT group are not significantly significant. The difference between improved results in the EXPT1 group versus the EXPT2 or CONT group is statistically significant.

Example 62

Treatment of Systemic Erythematosus Lupus (SLE)

Based on the inventor's clinical experience, the following results are projected using controlled studies.

Systemic Erythematosus Lupus (SLE) is an autoimmune disease which is characterized uncontrolled inflammation in different organs, including the joints, skin, kidneys, heart and lungs. Furthermore, there is an extensive activation of CD4 T cells in SLE patients, which secrete pro-inflammatory molecules causing organ damage. A cohort of 60 SLE patients, between the ages of 25 and 50 years of age is identified by a rheumatologist. All these patients have fatigue, skin rush, joint pain and proteinuria. The experimental group patients (n=20; "EXPT1") receive Compound 2 once a day orally. The experimental group patients (n=20; "EXPT2) receive Compound 400 once a day orally. The control group patients (n=20; "CONT") receive a placebo once a day orally. The study is conducted over a period of 52 weeks after which patient outcomes are measured by a rheumatologist. Patients receiving the EXPT1 report substantial improvement in each symptom and an SLEDA score of less than 2 (remission state). The number T systemic, circulating regulatory immune (FoxP3+) cells were found to be 5-10-fold increased in the EXPT1 group of patients. Alternatively, patients in EXPT2 or the CONT group show no decrease in symptoms and/or an increase in symptoms over the course of the study. The differences between the EXPT2 and CONT group are not significantly significant. The difference between improved results in the EXPT1 group versus the EXPT2 or CONT group is statistically significant.

Example 63

Treatment of Colon Cancer

Based on the inventor's clinical experience, the following results are projected using controlled studies.

Colon cancer is a type of cancer that begins in the large intestine (colon). The colon is the final part of the digestive tract. Colon cancer typically affects older adults, though it can happen at any age. It usually begins as small, noncancerous (benign) clumps of cells called polyps that form on the inside of the colon. Over time some of these polyps can become colon cancers. A cohort of 90 patients with colon tumors between the ages of 50 and 75 years of age is identified by an oncologist. A detailed examination report for each patent is prepared, complete with an indication of symptoms and their severity. Tumor size is measured using MRI imaging. Symptoms common to the patients include diarrhea and/or constipation, abdominal pain and cramping, rectal pain, rectal bleeding, weight loss, and fatigue. A colonoscopy is also performed to view the tumor(s) in the patient. This report establishes a patient baseline. The experimental group patients (n=30; "EXPT1") receive Compound 3 once a day orally. The experimental group patients (n=30; "EXPT2) receive Compound 400 once a day orally. The control group patients (n=30; "CONT") receive a placebo once a day orally. The study is conducted over a period of three months after which patient outcomes are measured by an oncologist. Patients receiving the EXPT1 report improvement in each symptom of colon cancer. They also experience a tumor size reduction on average of 80%. Alternatively, patients in EXPT2 or the CONT group show no decrease in symptoms and/or an increase in symptoms over the course of the study. Tumor size increases over the course of the study. The differences between the EXPT2 and CONT group is not significantly significant. The difference between improved results in the EXPT1 group versus the EXPT2 or CONT group is statistically significant.

While some embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

While the subject matter has been particularly shown and described with reference to a preferred embodiment and various alternate embodiments, it will be understood by persons skilled in the relevant art that various changes in form and details can be made therein without departing from the spirit and scope of the present disclosure.

All references, issued patents and patent applications cited within the body of the instant specification are hereby incorporated by reference in their entirety, for all purposes.

Although the subject matter has been described with reference to embodiments and examples, it should be understood that numerous and various modifications can be made without departing from the spirit of the present disclosure. Accordingly, the subject matter is limited only by the following claims.

What is claimed is:

1. A compound of Formula (I) or a stereoisomer, tautomer, or pharmaceutically acceptable salt thereof:

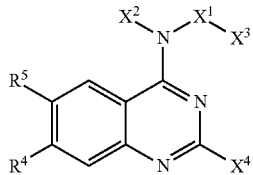
(I)

wherein:
X$^1$ is —(CH$_2$)$_o$— or a covalent bond;
o is an integer equal to 1, 2, 3, 4, 5, or 6;
X$^2$ is hydrogen and X$^3$ is represented by Formula (IX3):

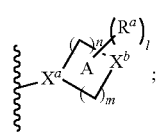
(IX3)

where
X$^a$ is selected from the group consisting of CH and N;
m is independently an integer selected from 1, 2, 3, or 4;
n is independently an integer selected from 0, 1, 2, 3, or 4;
X$^b$ is selected from the group consisting of CH$_2$, —NR$^a$, NH, O, S, and SO$_2$;
l is an integer selected from 0, 1, or 2;
each instance of R$^a$, where present, is independently selected from the group consisting of amino, —OH, halogen, cyano, hydroxy, optionally substituted C$_1$-C$_3$ alkyl, C-carboxy, and optionally substituted C$_1$-C$_6$ alkoxy(C$_1$-C$_6$)alkyl; and
wherein each R$^a$ can be provided at any position of the "A" ring by replacing one or more —H atoms of any carbon or nitrogen atom present within the "A" ring;
X$^4$ is selected from the group consisting of —CN, —OR$^1$, —SR$^1$, optionally substituted C$_1$-C$_{10}$ alkyl, optionally substituted C$_1$-C$_{10}$ alkenyl, optionally substituted C$_1$-C$_{10}$ alkynyl, optionally substituted 3-10 membered carbocyclyl, optionally substituted 6-10 membered aryl, optionally substituted 3-10 membered heterocyclyl, optionally substituted 5-10 membered heteroaryl, and —NR$^2$R$^3$;
R$^1$ is hydrogen or an optionally substituted C$_1$-C$_{10}$ alkyl;
each of R$^2$ and R$^3$ is independently selected from hydrogen and optionally substituted C$_{1-10}$ alkyl; or alternatively, R$^2$ and R$^3$ attached to the same nitrogen atom may be together with the atom to which they are attached, form an optionally substituted 3-10 membered heterocyclyl or an optionally substituted 5-10 membered heteroaryl;
R$^4$ is represented by one of:

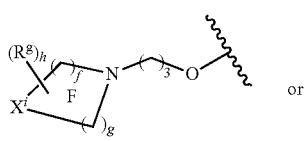
or

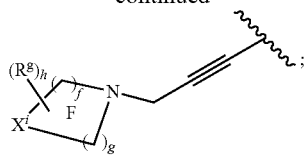
;

where
f is independently an integer selected from 1, 2, 3, or 4;
g is independently an integer selected from 0, 1, 2, 3, or 4;
X$^i$ is selected from the group consisting of CH$_2$, NH, O, S, and SO$_2$;
each instance of R$^g$, where present, is independently selected from the group consisting of amino, —OH, halogen, cyano, hydroxy, optionally substituted C$_1$-C$_6$ alkyl, C-carboxy, and optionally substituted C$_1$-C$_6$ alkoxy(C$_1$-C$_6$)alkyl;
h is an integer selected from 0, 1, 2, 3, or 4; and
wherein each R$^g$ can be provided at any position of the "F" ring by replacing one or more —H atoms of any carbon or nitrogen atom present within the "F" ring; and
R$^5$ is selected from the group consisting of hydrogen, halogen, and —OMe;
provided that, if X$^3$ is

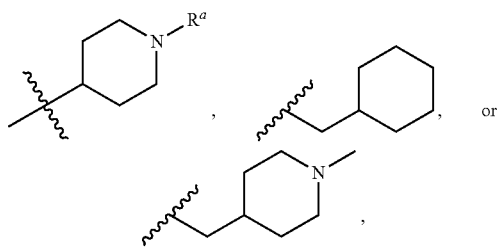

R$^5$ is —OMe, and R$^a$, where present, is methyl, isopropyl, cyclopropyl, cyclohexyl, or —CH$_2$-cyclohexyl, then X$^4$ is not optionally substituted cyclohexyl, an optionally substituted 5-membered to 7-membered heterocyclyl, an optionally substituted furanyl, or an optionally substituted pyrrolyl.

2. The compound of claim 1, wherein n is 1 and m is 1, n is 1 and m is 3, or n is 2 and m is 2.

3. The compound of claim 2, wherein X$^b$ is —NH, —NR$^a$, O or SO$_2$.

4. The compound of claim 3, where R$^4$ is one of the following structures:

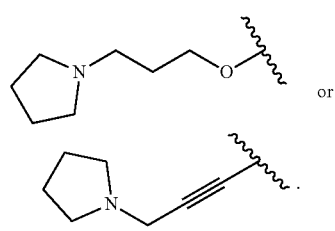

5. The compound of claim 1, wherein

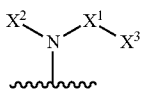

is represented by the following one of the following structures:

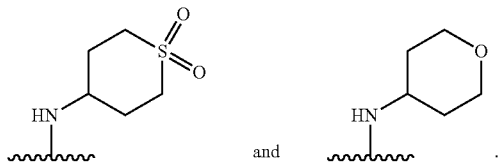 [SMILES: *NC1CCS(=O)(=O)CC1 ; *NC1CCOCC1]

6. The compound of claim 1, wherein X⁴ is represented by Formula (IX4):

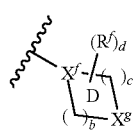

X$^f$ is selected from the group consisting of CH and N;
b is independently an integer selected from 1, 2, and 3;
c is independently an integer selected from 0, 1, 2, and 3;
d is independently an integer selected from 0, 1, 2, and 3;
X$^g$ is selected from the group consisting of CH$_2$, NH, O, and SO$_2$;
R$^f$ is optionally present and can be provided at any position of the "D" ring by replacing one or more —H of any carbon or nitrogen atom present within the "D" ring; and
R$^f$ is selected from the group consisting of halogen, amino, —OH, optionally substituted C$_1$-C$_6$ alkyl, and C-carboxy.

7. The compound of claim 6, wherein the optional substitutions of the "D" ring are selected from one or more of amino, —OH, optionally substituted C$_1$-C$_6$ alkyl, and halogen.

8. The compound of claim 1, wherein X⁴ is an optionally substituted 5-membered heteroaryl.

9. The compound of claim 1, wherein X⁴ is represented by:

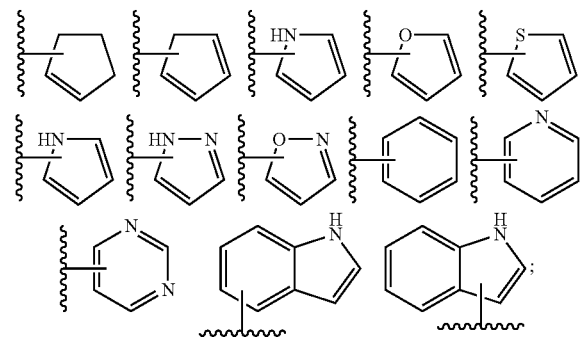

any one of which may be optionally substituted by replacing one or more —H atoms of any carbon or nitrogen atom present on X⁴.

10. The compound of claim 1, wherein X¹ is a covalent bond.

11. The compound of claim 1, wherein the compound is selected from the group consisting of:
- 4-((2-(4,4-difluoropiperidin-1-yl)-6-methoxy-7-(3-(pyrrolidin-1-yl)propoxy)quinazolin-4-yl)amino)tetrahydro-2H-thiopyran 1,1-dioxide;
- 2-(4,4-difluoropiperidin-1-yl)-6-methoxy-7-(3-(pyrrolidin-1-yl)propoxy)-N-(tetrahydro-2H-pyran-4-yl)quinazolin-4-amine;
- 2-(4,4-difluoropiperidin-1-yl)-6-methoxy-N-(1-(2-methoxyethyl)piperidin-4-yl)-7-(3-(pyrrolidin-1-yl)propoxy)quinazolin-4-amine;
- 2-(4,4-difluoropiperidin-1-yl)-6-methoxy-N-(2-methoxyethyl)-7-(3-(pyrrolidin-1-yl)propoxy)quinazolin-4-amine;
- 2-(4,4-difluoropiperidin-1-yl)-6-methoxy-N-((1-methylpiperidin-4-yl)methyl)-7-(3-(pyrrolidin-1-yl)propoxy)quinazolin-4-amine;
- (R)-6-methoxy-N-(piperidin-3-yl)-2-(pyrrolidin-1-yl)-7-(3-(pyrrolidin-1-yl)propoxy)quinazolin-4-amine;
- 2-(4-((2-(4,4-difluoropiperidin-1-yl)-6-methoxy-7-(3-(pyrrolidin-1-yl)propoxy)quinazolin-4-yl)amino)piperidin-1-yl)acetic acid;
- 2-(azetidin-1-yl)-N-(1-isopropylpiperidin-4-yl)-6-methoxy-7-(3-(pyrrolidin-1-yl)propoxy)quinazolin-4-amine;
- (S)-6-methoxy-N-(piperidin-3-yl)-2-(pyrrolidin-1-yl)-7-(3-(pyrrolidin-1-yl)propoxy)quinazolin-4-amine;
- N-(1-isopropylpiperidin-4-yl)-6-methoxy-2-(1H-pyrazol-1-yl)-7-(3-(pyrrolidin-1-yl)propoxy)quinazolin-4-amine;
- 4-((1-isopropylpiperidin-4-yl)amino)-6-methoxy-7-(3-(pyrrolidin-1-yl)propoxy)quinazoline-2-carbonitrile;
- 2-(4,4-difluoropiperidin-1-yl)-6-methoxy-N-(piperidin-4-yl)-7-(3-(pyrrolidin-1-yl)propoxy)quinazolin-4-amine;
- 2-(azetidin-1-yl)-6-methoxy-7-(3-(pyrrolidin-1-yl)propoxy)-N-(tetrahydro-2H-pyran-4-yl)quinazolin-4-amine;
- 6-methoxy-2-(pyrrolidin-1-yl)-7-(3-(pyrrolidin-1-yl)propoxy)-N-(tetrahydro-2H-pyran-4-yl)quinazolin-4-amine;
- 6-methoxy-2-morpholino-7-(3-(pyrrolidin-1-yl)propoxy)-N-(tetrahydro-2H-pyran-4-yl)quinazolin-4-amine;
- 6-methoxy-2-(4-methylpiperazin-1-yl)-7-(3-(pyrrolidin-1-yl)propoxy)-N-(tetrahydro-2H-pyran-4-yl)quinazolin-4-amine;
- 6-methoxy-2-(4-methyl-1,4-diazepan-1-yl)-7-(3-(pyrrolidin-1-yl)propoxy)-N-(tetrahydro-2H-pyran-4-yl)quinazolin-4-amine;
- 4-(6-methoxy-7-(3-(pyrrolidin-1-yl)propoxy)-4-((tetrahydro-2H-pyran-4-yl)amino)quinazolin-2-yl)thiomorpholine 1,1-dioxide;
- 4-((6-methoxy-2-(pyrrolidin-1-yl)-7-(3-(pyrrolidin-1-yl)propoxy)quinazolin-4-yl)amino)tetrahydro-2H-thiopyran 1,1-dioxide;
- 4-((6-methoxy-2-morpholino-7-(3-(pyrrolidin-1-yl)propoxy)quinazolin-4-yl)amino)tetrahydro-2H-thiopyran 1,1-dioxide;
- 4-((6-methoxy-2-(4-methylpiperazin-1-yl)-7-(3-(pyrrolidin-1-yl)propoxy)quinazolin-4-yl)amino)tetrahydro-2H-thiopyran 1,1-dioxide;

4-(4-(((1,1-dioxidotetrahydro-2H-thiopyran-4-yl)amino)-6-methoxy-7-(3-(pyrrolidin-1-yl)propoxy)quinazolin-2-yl)thiomorpholine 1,1-dioxide;

4-((6-methoxy-2-(4-methyl-1,4-diazepan-1-yl)-7-(3-(pyrrolidin-1-yl)propoxy)quinazolin-4-yl)amino)tetrahydro-2H-thiopyran 1,1-dioxide;

4-((2-(4,4-difluoropiperidin-1-yl)-6-methoxy-7-(3-(pyrrolidin-1-yl)prop-1-yn-1-yl)quinazolin-4-yl)amino)tetrahydro-2H-thiopyran 1,1-dioxide;

2-(4,4-difluoropiperidin-1-yl)-6-methoxy-N-(oxetan-3-yl)-7-(3-(pyrrolidin-1-yl)propoxy)quinazolin-4-amine;

2-(1H-imidazol-1-yl)-6-methoxy-7-(3-(pyrrolidin-1-yl)propoxy)-N-(tetrahydro-2H-pyran-4-yl)quinazolin-4-amine;

(R)-2-(4,4-difluoropiperidin-1-yl)-6-methoxy-7-(3-(pyrrolidin-1-yl)propoxy)-N-(tetrahydro-2H-pyran-3-yl)quinazolin-4-amine;

2-(4,4-difluoropiperidin-1-yl)-6-methoxy-7-(3-(pyrrolidin-1-yl)propoxy)-N-(tetrahydro-2H-pyran-3-yl)quinazolin-4-amine;

6-methoxy-N2,N2-dimethyl-7-(3-(pyrrolidin-1-yl)propoxy)-N4-(tetrahydro-2H-pyran-3-yl)quinazoline-2,4-diamine;

or a stereoisomer, tautomer, or pharmaceutically acceptable salt of any of the foregoing.

12. A pharmaceutical composition comprising a therapeutically effective amount of a compound of claim 1 and a pharmaceutically acceptable excipient.

\* \* \* \* \*

UNITED STATES PATENT AND TRADEMARK OFFICE
CERTIFICATE OF CORRECTION

PATENT NO. : 11,485,728 B2  
APPLICATION NO. : 17/531397  
DATED : November 1, 2022  
INVENTOR(S) : Dimitrios Iliopoulos Page 1 of 4

It is certified that error appears in the above-identified patent and that said Letters Patent is hereby corrected as shown below:

In the Specification

In Column 51, Lines 2-27, delete " 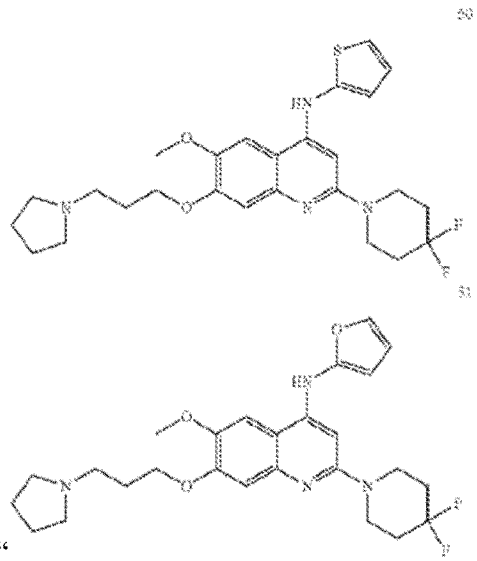 " and insert

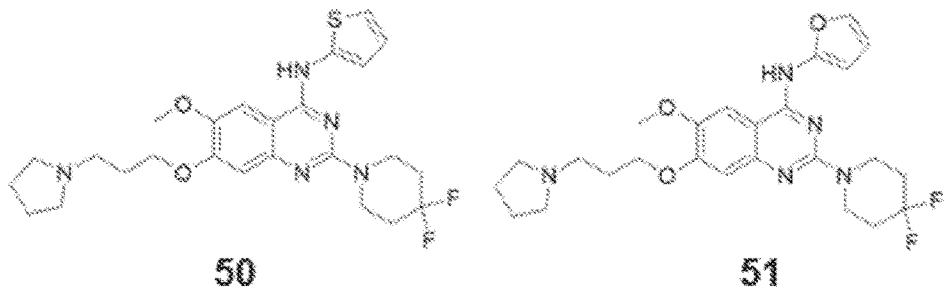

-- --.

Signed and Sealed this  
Sixth Day of February, 2024

Katherine Kelly Vidal  
*Director of the United States Patent and Trademark Office*

In Column 54, Lines 40-52, delete "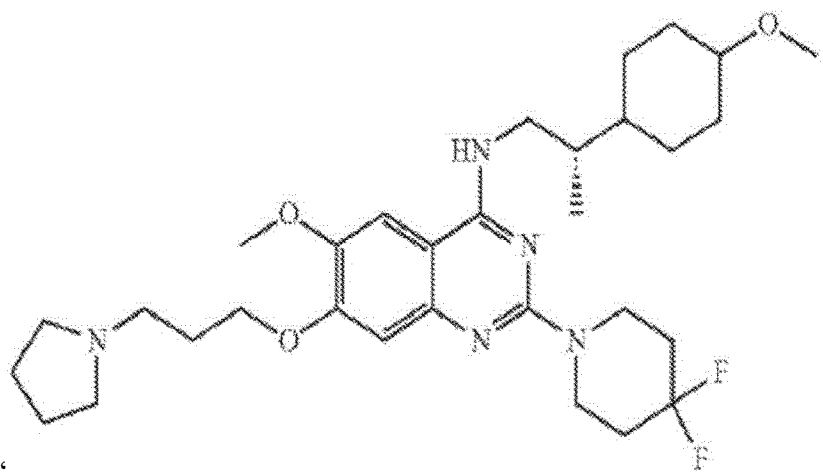" and insert
--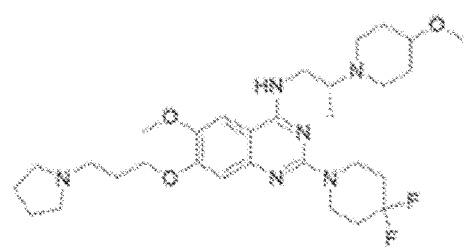--.
In Column 55, Lines 2-15, delete "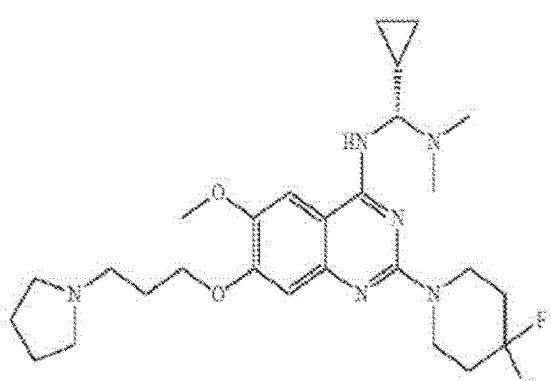" and insert

CERTIFICATE OF CORRECTION (continued)
U.S. Pat. No. 11,485,728 B2

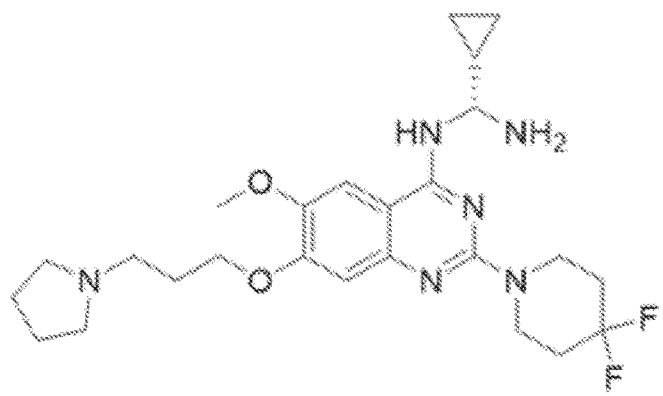

--                                                  --.

In Column 66, Lines 17-32, delete " 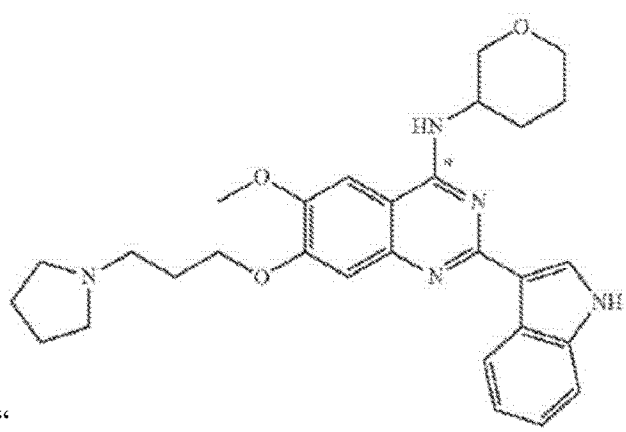 " and insert

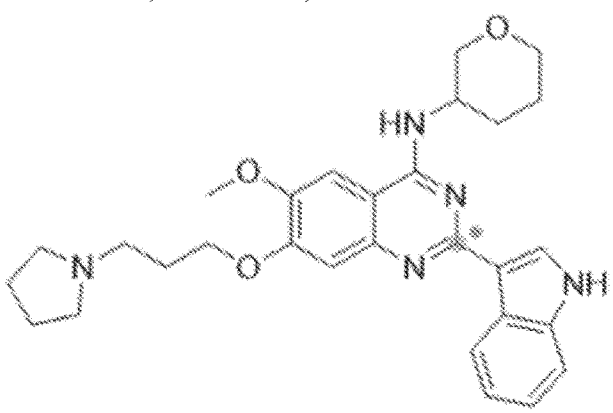

--                                                  --.

CERTIFICATE OF CORRECTION (continued)
U.S. Pat. No. 11,485,728 B2

In Column 83, Lines 25-37, delete " 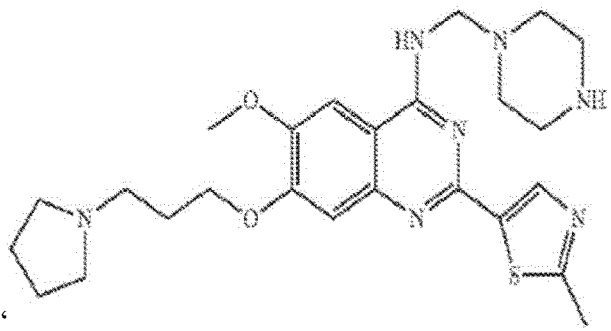 " and insert -- 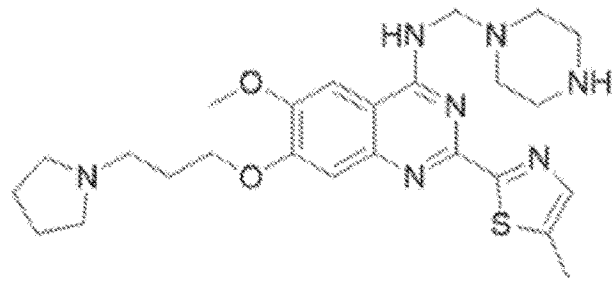 --.

In Column 112, Line 50-66, delete " 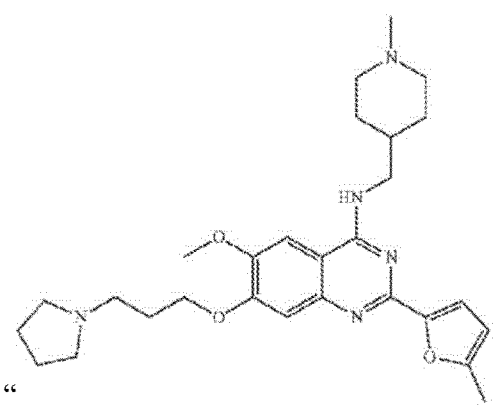 " and insert -- 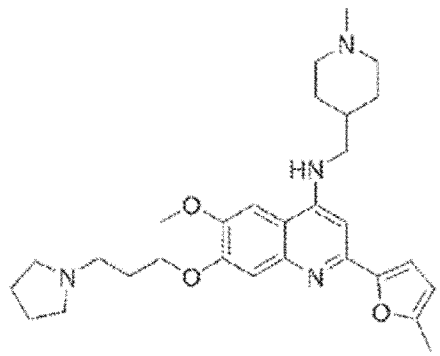 --.